United States Patent
Miller et al.

(10) Patent No.: US 10,358,463 B2
(45) Date of Patent: Jul. 23, 2019

(54) IMMUNOMODULATORS

(71) Applicant: BRISTOL-MYERS SQUIBB COMPANY, Princeton, NJ (US)

(72) Inventors: Michael Matthew Miller, Lambertville, NJ (US); Martin Patrick Allen, Flemington, NJ (US); Ling Li, Pennington, NJ (US); Michael S. Bowsher, Prospect, CT (US); Eric P. Gillis, Cheshire, CT (US); Eric Mull, Guilford, CT (US); Qian Zhao, Wallingford, CT (US); Li-Qiang Sun, Glastonbury, CT (US); David R. Langley, Meriden, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/475,227

(22) Filed: Mar. 31, 2017

(65) Prior Publication Data

US 2017/0283463 A1 Oct. 5, 2017

Related U.S. Application Data

(60) Provisional application No. 62/318,417, filed on Apr. 5, 2016.

(51) Int. Cl.
| | | |
|---|---|---|
| A61K 38/12 | (2006.01) | |
| C07K 7/56 | (2006.01) | |
| C07K 7/08 | (2006.01) | |
| C07K 7/54 | (2006.01) | |
| C07K 7/64 | (2006.01) | |
| A61K 38/00 | (2006.01) | |

(52) U.S. Cl.
CPC ............ *C07K 7/56* (2013.01); *A61K 38/12* (2013.01); *C07K 7/08* (2013.01); *C07K 7/54* (2013.01); *C07K 7/64* (2013.01); *A61K 38/00* (2013.01); *Y02A 50/463* (2018.01)

(58) Field of Classification Search
None
See application file for complete search history.

(56) References Cited

U.S. PATENT DOCUMENTS

| | | | |
|---|---|---|---|
| 5,869,451 A | 2/1999 | Dower et al. | |
| 9,090,668 B2 | 7/2015 | Suga et al. | |
| 9,410,148 B2 | 8/2016 | Suga et al. | |
| 9,732,119 B2 * | 8/2017 | Sun ................. | A61K 38/12 |
| 9,861,680 B2 * | 1/2018 | Mapelli ............ | A61K 38/12 |
| 9,879,046 B2 * | 1/2018 | Miller ............... | A61K 38/10 |
| 2014/0018257 A1 | 1/2014 | Suga et al. | |
| 2016/0158349 A1 | 6/2016 | Miller et al. | |
| 2016/0176928 A1 * | 6/2016 | Sun ................. | A61K 38/10 |
| | | | 424/278.1 |
| 2016/0272680 A1 | 9/2016 | Boy et al. | |
| 2016/0340391 A1 | 11/2016 | Miller et al. | |
| 2017/0260237 A1 * | 9/2017 | Miller .............. | C07K 7/64 |

FOREIGN PATENT DOCUMENTS

| | | | |
|---|---|---|---|
| WO | WO 00/26353 | 5/2000 | |
| WO | WO 2010/027828 A2 | 3/2010 | |
| WO | WO 2011/161699 A2 | 12/2011 | |
| WO | WO 2012/168944 A1 | 12/2012 | |
| WO | WO 2013/144704 A1 | 10/2013 | |
| WO | WO 2013/182240 A1 | 12/2013 | |
| WO | WO 2013/183707 A1 | 12/2013 | |
| WO | WO 2014/151006 A2 | 9/2014 | |
| WO | WO2014/151634 A1 | 9/2014 | |
| WO | WO-2014151634 A1 * | 9/2014 | ............ A61K 38/10 |
| WO | WO 2015/033303 A1 | 3/2015 | |
| WO | WO 2015/044900 A1 | 4/2015 | |
| WO | WO2016/039749 A1 | 3/2016 | |
| WO | WO 2016/057624 A1 | 4/2016 | |
| WO | WO2016/077518 A1 | 5/2016 | |
| WO | WO2016/100285 A1 | 6/2016 | |
| WO | WO2016/100608 A1 | 6/2016 | |
| WO | WO2016/126646 A1 | 8/2016 | |
| WO | WO 2017/151830 A1 | 9/2017 | |
| WO | WO 2017/201111 A1 | 11/2017 | |

OTHER PUBLICATIONS

Nowak, Mark W. et al, "In vivo incorporation of unnatural amino acids into ion channels in xenopus oocyte expression system." Methods Enzymol. (1988) 293 p. 504-529.*

Zhong, Wenge et al, "From ab initio quantum mechanics to molecular neurobiology: a cation-pi binding site in the nicotinic receptor." PNAS (1998) 95 p. 12088-12093.*

Zhang, Rumin et al, "Fluroescence polarization assay an inhibitor design for mdm2/p53 interaction." Anal. Biochem. (2004) 331 p. 138-146.*

Judd, A. K. et al, "Structure-activity studies on high affinity nop-active hexapeptides." J. Peptide. Res. (2004) 64(3) p. 87-94.*

Noichl, Benjamin P. et a, "Toward intrinsicallycolored peptides: synthesis and investigation of the spectral properteis of methyalted azatryptophans in tryptophan cage mutants." Biopolymers (2015) 104 p. 585-600.*

Dolušić, Eduard et al, "Tryptophan 2, 3 dioxygenase (tdo) inhibitors. 3-(2-(pyridyl)ethenyl)indoles as potential anticancer immunomodulators." J. Med. Chem. (2011) 54 p. 5320-5334.*

Hayashi, Y. et al., "In Vitro Selection of Anti-Akt2 Thioether-Macrocyclic Peptides Leading to Isoform-Selective Inhibitors", ACS Chemical Biology, vol. 7, pp. 607-613 (2012).

Morimoto, J. et al., "Discovery of Macrocyclic Peptides Armed with a Mechanism-Based Warhead: Isoform-Selective Inhibition of Human Deacetylase SIRT2", Angewandte Chemie, International Edition, vol. 51, pp. 3423-3427 (2012).

(Continued)

*Primary Examiner* — Fred H Reynolds
(74) *Attorney, Agent, or Firm* — Sterne, Kessler, Goldstein & Fox P.L.L.C.

(57) ABSTRACT

The present disclosure provides novel macrocyclic peptides which inhibit the PD-1/PD-L1 and PD-L1/CD80 protein/protein interaction, and thus are useful for the amelioration of various diseases, including cancer and infectious diseases.

15 Claims, No Drawings
Specification includes a Sequence Listing.

(56) References Cited

OTHER PUBLICATIONS

Yamagishi, Y. et al., "Natural Product-Like Macrocyclic N-Methyl-Peptide Inhibitors against a Ubiquitin Ligase Uncovered from a Ribosome-Expressed De Novo Library", Chemistry & Biology, vol. 18, pp. 1562-1570 (2011).
Cook, W. J. et al., Crystal Structure and Confirmation of the Cyclic Trimer of a Repeat Pentapeptide of Elastin, cyclo-(L-Valyl-L-prolylglycyl-L-valylglycyl)$_3$, J. Am. Chem. Soc., vol. 102, No. 17, p. 5502-5505 (1980).
Hoyer, K. M. et al., "The Iterative Gramicidin S Thioesterase Catalyzes Peptide Ligation and Cyclization," Chemistry & Biology, vol. 14, No. 1, p. 13-22 (2007).
Tamaki, M. et al., "Cyclization of Penta- and Hexapeptide Active Esters Related to Gramicidin S and Gratisin," Bulletin of the Chemical Society of Japan, vol. 62, No. 2, p. 594-596 (1989).
Karle, I. L., "Conformation of Cyclic Pentapeptides in the Crystalline State. Cyclic (D-Phe-L-Pro-Gly-D-Ala-L-Pro) with 3.fwdarw. 1 and 4.fwdarw. 1 Intramolecular Hydrogen Bonds", Database Accession No. 1981: 498291; Compound 78221-87-1, 1981.
Rothe, M. et al., Interchain Reactions (Cyclo-Oligomerizations) During the Cyclization of Resin-Bound Peptides, Database Accession No. 1978: 424771; Compound RN: 66517-17-7, 1977.

\* cited by examiner

SEQUENCE LISTING

<160> NUMBER OF SEQ ID NOS: 2

<210> SEQ ID NO 1
<211> LENGTH: 384
<212> TYPE: PRT
<213> ORGANISM: Homo sapiens

<400> SEQUENCE: 1

```
Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
                20                  25                  30

Ser Asn Thr Ser Glu Ser Phe Val Leu Asn Trp Tyr Arg Met Ser Pro
            35                  40                  45

Ser Asn Gln Thr Asp Lys Leu Ala Ala Phe Pro Glu Asp Arg Ser Gln
        50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Gly
    130                 135                 140

Ser Pro Gly Gly Gly Gly Arg Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285
```

```
Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
                340                 345                 350

Arg Trp Gln Gln Gly Asn Val Phe Ser Cys Ser Val Met His Glu Ala
                355                 360                 365

Leu His Asn His Tyr Thr Gln Lys Ser Leu Ser Leu Ser Pro Gly Lys
                370                 375                 380

<210> SEQ ID NO 2
<211> LENGTH: 237
<212> TYPE: PRT
<213> ORGANISM: Homo sapiens

<400> SEQUENCE: 2

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg Thr Gly Ser Ser
        210                 215                 220

Glu Thr Val Arg Phe Gln Gly His His His His His
225                 230                 235
```

IMMUNOMODULATORS

CROSS-REFERENCE TO RELATED APPLICATIONS

This application claims the benefit of U.S. provisional patent application Ser. No. 62/318,417, filed on Apr. 5, 2016, hereby incorporated by reference in its entirety.

The present disclosure provides novel macrocyclic peptides which inhibit the PD-1/PD-L1 and CD80/PD-L1 protein/protein interaction, and are thus useful for the amelioration of various diseases, including cancer and infectious diseases.

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al., Curr. Opin. Immunol., 14:779-782 (2002); Bennett et al., J. Immunol., 170:711-718 (2003)).

The PD-1 protein is a 55 kDa type I transmembrane protein that is part of the Ig gene superfamily (Agata et al., Int. Immunol., 8:765-772 (1996)). PD-1 contains a membrane proximal immunoreceptor tyrosine inhibitory motif (ITIM) and a membrane distal tyrosine-based switch motif (ITSM) (Thomas, M. L., J. Exp. Med, 181:1953-1956 (1995); Vivier, E. et al., Immunol. Today, 18:286-291 (1997)). Although structurally similar to CTLA-4, PD-1 lacks the MYPPY motif that is critical for CD80 CD86 (B7-2) binding. Two ligands for PD-1 have been identified, PD-L1 (B7-H1) and PD-L2 (b7-DC). The activation of T cells expressing PD-1 has been shown to be downregulated upon interaction with cells expressing PD-L1 or PD-L2 (Freeman et al., J. Exp. Med, 192:1027-1034 (2000); Latchman et al., Nat. Immunol., 2:261-268 (2001); Carter et al., Eur. J. Immunol., 32:634-643 (2002)). Both PD-L1 and PD-L2 are B7 protein family members that bind to PD-1, but do not bind to other CD28 family members. The PD-L1 ligand is abundant in a variety of human cancers (Dong et al., Nat. Med., 8:787-789 (2002)). The interaction between PD-1 and PD-L1 results in a decrease in tumor infiltrating lymphocytes, a decrease in T-cell receptor mediated proliferation, and immune evasion by the cancerous cells (Dong et al., J. Mol. Med, 81:281-287 (2003); Blank et al., Cancer Immunol. Immunother., 54:307-314 (2005); Konishi et al., Clin. Cancer Res., 10:5094-5100 (2004)). Immune suppression can be reversed by inhibiting the local interaction of PD-1 with PD-L1, and the effect is additive when the interaction of PD-1 with PD-L2 is blocked as well (Iwai et al., Proc. Natl. Acad. Sci. USA, 99:12293-12297 (2002); Brown et al., J. Immunol., 170:1257-1266 (2003)).

PD-L1 has also been shown to interact with CD80 (Butte M J et al, Immunity; 27:111-122 (2007)). The interaction P D-L1/CD80 on expressing immune cells has been shown to be an inhibitory one. Blockade of this interaction has been shown to abrogate this inhibitory interaction (Paterson A M, et al., J Immunol., 187:1097-1105 (2011); Yang J, et al. J Immunol. August 1; 187(3):1113-9 (2011)).

When PD-1 expressing T cells contact cells expressing its ligands, functional activities in response to antigenic stimuli, including proliferation, cytokine secretion, and cytotoxicity, are reduced. PD-1/PD-L1 or PD-L2 interactions down regulate immune responses during resolution of an infection or tumor, or during the development of self tolerance (Keir, M. E. et al., Annu. Rev. Immunol., 26:Epub (2008)). Chronic antigen stimulation, such as that which occurs during tumor disease or chronic infections, results in T cells that express elevated levels of PD-1 and are dysfunctional with respect to activity towards the chronic antigen (reviewed in Kim et al., Curr. Opin. Imm. (2010)). This is termed "T cell exhaustion". B cells also display PD-1/PD-ligand suppression and "exhaustion".

Blockade of PD-1/PD-L1 ligation using antibodies to PD-L1 has been shown to restore and augment T cell activation in many systems. Patients with advanced cancer benefit from therapy with a monoclonal antibody to PD-L1 (Brahmer et al., New Engl. J. Med. (2012)). Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors (Dong, H. et al., "B7-H1 pathway and its role in the evasion of tumor immunity", J. Mol. Med., 81(5):281-287 (2003); Dong, H. et al., "Tumor-associated B7-H1 promotes T-cell apoptosis: a potential mechanism of immune evasion", Nat. Med., 8(8):793-800 (2002)).

Interference with the PD-1/PD-L1 interaction causes enhanced T cell activity in systems with chronic infection. Blockade of PD-L1 caused improved viral clearance and restored immunity in mice with chromoic lymphocytic chorio meningitis virus infection (Barber, D. L. et al., "Restoring function in exhausted CD8 T cells during chronic viral infection", Nature, 439(7077):682-687 (2006)). Humanized mice infected with HIV-1 show enhanced protection against viremia and viral depletion of CD4+ T cells (Palmer et al., J. Immunol. (2013)). Blockade of PD-1/PD-L1 through monoclonal antibodies to PD-L1 can restore in vitro antigen-specific functionality to T cells from HIV patients (Day, Nature (2006); Petrovas, J. Exp. Med. (2006); Trautman, Nature Med. (2006); D'Souza, J. Immunol. (2007); Zhang, Blood (2007); Kaufmann, Nature Imm. (2007); Kasu, J. Immunol. (2010); Porichis, Blood (2011)), HCV patients (Golden-Mason, J. Virol. (2007); Jeung, J. Leuk. Biol. (2007); Urbani, J. Hepatol. (2008); Nakamoto, PLoS Path. (2009); Nakamoto, Gastroenterology (2008)) and HBV patients (Boni, Virol. (2007); Fisicaro, Gastro. (2010); Fisicaro et al., Gastroenterology (2012); Boni et al., Gastro. (2012); Penna et al., J Hep. (2012); Raziorrough, Hepatology (2009); Liang, World J Gastro. (2010); Zhang, Gastro. (2008)).

Blockade of the PD-L1/CD80 interaction has also been shown to stimulate immunity (Yang J., et al., J Immunol. August 1; 187(3):1113-9 (2011)). Immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., Nat Rev Immunol (2013)). These include increased levels of PD-1 and PD-L1 (Guignant, et al, Crit. Care (2011)). Cells from septic shock patients with increased levels of PD-1 and PD-L1 exhibit an increased level of T cell apoptosis. Antibodies directed to PD-L1, can reduce the level of Immune cell apoptosis (Zhang et al, Crit. Care (2011)). Furthermore, mice lacking PD-1 expression are more resistant to septic shock symptoms than wildtype mice. Yang J., et al. J Immunol. August 1; 187(3):1113-9 (2011)). Studies have revealed that blockade of the interactions of PD-L1 using antibodies can suppress inappropriate immune responses and ameliorate disease signs.

In addition to enhancing immunologic responses to chronic antigens, blockade of the PD-1/PD-L1 pathway has also been shown to enhance responses to vaccination, including therapeutic vaccination in the context of chronic infection (Ha, S. J. et al., "Enhancing therapeutic vaccination by blocking PD-1-mediated inhibitory signals during chronic infection", *J. Exp. Med*, 205(3):543-555 (2008); Finnefrock, A. C. et al., "PD-1 blockade in rhesus macaques: impact on chronic infection and prophylactic vaccination", *J. Immunol.*, 182(2):980-987 (2009); Song, M.-Y. et al., "Enhancement of vaccine-induced primary and memory CD8+t-cell responses by soluble PD-1", *J. Immunother.*, 34(3):297-306 (2011)).

The molecules described herein demonstrate the ability to block the interaction of PD-L1 with PD-1, in both biochemical and cell-based experimental systems. These results are consistent with a potential for therapeutic administration to enhance immunity in cancer or chronic infection, including therapeutic vaccine.

The macrocyclic peptides described herein are capable of inhibiting the interaction of PD-L1 with PD-1 and with CD80. These compounds have demonstrated highly efficacious binding to PD-L1, blockade of the interaction of PD-L1 with either PD-1 or CD80, and are capable of promoting enhanced T cell functional activity, thus making them candidates for parenteral, oral, pulmonary, nasal, buccal and sustained release formulations.

In a first aspect the present disclosure provides a compound of formula (I)

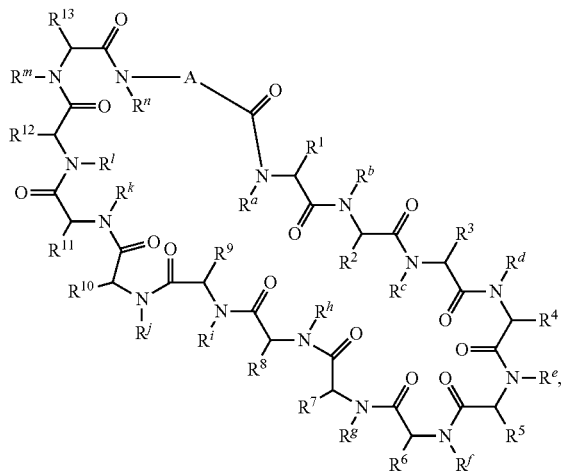

or a pharmaceutically acceptable salt thereof, wherein:
A is selected from a bond,

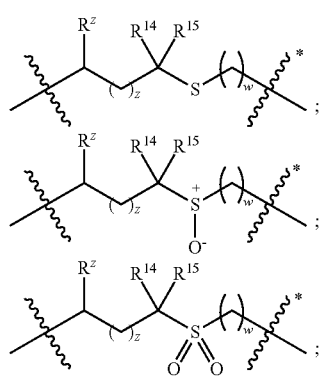

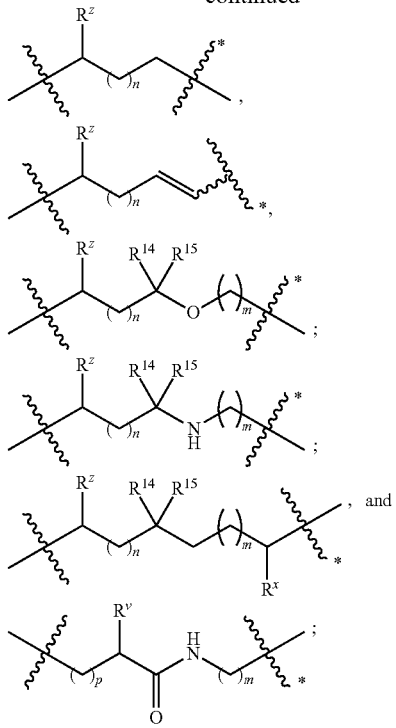

wherein:

$\sim\!\!\!\sim^*$ denotes the point of attachment to the carbonyl group and $\sim\!\!\!\sim$ denotes the point of attachment to the nitrogen atom;
z is 0, 1, or 2;
w is 1 or 2;
n is 0 or 1;
m is 1 or 2;
m' is 0 or 1;
p is 0, 1, or 2;
$R^x$ is selected from hydrogen, amino, hydroxy, and methyl;
$R^{14}$ and $R^{15}$ are independently selected from hydrogen and methyl; and
$R^z$ is selected from hydrogen and —C(O)NHR$^{16}$; wherein $R^{16}$ is selected from hydrogen, —CHR$^{17}$C(O)NH$_2$, —CHR$^{17}$C(O)NHCHR$^{18}$C(O)NH$_2$, and —CHR$^{17}$C(O)NHCHR$^{18}$C(O)NHCH$_2$C(O)NH$_2$; wherein $R^{17}$ is selected from hydrogen and —CH$_2$OH and wherein $R^{18}$ is selected from hydrogen and methyl;
$R^v$ is hydrogen or a natural amino acid side chain;

$\sim\!\!\!\sim^*$ denotes the point of attachment to the carbonyl group and $\sim\!\!\!\sim$ denotes the point of attachment to the nitrogen atom;
$R^c$, $R^f$, $R^h$, $R^i$, $R^m$, and $R^n$ are hydrogen;
$R^a$, $R^e$, $R^j$, and $R^k$, are each independently selected from hydrogen and methyl;
$R^{10}$ is indolylC$_1$-C$_3$alkyl, wherein the indolyl part is optionally substituted with one group selected from C$_1$-C$_6$alkoxy, C$_1$-C$_6$alkoxycarbonyl, C$_1$-C$_6$alkoxycarbonylC$_1$-C$_3$alkyl, (C$_1$-C$_6$alkyl)S(O)$_2$NHC(O)C$_1$-C$_3$alkyl, arylS(O)$_2$NHC(O)C$_1$-C$_3$alkyl, arylC$_1$-C$_3$alkylS(O)$_2$NHC(O)C$_1$-C$_3$alkyl, C$_3$-C$_6$cycloalkylS(O)$_2$NHC(O)C$_1$-C$_3$alkyl, C$_3$-C$_6$cycloalkylC$_1$-C$_3$alkylS(O)$_2$NHC(O)C$_1$-C$_3$alkyl, cyano, haloC$_1$-C$_3$alkoxy, haloC$_1$-C$_3$alkyl, heteroarylS(O)$_2$NHC(O)C$_1$-C$_3$alkyl, heteroarylC$_1$-C$_3$alkylS $(O)_2NHC(O)C_1$-$C_3$alkyl, —$NR^pR^q$, $(NR^pR^q)C_1$-$C_3$alkyl, and tetrazolyl$C_1$-$C_3$alkyl, or with two groups selected from $C_1$-$C_6$alkoxy, $C_1$-$C_6$alkoxycarbonyl, $C_1$-$C_6$alkoxycarbonyl$C_1$-$C_3$alkyl, $C_1$-$C_3$alkyl, ($C_1$-$C_6$alkyl)$S(O)_2NHC(O)C_1$-$C_3$alkyl, aryl$S(O)_2NHC(O)C_1$-$C_3$alkyl, aryl$C_1$-$C_3$alkyl$S(O)_2NHC(O)C_1$-$C_3$alkyl, carboxy, carboxy$C_1$-$C_3$alkyl, cyano, $C_3$-$C_6$cycloalkyl$S(O)_2NHC(O)C_1$-$C_3$alkyl, $C_3$-$C_6$cycloalkyl$C_1$-$C_3$alkyl$S(O)_2NHC(O)C_1$-$C_3$alkyl, halo, halo$C_1$-$C_3$alkoxy, halo$C_1$-$C_3$alkyl, heteroaryl$S(O)_2NHC(O)C_1$-$C_3$alkyl, heteroaryl$C_1$-$C_3$alkyl$S(O)_2NHC(O)C_1$-$C_3$alkyl, hydroxy, —$NR^pR^q$, $(NR^pR^qC_1$-$C_3$alkyl, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; or $R^{10}$ is azaindolyl$C_1$-$C_3$alkyl wherein the azaindolyl part of the azaindolyl$C_1$-$C_3$alkyl is substituted with one or two other groups independently selected from $C_1$-$C_6$alkoxy, $C_1$-$C_6$alkoxycarbonyl, $C_1$-$C_6$alkoxycarbonyl$C_1$-$C_3$alkyl, $C_1$-$C_3$alkyl, ($C_1$-$C_6$alkyl)$S(O)_2NHC(O)C_1$-$C_3$alkyl, aryl$S(O)_2NHC(O)C_1$-$C_3$alkyl, aryl$C_1$-$C_3$alkyl$S(O)_2NHC(O)C_1$-$C_3$alkyl, carboxy, carboxy$C_1$-$C_3$alkyl, cyano, $C_3$-$C_6$cycloalkyl$S(O)_2NHC(O)C_1$-$C_3$alkyl, $C_3$-$C_6$cycloalkyl$C_1$-$C_3$alkyl$S(O)_2NHC(O)C_1$-$C_3$alkyl, halo, halo$C_1$-$C_3$alkoxy, halo$C_1$-$C_3$alkyl, heteroaryl$S(O)_2NHC(O)C_1$-$C_3$alkyl, heteroaryl$C_1$-$C_3$alkyl$S(O)_2NHC(O)C_1$-$C_3$alkyl, hydroxy, —$NR^pR^q$, $(NR^pR^qC_1$-$C_3$alkyl, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; or $R^{10}$ is —$(CH_2)_nQ'$, wherein n is 1-3 and $Q'$ is a five, six-fused saturated or unsaturated ring system containing one, two, three, or four nitrogen atoms, wherein said ring system is optionally substituted with one, two, or three groups selected from $C_1$-$C_6$alkoxy, $C_1$-$C_6$alkoxycarbonyl, $C_1$-$C_6$alkoxycarbonyl$C_1$-$C_3$alkyl, $C_1$-$C_3$alkyl, ($C_1$-$C_6$alkyl)$S(O)_2NHC(O)C_1$-$C_3$alkyl, aryl$S(O)_2NHC(O)C_1$-$C_3$alkyl, aryl$C_1$-$C_3$alkyl$S(O)_2NHC(O)C_1$-$C_3$alkyl, carboxy, carboxy$C_1$-$C_3$alkyl, cyano, $C_3$-$C_6$cycloalkyl$S(O)_2NHC(O)C_1$-$C_3$alkyl, $C_3$-$C_6$cycloalkyl$C_1$-$C_3$alkyl$S(O)_2NHC(O)C_1$-$C_3$alkyl, halo, halo$C_1$-$C_3$alkoxy, halo$C_1$-$C_3$alkyl, heteroaryl$S(O)_2NHC(O)C_1$-$C_3$alkyl, heteroaryl$C_1$-$C_3$alkyl$S(O)_2NHC(O)C_1$-$C_3$alkyl, hydroxy, —$NR^pR^q$, $(NR^pR^q)C_1$-$C_3$alkyl, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; provided $Q'$ is other than azaindolyl or indolyl; or $R^{10}$ is —$(CH_2)_nZ'$, wherein n is 1-3 and $Z'$ is a six, six-fused saturated or unsaturated ring system containing one, two, three or four nitrogen atoms, wherein said ring system is optionally substituted with one, two, or three groups selected from $C_1$-$C_6$alkoxy, $C_1$-$C_6$alkoxycarbonyl, $C_1$-$C_6$alkoxycarbonyl$C_1$-$C_3$alkyl, $C_1$-$C_3$alkyl, ($C_1$-$C_6$alkyl)$S(O)_2NHC(O)C_1$-$C_3$alkyl, aryl$S(O)_2NHC(O)C_1$-$C_3$alkyl, aryl$C_1$-$C_3$alkyl$S(O)_2NHC(O)C_1$-$C_3$alkyl, carboxy, carboxy$C_1$-$C_3$alkyl, cyano, $C_3$-$C_6$cycloalkyl$S(O)_2NHC(O)C_1$-$C_3$alkyl, $C_3$-$C_6$cycloalkyl$C_1$-$C_3$alkyl$S(O)_2NHC(O)C_1$-$C_3$alkyl, halo, halo$C_1$-$C_3$alkoxy, halo$C_1$-$C_3$alkyl, heteroaryl$S(O)_2NHC(O)C_1$-$C_3$alkyl, heteroaryl$C_1$-$C_3$alkyl$S(O)_2NHC(O)C_1$-$C_3$alkyl, hydroxy, —$NR^pR^q$, $(NR^pR^q)C_1$-$C_3$alkyl, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo;

$R^p$ and $R^q$ are independently selected from hydrogen and $C_1$-$C_6$alkyl;

$R^{13}$ is selected from a natural amino acid side chain, an unnatural amino acid side chain, and —$(C(R^{17a})_2)_2$—X—$R^{30}$; —$C(R^{17a})_2C(O)N(R^{16a})C(R^{17a})_2$—$X'$—$R^{31}$; —$C(R^{17a})_2[C(O)N(R^{16a})C(R^{17a})_2]_{w'}$—X—$R^{31}$; —$(C(R^{17a})(R^{17})C(O)NR^{16a})_{n'}$—H; and —$(C(R^{17a})(R^{17})C(O)NR^{16a})_{m'}$—$C(R^{17a})(R^{17})$—$CO_2H$;

$w'$ is 2 or 3;

$n'$ is 1-6;

$m'$ is 0-5;

X is a chain of between 1 and 172 atoms wherein the atoms are selected from carbon and oxygen and wherein the chain may contain one, two, three, or four groups selected from —NHC(O)NH—, and —C(O)NH— embedded therein; and wherein the chain is optionally substituted with one to six groups independently selected from —$CO_2H$, —$C(O)NH_2$, —$CH_2C(O)NH_2$, and —$(CH_2)CO_2H$;

$X'$ is a chain of between 1 and 172 atoms wherein the atoms are selected from carbon and oxygen and wherein the chain may contain one, two, three, or four groups selected from —NHC(O)NH—, and —C(O)NH— embedded therein; and wherein the chain is optionally substituted with one to six groups independently selected from —$CO_2H$, —$C(O)NH_2$, and —$CH_2CO_2H$, provided that $X'$ is other than unsubstituted PEG;

$R^{30}$ is selected from —$CO_2H$, —$C(O)NR^wR^x$, and —$CH_3$ wherein $R^w$ and $R^x$ are independently selected from hydrogen and $C_1$-$C_6$alkyl, provided that when X is all carbon, $R^{30}$ is other than —$CH_3$;

$R^{31}$ is —$CO_2H$, —$C(O)NR^wR^x$, —$CH_3$, alexa-5-SDP, and biotin;

each $R^{17a}$ is independently selected from hydrogen, $C_1$-$C_6$alkyl, —$CH_2OH$, —$CH_2CO_2H$, —$(CH_2)_2CO_2H$, each $R^{17}$ is independently selected from hydrogen, —$CH_3$, $(CH_2)_zN_3$, —$(CH_2)_zNH_2$, —X—$R^{31}$, —$(CH_2)_zCO_2H$, —$CH_2OH$, $CH_2C\!\!=\!\!CH$, and —$(CH_2)_z$-triazolyl-X—$R^{35}$, wherein z is 1-6 and $R^{35}$ is selected from —$CO_2H$, —$C(O)NR^wR^x$, $CH_3$, biotin, -2-fluoropyridine, —$C(O)$—$(CH_2)_2$—$C(O)O$-vitamin E, —$C(O)O$-vitamin E; and

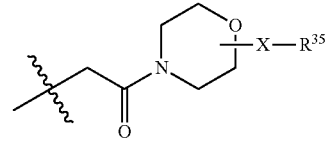

provided at least one $R^{17}$ is other than hydrogen, —$CH_3$, or —$CH_2OH$;

$R^1$, $R^2$, $R^3$, $R^4$, $R^5$, $R^6$, $R^7$, $R^8$, $R^9$, $R^{11}$, and $R^{12}$ are independently selected from a natural amino acid side chain and an unnatural amino acid side chain or form a ring with the corresponding vicinal R group as described below;

$R^e$ and $R^k$ can each form a ring with the corresponding vicinal R group and the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, and hydroxy;

$R^b$ is methyl or, $R^b$ and $R^2$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, and hydroxy;

$R^d$ is hydrogen or methyl, or, $R^d$ and $R^4$, together with the atoms to which they are attached, can form a ring selected from azetidine, pyrollidine, morpholine, piperidine, piperazine, and tetrahydrothiazole; wherein each ring is optionally substituted with one to four groups independently selected from amino, cyano, methyl, halo, hydroxy, and phenyl;

$R^g$ is hydrogen or methyl or $R^g$ and $R^7$, together with the atoms to which they are attached, can form a ring selected from azetidine, pyrollidine, morpholine, piperidine, piperazine, and tetrahydrothiazole; wherein each ring is optionally substituted with one to four groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and $R^L$ is methyl or, $R^L$ and $R^{12}$, together with the atoms to which they are attached, form a ring selected from azetidine and pyrollidine, wherein each ring is optionally substituted with one to four independently selected from amino, cyano, methyl, halo, and hydroxy.

In a first embodiment the present disclosure provides a compound of formula (I), or a pharmaceutically acceptable salt thereof, wherein $R^{13}$ is a natural amino acid side chain or an unnatural amino acid side chain.

In a second embodiment the present disclosure provides a compound of formula (I), or a pharmaceutically acceptable salt thereof, wherein:

$R^{13}$ is a natural amino acid side chain or an unnatural amino acid side chain; and $R^{10}$ is indolyl$C_1$-$C_3$alkyl, wherein the indolyl part is optionally substituted with one group selected from ($C_1$-$C_6$alkyl)S(O)$_2$NHC(O)$C_1$-$C_3$alkyl, $C_1$-$C_6$alkoxy, cyano, and tetrazolyl$C_1$-$C_3$alkyl, or with two groups selected from $C_1$-$C_6$alkoxy, $C_1$-$C_3$alkyl, ($C_1$-$C_6$alkyl)S(O)$_2$NHC(O)$C_1$-$C_3$alkyl, carboxy, carboxy$C_1$-$C_3$alkyl, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; or $R^{10}$ is azaindolyl$C_1$-$C_3$alkyl wherein the azaindolyl part of the azaindolyl$C_1$-$C_3$alkyl is substituted with a carboxy$C_1$-$C_3$alkyl and optionally one or two other groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; or $R^{10}$ is —(CH$_2$)$_n$Q', wherein n is 1-3 and Q' is a five, six-fused saturated or unsaturated ring system containing two, three, or four nitrogen atoms, wherein said ring system is optionally substituted with one, two, or three groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, carboxy$C_1$-$C_3$alkyl, cyano, halo, hydroxy, oxo, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; provided Q' is other than azaindolyl or indolyl; or $R^{10}$ is —(CH$_2$)$_n$Z', wherein n is 1-3 and Z' is a six, six-fused saturated or unsaturated ring system containing one, two, three or four nitrogen atoms, wherein said ring system is optionally substituted with one, two, or three groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo.

In a third embodiment, the present disclosure provides a compound of formula (I), or a pharmaceutically acceptable salt thereof, wherein:

$R^{13}$ is a natural amino acid side chain or an unnatural amino acid side chain;

$R^{10}$ is indolyl$C_1$-$C_3$alkyl, wherein the indolyl part is optionally substituted with one group selected from ($C_1$-$C_6$alkyl)S(O)$_2$NHC(O)$C_1$-$C_3$alkyl, $C_1$-$C_6$alkoxy, cyano, and tetrazolyl$C_1$-$C_3$alkyl, or with two groups selected from $C_1$-$C_6$alkoxy, $C_1$-$C_3$alkyl, ($C_1$-$C_6$alkyl)S(O)$_2$NHC(O)$C_1$-$C_3$alkyl, carboxy, carboxy$C_1$-$C_3$alkyl, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; or $R^{10}$ is azaindolyl$C_1$-$C_3$alkyl wherein the azaindolyl part of the azaindolyl$C_1$-$C_3$alkyl is substituted with a carboxy$C_1$-$C_3$alkyl and optionally one or two other groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; or $R^{10}$ is —(CH$_2$)$_n$Q', wherein n is 1-3 and Q' is a five, six-fused saturated or unsaturated ring system containing two, three, or four nitrogen atoms, wherein said ring system is optionally substituted with one, two, or three groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, carboxy$C_1$-$C_3$alkyl, cyano, halo, hydroxy, oxo, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; provided Q' is other than azaindolyl or indolyl; or $R^{10}$ is —(CH$_2$)$_n$Z', wherein n is 1-3 and Z' is a six, six-fused saturated or unsaturated ring system containing one, two, three or four nitrogen atoms, wherein said ring system is optionally substituted with one, two, or three groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; and A is

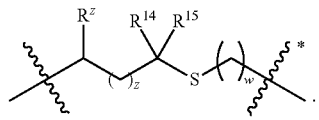

In a fourth embodiment, the present disclosure provides a compound of formula (I), or a pharmaceutically acceptable salt thereof, wherein:

$R^{13}$ is a natural amino acid side chain or an unnatural amino acid side chain;

$R^{10}$ is indolyl$C_1$-$C_3$alkyl, wherein the indolyl part is optionally substituted with one group selected from ($C_1$-$C_6$alkyl)S(O)$_2$NHC(O)$C_1$-$C_3$alkyl, $C_1$-$C_6$alkoxy, cyano, and tetrazolyl$C_1$-$C_3$alkyl, or with two groups selected from $C_1$-$C_6$alkoxy, $C_1$-$C_3$alkyl, ($C_1$-$C_6$alkyl)S(O)$_2$NHC(O)$C_1$-$C_3$alkyl, carboxy, carboxy$C_1$-$C_3$alkyl, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; or $R^{10}$ is azaindolyl$C_1$-$C_3$alkyl wherein the azaindolyl part of the azaindolyl$C_1$-$C_3$alkyl is substituted with a carboxy$C_1$-$C_3$alkyl and optionally one or two other groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; or $R^{10}$ is —(CH$_2$)$_n$Q', wherein n is 1-3 and Q' is a five, six-fused saturated or unsaturated ring system containing two, three, or four nitrogen atoms, wherein said ring system is optionally substituted with one, two, or three groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, carboxy$C_1$-$C_3$alkyl, cyano, halo, hydroxy, oxo, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; provided Q' is other than azaindolyl or indolyl; or $R^{10}$ is —(CH$_2$)$_n$Z', wherein n is 1-3 and Z' is a six, six-fused saturated or unsaturated ring system containing one, two, three or four nitrogen atoms, wherein said ring system is optionally substituted with one, two, or three groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo;

A is w is 1;

z is 0; and $R^z$ is —C(O)NHR$^{16}$; wherein R$^{16}$ is selected from hydrogen and —CHR$^{17}$C(O)NH$_2$, wherein R$^{17}$ is hydrogen.

In a fifth embodiment, the present disclosure provides a compound of formula (I), or a pharmaceutically acceptable salt thereof, wherein:

$R^{13}$ is a natural amino acid side chain or an unnatural amino acid side chain;

$R^{10}$ is indolyl$C_1$-$C_3$alkyl, wherein the indolyl part is optionally substituted with one group selected from ($C_1$-$C_6$alkyl)S(O)$_2$NHC(O)$C_1$-$C_3$alkyl, $C_1$-$C_6$alkoxy, cyano, and tetrazolyl$C_1$-$C_3$alkyl, or with two groups selected from $C_1$-$C_6$alkoxy, $C_1$-$C_3$alkyl, ($C_1$-$C_6$alkyl)S(O)$_2$NHC(O)$C_1$-$C_3$alkyl, carboxy, carboxy$C_1$-$C_3$alkyl, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; or $R^{10}$ is azaindolyl$C_1$-$C_3$alkyl wherein the azaindolyl part of the azaindolyl$C_1$-$C_3$alkyl is substituted with a carboxy$C_1$-$C_3$alkyl and optionally one or two other groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; or $R^{10}$ is —(CH$_2$)$_n$Q', wherein n is 1-3 and Q' is a five, six-fused saturated or unsaturated ring system containing two, three, or four nitrogen atoms, wherein said ring system is optionally substituted with one, two, or three groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, carboxy$C_1$-$C_3$alkyl, cyano, halo, hydroxy, oxo, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; provided Q' is other than azaindolyl or indolyl; or $R^{10}$ is —(CH$_2$)$_n$Z', wherein n is 1-3 and Z' is a six, six-fused saturated or unsaturated ring system containing one, two, three or four nitrogen atoms, wherein said ring system is optionally substituted with one, two, or three groups selected from $C_1$-$C_6$alkoxy, $C_1$-$C_6$alkyl, ($C_1$-$C_6$alkyl)S(O)$_2$NHC(O)$C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo;

A is w is 1;

z is 0;

$R^z$ is —C(O)NHR$^{16}$; wherein R$^{16}$ is selected from hydrogen and —CHR$^{17}$C(O)NH$_2$, wherein R$^{17}$ is hydrogen;

$R^d$ and $R^4$, together with the atoms to which they are attached, form a pyrollidine ring;

$R^g$ and $R^7$, together with the atoms to which they are attached, form a pyrollidine ring, wherein said ring is optionally substituted with one hydroxy group; and $R^k$ is methyl.

In a sixth embodiment, the present disclosure provides a compound of formula (I), or a pharmaceutically acceptable salt thereof, wherein:

A is w is 1;

z is 0;

$R^z$ is —C(O)NHR$^{16}$; wherein R$^{16}$ is selected from hydrogen and —CHR$^{17}$C(O)NH$_2$, wherein R$^{17}$ is hydrogen;

$R^d$ and $R^4$, together with the atoms to which they are attached, form a pyrollidine ring;

$R^g$ and $R^7$, together with the atoms to which they are attached, form a pyrollidine ring, wherein said ring is optionally substituted with one hydroxy group; and $R^k$ is methyl;

$R^a$, $R^e$, and $R^j$ hydrogen;

$R^b$ and $R^2$ are each methyl, or, $R^b$ and $R^2$, together with the atoms to which they are attached, form a piperidine ring;

$R^L$ is methyl;
$R''$ is hydrogen;
$R^1$ is phenylmethyl wherein the phenyl is optionally substituted with one group selected from $C_1$-$C_6$alkoxy, halo, and hydroxy;
$R^3$ is selected from —$CH_2C(O)NH_2$ and —$CH_2CO_2H$;
$R^5$ is selected from —$CH_2$(imidazolyl), —$CH_2NH_2$, and —$CH_2CH_2CO_2H$;
$R^6$ is selected from —$CH_2CH(CH_3)_2$, —$(CH_2)_4NH_2$, and $(CH_2)_2C(O)NH_2$;
$R^8$ is —$CH_2$(indolyl);
$R^9$ is selected from —$(CH_2)_2NH_2$ and $CH_2OH$;
$R^{10}$ is —$CH_2$(indolyl), wherein the indolyl part is optionally substituted with one group selected from —$CH_2C(O)NHS(O)_2CH_3$, cyano, and —$CH_2$(tetrazolyl), or with two groups selected from —$OCH_3$, —$CO_2H$, and —$CH_2CO_2H$ or
$R^{10}$ is —$CH_2$(azaindolyl) wherein the azaindolyl part of the azaindolyl$C_1$-$C_3$alkyl is substituted with —$CH_2CO_2H$; or
$R^{10}$ is —$(CH_2)_nQ'$, wherein n is 1 and Q' is a five, six-fused saturated or unsaturated ring system containing two or three nitrogen atoms, wherein said ring system is optionally substituted with one or two groups selected from —$CH_3$, —$CH_2CO_2H$, and oxo; provided Q' is other than azaindolyl or indolyl; or
$R^{10}$ is —$(CH_2)_nZ'$, wherein n is 1 and Z' is a six, six-fused saturated or unsaturated ring system containing one nitrogen atom;
$R^{11}$ and $R^{12}$ are —$(CH_2)_3CH_3$; and
$R^{13}$ is selected from methyl, —$CH_2CH(CH_3)_2$, and —$(CH_2)_3NHC(NH)NH_2$.

In a second aspect the present disclosure provides a method of enhancing, stimulating, and/or increasing the immune response in a subject in need thereof, said method comprising administering to the subject a therapeutically effective amount of a compound of formula (I) or a therapeutically acceptable salt thereof. In a first embodiment of the second aspect the method further comprises administering an additional agent prior to, after, or simultaneously with the compound of formula (I) or a therapeutically acceptable salt thereof. In a second embodiment of the second aspect the additional agent is an antimicrobial agent, an antiviral agent, a cytotoxic agent, and/or an immune response modifier. In a third embodiment of the second aspect the additional agent is an HDAC inhibitor. In a fourth embodiment of the second aspect the additional agent is a TLR7 and/or TLR8 agonist.

In a third aspect the present disclosure provides a method of inhibiting growth, proliferation, or metastasis of cancer cells in a subject in need thereof, said method comprising administering to the subject a therapeutically effective amount a compound of formula (I) or a therapeutically acceptable salt thereof. In a first embodiment of the third aspect the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and hematological malignancies.

In a fourth aspect the present disclosure provides a method of treating an infectious disease in a subject in need thereof, the method comprising administering to the subject a therapeutically effective amount of a compound of formula (I), or a therapeutically acceptable salt thereof. In a first embodiment of the fourth aspect the infectious disease is caused by a virus. In a second embodiment of the fourth aspect the virus is selected from HIV, Hepatitis A, Hepatitis B, Hepatitis C, herpes viruses, and influenza.

In a fifth aspect the present disclosure provides a method of treating septic shock in a subject in need thereof, the method comprising administering to the subject a therapeutically effective amount of a compound of formula (I), or a therapeutically acceptable salt thereof.

In a sixth aspect the present disclosure provides a method for blocking the interaction of PD-L1 with PD-1 and/or CD80 in a subject, said method comprising administering to the subject a therapeutically effective amount of a compound of formula (I), or a therapeutically acceptable salt thereof.

In compounds of formula (I) where the R side chains are part of a ring that is substituted with methyl, it is understood that the methyl group may be on any substitutable carbon atom in the ring, including the carbon that is part of the macrocyclic parent structure.

In compounds of formula (I), preferred $R^1$ side chains are: phenylalanine, tyrosine, 3-thien-2-yl, 4-methylphenylalanine, 4-chlorophenylalanine, 3-methoxyphenylalananie, isotryptophan, 3-methylphenylalanine, 1-naphthylalanine, 3,4-difluorophenylalanine, 4-fluorophenylalanine, 3,4-dimethoxyphenylalanine, 3,4-dichlorophenylalanine, 4-difluoromethylphenylalanine, 2-methylphenylalanine, 2-naphthylalanine, tryptophan, 4-pyridinyl, 4-bromophenylalanine, 3-pyridinyl, 4-trifluoromethylphenylalanine, 4-carboxyphenylalanine, 4-methoxyphenylalanine, biphenylalanine, and 3-chlorophenylalanine; and 2,4-diaminobutane.

In compounds of formula (I) where $R^2$ is not part of a ring, preferred $R^2$ side chains are: alanine, serine, and glycine.

In compounds of formula (I), preferred $R^3$ side chains are: asparagine, aspartic acid, glutamic acid, glutamine, serine, ornithine, lysine, histidine, threonine, leucine, alanine, 2,3-diaminopropane, and 2,4-diaminobutane.

In compounds of formula (I) where $R^4$ is not part of a ring, preferred $R^4$ side chains are: valine, alanine, isoleucine, and glycine.

In compounds of formula (I), preferred $R^5$ side chains are: aminomethane, glutamic acid, histidine, asparagine, 2,3-diaminopropane, serine, glycine, 2,4-diaminobutane, threonine, alanine, lysine, aspartic acid, alanine, and 3-thiazolylalanine.

In compounds of formula (I), preferred $R^6$ side chains are: leucine, aspartic acid, asparagine, glutamic acid, glutamine, serine, lysine, 3-cyclohexane, threonine, ornithine, 2,4-diaminobutane, alanine, arginine, and ornithine ($COCH_3$).

In compounds of formula (I) where $R^7$ is not part of a ring, preferred $R^7$ side chains are: glycine, 2,4-diaminobutane, serine, lysine, arginine, ornithine, histidine, asparagine, glutamine, alanine, and 2,4-diaminobutane (C(O)cyclobutane).

In compounds of formula (I) preferred $R^8$ side chains are tryptophan and 1,2-benzisothiazolinylalanine.

In compounds of formula (I) preferred $R^9$ side chains are: serine, aminoethane, histidine, lysine, ornithine, 2,4-dibutylamine, threonine, glycine, glutamic acid, valine, 2,3-diaminopropane, arginine, aspartic acid, and tyrosine.

In compounds of formula (I) it should be understood that the $R^{10}$ side chains can be attached through any substitutable carbon or nitrogen atom in the ring.

In compounds of formula (I) preferred $R^{11}$ side chains are: norleucine, leucine, asparagine, phenylalanine, methionine, ethoxymethane, alanine, tryptophan, isoleucine, phenylpropane, glutamic acid, hexane, and heptane.

In compounds of formula (I) where $R^{12}$ is not part of a ring, preferred $R^{12}$ side chains are: norleucine, alanine, ethoxymethane, methionine, serine, phenylalanine, methoxyethane, leucine, tryptophan, isoleucine, glutamic acid, hexane, heptane, and glycine.

In compounds of formula (I) preferred $R^{13}$ side chains: arginine, ornithine, alanine, 2,4-diaminobutane, 2,3-diaminopropane, leucine, aspartic acid, glutamic acid, serine, lysine, threonine, cyclopropylmethane, glycine, valine, isoleucine, histidine, and 2-aminobutane.

In accordance with the present disclosure, we have discovered peptides that specifically bind to PD-L1 and are capable of inhibiting the interaction of PD-L1 with PD-1 and CD80. These macrocyclic peptides exhibit in vitro immunomodulatory efficacy thus making them therapeutic candidates for the treatment of various diseases including cancer and infectious diseases.

The terms "specific binding" or "specifically bind" refer to the interaction between a protein and a binding molecule, such as a compound or ligand. The interaction is dependent upon the presence of a particular structure (i.e., an enzyme binding site, an antigenic determinant or epitope) of the protein that is recognized by the binding molecule. For example, if a compound has specific binding for protein binding site "A", the presence of the compound in a reaction containing a protein including binding site A, and a labeled peptide that specifically binds to protein binding site A will reduce the amount of labeled peptide bound to the protein. In contrast, nonspecific binding of a compound to the protein does not result in a concentration-dependent displacement of the labeled peptide from the protein.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

An additional aspect of the subject matter described herein is the use of the disclosed peptides as radiolabeled ligands for development of ligand binding assays or for monitoring of in vivo adsorption, metabolism, distribution, receptor binding or occupancy, or compound disposition. For example, a macrocyclic peptide described herein may be prepared using the radioactive isotope $^{125}I$ and the resulting radiolabeled peptide may be used to develop a binding assay or for metabolism studies. Alternatively, and for the same purpose, a macrocyclic peptide described herein may be converted to a radiolabeled form by catalytic tritiation using methods known to those skilled in the art.

The macrocyclic peptides of the present disclosure can also be used as PET imaging agents by adding a radioactive tracer using methods known to those skilled in the art.

Preferred peptides include at least one of the macrocyclic peptides provided herein and these peptides may be included in pharmaceutical compositions and combinations.

The definitions provided herein apply, without limitation, to the terms as used throughout this specification, unless otherwise limited in specific instances.

Those of ordinary skill in the art of amino acid and peptide chemistry are aware that an amino acid includes a compound represented by the general structure:

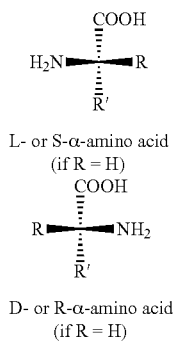

L- or S-α-amino acid (if R = H)

D- or R-α-amino acid (if R = H)

where R and R' are as discussed herein.

Unless otherwise indicated, the term "amino acid" as employed herein, alone or as part of another group, includes, without limitation, an amino group and a carboxyl group linked to the same carbon, referred to as "a" carbon, where R and/or R' can be a natural or an un-natural side chain, including hydrogen. The absolute "S" configuration at the "a" carbon is commonly referred to as the "L" or "natural" configuration. In the case where both the "R" and the "R'" (prime) substituents equal hydrogen, the amino acid is glycine and is not chiral.

The terms "natural amino acid side chain" and "naturally occurring amino acid side chain," as used herein, refer to side chain of any of the naturally occurring amino acids (i.e., alanine, arginine, asparagine, aspartic acid, cysteine, glutamine, glutamic acid, glycine,-histidine, isoleucine, leucine, lysine, methionine, phenylalanine, proline, serine, threonine, tryptophan, tyrosine, and valine) usually in the S-configuration (i.e., the L-amino acid).

The terms "unnatural amino acid side chain" and "non-naturally occurring amino acid side chain," as used herein, refer to a side chain of any naturally occurring amino acid usually in the R-configuration (i.e., the D-amino acid) or to a group other than a naturally occurring amino acid side chain in R- or S-configuration (i.e., the D- or L-amino acid, respectively) selected from:

$C_2$-$C_7$alkenyl, $C_1$-$C_3$alkoxy$C_1$-$C_3$alkyl, $C_1$-$C_6$alkoxycarbonyl$C_1$-$C_3$alkyl, $C_1$-$C_7$alkyl, $C_1$-$C_3$alkylsulfanyl$C_1$-$C_3$alkyl, amido$C_1$-$C_3$alkyl, amino$C_1$-$C_3$alkyl, benzothiazolyl$C_1$-$C_3$alkyl, benzothienyl$C_1$-$C_3$alkyl, benzyloxy$C_1$-$C_3$alkyl, carboxy$C_1$-$C_3$alkyl, $C_3$-$C_{14}$cycloalkyl$C_1$-$C_3$alkyl, $C_3$-$C_6$cycloalkyl$C_1$-$C_3$alkyl, diphenylmethyl, furanyl$C_1$-$C_3$alkyl, imidazolyl$C_1$-$C_3$alkyl, naphthyl$C_1$-$C_3$alkyl, pyridinyl$C_1$-$C_3$alkyl, thiazolyl$C_1$-$C_3$alkyl, thienyl$C_1$-$C_3$alkyl;

azaindolyl$C_1$-$C_3$alkyl, wherein the azaindolyl part of the azaindolyl$C_1$-$C_3$alkyl is optionally substituted with one or two substituents independently selected from $C_1$-$C_6$alkoxy, $C_1$-$C_6$alkyl, ($C_1$-$C_6$alkyl)S(O)$_2$NHC(O)$C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo;

biphenyl$C_1$-$C_3$alkyl wherein the biphenyl is optionally substituted with a methyl group;

—(CH$_2$)$_n$Q', wherein n is 1-3 and Q' is a five, six-fused saturated or unsaturated ring system containing two, three, or four nitrogen atoms, wherein said ring system is optionally substituted with one, two, or three groups selected from $C_1$-$C_6$alkoxy, $C_1$-$C_6$alkyl, $(C_1$-$C_6$alkyl)$S(O)_2NHC(O)C_1$-$C_3$alkyl, $(C_{1-6}$alkyl)sulfamidyl$C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; provided Q' is other than azaindolyl or indolyl; or —$(CH_2)_n Z'$, wherein n is 1-3 and Z' is a six, six-fused saturated or unsaturated ring system containing one, two, three or four nitrogen atoms, wherein said ring system is optionally substituted with one, two, or three groups selected from $C_1$-$C_6$alkoxy, $C_1$-$C_6$alkyl, $(C_1$-$C_6$alkyl)$S(O)_2NHC(O)$ $C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo;

heterocyclyl optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, —$NC(NH_2)_2$, nitro, and —$OP(O)(OH)_2$;

indolyl$C_1$-$C_3$alkyl, wherein the indolyl part is optionally substituted with one or two groups selected from $(C_{1-6}$alkyl)$S(O)_2NHC(O)C_1$-$C_3$alkyl, $C_1$-$C_6$alkoxy, $C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo;

phenyl optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, —$NC(NH_2)_2$, nitro, and —$OP(O)(OH)_2$;

$NR^a R^b (C_1$-$C_7$alkyl), wherein $R^a$ and $R^b$ are independently selected from hydrogen, $C_2$-$C_4$alkenyloxycarbonyl, $C_1$-$C_3$alkyl, $C_1$-$C_3$alkylcarbonyl, $C_3$-$C_6$cycloalkylcarbonyl, furanylcarbonyl, and phenylcarbonyl. When the alkyl linker contains more than one carbon an additional $NR^a R^b$ group can be on the chain.

$NR^c R^d$ carbonyl$C_1$-$C_3$alkyl, wherein $R^c$ and $R^d$ are independently selected from hydrogen, $C_1$-$C_3$alkyl, and triphenylmethyl;

phenyl$C_1$-$C_3$alkyl wherein the phenyl part is optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, —$NC(NH_2)_2$, nitro, and —$OP(O)(OH)_2$; and phenoxy$C_1$-$C_3$alkyl wherein the phenyl is optionally substituted with a $C_1$-$C_3$alkyl group.

The term "$C_2$-$C_4$alkenyl," as used herein, refers to a straight or branched chain group of two to four carbon atoms containing at least one carbon-carbon double bond.

The term "$C_2$-$C_7$alkenyl," as used herein, refers to a straight or branched chain group of two to seven carbon atoms containing at least one carbon-carbon double bond.

The term "$C_2$-$C_4$alkenyloxy," as used herein, refers to a $C_2$-$C_4$alkenyl group attached to the parent molecular moiety through an oxygen atom.

The term "$C_1$-$C_3$alkoxy," as used herein, refers to a $C_1$-$C_3$alkyl group attached to the parent molecular moiety through an oxygen atom.

The term "$C_1$-$C_4$alkoxy," as used herein, refers to a $C_1$-$C_4$alkyl group attached to the parent molecular moiety through an oxygen atom.

The term "$C_1$-$C_6$alkoxy," as used herein, refers to a $C_1$-$C_6$alkyl group attached to the parent molecular moiety through an oxygen atom.

The term "$C_1$-$C_3$alkoxy$C_1$-$C_3$alkyl," as used herein, refers to a $C_1$-$C_3$alkoxy group attached to the parent molecular moiety through a $C_1$-$C_3$alkyl group.

The term "$C_1$-$C_6$alkoxycarbonyl," as used herein, refers to a $C_1$-$C_6$alkoxy group attached to the parent molecular moiety through a carbonyl group.

The term "$C_1$-$C_6$alkoxycarbonyl$C_1$-$C_3$alkyl," as used herein, refers to a $C_1$-$C_6$alkoxycarbonyl group attached to the parent molecular moiety through a $C_1$-$C_3$alkyl group.

The term "$C_1$-$C_3$alkyl," as used herein, refers to a group derived from a straight or branched chain saturated hydrocarbon containing from one to three carbon atoms.

The term "$C_1$-$C_4$alkyl," as used herein, refers to a group derived from a straight or branched chain saturated hydrocarbon containing from one to four carbon atoms.

The term "$C_1$-$C_6$alkyl," as used herein, refers to a group derived from a straight or branched chain saturated hydrocarbon containing from one to six carbon atoms.

The term "$C_1$-$C_3$alkylcarbonyl," as used herein, refers to a $C_1$-$C_3$alkyl group attached to the parent molecular moiety through a carbonyl group.

The term "$(C_1$-$C_6$alkyl)$S(O)_2NHC(O)C_1$-$C_3$alkyl," as used herein, refers to:

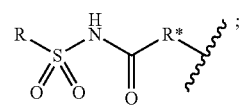

wherein R is a $C_1$-$C_6$alkyl group, R* is a $C_1$-$C_3$alkyl group, and ⁓ indicates the point of attachment to the parent molecular moiety.

The term "$C_1$-$C_3$alkylsulfanyl," as used herein, refers to a $C_1$-$C_3$alkyl group attached to the parent molecular moiety through a sulfur atom.

The term "$C_1$-$C_3$alkylsulfanyl$C_1$-$C_3$alkyl," as used herein, refers to a $C_1$-$C_3$alkylsulfanyl group attached to the parent molecular moiety through a $C_1$-$C_3$alkyl group.

The term "$C_1$-$C_3$alkylsulfonyl," as used herein, refers to a $C_1$-$C_3$alkyl group attached to the parent molecular moiety through a sulfonyl group.

The term "$C_1$-$C_3$alkylsulfonylamino," as used herein, refers to a $C_1$-$C_3$alkylsulfonyl group attached to the parent molecular moiety through an amino group.

The term "amido," as used herein, refers to —$C(O)NH_2$.

The term "amido$C_1$-$C_3$alkyl," as used herein, refers to an amido group attached to the parent molecular moiety through a $C_1$-$C_3$alkyl group.

The term "amino," as used herein, refers to —$NH_2$.

The term "amino$C_1$-$C_3$alkyl," as used herein, refers to an amino group attached to the parent molecular moiety through a $C_1$-$C_3$alkyl group.

The term "aminosulfonyl," as used herein, refers to an amino group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from $C_{1-3}$alkoxy, $C_{1-3}$alkyl, cyano, halo, halo$C_1$-$C_3$alkoxy, halo$C_1$-$C_3$alkyl, and hydroxy.

The term "aryl$C_1$-$C_3$alkyl," as used herein, refers to an aryl group attached to the parent molecular moiety through a $C_1$-$C_3$alkyl group.

The term "azaindolyl$C_1$-$C_3$alkyl," as used herein, refers to an azaindolyl group attached to the parent molecular through a $C_1$-$C_3$alkyl group. The azaindolyl group can be attached to the alkyl moiety through any substitutable atom in the group.

The term "benzothiazolyl$C_1$-$C_3$alkyl," as used herein, refers to an benzothiazolyl group attached to the parent molecular through a $C_1$-$C_3$alkyl group. The benzothiazolyl group can be attached to the alkyl moiety through any substitutable atom in the group.

The term "benzothienyl$C_1$-$C_3$alkyl," as used herein, refers to a benzothienyl group attached to the parent molecular through a $C_1$-$C_3$alkyl group. The benzothienyl group can be attached to the alkyl moiety through any substitutable atom in the group.

The term "benzyloxy," as used herein, refers to a benzyl group attached to the parent molecular moiety through an oxygen atom.

The term "benzyloxy$C_1$-$C_3$alkyl," as used herein, refers to a benzyloxy group attached to the parent molecular moiety through a $C_1$-$C_3$alkyl group.

The term "biphenyl$C_1$-$C_3$alkyl," as used herein, refers to a biphenyl group attached to the parent molecular moiety through a $C_1$-$C_3$alkyl group. The biphenyl group can be attached to the alkyl moiety through any substitutable atom in the group.

The term "carbonyl," as used herein, refers to —C(O)—.

The term "carboxy," as used herein, refers to —CO$_2$H.

The term "carboxy$C_1$-$C_3$alkyl," as used herein, refers to a carboxy group attached to the parent molecular moiety through a $C_1$-$C_3$alkyl group.

The term "cyano," as used herein, refers to —CN.

The term "$C_3$-$C_{14}$cycloalkyl," as used herein, refers to a saturated monocyclic, bicyclic, or tricyclic hydrocarbon ring system having three to fourteen carbon atoms and zero heteroatoms. The bicyclic and tricyclic rings may be fused, spirocyclic, or bridged. Representative examples of cycloalkyl groups include, but are not limited to, cyclopropyl, cyclopentyl, bicyclo[3.1.1]heptyl, and adamantyl.

The term "$C_3$-$C_{14}$cycloalkyl$C_1$-$C_3$alkyl," as used herein, refers to a $C_3$-$C_{14}$cycloalkyl group attached to the parent molecular moiety through a $C_1$-$C_3$alkyl group.

The term "$C_3$-$C_{14}$cycloalkylcarbonyl," as used herein, refers to a $C_3$-$C_{14}$ cycloalkyl group attached to the parent molecular moiety through a carbonyl group.

The term "$C_3$-$C_6$cycloalkyl," as used herein, refers to a saturated monocyclic, hydrocarbon ring system having three to six carbon atoms and zero heteroatoms.

The term "$C_3$-$C_6$cycloalkyl$C_1$-$C_3$alkyl," as used herein, refers to a $C_3$-$C_6$cycloalkyl group attached to the parent molecular moiety through a $C_1$-$C_3$alkyl group.

The term "$C_3$-$C_6$cycloalkylcarbonyl," as used herein, refers to a $C_3$-$C_6$ cycloalkyl group attached to the parent molecular moiety through a carbonyl group.

The term "furanyl$C_1$-$C_3$alkyl," as used herein, refers to a furanyl group attached to the parent molecular moiety through a $C_1$-$C_3$alkyl group. The furanyl group can be attached to the alkyl moiety through any substitutable atom in the group.

The term "furanylcarbonyl," as used herein, refers to a furanyl group attached to the parent molecular moiety through a carbonyl group.

The terms "halo" and "halogen," as used herein, refer to F, $C_1$, Br, or I.

The term "halo$C_1$-$C_3$alkoxy," as used herein, refers to a $C_1$-$C_3$alkoxy group substituted with one, two, or three halogen atoms.

The term "halo$C_1$-$C_3$alkyl," as used herein, refers to a $C_1$-$C_3$alkyl group substituted with one, two, or three halogen atoms.

The term "halomethyl," as used herein, refers to a methyl group substituted with one, two, or three halogen atoms.

The term "heteroaryl," as used herein, refers to an aromatic five- or six-membered ring where at least one atom is selected from N, O, and S, and the remaining atoms are carbon. The term "heteroaryl" also includes bicyclic systems where a heteroaryl ring is fused to a four- to six-membered aromatic or non-aromatic ring containing zero, one, or two additional heteroatoms selected from N, O, and S. The heteroaryl groups are attached to the parent molecular moiety through any substitutable carbon or nitrogen atom in the group. Representative examples of heteroaryl groups include, but are not limited to, benzoxadiazolyl, benzoxazolyl, benzofuranyl, benzothienyl, furanyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl. The heteroaryl groups of the present invention can be optionally substituted with one, two, three, four, or five substituents independently selected from $C_{1-3}$alkoxy, $C_{1-3}$alkyl, cyano, halo, halo$C_1$-$C_3$alkoxy, halo$C_1$-$C_3$alkyl, and hydroxy.

The term "heteroaryl$C_1$-$C_3$alkyl," as used herein, refers to a heteroaryl group attached to the parent molecular moiety through a $C_1$-$C_3$alkyl group.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four- to six-membered aromatic or non-aromatic carbocyclic ring or another monocyclic heterocyclyl group. The heterocyclyl groups of the present disclosure are attached to the parent molecular moiety through a carbon atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl.

The term "hydroxy," as used herein, refers to —OH.

The term "imidazolyl$C_1$-$C_3$alkyl," as used herein, refers to an imidazolyl group attached to the parent molecular moiety through a $C_1$-$C_3$alkyl group. The imidazolyl group can be attached to the alkyl moiety through any substitutable atom in the group.

The term "indolylC$_1$-C$_3$alkyl," as used herein, refers to an indolyl group attached to the parent molecular moiety through a C$_1$-C$_3$alkyl group. The indolyl group can be attached to the alkyl moiety through any substitutable atom in the group.

The term "naphthylC$_1$-C$_3$alkyl," as used herein, refers to a naphthyl group attached to the parent molecular moiety through a C$_1$-C$_3$alkyl group. The naphthyl group can be attached to the alkyl moiety through any substitutable atom in the group.

The term "nitro," as used herein, refers to —NO$_2$.

The term "NR$^a$R$^b$," as used herein, refers to two groups, R$^a$ and R$^b$, which are attached to the parent molecular moiety through a nitrogen atom. R$^a$ and R$^b$ are independently selected from hydrogen, C$_2$-C$_4$alkenyloxycarbonyl, C$_1$-C$_3$alkylcarbonyl, C$_3$-C$_6$cycloalkylcarbonyl, furanylcarbonyl, and phenylcarbonyl.

The term "NR$^a$R$^b$(C$_1$-C$_3$)alkyl," as used herein, refers to an NR$^a$R$^b$ group attached to the parent molecular moiety through a C$_1$-C$_3$alkyl group.

The term "NR$^c$R$^d$," as used herein, refers to two groups, R$^c$ and R$^d$, which are attached to the parent molecular moiety through a nitrogen atom. R$^c$ and R$^d$ are independently selected from hydrogen, C$_1$-C$_3$alkyl, and triphenylmethyl.

The term "NR$^c$R$^d$carbonyl," as used herein, refers to an NR$^c$R$^d$ group attached to the parent molecular moiety through a carbonyl group.

The term "NR$^c$R$^d$carbonylC$_1$-C$_3$alkyl," as used herein, refers to an NR$^c$R$^d$carbonyl group attached to the parent molecular moiety through a C$_1$-C$_3$alkyl group.

The term "phenoxy," as used herein, refers to a phenyl group attached to the parent molecular moiety through an oxygen atom.

The term "phenoxyC$_1$-C$_3$alkyl," as used herein, refers to a phenoxy group attached to the parent molecular moiety through a C$_1$-C$_3$alkyl group.

The term "phenylC$_1$-C$_3$alkyl," as used herein, refers to a phenyl group attached to the parent molecular moiety through a C$_1$-C$_3$alkyl group.

The term "phenylcarbonyl," as used herein, refers to a phenyl group attached to the parent molecular moiety through a carbonyl group.

The term "pyridinylC$_1$-C$_3$alkyl," as used herein, refers to a pyridinyl group attached to the parent molecular moiety through a C$_1$-C$_3$alkyl group. The pyridinyl group can be attached to the alkyl moiety through any substitutable atom in the group.

The term "sulfanyl," as used herein, refers to —S—.

The term "sulfonyl," as used herein, refers to —SO$_2$—.

The term "tetrazolylC$_1$-C$_3$alkyl," as used herein, refers to a tetrazolyl group attached to the parent molecular moiety through a C$_1$-C$_3$alkyl group. The thiazolyl group can be attached to the alkyl moiety through any substitutable atom in the group.

The term "thiazolylC$_1$-C$_3$alkyl," as used herein, refers to a thiazolyl group attached to the parent molecular moiety through a C$_1$-C$_3$alkyl group. The thiazolyl group can be attached to the alkyl moiety through any substitutable atom in the group.

The term "thienylC$_1$-C$_3$alkyl," as used herein, refers to a thienyl group attached to the parent molecular moiety through a C$_1$-C$_3$alkyl group. The thienyl group can be attached to the alkyl moiety through any substitutable atom in the group.

The term "treating" refers to: (i) preventing a disease, disorder, or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition and/or symptoms associated with the disease, disorder, and/or condition.

Binding of the macrocyclic peptides to PD-L1 can be measured, for example, by methods such as homogeneous time-resolved fluorescence (HTRF), Surface Plasmon Resonance (SPR), isothermal titration calorimetry (ITC), nuclear magnetic resonance spectroscopy (NMR), and the like. Further, binding of the macrocyclic peptides to PD-L1 expressed on the surface of cells can be measured as described herein in cellular binding assays.

Administration of a therapeutic agent described herein includes, without limitation, administration of a therapeutically effective amount of therapeutic agent. The term "therapeutically effective amount" as used herein refers, without limitation, to an amount of a therapeutic agent to treat or prevent a condition treatable by administration of a composition of the PD-1/PD-L1 binding inhibitors described herein. That amount is the amount sufficient to exhibit a detectable therapeutic or preventative or ameliorative effect. The effect may include, for example and without limitation, treatment or prevention of the conditions listed herein. The precise effective amount for a subject will depend upon the subject's size and health, the nature and extent of the condition being treated, recommendations of the treating physician, and therapeutics or combination of therapeutics selected for administration. Thus, it is not useful to specify an exact effective amount in advance.

In another aspect, the disclosure pertains to methods of inhibiting growth of tumor cells in a subject using the macrocyclic peptides of the present disclosure. As demonstrated herein, the macrocyclic peptides of the present disclosure are capable of binding to PD-L1, disrupting the interaction between PD-L1 and PD-1, competing with the binding of PD-L1 with anti-PD-1 monoclonal antibodies that are known to block the interaction with PD-1, enhancing CMV-specific T cell IFNγ secretion, and enhancement of HIV-specific T cell IFNg secretion. As a result, the macrocyclic peptides of the present disclosure are useful for modifying an immune response, treating diseases such as cancer or infectious disease, stimulating a protective auto-immune response or to stimulate antigen-specific immune responses (e.g., by coadministration of PD-L1 blocking peptides with an antigen of interest).

In order that the present disclosure may be more readily understood, certain terms are first defined. Additional definitions are set forth throughout the detailed description.

The terms "Programmed Death Ligand 1", "Programmed Cell Death Ligand 1", "Protein PD-L1", "PD-L1", "PDL1", "PDCDL1", "hPD-L1", "hPD-L1", "CD274" and "B7-H1" are used interchangeably, and include variants, isoforms, species homologs of human PD-L1, and analogs having at least one common epitope with PD-L1. The complete PD-L1 sequence can be found under GENBANK® Accession No. NP_054862.

The terms "Programmed Death 1", "Programmed Cell Death 1", "Protein PD-1", "PD-1", "PD1", "PDCD1", "hPD-1" and "hPD-1" are used interchangeably, and include variants, isoforms, species homologs of human PD-1, and analogs having at least one common epitope with PD-1. The complete PD-1 sequence can be found under GENBANK® Accession No. U64863.

The terms "cytotoxic T lymphocyte-associated antigen-4", "CTLA-4", "CTLA4", "CTLA-4 antigen" and "CD152"

(see, e.g., Murata, *Am. J. Pathol.*, 155:453-460 (1999)) are used interchangeably, and include variants, isoforms, species homologs of human CTLA-4, and analogs having at least one common epitope with CTLA-4 (see, e.g., Balzano, *Int. J. Cancer Suppl.*, 7:28-32 (1992)). The complete CTLA-4 nucleic acid sequence can be found under GEN-BANK® Accession No. L15006.

The term "immune response" refers to the action of, for example, lymphocytes, antigen presenting cells, phagocytic cells, granulocytes, and soluble macromolecules produced by the above cells or the liver (including macrocyclic peptides, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "adverse event" (AE) as used herein is any unfavorable and generally unintended, even undesirable, sign (including an abnormal laboratory finding), symptom, or disease associated with the use of a medical treatment. For example, an adverse event may be associated with activation of the immune system or expansion of immune system cells (e.g., T cells) in response to a treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

As used herein, "hyperproliferative disease" refers to conditions wherein cell growth is increased over normal levels. For example, hyperproliferative diseases or disorders include malignant diseases (e.g., esophageal cancer, colon cancer, biliary cancer) and non-malignant diseases (e.g., atherosclerosis, benign hyperplasia, and benign prostatic hypertrophy).

As used herein, "about" or "comprising essentially of" mean within an acceptable error range for the particular value as determined by one of ordinary skill in the art, which will depend in part on how the value is measured or determined, i.e., the limitations of the measurement system. For example, "about" or "comprising essentially of" can mean within one or more than one standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

As described herein, any concentration range, percentage range, ratio range or integer range is to be understood to include the value of any integer within the recited range and, when appropriate, fractions thereof (such as one tenth and one hundredth of an integer), unless otherwise indicated.

Competition Assays

The present disclosure is also directed to macrocyclic peptides that are capable of competing with the binding of a reference anti-PD-L1 antibody (MDX-1105) by at least about 20%, at least about 30%, at least about 40%, at least about 50%, at least about 60%, at least about 70%, at least about 80%, at least about 90%, and at least about 100%. Such macrocyclic peptides may share structural homology with one or more macrocyclic peptides disclosed herein, including mutant, conservative substitution, functional substitution, and deletion forms, provided they specific bind to PD-L1. For example, if a macrocyclic peptide binds substantially to the same region of PD-L1 as a reference anti-PD-L1 antibody, the macrocyclic peptide should bind to an epitope of PD-L1 that at least overlaps with the PD-L1 epitope that the anti-PD-L1 monoclonal antibody binds to. The overlapping region can range from one amino acid residue to several hundred amino acid residues. The macrocyclic peptide should then compete with and/or block the binding of the anti-PD-L1 monoclonal antibody to PD-L1 and thereby decrease the binding of the anti-PD-L1 monoclonal antibody to PD-L1, preferably by at least about 50% in a competition assay.

Anti-PD-L1 antibodies that may be used as reference antibodies for competition assay purposes are known in the art. For example, the following representative anti-PD-L1 antibodies may be used: MDX-1105 (BMS); L01X-C(Serono), L1X3 (Serono), MSB-0010718C (Serono), and PD-L1 Probody (CytomX), and the PD-L1 antibodies disclosed in co-owned WO 2007/005874.

Anti-PD-1 antibodies that may be used as reference antibodies for competition assay purposes are known in the art. For example, the following representative anti-PD-1 antibodies may be used: nivolumab (BMS); 17D8, 2D3, 4H1, 4A11, 7D3 and 5F4 each disclosed in co-owned U.S. Pat. No. 8,008,449 (BMS), MK-3475 (Merck, disclosed in U.S. Pat. No. 8,168,757), and the antibodies disclosed in U.S. Pat. No. 7,488,802.

Pharmaceutical Compositions

In another aspect, the present disclosure provides a composition, e.g., a pharmaceutical composition, containing one or a combination of macrocyclic peptides of the present disclosure, formulated together with a pharmaceutically acceptable carrier. Such compositions may include one or a combination of (e.g., two or more different) macrocyclic peptides, or immunoconjugates or bispecific molecules of the disclosure. For example, a pharmaceutical composition of the disclosure can comprise a combination of macrocyclic peptides (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include a macrocyclic peptide combined with at least one other anti-inflammatory or immunosuppressant agent. Examples of therapeutic agents that can be used in combination therapy are described in greater detail below in the section on uses of the macrocyclic peptides of the disclosure.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., a macrocyclic peptide, immunoconjugate, or bispecific molecule, may be coated in a material to protect the compound from the action of acids and other natural conditions that may inactivate the compound.

The pharmaceutical compounds of the disclosure may include one or more pharmaceutically acceptable salts. A "pharmaceutically acceptable salt" or "therapeutically acceptable salt" refers to a salt that retains the desired biological activity of the parent compound and does not impart any undesired toxicological effects (see e.g., Berge, S. M. et al., *J. Pharm. Sci.,* 66:1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the macrocyclic peptide, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per day, twice per day, bi-weekly, tri-weekly, weekly, once every two weeks, once every three weeks, once every four weeks, once a month, once every 3 months or once every three to 6 months. Preferred dosage regimens for a macrocyclic peptide of the disclosure include 1 mg/kg body weight or 3 mg/kg body weight via intravenous administration, with the macrocycle being given using one of the following dosing schedules: (i) every four weeks for six dosages, then every three months; (ii) every three weeks; (iii) 3 mg/kg body weight once followed by 1 mg/kg body weight every three weeks.

In some methods, two or more macrocyclic peptides with different binding specificities are administered simultaneously, in which case the dosage of each compound administered falls within the ranges indicated. The compounds are usually administered on multiple occasions. Intervals between single dosages can be, for example, weekly, monthly, every three months or yearly. Intervals can also be irregular as indicated by measuring blood levels of macrocyclic peptide to the target antigen in the patient. In some methods, dosage is adjusted to achieve a plasma concentration of about 1-1000 .mu.g/ml and in some methods about 25-300 .mu.g/ml.

Alternatively, the macrocyclic peptide can be administered as a sustained release formulation, in which case less frequent administration is required. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a macrocyclic peptide of the disclosure preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth and/or HIV can be evaluated in an animal model system predictive of efficacy in human tumors or viral efficacy. Alternatively, this property of a composition can be evaluated by examining the ability of the compound to inhibit, such inhibition in vitro by assays known to the skilled practitioner. A therapeutically effective amount of a therapeutic compound can decrease tumor size, decrease viral load, or otherwise ameliorate symptoms in a subject. One of ordinary skill in the art would be able to determine such amounts based on such factors as the subject's size, the severity of the subject's symptoms, and the particular composition or route of administration selected.

In another aspect, the instant disclosure provides a pharmaceutical kit of parts comprising a macrocyclic peptide and an another immumodulator, as described herein. The kit may also further comprise instructions for use in the treatment of a hyperproliferative disease (such as cancer as described herein) and/or anti-viral disease.

A composition of the present disclosure can be administered via one or more routes of administration using one or more of a variety of methods known in the art. As will be appreciated by the skilled artisan, the route and/or mode of administration will vary depending upon the desired results. Preferred routes of administration for macrocyclic peptides of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a macrocyclic peptide of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, J. R., ed., *Sustained and Controlled Release Drug Delivery Systems*, Marcel Dekker, Inc., New York (1978).

Therapeutic compositions can be administered with medical devices known in the art. For example, in a preferred embodiment, a therapeutic composition of the disclosure can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medication through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the macrocyclic peptides of the disclosure can be formulated to ensure proper distribution in vivo. For example, the blood-brain barrier (BBB) excludes many highly hydrophilic compounds. To ensure that therapeutic compounds of the disclosure cross the BBB (if desired), they can be formulated, for example, in liposomes. For methods of manufacturing liposomes, see, e.g., U.S. Pat. Nos. 4,522,811, 5,374,548, and 5,399,331. The liposomes may comprise one or more moieties which are selectively transported into specific cells or organs, thus enhance targeted drug delivery (see, e.g., Ranade, V. V., *J. Clin. Pharmacol.*, 29:685 (1989)). Exemplary targeting moieties include folate or biotin (see, e.g., U.S. Pat. No. 5,416,016 to Low et al.); mannosides (Umezawa et al., *Biochem. Biophys. Res. Commun.*, 153:1038 (1988)); macrocyclic peptides (Bloeman, P. G. et al., *FEBS Lett*, 357:140 (1995); Owais, M. et al., *Antimicrob. Agents Chemother.*, 39:180 (1995)); surfactant protein A receptor (Briscoe et al., *Am. J. Physiol.*, 1233:134 (1995)); p 120 (Schreier et al., *J. Biol. Chem.*, 269:9090 (1994)); see also Keinanen, K. et al., *FEBS Lett.*, 346:123 (1994); Killion, J. J. et al., *Immunomethods* 4:273 (1994).

Uses and Methods of the Disclosure

The macrocyclic peptides, compositions and methods of the present disclosure have numerous in vitro and in vivo utilities involving, for example, detection of PD-L1 or enhancement of immune response by blockade of PD-L1. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject the macrocyclic peptide of the disclosure such that the immune response in the subject is modified. Preferably, the response is enhanced, stimulated or up-regulated. In other respects, the macrocyclic peptide may have anti-cyno, anti-mouse, and/or anti-woodchuck binding and therapeutic activity.

As used herein, the term "subject" is intended to include human and non-human animals. Non-human animals includes all vertebrates, e.g., mammals and non-mammals, such as non-human primates, sheep, dogs, cats, cows, horses, chickens, woodchuck, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo. To achieve antigen-specific enhancement of immunity, the macrocyclic peptides can be administered together with an antigen of interest. When macrocyclic peptides to PD-L1 are administered together with another agent, the two can be administered in either order or simultaneously.

The disclosure further provides methods for detecting the presence of human, woodchuck, cyno, and/or mouse PD-L1 antigen in a sample, or measuring the amount of human, woodchuck, cyno, and/or mouse PD-L1 antigen, comprising contacting the sample, and a control sample, with a reference macrocyclic peptide which specifically binds to human, woodchuck, cyno, and/or mouse PD-L1, under conditions that allow for formation of a complex between the macrocycle and human, woodchuck, cyno, and/or mouse PD-L1. The formation of a complex is then detected, wherein a difference complex formation between the sample compared to the control sample is indicative the presence of human, woodchuck, cyno, and/or mouse PD-L1 antigen in the sample.

Given the specific binding of the macrocyclic peptides of the disclosure for PD-L1, compared to CD28, ICOS and CTLA-4, the macrocyclic peptides of the disclosure can be used to specifically detect PD-L1 expression on the surface of cells and, moreover, can be used to purify PD-L1 via immunoaffinity purification.

Cancer

Blockade of PD-1 by macrocyclic peptides can enhance the immune response to cancerous cells in the patient. The ligand for PD-1, PD-L1, is not expressed in normal human cells, but is abundant in a variety of human cancers (Dong et al., *Nat. Med.*, 8:787-789 (2002)). The interaction between PD-1 and PD-L1 results in a decrease in tumor infiltrating lymphocytes, a decrease in T-cell receptor mediated proliferation, and immune evasion by the cancerous cells (Dong et al., *J. Mol. Med*, 81:281-287 (2003); Blank et al., *Cancer Immunol. Immunother.*, 54:307-314 (2005); Konishi et al., *Clin. Cancer Res.*, 10:5094-5100 (2004)). Immune suppression can be reversed by inhibiting the local interaction of PD-1 to PD-L1 and the effect is additive when the interaction of PD-1 to PD-L2 is blocked as well (Iwai et al., *Proc. Natl. Acad. Sci.*, 99:12293-12297 (2002); Brown et al., *J. Immunol.*, 170:1257-1266 (2003)). While previous studies have shown that T-cell proliferation can be restored by inhibiting the interaction of PD-1 to PD-L1, there have been no reports of a direct effect on cancer tumor growth in vivo by blocking the PD-1/PD-L1 interaction. In one aspect, the present disclosure relates to treatment of a subject in vivo using a macrocyclic peptide such that growth of cancerous tumors is inhibited. A macrocyclic peptide may be used alone to inhibit the growth of cancerous tumors. Alternatively, a macrocyclic peptide may be used in conjunction with other immunogenic agents, standard cancer treatments, or other macrocyclic peptides, as described below.

Accordingly, in one embodiment, the disclosure provides a method of inhibiting growth of tumor cells in a subject, comprising administering to the subject a therapeutically effective amount of a macrocyclic peptide.

Preferred cancers whose growth may be inhibited using the macrocyclic peptides of the disclosure include cancers typically responsive to immunotherapy. Non-limiting examples of preferred cancers for treatment include melanoma (e.g., metastatic malignant melanoma), renal cell carcinoma (e.g., clear cell carcinoma), prostate cancer (e.g., hormone refractory prostate adenocarcinoma and castration-resistant prostate cancer), breast cancer, colorectal cancer and lung cancer (e.g., squamous and non-squamous non-small cell lung cancer). Additionally, the disclosure includes refractory or recurrent malignancies whose growth may be inhibited using the macrocyclic peptides of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, colon cancer, rectal cancer, cancer of the anal region, stomach/gastric cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al., *Int. Immunol.*, 17:133-144 (2005)).

Optionally, macrocyclic peptides to PD-L1 can be combined with an immunogenic agent, such as cancerous cells, purified tumor antigens (including recombinant proteins, peptides, and carbohydrate molecules), cells, and cells transfected with genes encoding immune stimulating cytokines (He et al., *J. Immunol.*, 173:4919-4928 (2004)). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. It is anticipated that by raising the threshold of T cell activation by PD-L1 blockade, we may expect to activate tumor responses in the host.

PD-L1 blockade is likely to be most effective when combined with a vaccination protocol. Many experimental strategies for vaccination against tumors have been devised (see Rosenberg, S., Development of Cancer Vaccines, ASCO Educational Book Spring: 60-62 (2000); Logothetis, C., ASCO Educational Book Spring: 300-302 (2000); Khayat, D., ASCO Educational Book Spring: 414-428 (2000); Foon, K., ASCO Educational Book Spring: 730-738 (2000); see also Restifo, N. et al., Cancer Vaccines, Chapter 61, pp. 3023-3043, in DeVita, V. et al., eds., *Cancer: Principles and Practice of Oncology*, Fifth Edition (1997)). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., *Proc. Natl. Acad. Sci. USA*, 90: 3539-3543 (1993)).

The study of gene expression and large scale gene expression patterns in various tumors has led to the definition of so called tumor specific antigens (Rosenberg, S. A., *Immunity*, 10:281-287 (1999)). In many cases, these tumor specific antigens are differentiated antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al., *Science*, 266:2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R. et al., *Science*, 269:1585-1588 (1995); Tamura, Y. et al., *Science*, 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle, F. et al., *Nat. Med*, 4:328-332 (1998)). DCs may also be transduced by genetic means to express these tumor antigens as well. DCs have also been fused directly to tumor cells for the purposes of immunization (Kugler, A. et al., *Nat. Med.*, 6:332-336 (2000)). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al., *Cancer Res.*, 58:5301-5304 (1998)). An example of such a combination is a macrocyclic peptide in combination with decarbazine for the treatment of melanoma. Another example of such a combination is a macrocyclic peptide in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

PD-L1 blocking macrocyclic peptides can also be used in combination with bispecific macrocyclic peptides that target Fc alpha or Fc gamma receptor-expressing effectors cells to tumor cells (see, e.g., U.S. Pat. Nos. 5,922,845 and 5,837, 243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific macrocyclic peptides which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al., *J. Exp. Med.*, 163:1037-1050 (1986)), IL-10 (Howard, M. et al., *Immunology Today*, 13:198-200 (1992)), and Fas ligand (Hahne, M. et al., *Science*, 274:1363-1365 (1996)). Macrocyclic peptides to each of these entities may be used in combination with anti-PD-L1 to counteract the effects of the immunosuppressive agent and favor tumor immune responses by the host.

Other macrocyclic peptides which may be used to activate host immune responsiveness can be used in combination with anti-PD-L1. These include molecules on the surface of dendritic cells which activate DC function and antigen presentation. Anti-CD40 macrocyclic peptides are able to substitute effectively for T cell helper activity (Ridge, J. et al., *Nature*, 393:474-478 (1998)) and can be used in conjunction with PD-1 antibodies (Ito, N. et al., *Immunobiology*, 201(5):527-540 (2000)). Activating macrocyclic peptides to T cell costimulatory molecules such as CTLA-4 (e.g., U.S. Pat. No. 5,811,097), OX-40 (Weinberg, A. et al., *Immunol.*, 164:2160-2169 (2000)), 4-1BB (Melero, I. et al., *Nat. Med.*, 3:682-685 (1997), and ICOS (Hutloff, A. et al., *Nature*, 397:262-266 (1999)) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. et al., *Science*, 285:546-551 (1999)). These methods may also be used to activate T cell responses to infectious agents such as CMV. Ex vivo activation in the presence of macrocyclic peptides may be expected to increase the frequency and activity of the adoptively transferred T cells.

Infectious Diseases

Other methods of the disclosure are used to treat patients that have been exposed to particular toxins or pathogens. Accordingly, another aspect of the disclosure provides a method of treating an infectious disease in a subject comprising administering to the subject a macrocyclic peptide of the present disclosure such that the subject is treated for the infectious disease.

Similar to its application to tumors as discussed above, PD-L1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, and C), Influenza, Herpes, Giardia, Malaria (Butler, N. S. et al., *Nature Immunology* 13, 188-195 (2012); Hafalla, J. C. R., et al. *PLOS Pathogens*; Feb. 2, 2012)), Leishmania, Staphylococcus aureus, Pseudomonas Aeruginosa. PD-L1 blockade is particularly useful against established infections by agents such as HIV that present altered antigens over the course of the infections. These novel epitopes are recognized as foreign at the time of anti-human PD-L1 administration, thus provoking a strong T cell response that is not dampened by negative signals through PD-L1.

Some examples of pathogenic viruses causing infections treatable by methods of the disclosure include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme disease bacteria.

Some examples of pathogenic fungi causing infections treatable by methods of the disclosure include *Candida (albicans, krusei, glabrata, tropicalis*, etc.), *Cryptococcus neoformans, Aspergillus (fumigatus, niger*, etc.), Genus *Mucorales (mucor, absidia, rhizophus), Sporothrix schenkii, Blastomyces dermatitidis, Paracoccidioides brasiliensis, Coccidioides immitis* and *Histoplasma capsulatum.*

Some examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

In all of the above methods, PD-L1 blockade can be combined with other forms of immunotherapy such as cytokine treatment (e.g., interferons, agents targeting VEGF activity or VEGF-receptors, GM-CSF, G-CSF, IL-2), or bispecific antibody therapy, which provides for enhanced presentation of tumor antigens (see, e.g., Holliger, *Proc. Natl. Acad. Sci. USA*, 90:6444-6448 (1993); Poljak, *Structure*, 2:1121-1123 (1994)).

Autoimmune Reactions

The macrocyclic peptides may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al., *Proc. Natl. Acad. Sci. USA*, 96:2982-2987 (1999)); autoimmune prostatitis evoked by TRAMP tumor cell vaccines (Hurwitz, A., supra (2000)), melanoma peptide antigen vaccination and vitiligo observed in human clinical trials (Rosenberg, S. A. et al., *J. Immunother. Emphasis Tumor Immunol.*, 19(1):81-84 (1996)).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta. peptide in amyloid deposits in the brain; antibody responses against amyloid are able to clear these amyloid deposits (Schenk et al., *Nature*, 400:173-177 (1999)).

Other self proteins may also be used as targets such as IgE for the treatment of allergy and asthma, and TNF.alpha for rheumatoid arthritis. Finally, antibody responses to various hormones may be induced by the use of the macrocycles disclosed herein. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 macrocycles can be used for induction of therapeutic autoimmune responses to treat patients having an inappropriate accumulation of other self-antigens, such as amyloid deposits, including A.beta. in Alzheimer's disease, cytokines such as TNF.alpha., and IgE.

Vaccines

The macrocyclic peptides may be used to stimulate antigen-specific immune responses by coadministration of an anti-PD-1 macrocycle with an antigen of interest (e.g., a vaccine). Accordingly, in another aspect the disclosure provides a method of enhancing an immune response to an antigen in a subject, comprising administering to the subject: (i) the antigen; and (ii) an anti-PD-1 macrocycle such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the compositions (e.g., macrocyclic peptides, multispecific and bispecific molecules and immunoconjugates) of the disclosure in vivo and in vitro are well known in the art and can be selected by those of ordinary skill. For example, the compositions can be administered by injection (e.g., intravenous or subcutaneous). Suitable dosages of the molecules used will depend on the age and weight of the subject and the concentration and/or formulation of the composition.

As previously described the macrocyclic peptides of the disclosure can be co-administered with one or other more therapeutic agents, e.g., a cytotoxic agent, a radiotoxic agent or an immunosuppressive agent. The peptide can be linked to the agent (as an immunocomplex) or can be administered separate from the agent. In the latter case (separate administration), the peptide can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the macrocyclic peptides of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the peptides.

Also within the scope of the present disclosure are kits comprising the compositions of the disclosure (e.g., macrocyclic peptides, bispecific or multispecific molecules, or immunoconjugates) and instructions for use. The kit can further contain at least one additional reagent, or one or more additional macrocyclic peptides of the disclosure (e.g., a human antibody having a complementary activity which binds to an epitope in PD-L1 antigen distinct from the macrocycle). Kits typically include a label indicating the intended use of the contents of the kit. The term label includes any writing, or recorded material supplied on or with the kit, or which otherwise accompanies the kit.

Combination Therapy

The combination of the macrocyclic peptides of the present disclosure with another PD-L1 antagonist and/or other immunomodulator is useful for enhancement of an immune response against a hyperproliferative disease. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject a macrocyclic peptide of the disclosure such that the immune response in the subject is modified. Preferably, the response is enhanced, stimulated or up-regulated. In another embodiment, the instant disclosure provides a method of altering adverse events associated with treatment of a hyperproliferative disease with an immunostimulatory therapeutic agent, comprising administering a macrocyclic peptide of the present disclosure and a subtherapeutic dose of another immunomodulator to a subject.

Blockade of PD-L1 by macrocyclic peptides can enhance the immune response to cancerous cells in the patient. Cancers whose growth may be inhibited using the macrocyclic peptides of the instant disclosure include cancers typically responsive to immunotherapy. Representative examples of cancers for treatment with the combination therapy of the instant disclosure include melanoma (e.g., metastatic malignant melanoma), renal cancer, prostate cancer, breast cancer, colon cancer and lung cancer. Examples of other cancers that may be treated using the methods of the instant disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers.

In certain embodiments, the combination of therapeutic agents containing at least one macrocyclic peptide discussed herein may be administered concurrently as a single composition in a pharmaceutically acceptable carrier, or concurrently as separate compositions wherein each agent can be administered sequentially. For example, a second immunomodulator and a macrocyclic peptide of the present disclosure can be administered sequentially, such as the second immunomodulator administered first and the macrocyclic peptide second, or the macrocyclic peptide being administered first and the second immunomodulator second. Furthermore, if more than one dose of the combination therapy is administered sequentially, the order of the sequential administration can be reversed or kept in the same order at each time point of administration, sequential administrations may be combined with concurrent administrations, or any combination thereof. For example, the first administration of a second immunomodulator and the macrocyclic peptide may be concurrent, the second administration may be sequential with the second immunomodulator first and the macrocyclic peptide second, and the third administration may be sequential with the macrocyclic peptide first and second immunomodulator second, etc. Another representative dosing scheme may involve a first administration that is sequential with the macrocyclic peptide first and the second immunomodulator second, and subsequent administrations may be concurrent.

Optionally, the combination of the macrocyclic peptide and a second immunomodulator can be further combined with an immunogenic agent, such as cancerous cells, purified tumor antigens (including recombinant proteins, peptides, and carbohydrate molecules), cells, and cells transfected with genes encoding immune stimulating cytokines (He et al., *J. Immunol.*, 173:4919-4928 (2004)). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

A combined PD-L1 macrocyclic peptide and a second immunomodulator can be further combined with a vaccination protocol. Many experimental strategies for vaccination against tumors have been devised (see Rosenberg, S., Development of Cancer Vaccines, ASCO Educational Book Spring: 60-62 (2000); Logothetis, C., ASCO Educational Book Spring: 300-302 (2000); Khayat, D., ASCO Educational Book Spring: 414-428 (2000); Foon, K., ASCO Educational Book Spring: 730-738 (2000); see also Restifo et al., Cancer Vaccines, Chapter 61, pp. 3023-3043 in DeVita et al., eds., *Cancer: Principles and Practice of Oncology*, Fifth Edition (1997)). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., *Proc. Natl. Acad. Sci. USA*, 90:3539-3543 (1993)).

The study of gene expression and large scale gene expression patterns in various tumors has led to the definition of so called tumor specific antigens (Rosenberg, *Immunity*, 10:281-287 (1999)). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. In certain embodiments, a combined PD-L1 macrocyclic peptide and a second immunomodulator may be used in conjunction with a collection of recombinant proteins and/or peptides expressed in a tumor in order to generate an immune response to these proteins. These proteins are normally viewed by the immune system as self-antigens and are, therefore, tolerant to them. The tumor antigen may also include the protein telomerase, which is required for the synthesis of telomeres of chromosomes and which is expressed in more than 85% of human cancers and in only a limited number of somatic tissues (Kim et al., *Science*, 266:2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 macrocyclic peptide blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot et al., *Science*, 269:1585-1588 (1995); Tamura et al., *Science*, 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle et al., *Nat. Med.*, 4:328-332 (1998)). DCs may also be transduced by genetic means to express these tumor antigens as well. DCs have also been fused directly to tumor cells for the purposes of immunization (Kugler et al., *Nat. Med.*, 6:332-336 (2000)). As a method of vaccination, DC immunization may be effectively further combined with a combined anti-PD-L1 macrocyclic peptide and a second immunomodulator to activate more potent anti-tumor responses.

A combined anti-PD-L1 macrocyclic peptide and additional immunomodulator may also be further combined with standard cancer treatments. For example, a combination of a macrocyclic peptide and a second immunomodulator may be effectively combined with chemotherapeutic regimes. In these instances, as is observed with the combination of a macrocyclic peptide and a second immunomodulator, it may be possible to reduce the dose of other chemotherapeutic reagent administered with the combination of the instant disclosure (Mokyr et al., *Cancer Res.*, 58:5301-5304 (1998)). An example of such a combination is a combination of a macrocyclic peptide and a second immunomodulator further in combination with decarbazine for the treatment of melanoma. Another example is a combination of a macrocyclic peptide and a second immunomodulatory agent further in combination with interleukin-2 (IL-2) for the treatment of melanoma. The scientific rationale behind the combined use of PD-L1 macrocyclic peptide and another immunomodulator with chemotherapy is that cell death, which is a consequence of the cytotoxic action of most chemotherapeutic compounds, should result in increased levels of tumor antigen in the antigen presentation pathway. Other combination therapies that may result in synergy with a combined anti-PD-L1 macrocyclic peptide and additional immunomodulator through cell death include radiation, surgery, or hormone deprivation. Each of these protocols creates a source of tumor antigen in the host. Angiogenesis inhibitors may also be combined with a combined PD-L1 and second immunomodulator. Inhibition of angiogenesis leads to tumor cell death, which may also be a source of tumor antigen to be fed into host antigen presentation pathways.

A combination of PD-L1 and another immunomodulator can also be used in combination with bispecific macrocyclic peptides that target Fc.alpha. or Fc.gamma. receptor-expressing effector cells to tumor cells (see, e.g., U.S. Pat. Nos. 5,922,845 and 5,837,243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of a combined PD-L1 and a second immunomodulator. Alternatively, antigen may be delivered directly to DCs by the use of bispecific macrocyclic peptides which bind to tumor antigen and a dendritic cell specific cell surface marker.

In another example, a combination of a macrocyclic peptide and a second immunomodulator can be used in conjunction with anti-neoplastic macrocyclic agents, such as RITUXAN® (rituximab), HERCEPTIN® (trastuzumab), BEXXAR® (tositumomab), ZEVALIN® (ibritumomab), CAMPATH® (alemtuzumab), Lymphocide (eprtuzumab), AVASTIN® (bevacizumab), and TARCEVA® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by the second immunomodulator target or PD-L1. In an exemplary embodiment, a treatment of a hyperproliferative disease (e.g., a cancer tumor) may include an anti-cancer antibody in combination with a macrocyclic peptide and a second immunomodulator concurrently or sequentially or any combination thereof, which may potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-.beta. (Kehrl, J. et al., *J. Exp. Med.*, 163:1037-1050 (1986)), IL-10 (Howard, M. et al., *Immunology Today*, 13:198-200 (1992)), and Fas ligand (Hahne, M. et al., *Science*, 274:1363-1365 (1996)). In another example, antibodies to each of these entities may be further combined with a macrocyclic peptide and another immunomodulator to counteract the effects of immunosuppressive agents and favor anti-tumor immune responses by the host.

Other agents that may be used to activate host immune responsiveness can be further used in combination with a macrocyclic peptide of the present disclosure. These include molecules on the surface of dendritic cells that activate DC function and antigen presentation. Anti-CD40 macrocyclic peptides are able to substitute effectively for T cell helper activity (Ridge, J. et al., *Nature*, 393:474-478 (1998)) and can be used in conjunction with the macrocyclic peptides of the present disclosure, either alone or in combination with an anti-CTLA-4 combination (Ito, N. et al., *Immunobiology*, 201(5):527-540 (2000)). Activating macrocyclic peptides to T cell costimulatory molecules, such as OX-40 (Weinberg, A. et al., *Immunol.*, 164:2160-2169 (2000)), 4-1BB (Melero, I. et al., *Nat. Med.*, 3:682-685 (1997), and ICOS (Hutloff, A. et al., *Nature*, 397:262-266 (1999)) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. A macrocyclic peptide of the present disclosure, either alone or in combination with another immunomodulator, can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. et al., *Science*, 285:546-551 (1999)). These methods may also be used to activate T cell responses to infectious agents such as CMV. Ex vivo activation in the presence a macrocyclic peptide of the present disclosure, either alone or in combination with another innumomodulator, may be expected to increase the frequency and activity of the adoptively transferred T cells.

In certain embodiments, the present disclosure provides a method for altering an adverse event associated with treatment of a hyperproliferative disease with an immunostimulatory agent, comprising administering a macrocyclic peptide of the present disclosure in combination with a subtherapeutic dose of another immunomodulator to a subject. For example, the methods of the present disclosure provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such treatment, this entire patient population is suitable for therapy according to the methods of the present disclosure. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a macrocyclic peptide of the present disclosure, either alone or in combination with another immunomodulator, can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the disclosure, the non-absorbable steroid is budesonide. Budesonide is a locally-acting glucocorticosteroid, which is extensively metabolized, primarily by the liver, following oral administration. ENTOCORT® EC (Astra-Zeneca) is a pH- and time-dependent oral formulation of budesonide developed to optimize drug delivery to the ileum and throughout the colon. ENTOCORT® EC is approved in the U.S. for the treatment of mild to moderate Crohn's disease involving the ileum and/or ascending colon. The usual oral dosage of ENTOCORT® EC for the treatment of Crohn's disease is 6 to 9 mg/day. ENTOCORT® EC is released in the intestines before being absorbed and retained in the gut mucosa. Once it passes through the gut mucosa target tissue, ENTOCORT® EC is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT® EC can result in systemic glucocorticoid effects such as hypercorticism and adrenal suppression. See *Physicians' Desk Reference Supplement*, 58th Edition, 608-610 (2004).

In still further embodiments, a combination PD-L1 and another immunomodulator in conjunction with a non-absorbable steroid can be further combined with a salicylate. Salicylates include 5-ASA agents such as, for example: sulfasalazine (AZULFIDINE®, Pharmacia & Upjohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

Dosage and Formulation

A suitable peptide of Formula I, or more specifically a macrocyclic peptide described herein, can be administered to patients to treat diabetes and other related diseases as the compound alone and or mixed with an acceptable carrier in the form of pharmaceutical formulations. Those skilled in the art of treating diabetes can easily determine the dosage and route of administration of the compound to mammals, including humans, in need of such treatment. The route of administration may include but is not limited to oral, intraoral, rectal, transdermal, buccal, intranasal, pulmonary, subcutaneous, intramuscular, intradermal, sublingual, intracolonic, intraoccular, intravenous, or intestinal administration. The compound is formulated according to the route of administration based on acceptable pharmacy practice (Fingl et al., in *The Pharmacological Basis of Therapeutics, Chapter 1, p. 1* (1975); *Remington's Pharmaceutical Sciences,* 18th Edition, Mack Publishing Co., Easton, Pa. (1990)).

The pharmaceutically acceptable peptide compositions described herein can be administered in multiple dosage forms such as tablets, capsules (each of which includes sustained release or timed release formulations), pills, powders, granules, elixirs, in situ gels, microspheres, crystalline complexes, liposomes, micro-emulsions, tinctures, suspensions, syrups, aerosol sprays and emulsions. The compositions described herein can also be administered in oral, intravenous (bolus or infusion), intraperitoneal, subcutaneous, transdermally or intramuscular form, all using dosage forms well known to those of ordinary skill in the pharmaceutical arts. The compositions may be administered alone, but generally will be administered with a pharmaceutical carrier selected on the basis of the chosen route of administration and standard pharmaceutical practice.

The dosage regimen for the compositions described herein will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 0.6 to 20 mg/kg/day. Intravenously, the daily dosage of the active ingredient when used for the indicated effects will range between 0.001 ng to 100.0 ng per min/per Kg of body weight during a constant rate infusion. Such constant intravenous infusion can be preferably administered at a rate of 0.01 ng to 50 ng per min per Kg body weight and most preferably at 0.01 ng to 10.0 mg per min per Kg body weight. The compositions described herein may be administered in a single daily dose, or the total daily dosage may be administered in divided doses of two, three, or four times daily. The compositions described herein may also be administered by a depot formulation that will allow sustained release of the drug over a period of days/weeks/months as desired.

The compositions described herein can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compositions are typically administered in a mixture with suitable pharmaceutical diluents, excipients, or carriers (collectively referred to herein as pharmaceutical carriers) suitably selected with respect to the intended form of administration, that is, oral tablets, capsules, elixirs, aerosol sprays generated with or without propellant and syrups, and consistent with conventional pharmaceutical practices.

For instance, for oral administration in the form of a tablet or capsule, the active drug component can be combined with an oral, non-toxic, pharmaceutically acceptable, inert carrier such as but not limited to, lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as, but not limited to, ethanol, glycerol, and water. Moreover, when desired or necessary, suitable binders, lubricants, disintegrating agents, and coloring agents can also be incorporated into the mixture. Suitable binders include, but not limited to, starch, gelatin, natural sugars such as, but not limited to, glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrants include, but are not limited to, starch, methyl cellulose, agar, bentonite, and xanthan gum.

The compositions described herein may also be administered in the form of mixed micellar or liposome delivery systems, such as small unilamellar vesicles, large unilamellar vesicles, and multilamellar vesicles. Liposomes can be formed from a variety of phospholipids, such as cholesterol, stearylamine, or phosphatidylcholines. Permeation enhancers may be added to enhance drug absorption.

Since prodrugs are known to enhance numerous desirable qualities of pharmaceuticals (i.e., solubility, bioavailability, manufacturing, etc.) the compounds described herein may be delivered in prodrug form. Thus, the subject matter described herein is intended to cover prodrugs of the presently claimed compounds, methods of delivering the same, and compositions containing the same.

The compositions described herein may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the compositions described herein may be combined with a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 0.01 milligram to about 500 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivative, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration preferably contains a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington: The Science and Practice of Pharmacy*, Nineteenth Edition, Mack Publishing Company (1995), a standard reference text in this field.

Representative useful pharmaceutical dosage forms for administration of the compounds described herein can be illustrated as follows:

Capsules

A large number of unit capsules can be prepared by filling standard two-piece hard gelatin capsules with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit, for example is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

An injectable formulation of a peptide composition described herein may or may not require the use of excipients such as those that have been approved by regulatory bodies. These excipients include, but are not limited to, solvents and co-solvents, solubilizing, emulsifying or thickening agents, chelating agents, anti-oxidants and reducing agents, antimicrobial preservatives, buffers and pH adjusting agents, bulking agents, protectants and tonicity adjustors and special additives. An injectable formulation has to be sterile, pyrogen free and, in the case of solutions, free of particulate matter.

A parenteral composition suitable for administration by injection may be prepared by stirring for example, 1.5% by weight of active ingredient in a pharmaceutically acceptable buffer that may or may not contain a co-solvent or other excipient. The solution should be made isotonic with sodium chloride and sterilized.

Suspension

An aqueous suspension can be prepared for oral and/or parenteral administration so that, for example, each 5 mL contains 100 mg of finely divided active ingredient, 20 mg of sodium carboxymethyl cellulose, 5 mg of sodium benzoate, 1.0 g of sorbitol solution, U.S.P., and 0.025 mL of vanillin or other palatable flavoring.

Biodegradable Microparticles

A sustained-release parenteral composition suitable for administration by injection may be prepared, for example, by dissolving a suitable biodegradable polymer in a solvent, adding to the polymer solution the active agent to be incorporated, and removing the solvent from the matrix thereby forming the matrix of the polymer with the active agent distributed throughout the matrix.

The abbreviations used in the present application, including particularly in the illustrative examples which follow, are well-known to those skilled in the art. Some of the abbreviations used are as follows: HOBt for hydroxybenzotriazole; HOAt for 1-hydroxy-7-azabenzotriazole; DIC for N,N'-diisopropylcarbodiimide; BOP for benzotriazol-1-yloxy tris(dimethylamino)phosphonium hexafluorophosphate; PyBOP for benzotriazol-1-yl-oxytripyrrolidinophosphonium hexafluorophosphate; HCTU for 1H-benzotriazolium 1-[bis(dimethylamino)methylene]-5chloro-,hexafluorophosphate (1-),3-oxide; HATU for 1-[Bis(dimethylamino)methylene]-1H-1,2,3-triazolo[4,5-b]pyridinium 3-oxid hexafluorophosphate; TFA for trifluoroacetic acid; TIS for triisopropylsilane; DMSO for dimethylsulfoxide; MeCN or ACN or AcCN for acetonitrile; DMF for N,N-dimethylformamide; DCM for dichloromethane; DIPEA or DIEA for diisopropylethylamine; Et$_2$O for diethyl ether; MeOH for methanol; rt for room temperature; h for hours; min for minutes; and iPr for isopropyl.

Peptide Synthesis

The description of the present disclosure herein should be construed in congruity with the laws and principals of chemical bonding. It should be understood that the compounds encompassed by the present disclosure are those that are suitably stable for use as pharmaceutical agent. One of skill in the art will know what compounds would and would not be stable based on the general principles of chemical bonding and stability.

Chemical synthesis of a macrocyclic peptide of the present disclosure can be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. A preferred method to synthesize the macrocyclic peptides and analogs thereof described herein is chemical synthesis using various solid-phase techniques such as those described in Chan, W. C. et al., eds., *Fmoc Solid Phase Synthesis*, Oxford University Press, Oxford (2000); Barany, G. et al., *The Peptides: Analysis, Synthesis, Biology*, Vol. 2: "Special Methods in Peptide Synthesis, Part A", pp. 3-284, Gross, E. et al., eds., Academic Press, New York (1980); and in Stewart, J. M. et al., *Solid-Phase Peptide Synthesis*, 2nd Edition, Pierce Chemical Co., Rockford, Ill. (1984). The preferred strategy is based on the Fmoc (9-Fluorenylmethyl methyl-oxycarbonyl) group for temporary protection of the α-amino group, in combination with the tert-butyl group for temporary protection of the amino acid side chains (see for example Atherton, E. et al., "The Fluorenylmethoxycarbonyl Amino Protecting Group", in *The Peptides: Analysis, Synthesis, Biology*, Vol. 9: "Special Methods in Peptide Synthesis, Part C", pp. 1-38, Undenfriend, S. et al., eds., Academic Press, San Diego (1987).

The peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively.

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.; Applied Biosystems, Foster City, Calif.). Preferred solid supports are: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-Fmoc)aminomethyl-3,5-dimethoxyphenoxy)valeryl-aminomethyl-Merrifield resin (PAL resin), for C-terminal carboxamides. Coupling of first and subsequent amino acids can be accomplished using HOBt, 6-Cl-HOBt or HOAt active esters produced from DIC/HOBt, HBTU/HOBt, BOP, PyBOP, or from DIC/6-Cl-HOBt, HCTU, DIC/HOAt or HATU, respectively. Preferred solid supports are: 2-Chlorotrityl chloride resin and 9-Fmoc-amino-xanthen-3-yloxy-Merrifield resin (Sieber amide resin) for protected peptide fragments. Loading of the first amino acid onto the 2-chlorotrityl chloride resin is best achieved by reacting the Fmoc-protected amino acid with the resin in dichloromethane and DIEA. If necessary, a small amount of DMF may be added to facilitate dissolution of the amino acid.

The syntheses of the peptide analogs described herein can be carried out by using a single or multi-channel peptide synthesizer, such as an CEM Liberty Microwave synthesizer, or a Protein Technologies, Inc. Prelude (6 channels) or Symphony (12 channels) synthesizer.

The peptidyl-resin precursors for their respective peptides may be cleaved and deprotected using any standard procedure (see, for example, King, D. S. et al., *Int. J. Peptide Protein Res.*, 36:255-266 (1990)). A desired method is the use of TFA in the presence of water and TIS as scavengers. Typically, the peptidyl-resin is stirred in TFA/water/TIS (94:3:3, v:v:v; 1 mL/100 mg of peptidyl resin) for 2-6 hrs at room temperature. The spent resin is then filtered off and the TFA solution is concentrated or dried under reduced pressure. The resulting crude peptide is either precipitated and washed with $Et_2O$ or is redissolved directly into DMSO or 50% aqueous acetic acid for purification by preparative HPLC.

Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

The following analytical protocols and synthetic methods pertain for Examples 1253 through 1288:

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS(+)" signifies high-resolution electrospray ionization mass spectrometry performed in positive ion mode; "ESI-HRMS(−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analysis LCMS Condition A:
Column: BEH C18, 2.1×50 mm, 1.7-μm particles; Mobile Phase A: water with 0.05% TFA; Mobile Phase B: Acetonitrile with 0.05% TFA; Temperature: 50° C.; Gradient: 2% B to 98% B over 2 minutes, then a 0.5 minutes hold at 98% B; Flow: 0.8 mL/min; Detection: UV at 220 nm.

Analysis LCMS Condition B:
Column: BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Analysis LCMS Condition C:
Column: BEH C18, 2.1×50 mm, 1.7-μm particles; Mobile Phase A: water with 0.2% Formic Acid and 0.01% TFA; Mobile Phase B: Acetonitrile with 0.2% Formic acid an 0.01% TFA; Temperature: 50° C.; Gradient: 2% B to 80% B over 2 minutes, 80% B to 98% B over 0.1 minute then a 0.5 minutes hold at 98% B; Flow: 0.8 mL/min; Detection: UV at 220 nm.

Analysis LCMS Condition D:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

Analysis LCMS Condition E:
Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; temperature: 50° C.; Gradient: 0-100% B over 3 minutes, then a 0.75-minute hold at 100% B; Flow: 1.11 mL/min; Detection: UV at 220 nm.
Analysis LCMS Condition F:
Column: Waters Xbridge C18, 2.1×50 mm; Mobile Phase A: 5:95 acetonitrile:water with 10 mM ammonium acetate; Mobile Phase B: 95:5 acetonitrile:water with 10 mM ammonium acetate; Temperature: 35° C.; Gradient: 0-100% B over 4 minutes, then a 1-minute hold at 100% B; Flow: 4 mL/min; Detection: UV at 220 nm.
Analysis LCMS Condition G:
Finnigan LTQ Mass Spectrometer; column: Phenomenex Jupiter C4, 1×50 mm; Mobile Phase A: 1% formic acid in water; Mobile Phase B: 0.1% formic acid in acetonitrile; Temperature: 30° C.; Gradient: 1% B, 1 min. hold; 1-95% B over 3 min., then a 3-min. hold at 95% B; Flow: 0.15 mL/min.
Analysis LCMS Condition H:
Column: Waters BEH C18, 2.0×50 mm, 1.7-μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0-100% B over 3 minutes, then a 0.5-minute hold at 100% B; Flow: 1.0 mL/min; Detection: UV at 220 nm.
Analysis LCMS Condition I:
Column: Waters BEH C18, 2.0×50 mm, 1.7-μm particles; Mobile Phase A: 5:95 methanol:water with 10 mM ammonium
acetate; Mobile Phase B: 95:5 methanol:water with 10 mM ammonium acetate; Temperature: 50° C.; Gradient: 0-100% B over 3 minutes,
then a 0.5-minute hold at 100% B; Flow: 0.5 mL/min; Detection: UV at 220 nm.
Analysis HPLC Condition A:
Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 35% B to 80% B over 25 min.; Flow: 1 mL/min; Detection: UV at 217 nm.
Analysis HPLC Condition B:
Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 25% B to 75% B over 25 min.; Flow: 1 mL/min; Detection: UV at 217 nm.
Analysis HPLC Condition C:
Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 20% B to 70% B over 25 min.; Flow: 1 mL/min; Detection: UV at 217 nm.
Analysis HPLC Condition D:
Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 15% B to 65% B over 25 min.; Flow: 1 mL/min; Detection: UV at 217 nm.
Analysis HPLC Condition E:
Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 25% B to 60% B over 20 min.; Flow: 1.25 mL/min; Detection: UV at 217 nm.
Analysis HPLC Condition F:
Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 25% B to 65% B over 20 min.; Flow: 1.25 mL/min; Detection: UV at 217 nm.
Analysis HPLC condition G
Column: Sunfire C18 3.5 um, 3.0×150 mm; Mobile Phase A: 5:95 acetonitrile:water with 0.05% trifluoroacetic acid; Mobile Phase B: 95:5 acetonitrile:water with 0.05% trifluoroacetic acid; temperature: 50° C.; Gradient: 10-100% B over 12 minutes, then a 3-minute hold at 100% B; Flow: 1 mL/min; Detection: UV at 220 nm.
Analysis HPLC condition H
Column: Xbridge Phenyl 3.5×150 um, Mobile Phase A: 5:95 acetonitrile:water with 0.05% trifluoroacetic acid; Mobile Phase B: 95:5 acetonitrile:water with 0.05% trifluoroacetic acid; temperature: 50° C.; Gradient: 10-100% B over 12 minutes, then a 3-minute hold at 100% B; Flow: 1 mL/min; Detection: UV at 220 nm.
Analysis HPLC Condition I:
Column: Phenomenex Luna 5u C18(2) 150×4.6 mm; mobile Phase A: water with 0.1% triflouroacetic acid, mobile Phase B: acetonitrile with 0.1% triflouroacetic acid, Gradient 5-100% B over 20 min, then a 5 minute hold at 100% B; Flow 1 mL/min, Detection: UV at 220
Analysis HPLC Condition J:
Column: Phenomenex Luna 5u C18(2) 150×4.6 mm; mobile Phase A: water with 0.1% triflouroacetic acid, mobile Phase B: acetonitrile with 0.1% triflouroacetic acid, Gradient 10-100% B over 20 min, then a 5 minute hold at 100% B; Flow 1 mL/min, Detection: UV at 220
General Procedures:
Prelude Method A:

All manipulations were performed under automation on a Prelude peptide synthesizer (Protein Technologies). All procedures unless noted were performed in a 10 or 45 mL polypropylene tube fitted with a bottom frit. The tube connects to the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were generally not used beyond three weeks from preparation. DMF=dimethylformamide; DIC=N,N'-diisopropylcarbodiimide; HOAt=1-hydroxy 7-azabenzotriazole; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Prelude Method A" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of Fmoc-N-methyl amino acids and coupling to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed below.

Resin-Swelling Procedure:

To a 40 mL polypropylene solid-phase reaction vessel was added Merrifield: Sieber resin (140 mg, 0.100 mmol). The resin was washed three times as follows: to the reaction vessel was added DMF (5.0 mL) and DCM (5.0 mL), upon which the mixture was periodically agitated with N2 bubbling from the bottom of the reaction vessel for 10 minutes before the solvent was drained.

Single-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperdine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added a solution of the amino acid and HOAt (0.2M in DMF, 5.0 mL, 10 eq), then DIC (0.2M in DMF, 5.0 mL, 10 eq). The mixture was periodically agitated for 60 min, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Secondary Amine-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperdine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added a solution of the amino acid and HOAt (0.2M in DMF, 5.0 mL, 5 eq), then DIC (0.2M in DMF, 5.0 mL, 5 eq). The mixture was periodically agitated for 300 min, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Chloroacetyl Chloride Coupling Procedure:

To the reaction vessel containing the resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added 3.0 mL of a solution of DIPEA (4.0 mmol, 0.699 mL, 40 eq), and chloroacetyl chloride (2.0 mmol, 0.160 mL, 20 eq) in DMF. The mixture was periodically agitated for 12 to 18 hours, then the solution was drained. The resin was washed successively three times as follows: for each wash, DMF (4.0 mL) was added to top of the vessel and the resulting mixture was periodically agitated for 90 seconds before the solution was drained. The resin was washed successively four times as follows: for each wash, DCM (4.0 mL) was added to top of the vessel and the resulting mixture was periodically agitated for 90 seconds before the solution was drained.

Prelude Method B:

All manipulations were performed under automation on a Prelude peptide synthesizer (Protein Technologies). All procedures were performed in a 10 or 45 mL polypropylene tube fitted with a bottom frit. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were generally not used beyond three weeks from preparation. DMF=dimethylformamide; HCTU=2-(6-Chloro-1-H-benzotriazol-1-yl)-1,1,3,3-tetramethyluronium; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH;

Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Prelude Method B" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed below.

Resin-Swelling Procedure:

To a 40 mL polypropylene solid-phase reaction vessel was added Merrifield:Sieber resin (140 mg, 0.100 mmol). The resin was washed (swelled) three times as follows: to the reaction vessel was added DMF (5.0 mL) and DCM (5.0 mL), upon which the mixture was periodically agitated with N2 bubbling from the bottom of the reaction vessel for 10 minutes before the solvent was drained through the frit.

Single-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperdine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 5.0 mL, 10 eq), then HCTU (0.2M in DMF, 5.0 mL, 10 eq), and finally DIPEA (0.8M in DMF, 2.5 mL, 20 eq). The mixture was periodically agitated for 30 minutes, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Double-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 5.0 mL, 10 eq), then HCTU (0.2M in DMF, 5.0 mL, 10 eq), and finally DIPEA (0.8M in DMF, 2.5 mL, 20 eq). The mixture was periodically agitated for 15 minutes, then the reaction solution was drained through the frit. The resin was washed successively 3 times with DMF (4.0 mL) through the top of the vessel and the resulting mixture was periodically agitated for 60 seconds before the solution was drained through the frit. To the reaction vessel was added the amino acid (0.2M in DMF, 5.0 mL, 10 eq), then HCTU (0.2M in DMF, 5.0 mL, 10 eq), and finally DIPEA (0.8M in DMF, 2.5 mL, 20 eq). The mixture was periodically agitated for 15 minutes, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. The resulting resin was used directly in the next step.

Secondary Amine-Coupling Procedure:

To the reaction vessel containing resin from the previous step was added piperdine:DMF (20:80 v/v, 5.0 mL). The mixture was periodically agitated for 3 minutes and then the solution was drained through the frit. To the reaction vessel was added piperdine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 2.5 mL, 10 eq), then HCTU (0.2M in DMF, 2.5 mL, 10 eq), and finally NMM (0.8M in DMF, 1.5 mL, 12 eq). The mixture was periodically agitated for 12 hrs, then the reaction solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Chloroacetyl Chloride Coupling Procedure A:

To the reaction vessel containing the resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added 3.0 mL of a solution of DIPEA (4.0 mmol, 0.699 mL, 40 eq), and chloroacetyl chloride (2.0 mmol, 0.160 mL, 20 eq) in DMF. The mixture was periodically agitated for 12 to 18 hours, then the solution was drained through the frit. The resin was washed successively three times as follows: for each wash, DMF (4.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit.

Chloroacetic Acid Coupling Procedure B:

To the reaction vessel containing the resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added DMF (2.0 mL), chloroacetic acid (1.2 mmol, 113 mg, 12 eq), and N,N'-Diisopropylcarbodiimide (1.2 mmol, 0.187 mL, 12 eq). The mixture was periodically agitated for 12 to 18 hours, then the solution was drained through the frit. The resin was washed successively three times as follows: for each wash, DMF (4.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit.

Prelude Method C:

All manipulations were performed under automation on a Prelude peptide synthesizer (Protein Technologies). All procedures unless noted were performed in a 10 or 45 mL polypropylene tube fitted with a bottom frit. The tube connects to a the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were generally not used beyond three weeks from preparation. HATU solution were used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Prelude Method C" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. The Final wash of the Resin used the "Final Wash procedure" described below Resin-Swelling Procedure:

To a 40 mL polypropylene solid-phase reaction vessel was added Merrifield:Sieber resin (140 mg, 0.100 mmol). The resin was washed (swelled) three times as follows: to the reaction vessel was added DMF (5.0 mL) and DCM (5.0 mL), upon which the mixture was periodically agitated with $N_2$ bubbling from the bottom of the reaction vessel for 10 minutes before the solvent was drained through the frit.

Single-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperdine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 5.0 mL, 10 eq), then HATU (0.2M in DMF, 5.0 mL, 10 eq), and finally DIPEA (0.8M in DMF, 2.5 mL, 20 eq). The mixture was periodically agitated for 60 minutes, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Secondary Amine-Coupling Procedure:

To the reaction vessel containing resin from the previous step was added piperdine:DMF (20:80 v/v, 5.0 mL). The mixture was periodically agitated for 3 minutes and then the solution was drained through the frit. To the reaction vessel was added piperdine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 2.5 mL, 5 eq), then HATU (0.2M in DMF, 2.5 mL, 5 eq), and finally DIPEA (0.8M in DMF, 1.5 mL, 12 eq). The mixture was periodically agitated for 300 minutes, then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 2.5 mL, 5 eq), then HATU (0.2M in DMF, 2.5 mL, 5 eq), and finally DIPEA (0.8M in DMF, 1.5 mL, 12 eq). The mixture was periodically agitated for 300 minutes, then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Custom Amino Acids-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperdine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 0.5 to 2.5 mL, 1 to 5 eq), then HATU (0.2M in DMF, 0.5 to 2.5 mL, 1 to 5 eq), and finally DIPEA (0.8M in DMF, 0.5 to 1.5 mL, 4 to 12 eq). The mixture was periodically agitated for 60 minutes to 600 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Final Wash Procedure:

The resin was washed successively two times as follows: for each wash, DMF (4.0 mL) was added through the top of the vessel and the resulting mixture was periodically agitated for 90 seconds before the solution was drained through the frit. The resin was washed successively four times as follows: for each wash, DCM (4.0 mL) was added through the top of the vessel and the resulting mixture was periodically agitated for 90 seconds before the solution was drained through the frit. The resulting resin was used directly in the next step.

Chloroacetic Acid Coupling Procedure:

Note Manual step. To the reaction vessel containing the resin from the previous step was added piperidine:DMF (20:80 v/v, 5.0 mL). The mixture was shaken at Room temperature for 5 minutes and then the solution was drained through the frit. The resin was washed successively five times as follows: for each wash, DMF (4.0 mL) was added through the top of the vessel and the resulting mixture was agitated before the solution was drained through the frit. To the reaction vessel was added DMF (2.0 mL), chloroacetic acid (1.2 mmol, 113 mg, 12 eq), and N,N'-Diisopropylcarbodiimide (1.2 mmol, 0.187 mL, 12 eq). The mixture was shaken at room temperature for 12 to 18 hours, then the solution was drained through the frit. The resin was washed successively three times as follows: for each wash, DMF (4.0 mL) was added to top of the vessel and the resulting mixture was agitated for 90 seconds before the solution was drained through the frit. The resin was washed successively four times as follows: for each wash, $CH_2Cl_2$ (4.0 mL) was added to top of the vessel and the resulting mixture was periodically agitated for 90 seconds before the solution was drained through the frit.

Prelude Method D:

All manipulations were performed under automation on a Prelude peptide synthesizer (Protein Technologies). All procedures unless noted were performed in a 10 or 45 mL polypropylene tube fitted with a bottom frit. The tube connects to a the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were generally not used beyond three weeks from preparation. HATU solution were used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Prelude Method D" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. The Final wash of the Resin used the "Final Wash procedure" described below Resin-Swelling Procedure:

To a 40 mL polypropylene solid-phase reaction vessel was added Merrifield:Sieber resin (140 mg, 0.100 mmol). The resin was washed (swelled) three times as follows: to the reaction vessel was added DMF (5.0 mL) and DCM (5.0 mL), upon which the mixture was periodically agitated with $N_2$ bubbling from the bottom of the reaction vessel for 10 minutes before the solvent was drained through the frit.

Single-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperdine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 1.25 mL, 2.5 eq), then HATU (0.2M in DMF, 1.25 mL, 2.5 eq), and finally DIPEA (0.8M in DMF, 0.75 mL, 5 eq). The mixture was periodically agitated for 30 minutes, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 15 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Secondary Amine-Coupling Procedure:

To the reaction vessel containing resin from the previous step was added piperdine:DMF (20:80 v/v, 5.0 mL). The mixture was periodically agitated for 3 minutes and then the solution was drained through the frit. To the reaction vessel was added piperdine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 1.25 mL, 2.5 eq), then HATU (0.2M in DMF, 1.25 mL, 2.5 eq), and finally DIPEA (0.8M in DMF, 0.75 mL, 5 eq). The mixture was periodically agitated for 30 minutes, then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added the amino (0.2M in DMF, 1.25 mL, 2.5 eq), then HATU (0.2M in DMF, 1.25 mL, 2.5 eq), and finally DIPEA (0.8M in DMF, 0.75 mL, 5 eq). The mixture was periodically agitated for 30 minutes, then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 15 minutes, then the solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 15 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Final Wash procedure:

The resin was washed successively two times as follows: for each wash, DMF (4.0 mL) was added through the top of the vessel and the resulting mixture was periodically agitated for 90 seconds before the solution was drained through the frit. The resin was washed successively four times as follows: for each wash, DCM (4.0 mL) was added through the top of the vessel and the resulting mixture was periodically agitated for 90 seconds before the solution was drained through the frit. The resulting resin was used directly in the next step.

Chloroacetic Acid Coupling Procedure:

Note Manual step. To the reaction vessel containing the resin from the previous step was added piperidine:DMF (20:80 v/v, 5.0 mL). The mixture was shaken at Room temperature for 5 minutes and then the solution was drained through the frit. The resin was washed successively five times as follows: for each wash, DMF (4.0 mL) was added through the top of the vessel and the resulting mixture was agitated before the solution was drained through the frit. To the reaction vessel was added DMF (2.0 mL), chloroacetic acid (1.2 mmol, 113 mg, 12 eq), and N,N'-Diisopropylcarbodiimide (1.2 mmol, 0.187 mL, 12 eq). The mixture was shaken at room temperature for 12 to 18 hours, then the solution was drained through the frit. The resin was washed successively three times as follows: for each wash, DMF (4.0 mL) was added to top of the vessel and the resulting mixture was agitated for 90 seconds before the solution was drained through the frit. The resin was washed successively four times as follows: for each wash, $CH_2Cl_2$ (4.0 mL) was added to top of the vessel and the resulting mixture was periodically agitated for 90 seconds before the solution was drained through the frit.

CEM Method A:

All manipulations were performed under automation on a CEM Liberty microwave peptide synthesizer (CEM Corporation). All procedures unless noted were performed in a 30 or 125 mL polypropylene tube fitted with a bottom frit to a CEM Discovery microwave unit. The tube connects to a the CEM Liberty synthesizer through both the bottom and the top of the tube. DMF and DCM can be added through the top and bottom of the tube, which washes down the sides of the tube equally. All solutions are removed through the bottom of the tube except while transferring resin from the top. "Periodic bubbling" describes a brief bubbling of $N_2$ gas through the bottom frit. Amino acid solutions were generally not used beyond three weeks from preparation. HATU solution were used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Other Common resins Such as Rink, ChloroTrityl, or other acid sensitive linkers can be employed in the synthesis, Seiber amide resin is used unless otherwise noted in specific examples. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc[N-Me]Nle-OH; Fmoc-Orn(Boc)-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "CEM Method A" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed above.

Resin-Swelling Procedure:

To 50 mL polypropylene conical tube was added Merrifield:Sieber resin (140 mg, 0.100 mmol). Then DMF (7 mL) was added to the tube followed by DCM (7 mL). The resin was then transferred to the reaction vessel from top of the vessel. The procedure is repeated additionally two times. DMF (7 mL) was added followed by DCM (7 mL). The resin was allowed to swell with N2 bubbling from the bottom of the reaction vessel for 15 minutes before the solvent was drained through the frit.

Standard Coupling Procedure:

To the reaction vessel containing resin from the previous step was added a solution of piperidine:DMF (20:80 v/v, 5.0 mL). The mixture was periodically agitated for 3 minutes and then the solution was drained through the frit. To the reaction vessel was added a solution of piperidine:DMF (20:80 v/v, 5.0 mL). The mixture was periodically agitated for 3 minutes and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 minutes at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 minutes at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Double-Couple Coupling Procedure:

To the reaction vessel containing resin from the previous step was added a solution of piperidine:DMF (20:80 v/v, 5.0 mL). The mixture was periodically agitated for 3 minutes and then the solution was drained through the frit. To the reaction vessel was added a solution of piperidine:DMF (20:80 v/v, 5.0 mL). The mixture was periodically agitated for 3 minutes and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 minutes at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 minutes at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 minutes at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Secondary Amine Coupling Procedure:

To the reaction vessel containing resin from the previous step was added a solution of 5% piperazine and 0.1 M HOBt in DMF (7 mL). The mixture was periodically agitated for 3 minutes at 75° C. and then the solution was drained. This procedure was repeated one more time. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HCTU (0.5M in DMF, 1.0 mL, 5 eq), and DIPEA (2M in NMP, 0.5 mL, 10 eq). The mixture was mixed by $N_2$ bubbling for 5 minutes at 75° C. for all amino acids (50° C. for Fmoc-Cys(Trt)-OH and Fmoc-His(Trt)-OH), followed by 6 hrs with no heating. After draining, the resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 minutes at 65° C., then the solution was drained. The resin was washed successively three times as follows: DMF (7 mL) wash from top, followed by DMF (7 mL) wash from bottom and finally with DMF (7 mL) wash from top. The resulting resin was used directly in the next step.

Custom Amino Acids-Coupling Procedure:

To the reaction vessel containing resin from the previous step was added a solution of piperidine:DMF (20:80 v/v, 5.0 mL). The mixture was periodically agitated for 3 minutes and then the solution was drained through the frit. To the reaction vessel was added a solution of piperidine:DMF (20:80 v/v, 5.0 mL). The mixture was periodically agitated for 3 minutes and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid solution (1.25 mL to 5 mL, 2.5 eq to 10 eq) containing HATU (2.5 eq to 10 eq), and finally DIPEA (2M in NMP, 0.5 mL to 1 mL, 20 eq). The mixture was mixed by $N_2$ bubbling for 5 minutes to 2 hours at 25° C. to 75° C., then the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 minutes at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Symphony Method A:

All manipulations were performed under automation on a Symphony peptide synthesizer (Protein Technologies). All procedures unless noted were performed in a Symphony polypropylene tube fitted with a bottom frit. The tube connects to a the Symphony peptide synthesizer through both the bottom and the top of the tube. All Solvents, DMF, DCM, amino acids and reagents are added through the bottom of the tube and pass up through the frit to contact the resin. All solutions are removed through the bottom of the tube. "Periodic agitation" describes a brief pulse of N2 gas through the bottom frit; the pulse lasts approximately 5 seconds and occurs every 15 seconds. Amino acid solutions were generally not used beyond three weeks from preparation. HATU solution were used within 5 days of preparation. DMF=dimethylformamide; HCTU=2-(6-Chloro-1-H-benzotriazol-1-yl)-1,1,3,3-tetramethyluronium; HATU=1-[Bis (dimethylamino)methylene]-1H-1,2,3-triazolo[4,5-b]pyridinium 3-oxid hexafluorophosphate; NMM=n-Methyl morpholine; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Other common Acid sensitive resins can also be used in the synthesis such as Rink or functionalized Chloro trityl Resin. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Symphony Method A" describes an experiment performed on a 0.050 mmol scale, where the scale is determined by the amount of Sieber linker bound to the resin. This scale corresponds to approximately 70 mg of the Sieber-Merrifield resin described above. All procedures can be scaled beyond 0.050 mmol scale by adjusting the described volumes by the multiple of the scale. Prior to amino acid coupling, all peptide synthesis sequences began with a resin-swelling procedure, described below as "Swelling procedure". Coupling of amino acids to a primary amine N-terminus used the "Standard-coupling procedure" described below. Coupling of amino acids to a secondary amine N-terminus used the "Double-coupling", custom amino acids are coupled via a manual Blank addition of the amino acid "Blank coupling" described below.

Swelling Procedure:

To a Symphony polypropylene solid-phase reaction vessel was added Merrifield:Sieber resin (70 mg, 0.050 mmol). The resin was washed (swelled) three times as follows: to the reaction vessel was added DMF (2.5 mL) upon which the mixture was periodically agitated with N2 bubbling from the bottom of the reaction vessel for 10 minutes before the solvent was drained through the frit. To the reaction vessel was added piperdine:DMF (20:80 v/v, 2.5 mL). The mixture was periodically agitated for 2.5 minutes and then the solution was drained through the frit. The resin was washed successively six times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed with DMF (6.25 mL) added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. The resulting resin was used directly in the next step.

Standard-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine:DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed successively three times as follows: for each wash, DMF (2.5 mL) was added through the bottom of the vessel and the resulting mixture was periodically agitated for 30 seconds before the solution was drained through the frit. The resulting resin was used directly in the next step.

Secondary Amine-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine:DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 300 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 300 minutes, then the reaction solution was drained through the frit. The resin was washed successively three times as follows: for each wash, DMF (2.5 mL) was added through the bottom of the vessel and the resulting mixture was periodically agitated for 30 seconds before the solution was drained through the frit. The resulting resin was used directly in the next step.

Custom Amino Acids-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine:DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. The synthesis was paused by the Symphony software to add to the reaction vessel manually the custom amino acid (0.2M in DMF, 1.25 mL, 5 eq), then restart automation: to add HATU (0.2M in DMF, 1.25 mL, 5 eq), and finally NMM (0.8M in DMF, 1.25 mL, 10 eq). The mixture was periodically agitated for 300 minutes, then the reaction solution was drained through the frit. The resin was washed six times as follows with DMF (2.5 mL) was added through the bottom of the vessel and the resulting mixture was periodically agitated for 30 seconds before the solution was drained through the frit. To the reaction vessel was added the $Ac_2O$/DIPEA/DMF (v/v/v 1:1:3 2.5 mL) the mixture was periodically agitated for 10 minutes, then the reaction solution was drained through the frit. The resin was washed successively three times as follows: for each wash, DMF (2.5 mL) was added through the bottom of the vessel and the resulting mixture was periodically agitated for 90 seconds before the solution was drained through the frit. The resulting resin was used directly in the next step.

Symphony Method B:

All manipulations were performed under automation on a Symphony peptide synthesizer (Protein Technologies). All procedures unless noted were performed in a Symphony polypropylene tube fitted with a bottom frit. The tube connects to a the Symphony peptide synthesizer through both the bottom and the top of the tube. All Solvents, DMF, DCM, amino acids and reagents are added through the bottom of the tube and pass up through the frit to contact the resin. All solutions are removed through the bottom of the tube. "Periodic agitation" describes a brief pulse of N2 gas through the bottom frit; the pulse lasts approximately 5 seconds and occurs every 15 seconds. Amino acid solutions were generally not used beyond three weeks from preparation. HATU solution were used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; NMM=n-Methyl morpholine; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Other common Acid sensitive resins can also be used in the synthesis such as Rink or functionalized Chloro trityl Resin. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Symphony Method B" describes an experiment performed on a 0.050 mmol scale, where the scale is determined by the amount of Sieber linker bound to the resin. This scale corresponds to approximately 70 mg of the Sieber-Merrifield resin described above. All procedures can be scaled beyond 0.050 mmol scale by adjusting the described volumes by the multiple of the scale. Prior to amino acid coupling, all peptide synthesis sequences began with a resin-swelling procedure, described below as "Swelling procedure". Coupling of amino acids to a primary amine N-terminus used the "Standard-coupling procedure" described below. Coupling of amino acids to a secondary amine N-terminus used the "Secondary amine-coupling procedure B", Custom amino acids are coupled via a manual Blank addition of the amino acid "Custom amino acids-coupling procedure" described below, and ChloroAcetyl Anhydride is added to the final position of the sequence using the "final capping procedure" described below.

Swelling Procedure:

To a Symphony polypropylene solid-phase reaction vessel was added Merrifield:Sieber resin (70 mg, 0.050 mmol). The resin was washed (swelled) three times as follows: to the reaction vessel was added DMF (2.5 mL) upon which the mixture was periodically agitated with $N_2$ bubbling from the bottom of the reaction vessel for 10 minutes before the solvent was drained through the frit. To the reaction vessel was added piperdine:DMF (20:80 v/v, 2.5 mL). The mixture was periodically agitated for 2.5 minutes and then the solution was drained through the frit. The resin was washed successively six times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed with DMF (6.25 mL) added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. The resulting resin was used directly in the next step.

Standard-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine:DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 15 minutes, then the reaction solution was drained through the frit. The resin was washed 6 times as follows: DMF (2.5 mL) was added through the bottom of the vessel and the resulting mixture was periodically agitated for 30 seconds before the solution was drained through the frit. To the reaction vessel was added $Ac_2O$/DIPEA/DMF (v/v/v 1:1:3 2.5 mL) the mixture was periodically agitated for 10 minutes, then the reaction solution was drained through the frit. The resin was washed successively six times as follows: for each wash, DMF (2.5 mL) was added through the bottom of the vessel and the resulting mixture was periodically agitated for 90 seconds before the solution was drained through the frit. The resulting resin was used directly in the next step.

Secondary Amine-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine:DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 15 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 15 minutes, then the reaction solution was drained through the frit. The resin was washed successively three times as follows: for each wash, DMF (2.5 mL) was added through the bottom of the vessel and the resulting mixture was periodically agitated for 30 seconds before the solution was drained through the frit. To the reaction vessel was added $Ac_2O$/DIPEA/DMF (v/v/v 1:1:3 2.5 mL) the mixture was periodically agitated for 10 minutes, then the reaction solution was drained through the frit. The resin was washed successively six times as follows: for each wash, DMF (2.5 mL) was added through the bottom of the vessel and the resulting mixture was periodically agitated for 90 seconds before the solution was drained through the frit. The resulting resin was used directly in the next step.

Custom Amino Acids-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine:DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. The System was paused by the system for the Manual addition of the custom amino acid to the reaction vessel (0.2M in DMF, 1.25 mL, 5 eq), then the automation was restarted to add to the reaction vesicle HATU (0.2M in DMF, 1.25 mL, 5 eq), and finally NMM (0.8M in DMF, 1.25 mL, 10 eq). The mixture was periodically agitated for 15 minutes, then the reaction solution was drained through the frit. The resin was washed 6 times as follows: DMF (2.5 mL) was added through the bottom of the vessel and the resulting mixture was periodically agitated for 30 seconds before the solution was drained through the frit. To the reaction vessel was added $Ac_2O$/DIPEA/DMF (v/v/v 1:1:3 2.5 mL) the mixture was periodically agitated for 10 minutes, then the reaction solution was drained through the frit. The resin was washed successively six times as follows: for each wash, DMF (2.5 mL) was added through the bottom of the vessel and the resulting mixture was periodically agitated for 90 seconds before the solution was drained through the frit. The resulting resin was used directly in the next step.

Final Capping Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine:DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added NMM (0.8M in DMF, 1.25 mL, 10 eq) followed by the addition of the Chloroacetic anhydride (0.4M in DMF, 1.25 mL, 10 eq). The mixture was periodically agitated for 15 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added NMM (0.8M in DMF, 1.25 mL, 10 eq) followed by the addition of the Chloroacetic anhydride (0.4M in DMF, 1.25 mL, 10 eq). The mixture was periodically agitated for 15 minutes, then the reaction solution was drained through the frit. The resin was washed 6 times as follows: DMF (2.5 mL) was added through the bottom of the vessel and the resulting mixture was periodically agitated for 30 seconds before the solution was drained through the frit. To the reaction vessel was added $Ac_2O$/DIPEA/DMF (v/v/v 1:1:3 2.5 mL) the mixture was periodically agitated for 10 minutes, then the reaction solution was drained through the frit. The resin was washed successively six times as follows: for each wash, DMF (2.5 mL) was added through the bottom of the vessel and the resulting mixture was periodically agitated for 30 seconds before the solution was drained through the frit. The resin was washed successively four times as follows: for each wash, DCM (2.5 mL) was added through the bottom of the vessel and the resulting mixture was periodically agitated for 30 seconds before the solution was drained through the frit. The resulting resin was then dried with a stream of Nitrogen for 10 mins.

Global Deprotection Method A:

All manipulations were performed manually unless noted otherwise. The procedure of "Global Deprotection Method A" describes an experiment performed on a 0.100 mmol scale, where the scale is determined by the amount of Sieber linker bound to the resin. The procedure can be scaled beyond 0.100 mmol scale by adjusting the described volumes by the multiple of the scale. A "deprotection solution" was prepared using trifluoroacetic acid:water:triisopropylsilane:dithiothreitol (92.5:2.5:2.5:2.5 v:v:v:w). The resin was removed from the reaction vessel and transferred to a 25 mL syringe equipped with a frit. To the syringe was added the "deprotection solution" (5.0 mL). The mixture was mixed in a shaker for 85 min. The solution was filtered through, concentrated and diluted in diethyl ether (30 mL). The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Global Deprotection Method B:

All manipulations were performed manually unless noted otherwise. The procedure of "Global Deprotection Method B" describes an experiment performed on a 0.04 mmol scale, where the scale is determined by the amount of Sieber linker bound to the resin. The procedure can be scaled beyond 0.04 mmol scale by adjusting the described volumes by the multiple of the scale. A "deprotection solution" was prepared using trifluoroacetic acid:triisopropylsilane (96:4; v:v). The resin was removed from the reaction vessel and transferred to a 10 mL syringe equipped with a frit. To the syringe was added the "deprotection solution" (2.0-3.0 mL). The mixture was mixed in a shaker for 1 h or 1.5 h. The solution was filtered through, washed with deprotection solution (0.5 mL), concentrated and diluted in diethyl ether (30 mL). The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Global Deprotection Method C:

All manipulations were performed manually unless noted. The procedure of "Global Deprotection Method C" describes an experiment performed on a 0.100 mmol scale, where the scale is determined by the amount of Sieber linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (95:2.5:2.5 v:v:w). The resin was removed from the reaction vessel and transferred to a Bio-Rad tube. To the Bio-Rad tube was added the "deprotection solution" (4.0 mL). The mixture was mixed in a shaker for 60 minutes. The solution was filtered through and diluted in diethyl ether (30 mL). The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Global Deprotection Method D:

All manipulations were performed manually unless noted otherwise. The procedure of "Global Deprotection Method B" describes an experiment performed on a 0.100 mmol scale, where the scale is determined by the amount of Sieber linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (94:3:3 v:v:w). The resin was removed from the reaction vessel and transferred to a 25 mL syringe equipped with a frit. To the syringe was added the "deprotection solution" (5.0 mL). The mixture was mixed in a shaker for 5 minutes. The solution was filtered through and diluted in diethyl ether (30 mL). The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Global Deprotection Method E:

All manipulations were performed manually unless noted. The procedure of "Global Deprotection Method E" describes an experiment performed on a 0.100 mmol scale, where the scale is determined by the amount of Fmoc Gly-ClTrt linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (95:2.5:2.5 v:v:w). The resin was removed from the reaction vessel and transferred to a Bio-Rad tube. To the Bio-Rad tube was added the "deprotection solution" (2.0 mL). The mixture was mixed in a shaker for 3 minutes. The solution was filtered, and collected in a Centrifuge tube. To the Bio-Rad tube was added the "deprotection solution" (2.0 mL). The mixture was mixed in a shaker for 3 minutes. The solution was filtered, and collected in a Centrifuge tube. To the Bio-Rad tube was added the "deprotection solution" (2.0 mL). The mixture was mixed in a shaker for 3 minutes. The solution was filtered, and collected in a Centrifuge tube. The solution in the Centrifuge tube was allowed to stand for 60 minutes. The collected solution was then diluted with diethyl ether (30 mL), and precipitate formed. The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Global Deprotection Method F:

All manipulations were performed manually unless noted. The procedure of "Global Deprotection Method F" describes an experiment performed on a 0.100 mmol scale, where the scale is determined by the amount of Rink linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (95:2.5:2.5 v:v:w). The resin was removed from the reaction vessel and transferred to a 6 mls Bio-Rad tube. To the Bio-Rad was added the "deprotection solution" (4.0 mL). The mixture was mixed in a shaker for 90 minutes. The solution was filtered through and diluted in diethyl ether (30 mL). The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Cyclization Method A

All manipulations were performed manually unless noted otherwise. The procedure of "Cyclization Method A" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of acetonitrile:aqueous 8M Guanidine/50 mM TRIS (1:3) (pH 8.6) (7 mL:18 mL or similar ratio), and the solution was then adjusted to pH=8.5-9.0 using aq NaOH (1.0M), if necessary. The solution was then mixed using a shaker for 12 to 18 hours. The reaction solution was concentrated and the residue was then dissolved in acetonitrile:water. This solution was subjected to reverse-phase HPLC purification to afford the desired cyclic peptide.

Cyclization Method C:

All manipulations were performed manually unless noted. The procedure of "Cyclization Method C" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of acetonitrile:aqueous 0.1M ammonium bicarbonate buffer (11 mL:24 mL or similar ratio), and the solution was then carefully adjusted to pH=8.5-9.0 using aq NaOH (1.0M). The solution was then mixed using a shaker for 12 to 18 hours. The reaction solution was concentrated and the residue was then dissolved in acetonitrile:water. This solution was subjected to reverse-phase HPLC purification to afford the desired cyclic peptide.

Cyclization Method D:

All manipulations were performed manually unless noted. The procedure of "Cyclization Method D" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of acetonitrile:aqueous 0.1M ammonium bicarbonate buffer (11 mL:24 mL), and the solution was then carefully adjusted to pH=8.5-9.0 using aq NaOH (1.0M). The solution was then mixed with stirring for 12 to 18 hours. The reaction solution was concentrated and the residue was then dissolved in acetonitrile:water. This solution was subjected to reverse-phase HPLC purification to afford the desired cyclic peptide.

Cyclization Method E:

All manipulations were performed manually unless noted. The procedure of "Cyclization Method E" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of aqueous 6M guanidine HCl buffer (15 mL), the solution was then mixed with stirring for 12 to 18 hours. The reaction solution was concentrated and 15 mL of DMSO was added to the residue affording a slurry which was filtered. This filtered solution was subjected to reverse-phase HPLC purification to afford the desired cyclic peptide.

Manual Coupling procedure A:

To Bio-Rad reaction vessel containing resin from the previous step was added piperidine:DMF (20:80 v/v, 5.0 mL). The mixture was periodically shaken for 5 minutes and then the solution was drained through the frit. The resin was washed successively five times as follows: for each wash, DMF (4.0 mL) was added through the top of the vessel and the resulting mixture was shaken for 60 seconds before the solution was drained through the frit. To the reaction vessel was added the amino acid (1.2-10 equivalents) typical (0.2M in DMF, 2.5 mL, 5 eq), then HATU (1.210 equivalents) typical (0.2M in DMF, 2.5 mL, 5 eq), and finally DIPEA (2.4-20 equivalents) typical (0.8M in DMF, 1.25 mL, 10 eq). The mixture was shaken for 60 minutes to 18 hours, then the reaction solution was drained through the frit. The resin was washed successively four times as follows: for each wash, DMF (4.0 mL) was added through the top of the vessel and the resulting mixture was shaken for 60 seconds before the solution was drained through the frit.

N-Methylation On-Resin Method A.

(Turner, R. A.; Hauksson, N. E.; Gipe, J. H.; Lokey, R. S. Org. Lett. 2013, 15(19), 5012-5015):

All manipulations were performed manually unless noted. The procedure of "N-methylation on-resin Method A" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale.

The resin was transferred into a 25 mL fritted syringe. To the resin was added piperidine:DMF (20:80 v/v, 5.0 mL). The mixture was shaken for 3 min. and then the solution was drained through the frit. The resin was washed 3 times with DMF (4.0 mL). To the reaction vessel was added piperdine:DMF (20:80 v/v, 4.0 mL). The mixture was shaken for 3 min. and then the solution was drained through the frit. The resin was washed successively three times with DMF (4.0 mL) and three times with DCM (4.0 mL). The resin was suspended in DMF (2.0 mL) and ETHYL TRIFLUORO-ACETATE (0.119 ml, 1.00 mmol), 1,8-DIAZABICYCLO[5.4.0]UNDEC-7-ENE (0.181 ml, 1.20 mmol). The mixture was placed on a shaker for 60 min. The solution was drained through the frit. The resin was washed successively three times with DMF (4.0 mL) and three times with DCM (4.0 mL).

The resin was washed three times with dry THF (2.0 mL) to remove any residual water. In an oven dried 4.0 mL vial was added THF (1.0 mL) and TRIPHENYLPHOSPHINE (131 mg, 0.500 mmol) on dry 4 Å molecular sieves (20 mg). The solution was transferred to the resin and diisopropyl azodicarboxylate (0.097 mL, 0.5 mmol) was added slowly. The resin was stirred for 15 min. The solution was drained through the frit and the resin was washed with three times with dry THF (2.0 mL) to remove any residual water. In an oven dried 4.0 mL vial was added THF (1.0 mL), TRIPHENYLPHOSPHINE (131 mg, 0.500 mmol) on dry 4 Å molecular sieves (20 mg). The solution was transferred to the resin and diisopropyl azodicarboxylate (0.097 mL, 0.5 mmol) was added slowly. The resin was stirred for 15 min. The solution was drained through the frit. The resin was washed successively three times with DMF (4.0 mL) and three times with DCM (4.0 mL). The resin was suspended in Ethanol (1.0 mL) and THF (1.0 mL), and SODIUM BOROHYDRIDE (37.8 mg, 1.000 mmol) was added. The mixture was stirred for 30 min. and drained. The resin was washed successively three times with DMF (4.0 mL) and three times with DCM (4.0 mL).

Microcleavage A:

To a small <10 mg sample of resin is added 2 drops of TIS and 1 mL of Triflouroacetic acid, shake at rt. After 1 h, remove a small aliquot and dilute with 0.5 mL Acetonitrile, filter, and obtain analysis by LC-MS.

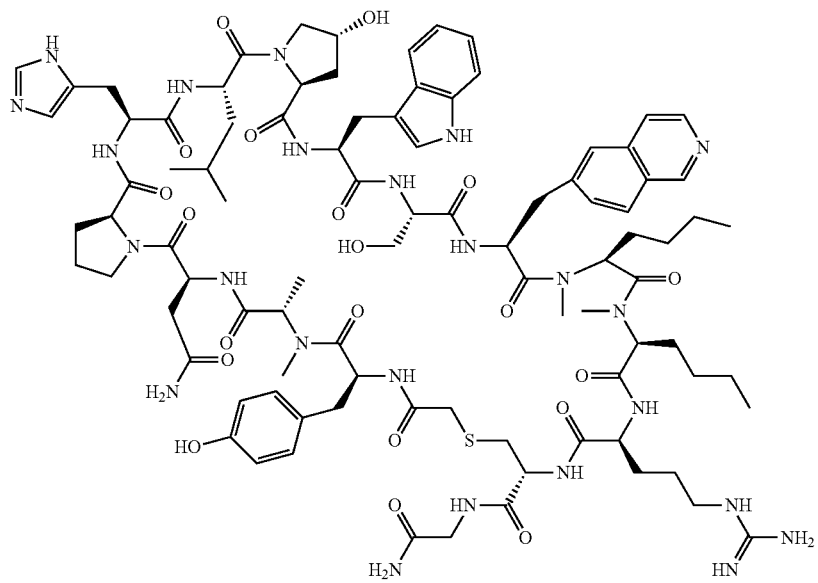

Preparation of Example 0001

Example 0001 was prepared one Rink amide resin using the following synthetic sequence described below:
"Symphony Method B: Resin-swelling procedure",
Fmoc-Glycine-OH: "Symphony Method B: Standard-coupling procedure",
Fmoc-Cystine(Trt)-OH: "Symphony Method B: Standard-coupling procedure",
Fmoc-Arginine(Pfp)-OH: "Symphony Method B: Secondary amine-coupling procedure",
Fmoc-N-Methyl Norleucine: "Symphony Method B: Secondary amine-coupling procedure",
Fmoc-N-Methyl Norleucine: "Symphony Method B: Secondary amine-coupling procedure",
(S)-2-4((9H-fluoren-9-yl)methoxy)carbonyl)amino)-3-(isoquinolin-7-yl)propanoic acid: "Manual Coupling procedure A",
Fmoc-Serine(OtBu)-OH: "Symphony Method B: Standard-coupling procedure",
Fmoc-Tryptophan(Boc)-OH: "Symphony Method B: Standard-coupling procedure",
Fmoc-trans-Hydoxyproline(tBu)-OH: "Symphony Method B: Standard-coupling procedure",
Fmoc-Leucine-OH: "Symphony Method B: Secondary amine-coupling procedure",
Fmoc-Histidine-OH: "Symphony Method B: Standard-coupling procedure",
Fmoc-Proline-OH: "Symphony Method B: Standard-coupling procedure",
Fmoc-Asparagine-OH: "Symphony Method B: Secondary amine-coupling procedure",
Fmoc-N-methyl-Alanine-OH: "Symphony Method B: Standard-coupling procedure",
Fmoc-Tyrosine(OtBu)-OH: "Symphony Method B: Secondary amine-coupling procedure",
"Symphony Method B: Final capping procedure",
"Global Deprotection Method D"
"Cyclization Method D".
The crude material was purified via preparative LC/MS with the following conditions: Column: Waters XBridge C18, 19×250 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-50% B over 25 minutes, then a 5-minute hold at 100% B; Flow: 20 mL/min. Fractions containing the desired product were combined and dried via centrifugal evaporation. The yield of the product was 1.2 mg, and its estimated purity by LCMS analysis was 93%. Analysis LCMS Condition D: Retention time=1.32 min; ESI-MS(+) m/z 961.8 (M+2H). Analysis LCMS Condition E: Retention time=1.10 min; ESI-MS(+) m/z 961.7 (M+2H). ESI-HRMS(+) m/z: Calculated: 962.9380 (M+2H); Found: 962.9370 (M+2H).

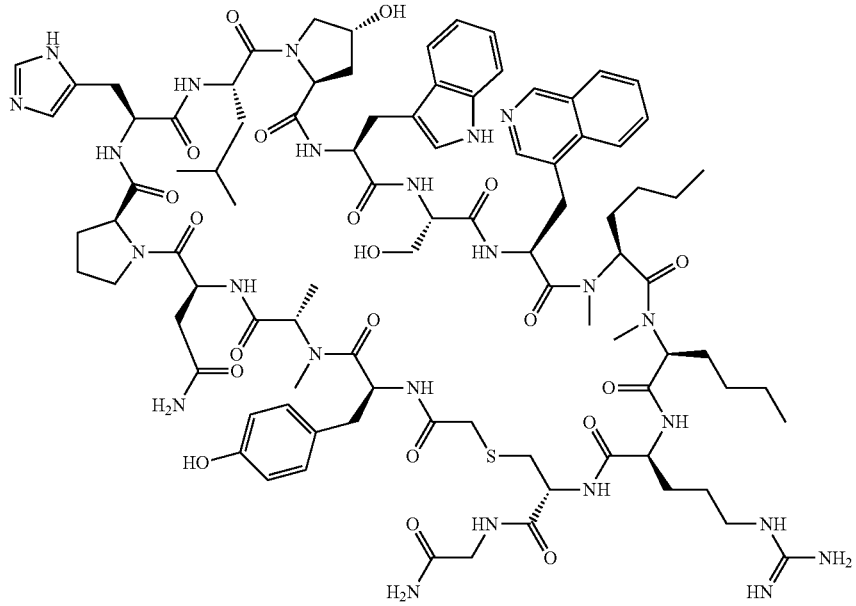

Preparation of Example 1254

Example 1254 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Manual Coupling procedure A "Symphony Method B: Final capping procedure", "Global Deprotection Method D", and "Cyclization Method D". The crude material was purified via preparative LC/MS with the following conditions: Column: Waters XBridge C18, 19×250 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-50% B over 25 minutes, then a 5-minute hold at 100% B; Flow: 20 mL/min. Fractions containing the desired product were combined and dried via centrifugal evaporation. The yield of the product was 3.1 mg, and its estimated purity by LCMS analysis was 99%. Analysis LCMS Condition D: Retention time=1.39 min; ESI-MS(+) m/z 961.8 (M+2H). Analysis LCMS Condition E: Retention time=1.13 min; ESI-MS(+) m/z 962.5 (M+2H).

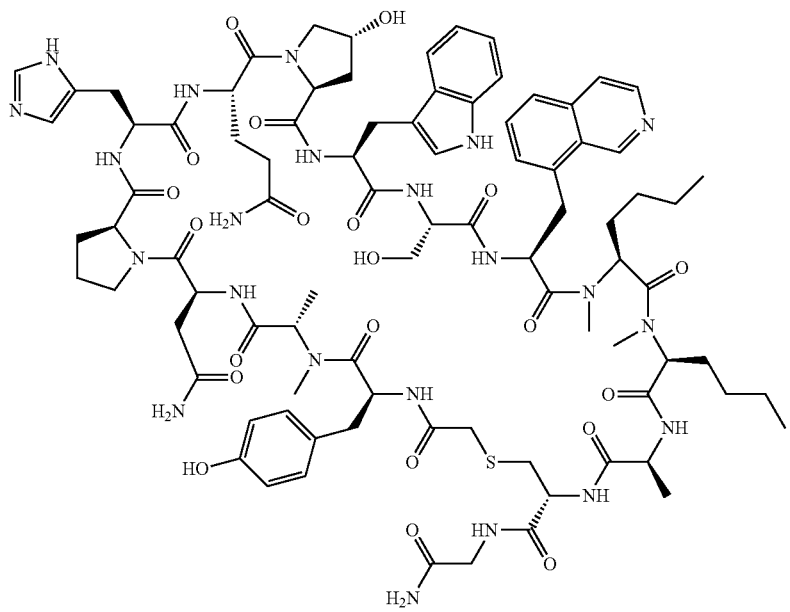

Preparation of Example 1271

Example 1271 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Manual Coupling procedure A", "Symphony Method B: Final capping procedure", "Global Deprotection Method F", and "Cyclization Method D". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.8 mg, and its estimated purity by LCMS analysis was 100%. Analysis LCMS Condition H: retention time=1.48 min.; ESI-MS(+) m/z 926.9 (M+2H). Analysis LCMS Condition I: retention time=2.96 min.; ESI-MS(+) m/z 926.9 (M+2H). ESI-HRMS(+) m/z: Calculated: 926.4354 (M+2H); Found: 926.4331 (M+2H).

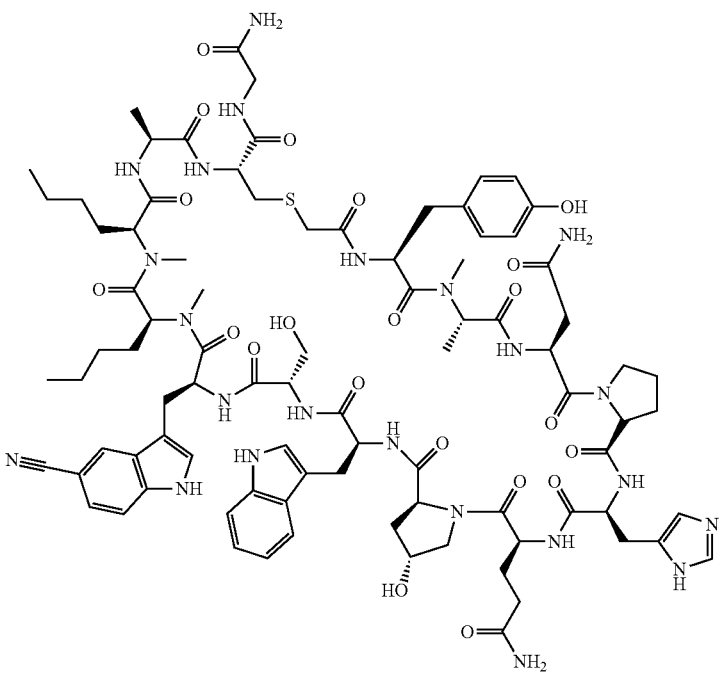

Preparation of Example 1284

Example 1284 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Manual Coupling procedure A", "Symphony Method B: Final capping procedure", "Global Deprotection Method F", and "Cyclization Method D". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 0.9 mg, and its estimated purity by LCMS analysis was 90%. Analysis LCMS Condition H: retention time=1.53 min.; ESI-MS(+) m/z 934.3 (M+2H) Analysis LCMS Condition I: retention time=2.57 min.; ESI-MS(+) m/z 933.7 (M+2H) ESI-HRMS(+) m/z: Calculated: 932.9330 (M+2H); Found: 932.9313 (M+2H).

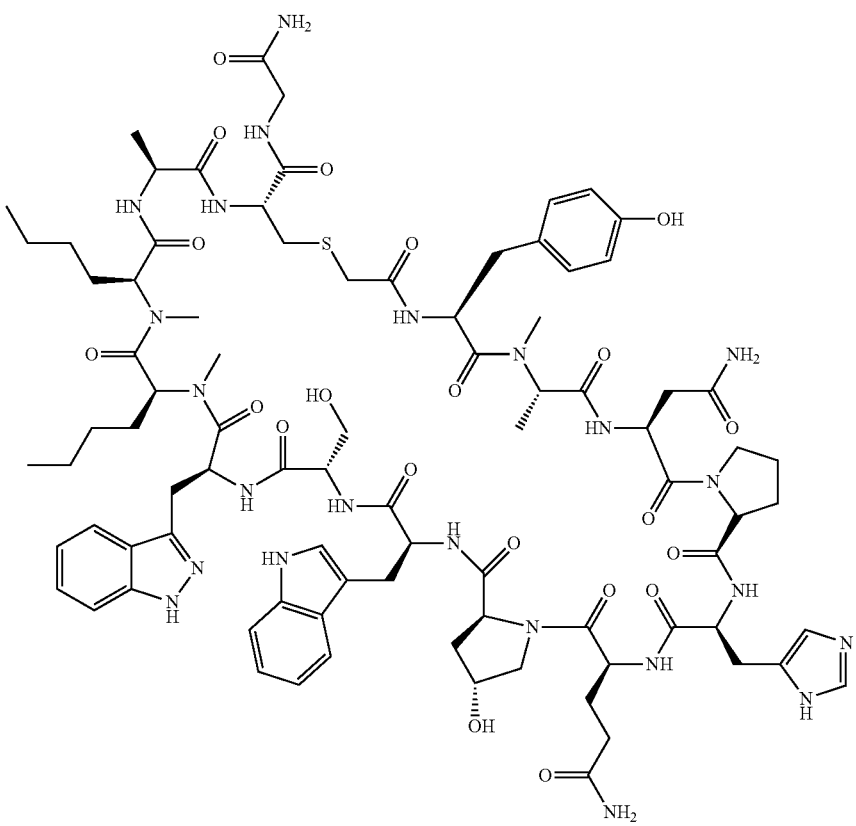

Preparation of Example 1286

Example 1286 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Manual Coupling procedure A", "Symphony Method B: Final capping procedure", "Global Deprotection Method F", and "Cyclization Method D". The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 1.8 mg, and its estimated purity by LCMS analysis was 97%. Analysis LCMS Condition H: retention time=1.45 min.; ESI-MS(+) m/z 921.5 (M+2H). Analysis LCMS Condition I: retention time=2.59 min.; ESI-MS(+) m/z 921.4 (M+2H). ESI-HRMS(+) m/z: Calculated: 920.9330 (M+2H); Found: 920.9320 (M+2H).

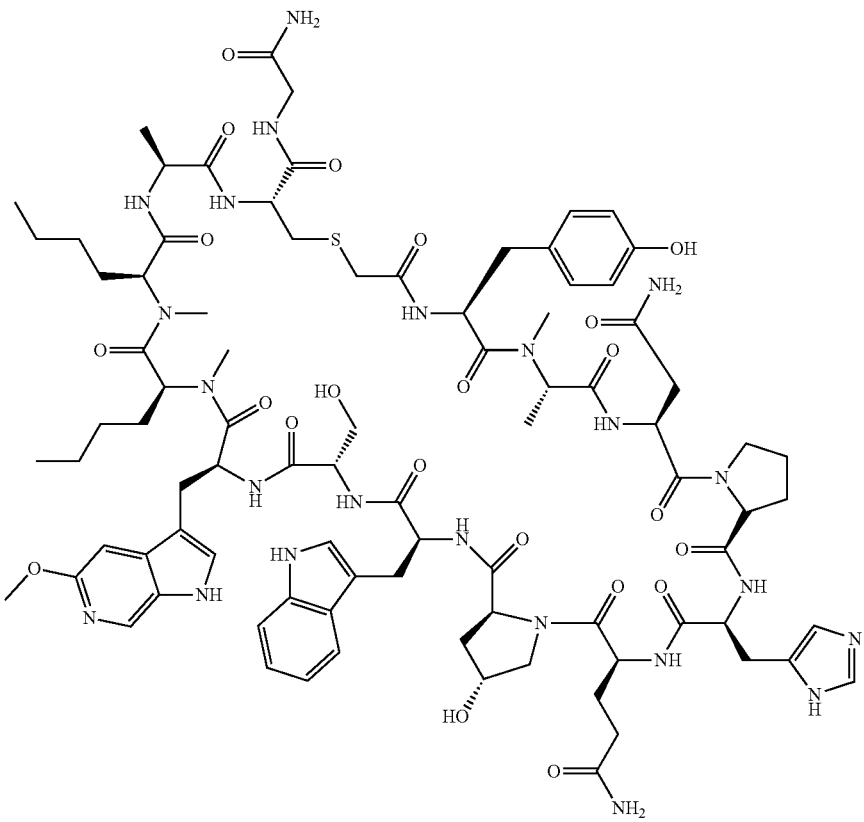

Preparation of Example 1287

Example 1287 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Manual Coupling procedure A", "Symphony Method B: Final capping procedure", "Global Deprotection Method F", and "Cyclization Method D". The crude material was purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 0.7 mg, and its estimated purity by LCMS analysis was 81%. Analysis LCMS Condition H: retention time=1.66 min.; ESI-MS(+) m/z 942.7 (M+2H) Analysis LCMS Condition I: retention time=2.80 min.; ESI-MS(+) m/z 943.6 (M+2H).

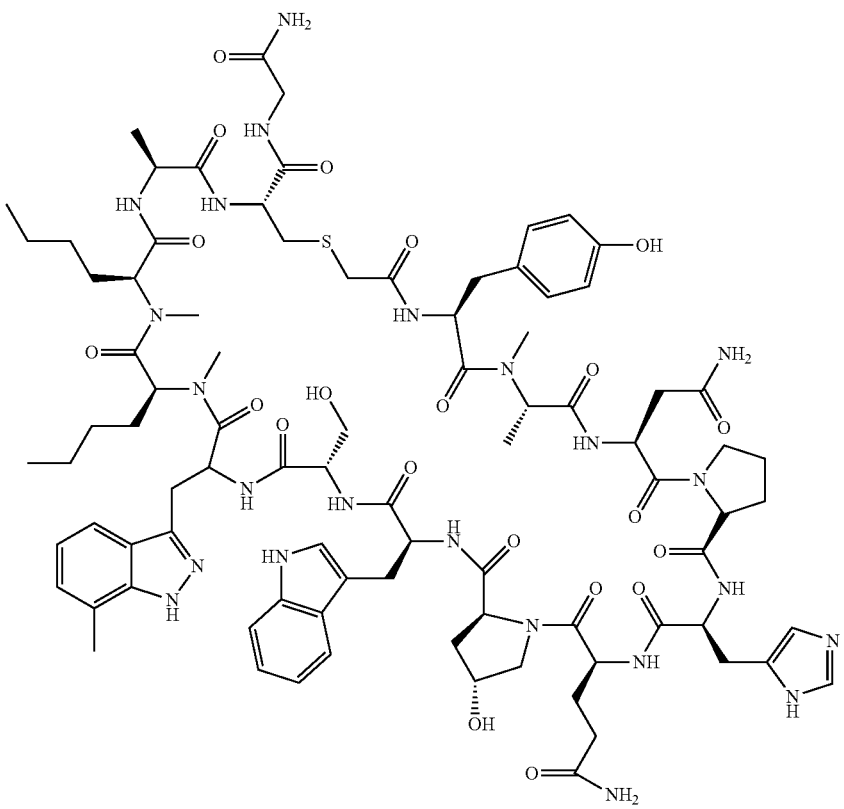

Preparation of Example 1288

Example 1288 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.0 mg, and its estimated purity by LCMS analysis was 100%. Analysis LCMS Condition H: retention time=1.45 min.; ESI-MS(+) m/z 928.2 (M+2H). Analysis LCMS Condition I: retention time=2.07 min.; ESI-MS(+) m/z 928.2 (M+2H). ESI-HRMS(+) m/z: Calculated: 927.9409 (M+2H) Found: 927.9381 (M+2H).

The following analytical protocols and synthetic methods pertain for Examples 1001 through 10505.
Analysis LCMS Condition A:
Column: Waters BEH C18, 2.1×50 mm, 1.7-μm particles; Mobile Phase A: water with 0.05% TFA; Mobile Phase B: Acetonitrile with 0.05% TFA; Temperature: 40° C.; Gradient: 2% B to 98% B over 2 min., then a 0.5 min. hold at 98% B; Flow: 0.8 mL/min; Detection: UV at 220 nm.

Analysis LCMS Condition B:
Column: Phenomenex una C18 2.0×30 mm 3-μm particles; Mobile Phase A: water with 0.05% ammonium acetate; Mobile Phase B: Acetonitrile with 0.05% ammonium acetate; Temperature: 40° C.; Gradient: 0% B to 100% B over 2 min., then a 1 min. hold at 100% B; Flow: 1.0 mL/min; Detection: UV at 220 nm.

Analysis LCMS Condition C:
Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0% B, 0-100% B over 3 minutes, then a 2.0-minute hold at 100% B; Flow: 0.75 mL/min; Detection: UV at 220 nm.

Analysis LCMS Condition D:
Column: Waters CSH C18, 2.1×50 mm, 1.7-μm particles; Mobile Phase A: 5:95 acetonitrile:water with trifluoroacetic acid; Mobile Phase B: 95:5 acetonitrile:water with trifluoroacetic acid; Temperature: 70° C.; Gradient: 0% B, 0-100% B over 3 minutes, then a 2.0-minute hold at 100% B; Flow: 0.75 mL/min; Detection: UV at 220 nm.

Analysis LCMS Condition E:
Column: Waters CSH C18, 2.1×50 mm, 1.7-μm particles; Mobile Phase A: 5:95 acetonitrile:water with 0.05% trifluoroacetic acid; Mobile Phase B: 95:5 acetonitrile:water with 0.05% trifluoroacetic acid; Temperature: 70° C.; Gradient: 0-100% B over 3 minutes, then a 2.0-minute hold at 100% B; Flow: 0.75 mL/min; Detection: UV at 220 nm.

General Procedures:
Prelude Method A:
  All manipulations were performed under automation on a Prelude peptide synthesizer (Protein Technologies). All procedures unless noted were performed in a 10 mL polypropylene tube fitted with a bottom frit. The tube connects to a the Prelude peptide synthesizer through both the bottom and the top of the tube. DMF and DCM are added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were not used beyond two weeks from preparation. HATU solutions were used within 5 days of preparation. DMF=dimethylformamide; HATU=1-[Bis(dimethylamino) methylene]-1H-1,2,3-triazolo[4,5-b]pyridinium 3-oxid hexafluorophosphate; DIPEA=diisopropylethylamine; The resin used is Merrifield polymer (polystyrene) functionalized with a Rink linker; 100-200 mesh, 1% DVB, 0.53 mmol/g loading. Common amino acids used are listed below with side-chain protecting groups indicated inside parenthesis. Fmoc-Asn(Trt)-OH; Fmoc-Asp(OtBu)-OH; Fmoc-Dab (Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Leu-OH; Fmoc-Lys(Boc)-OH; Fmoc-Nle-OH; Fmoc [N-Me]Ala-OH; Fmoc-[N-Me]Nle-OH; Fmoc-Pro-OH; Fmoc-Trp(Boc)-OH; Fmoc-Tyr(tBu)-OH The procedures of "Prelude Method A" describe an experiment performed on a 0.050 mmol scale, where the scale is determined by the amount amino acid used in the initial resin loading step. This scale uses 96 mg of the Rink Amide-Merrifield resin described above. All procedures can be scaled beyond 0.050 mmol scale by adjusting the described volumes by the multiple of the scale. Coupling of amino acids to a primary amine N-terminus used the "Single-coupling procedure" described below. Coupling of amino acids to a secondary amine N-terminus used the "Double-coupling procedure" described below. Coupling of chloroacetic acid to the N-terminus of the peptide is described by the "Chloroacetic acid coupling procedure" detailed below.

Resin-Swelling Procedure:

Repeated three times: To the reaction vessel containing resin was added DMF (1.0 mL). The mixture was periodically agitated for 10 minutes and then the solution was drained through the frit.

Single-Coupling Procedure:

To the reaction vessel containing resin was added piperidine:DMF (20:80 v/v, 1.0 mL). The mixture was periodically agitated for 4 minutes and then the solution was drained through the frit. To the reaction vessel was added piperidine:DMF (20:80 v/v, 1.0 mL). The mixture was periodically agitated for 4 minutes and then the solution was drained through the frit. The resin was washed successively six times as follows: for each wash, DMF (1.0 mL) was added through the top of the vessel and the resulting mixture was periodically agitated for 30 seconds before the solution was drained through the frit. To the reaction vessel was added the amino acid (0.2M in DMF, 0.5 mL, 2 eq), then HATU (0.2M in DMF, 0.5 mL, 2 eq), and finally DIPEA (0.8M in DMF, 0.3 mL, 4 eq). The mixture was periodically agitated for 15 minutes, then the reaction solution was drained through the frit. The resin was washed successively four times as follows: for each wash, DMF (1.0 mL) was added through the top of the vessel and the resulting mixture was periodically agitated for 30 seconds before the solution was drained through the frit. To the reaction vessel was added a solution of acetic anhydride in DMF (1M, 0.8 mL) followed by DIPEA (0.8M, 0.3 mL). The mixture was periodically agitated for 10 minutes, then the solution was drained through the frit. The resin was washed successively four times as follows: for each wash, DMF (1.0 mL) was added through the top of the vessel and the resulting mixture was periodically agitated for 90 seconds before the solution was drained through the frit. The resulting resin was used directly in the next step.

Single-Coupling Procedure—30 Min:

This method is identical to "Single-coupling procedure" except that following addition of DIPEA the mixture was periodically agitated for 30 minutes instead of 15 minutes.

Double-Coupling Procedure:

To the reaction vessel containing resin from the previous step was added piperidine:DMF (20:80 v/v, 1.0 mL). The mixture was periodically agitated for 4 minutes and then the solution was drained through the frit. To the reaction vessel was added piperidine:DMF (20:80 v/v, 1.0 mL). The mixture was periodically agitated for 4 minutes and then the solution was drained through the frit. The resin was washed successively six times as follows: for each wash, DMF (1.0 mL) was added through the top of the vessel and the resulting mixture was periodically agitated for 30 seconds before the solution was drained through the frit. To the reaction vessel was added the amino acid (0.2M in DMF, 0.5 mL, 2 eq), then HATU (0.2M in DMF, 0.5 mL, 2 eq), and finally DIPEA (0.8M in DMF, 0.3 mL, 4 eq). The mixture was periodically agitated for 15 minutes, then the reaction solution was drained through the frit. The resin was twice washed as follows: for each wash, DMF (1.0 mL) was added through the top of the vessel and the resulting mixture was periodically agitated for 30 seconds before the solution was drained through the frit. To the reaction vessel was added the amino acid (0.2M in DMF, 0.5 mL, 2 eq), then HATU (0.2M in DMF, 0.5 mL, 2 eq), and finally DIPEA (0.8M in DMF, 0.3 mL, 4 eq). The mixture was periodically agitated for 15 minutes, then the reaction solution was drained through the frit. The resin was twice washed as follows: for each wash, DMF (1.0 mL) was added through the top of the vessel and the resulting mixture was periodically agitated for 30 seconds before the solution was drained through the frit. To the reaction vessel was added a solution of acetic anhydride in DMF (1M, 0.8 mL) followed by DIPEA (0.8M, 0.3 mL). The mixture was periodically agitated for 10 minutes, then the solution was drained through the frit. The resin was washed successively four times as follows: for each wash, DMF (1.0 mL) was added through the top of the vessel and the resulting mixture was periodically agitated for 90 seconds before the solution was drained through the frit. The resulting resin was used directly in the next step.

Chloroacetic Acid Coupling Procedure:

To the reaction vessel containing the resin from the previous step was added piperidine:DMF (20:80 v/v, 1.0 mL). The mixture was periodically agitated for 3 minutes and then the solution was drained through the frit. To the reaction vessel was added piperidine:DMF (20:80 v/v, 1.0 mL). The mixture was periodically agitated for 3 minutes and then the solution was drained through the frit. The resin was washed successively six times as follows: for each wash, DMF (1.0 mL) was added through the top of the vessel and the resulting mixture was periodically agitated for 30 seconds before the solution was drained through the frit. To the reaction vessel was added chloroacetic acid (0.2M, 0.5 mL), HATU (0.2M, 0.5 mL, 2 eq.), then DIPEA (0.8M in DMF, 0.3 mL, 4 eq.). The mixture was periodically agitated for 30 minutes, then the solution was drained through the frit. The resin was washed successively three times as follows: for each wash, DMF (2.0 mL) was added to top of the vessel and the resulting mixture was periodically agitated for 90 seconds before the solution was drained through the frit. The resin was washed successively four times as follows: for each wash, CH$_2$Cl$_2$ (2.0 mL) was added to top of the vessel and the resulting mixture was periodically agitated for 90 seconds before the solution was drained through the frit. The resulting resin was placed under a N$_2$ stream for 8 minutes.

Symphony Method A:

For all procedures a Symphony X peptide synthesizer (Protein Technologies) was used instead of a Prelude peptide synthesizer and all reagents were added through the top of the reaction vessel. The Symphony X synthesizer performs reactions at a 1.0 mmol scale or greater. Therefore, the procedure below describe a synthesis on a 1.0 mmol scale.

Resin-Swelling Procedure:

Repeated three times: To the reaction vessel containing resin was added DMF (2.0 mL). The mixture was periodically agitated for 10 minutes and then the solution was drained through the frit.

Single-Coupling Procedure:

To the reaction vessel containing resin was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added a solution of acetic anhydride (2.0 mL). The mixture was periodically agitated for 10 minutes, then the solution was drained through the frit. The resin was washed successively three times as follows: for each wash, DMF (2.0 mL) was added through the top of the vessel and the resulting mixture was periodically agitated for 90 seconds before the solution was drained through the frit. The resulting resin was used directly in the next step.

Single-Coupling Procedure—30 Min:

This method is identical to "Single-coupling procedure" except that following addition of DIPEA the mixture was periodically agitated for 30 minutes instead of 15 minutes.

Double-Coupling Procedure:

To the reaction vessel containing resin was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was washed successively twice as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added a solution of acetic anhydride (2.0 mL). The mixture was periodically agitated for 10 minutes, then the solution was drained through the frit. The resin was washed successively three times as follows: for each wash, DMF (2.0 mL) was added through the top of the vessel and the resulting mixture was periodically agitated for 90 seconds before the solution was drained through the frit. The resulting resin was used directly in the next step.

Chloroacetyl Chloride Coupling Procedure:

To the reaction vessel containing the resin from the previous step was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added chloroacetic acid (0.2M, 1.0 mL), HATU (0.2M, 1.0 mL, 2 eq.), then DIPEA (0.4M in DMF, 1.0 mL, 4 eq.). The mixture was periodically agitated for 30 minutes, then the solution was drained through the frit. The resin was washed successively three times as follows: for each wash, DMF (2.0 mL) was added to top of the vessel and the resulting mixture was periodically agitated for 90 seconds before the solution was drained through the frit. The resin was washed successively four times as follows: for each wash, CH$_2$Cl$_2$ (2.0 mL) was added to top of the vessel and the resulting mixture was periodically agitated for 90 seconds before the solution was drained through the frit. The resulting resin was placed under a N$_2$ stream for 5 minutes.

Global Deprotection Method A:

All manipulations were performed manually unless noted. The procedure of "Global Deprotection Method A" describes an experiment performed on a 0.050 mmol scale, where the scale is determined by the scale of the initial loaded amino acid theoretically bound to the resin. The procedure can be scaled beyond 0.050 mmol scale by adjusting the described volumes by the multiple of the scale. A "deprotection solution" was prepared by combining in a 40 mL glass vial trifluoroacetic acid (22 mL), water (1.25 mL), DTT (250 mg), and triisopropylsilane (0.5 mL). The resin was removed from the reaction vessel and transferred to a 4 mL glass vial. To the vial was added the resin followed by the "deprotection solution" (1.0 mL). The mixture was vigorously mixed in a shaker (approximately 500 RPM for 40 minutes). The mixture was filtered through a 0.2 micron syringe filter and the solids were extracted with TFA (1.0 mL). To a 24 mL test tube charged with the combined filtrates was added Et$_2$O (15 mL). The mixture was vigorously mixed upon which a significant amount of a white solid precipitated. The mixture was centrifuged for 5 minutes, then the solution was decanted away from the solids and discarded. The solids were suspended in Et$_2$O (20 mL); then the mixture was centrifuged for 5 minutes; and the solution was decanted away from the solids and discarded to afford the crude peptide as a white to off-white solid.

Cyclization Method A:

All manipulations were performed manually unless noted. The procedure of "Cyclization Method A" describes an experiment performed on a 0.050 mmol scale, where the scale is determined by the amount of initial amino acid used theoretically bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in MeCN:aq. 0.2M ammonium bicarbonate (1:1) to a total volume of 18-22 mL. The target pH is 8.5-9.0. The solution was then allowed to stand without stirring for 12-18 h. The reaction solution was concentrated via centrifugal concentration overnight without heating, and the residue was then dissolved in DMSO: MeOH (1 mL:1 mL). This solution was subjected to reverse-phase HPLC purification to afford the desired cyclic peptide.

General Synthetic Sequence A:

"General Synthetic Sequence A" describes a general sequence of procedures that were used to afford the cyclic peptides described herein. For the purposes of this general procedure, the procedures of "Symphony Method A" are interchangeable with those of "Prelude Method A". To a 10 mL polypropylene solid-phase reaction vessel was added Rink Amide-Merrifield resin (96 mg), and the reaction vessel was placed on the Prelude peptide synthesizer. Then a series of amino acid couplings was sequentially performed on the Prelude following "Prelude Method A: Single-coupling procedure" if the N-terminus of the resin-bound peptide was a primary, "Prelude Method A: Double-coupling procedure" if the N-terminus of the resin-bound peptide was a secondary amine, or in a "Single-coupling procedure—30 min" if the AA being coupled was incorporated at the AA10 position. "Prelude Method A: Chloroacetic acid coupling procedure" was followed; then "Global Deprotection Method A" was followed; then "Cyclization Method A" was followed.

Preparation of (S)-2-(((((9H-fluoren-9-yl)methoxy)carbonyl)amino)-3-(1-(2-(tert-butoxy)-2-oxoethyl)-1H-indazol-3-yl)propanoic acid

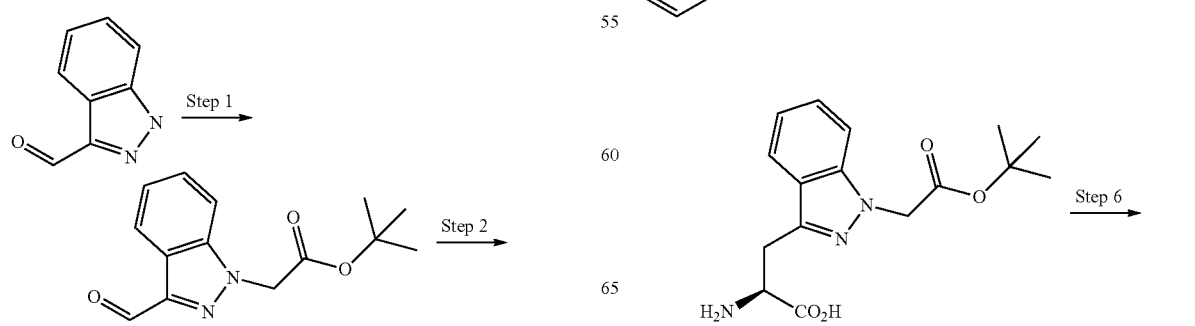

-continued

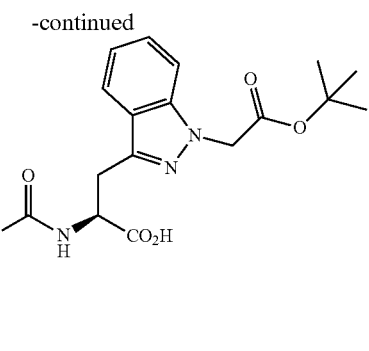

Step 1:

To a 0° C. solution of 1H-indazole-3-carbaldehyde (3 g, 20.53 mmol) and cesium carbonate (7.36 g, 22.58 mmol) in DMF (82 ml) was added tert-butyl 2-bromoacetate (3.29 ml, 22.58 mmol) and was allowed to warm up to RT by removing from ice bath. The reaction was stirred for 2 h. The reaction was poured onto water (500 mL) and Et$_2$O (200 mL) was added. The product was extracted in the Et$_2$O layer. They layers were separated and the aqueous phase was extracted a second time with Et$_2$O (100 mL). The combined Et$_2$O layers were washed 2× with water then brine. The organic layer was collected dried over sodium sulfate and concentrated under vacuum. The crude material was purified by flash silica gel chromatography using a gradient of 0-30% EtOAc/Hexanes. The product fractions were collected and the solvent removed under vacuum to give tert-butyl 2-(3-formyl-1H-indazol-1-yl)acetate, 5.23 (98%). ESI-MS(+) m/z 205.1 (M+1-tBu). $^1$H NMR (400 MHz, CHLOROFORM-d) δ 10.28 (s, 1H), 8.35 (d, J=8.1 Hz, 1H), 7.56-7.49 (m, 1H), 7.45-7.36 (m, 2H), 5.18 (s, 2H), 1.48 (s, 9H).

Step 2:

(±)-Methyl 2-benzyloxycarbonylamino-2-(dimethoxyphosphinyl)acetate (7.32 g, 22.10 mmol) was dissolved in CH$_2$Cl$_2$ (50 mL) and stirred under nitrogen. To this solution was added DBU (3.33 mL, 22.10 mmol) and the mixture was stirred for 10 min, followed by dropwise addition of a solution of tert-butyl 2-(3-formyl-1H-indazol-1-yl)acetate (5.23 g, 20.09 mmol) in CH$_2$Cl$_2$ (50 mL) over 15-20 min. Stirring was continued at room temperature for 16 h. The reaction mixture was concentrated under vacuum. The residue was diluted with EtOAc and washed with 5% aq. citric acid, then brine, then dried over anhydrous Na$_2$SO$_4$, filtered and evaporated. The crude material was purified by flash silica gel chromatography using a gradient of 0-50% EtOAc/Hexanes. The product fractions were collected and the solvent removed under vacuum to give methyl (E)-2-(((benzyloxy)carbonyl)amino)-3-(1-(2-(tert-butoxy)-2-oxoethyl)-1H-indazol-3-yl)acrylate, 7.4 g (79%). ESI-MS(+) m/z 466.0 (M+1). $^1$H NMR (400 MHz, CHLOROFORM-d) δ 9.21 (s, 1H), 7.82 (d, J=8.3 Hz, 1H), 7.52-7.23 (m, 8H), 6.90 (s, 1H), 5.23 (s, 2H), 5.08 (s, 2H), 3.86 (s, 3H), 1.44 (s, 9H).

Step 3:

(Z)-Methyl 2-(((benzyloxy)carbonyl)amino)-3-(1-(2-(tert-butoxy)-2-oxoethyl)-1H-indazol-3-yl)acrylate (7.4 g, 15.90 mmol) was dissolved in MeOH (80 mL) and benzene (80 mL) in a parr bottle. N$_2$ gas was bubbled through the solution for 15 min followed by the addition of (+)-1,2-BIS ((2S,5S)-2,5-DIETHYLPHOSPHOLANO)BENZENE(CYCLOOCTADIENE)RHODIUM(I) TRIFLUOROMETHANESULFONATE (0.115 g, 0.159 mmol), and placed under a hydrogen atmosphere (60 psi) for 3 days. The reaction was filtered through diatomaceous earth (Celite®) and concentrated under vacuum. The crude material was purified by flash silica gel chromatography using a gradient of 0-50% EtOAc/Hexanes. The product fractions were collected and the solvent removed under vacuum to give methyl (S)-2-(((benzyloxy)carbonyl)amino)-3-(1-(2-(tert-butoxy)-2-oxoethyl)-1H-indazol-3-yl)propanoate, 7.43 g, (100%). ESI-MS (+) m/z 468.0 (M+1). $^1$H NMR (400 MHz, CHLOROFORM-d) δ 7.64 (d, J=8.1 Hz, 1H), 7.44-7.26 (m, 7H), 7.15 (t, J=7.5 Hz, 1H), 5.87 (d, J=7.8 Hz, 1H), 5.13 (s, 2H), 4.99 (s, 2H), 4.90-4.80 (m, 1H), 3.66 (s, 3H), 3.63-3.55 (m, 1H), 3.46 (dd, J=14.8, 4.8 Hz, 1H), 1.42 (s, 9H).

Step 4:

A solution of LITHIUM HYDROXIDE (1.142 g, 47.7 mmol) in Water (39.7 ml) was added to a solution of (S)-methyl 2-(((benzyloxy)carbonyl)amino)-3-(1-(2-(tert-butoxy)-2-oxoethyl)-1H-indazol-3-yl)propanoate (7.43 g, 15.89 mmol) in THF (39.7 ml). The reaction was stirred at RT for 30 min. EtOAc was added to the reaction and the pH was made acidic with 1 N HCl. The organic phase was collected, dried over sodium sulfate, and concentrated under vacuum. The crude material was purified by flash chromatography using 0-10% MeOH/DCM w/0.1% AcOH. The product fractions were collected and the solvent removed under vacuum to give (S)-2-(((benzyloxy)carbonyl)amino)-3-(1-(2-(tert-butoxy)-2-oxoethyl)-1H-indazol-3-yl)propanoic acid, 3.9 g (54%). ESI-MS(+) m/z 454.0 (M+1). $^1$H NMR (400 MHz, DMSO-d$_6$) δ12.73 (br. s., 1H), 7.77 (d, J=8.3 Hz, 1H), 7.56-7.50 (m, 2H), 7.40-7.24 (m, 5H), 7.14-7.08 (m, 1H), 5.15 (s, 2H), 5.00-4.89 (m, 2H), 4.42 (td, J=8.6, 5.1 Hz, 1H), 3.39-3.24 (m, 2H), 1.37 (s, 9H).

Step 5:

(S)-2-(((Benzyloxy)carbonyl)amino)-3-(1-(2-(tert-butoxy)-2-oxoethyl)-1H-indazol-3-yl)propanoic acid (3.88 g, 8.56 mmol) was dissolved in MeOH (80 ml)/Benzene (20 mL) and placed under an atmosphere of N$_2$. Pd—C (0.455 g, 0.428 mmol) was added to the solution with vigorous stirring. The reaction was placed under an atmosphere of H$_2$ gas and stirred for 16 h. The reaction was filtered through diatomaceous earth (Celite®) and concentrated under vacuum to give (S)-2-amino-3-(1-(2-(tert-butoxy)-2-oxoethyl)-1H-indazol-3-yl)propanoic acid, 2.74 g (100%), which was used in Step 6 as is. ESI-MS(+) m/z 320.1 (M+H). $^1$H NMR (400 MHz, DMSO-d$_6$) δ 7.78 (d, J=8.0 Hz, 1H), 7.54 (d, J=8.5 Hz, 1H), 7.38 (ddd, J=8.3, 7.0, 1.0 Hz, 1H), 7.13 (t, J=7.2 Hz, 1H), 5.23-5.10 (m, 2H), 3.58 (dd, J=9.0, 4.0 Hz, 1H), 3.49 (dd, J=15.6, 4.0 Hz, 1H), 3.28 (br. s., 2H), 3.17 (dd, J=15.7, 8.9 Hz, 1H), 1.41 (s, 9H).

Step 6:

(S)-2-amino-3-(1-(2-(tert-butoxy)-2-oxoethyl)-1H-indazol-3-yl)propanoic acid (2.74 g, 8.58 mmol) was dissolved in THF (34.3 ml) followed by the addition of Water (34.3 ml). SODIUM BICARBONATE (1.442 g, 17.16 mmol) was then added followed by the addition of (9H-fluoren-9-yl) methyl (2,5-dioxopyrrolidin-1-yl) carbonate (2.89 g, 8.58 mmol). The reaction was stirred for 2 h. Most of the THF was removed under vacuum then EtOAc was added. The mixture was acidified to pH7 with 1 N HCl, and extracted with EtOAc. The organic layer was collected, dried over sodium sulfate, and concentrated under vacuum to give (S)-2-((((9H-fluoren-9-yl)methoxy)carbonyl)amino)-3-(1-(2-(tert-butoxy)-2-oxoethyl)-1H-indazol-3-yl)propanoic acid (4.9 g, 105%) which was used as is. ESI-MS(+) m/z 542.1 (M+H). $^1$H NMR (400 MHz, DMSO-d$_6$) δ7.87 (d, J=7.5 Hz, 2H), 7.82 (d, J=8.0 Hz, 1H), 7.70 (d, J=8.3 Hz, 1H), 7.64 (t, J=8.2 Hz, 2H), 7.52 (d, J=8.3 Hz, 1H), 7.43-7.34 (m, 3H), 7.32-7.23 (m, 2H), 7.10 (t, J=7.4 Hz, 1H), 5.15 (s, 2H), 4.42 (td, J=8.8, 5.0 Hz, 1H), 4.20-4.11 (m, 3H), 3.42-3.25 (m, 2H), 1.36 (s, 9H).

Preparation of (S)-2-(((((9H-fluoren-9-yl)methoxy)carbonyl)amino)-3-(1-(2-(tert-butoxy)-2-oxoethyl)-1H-pyrrolo[3,2-b]pyridin-3-yl)propanoic acid

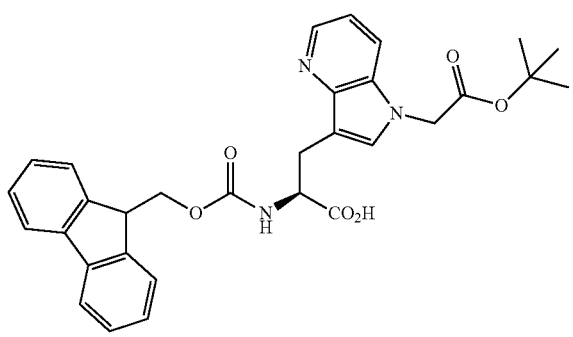 [SMILES: CC(C)(C)OC(=O)Cn1cc(C[C@H](NC(=O)OCC2c3ccccc3-c3ccccc32)C(=O)O)c2ncccc21]

(S)-2-(((((9H-Fluoren-9-yl)methoxy)carbonyl)amino)-3-(1-(2-(tert-butoxy)-2-oxoethyl)-1H-pyrrolo[3,2-b]pyridin-3-yl)propanoic acid was prepared by the same method as (S)-2-(((((9H-fluoren-9-yl)methoxy)carbonyl)amino)-3-(1-(2-(tert-butoxy)-2-oxoethyl)-1H-indazol-3-yl)propanoic acid with the following modifications: 1H-pyrrolo[3,2-b]pyridine-3-carbaldehyde instead of 1H-indazole-3-carbaldehyde in Step 1 was used as a starting material. The hydrolysis of the methyl ester in step 4 was run at 0° C. for 20 min instead of room temperature for 30 min. ESI-MS(+) m/z 542.2 (M+H). $^1$H NMR (400 MHz, DMSO-$d_6$) δ8.34 (dd, J=4.8, 1.3 Hz, 1H), 8.23 (d, J=7.5 Hz, 1H), 7.89 (d, J=7.5 Hz, 2H), 7.81 (dd, J=8.5, 1.3 Hz, 1H), 7.65 (t, J=8.4 Hz, 2H), 7.46 (s, 1H), 7.44-7.37 (m, 2H), 7.29 (dtd, J=10.9, 7.4, 0.9 Hz, 2H), 7.19 (dd, J=8.3, 4.5 Hz, 1H), 5.06-4.92 (m, 2H), 4.37-4.30 (m, 1H), 4.23-4.14 (m, 3H), 3.28 (dd, J=14.7, 4.1 Hz, 1H), 3.09 (dd, J=14.6, 9.0 Hz, 1H), 1.38 (s, 9H).

Preparation of (S)-2-(((((9H-fluoren-9-yl)methoxy)carbonyl)amino)-3-(1-(2-(tert-butoxy)-2-oxoethyl)-5-methoxy-1H-indol-3-yl)propanoic acid Scheme:

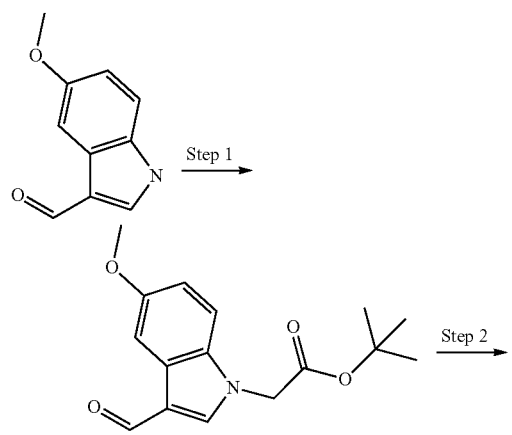

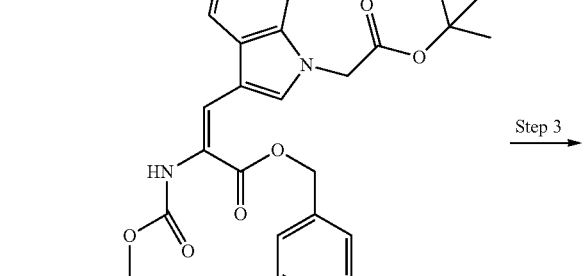

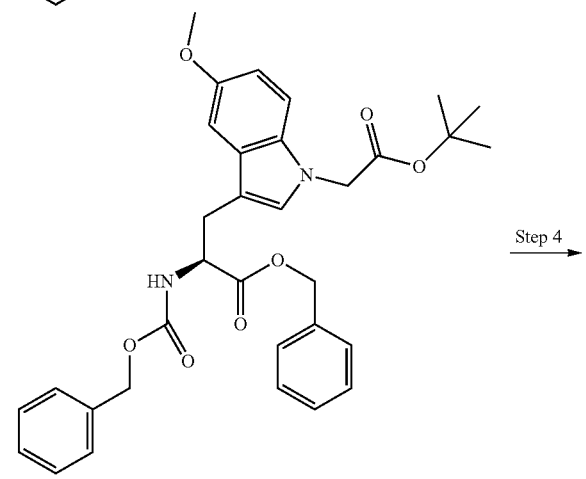

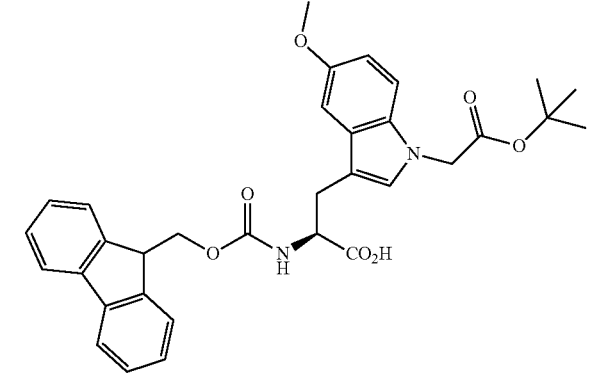 [SMILES: COc1ccc2c(c1)c(C[C@H](NC(=O)OCC1c3ccccc3-c3ccccc31)C(=O)O)cn2CC(=O)OC(C)(C)C]

Step 1:

To a 0° C. solution of 5-methoxy-1H-indole-3-carbaldehyde (1.5 g, 8.56 mmol) and cesium carbonate (3.07 g, 9.42 mmol) in DMF (34.2 ml) was added tert-butyl 2-bromoacetate (1.373 ml, 9.42 mmol) and was allowed to warm up to RT by removing from ice bath. The reaction was stirred for 2 h. The reaction was poured onto water and Et₂O was added. The product was extracted in the Et₂O layer. They layers were separated and the aqueous phase was extracted a second time with Et₂O. The combined Et₂O layers were washed twice with water then brine. The organic layer was collected dried over sodium sulfate and concentrated under vacuum to give tert-butyl 2-(3-formyl-5-methoxy-1H-indol-1-yl)acetate, 2.1 g (85%), which was used in the next step as is. ESI-MS(+) m/z 290.1 (M+H).

Step 2:

Benzyl 2-(((benzyloxy)carbonyl)amino)-2-(dimethoxyphosphoryl)acetate (1.55 g, (3.8 mmol) was dissolved in DCM (11.52 mL) and stirred under nitrogen. To this solution was added DBU (0.573 mL, 3.80 mmol) and the mixture was stirred for 10 min, followed by dropwise addition of a solution of tert-butyl 2-(3-formyl-5-methoxy-1H-indol-1-yl)acetate (1.0 g, 3.46 mmol) in DCM (11.52 mL) over 15-20 min. Stirring was continued at room temperature for 16 h. The reaction mixture was concentrated under vacuum. The residue was diluted with EtOAc and washed with 5% aq. citric acid, then brine, then dried over anhydrous Na₂SO₄, filtered and evaporated. The crude material was purified by flash chromatography using a gradient of 20-70% EtOAc/Hexanes. The product fractions were collected and the solvent removed under vacuum to give benzyl (E)-2-(((benzyloxy)carbonyl)amino)-3-(1-(2-(tert-butoxy)-2-oxoethyl)-5-methoxy-1H-indol-3-yl)acrylate, 1.6 g, 80%. ESI-MS(+) m/z 571.2 (M+H).

Step 3:

(Z)-Benzyl 2-(((benzyloxy)carbonyl)amino)-3-(1-(2-(tert-butoxy)-2-oxoethyl)-5-methoxy-1H-indol-3-yl)acrylate (700 mg, 1.227 mmol) was dissolved in MeOH (12 ml) treated with (+)-1,2-BIS((2S,5S)-2,5-DIETHYLPHOSPHOLANO)BENZENE(CYCLOOCTADIENE)RHODIUM(I) TRIFLUOROMETHANESULFONATE (8.86 mg, 0.012 mmol), and placed under a hydrogen atmosphere (60 psi) 3 days. The reaction was filtered through diatomaceous earth (Celite®) concentrated under vacuum to give benzyl (S)-2-(((benzyloxy)carbonyl)amino)-3-(1-(2-(tert-butoxy)-2-oxoethyl)-5-methoxy-1H-indol-3-yl)propanoate, 702 mg (100%), which was used in the next step as is. ESI-MS(+) m/z 573.2 (M+H). ¹H NMR (400 MHz, DMSO-d₆) δ7.87 (d, J=7.8 Hz, 1H), 7.38-7.13 (m, 11H), 7.10-7.02 (m, 2H), 6.77 (dd, J=8.8, 2.3 Hz, 1H), 5.13-5.04 (m, 2H), 5.04-4.94 (m, 2H), 4.86 (s, 2H), 4.32 (td, J=8.3, 5.8 Hz, 1H), 3.72 (s, 3H), 1.39 (s, 9H).

Step 4:

(S)-Benzyl 2-(((benzyloxy)carbonyl)amino)-3-(1-(2-(tert-butoxy)-2-oxoethyl)-5-methoxy-1H-indol-3-yl)propanoate (700 mg, 1.222 mmol) was dissolved in MeOH (12 ml) and placed under an atmosphere of N₂. Pd—C (65.0 mg, 0.061 mmol) was added to the solution with vigorous stirring. The reaction was placed under an atmosphere of H2 and stirred for 16 h. The reaction was filtered through diatomaceous earth (Celite®) and concentrated under vacuum to give (S)-2-amino-3-(1-(2-(tert-butoxy)-2-oxoethyl)-5-methoxy-1H-indol-3-yl)propanoic acid, 426 mg (100%), which was used in step 5 as is. ESI-MS(+) m/z 349.1 (M+H).

Step 5:

(S)-2-Amino-3-(1-(2-(tert-butoxy)-2-oxoethyl)-5-methoxy-1H-indol-3-yl)propanoic acid (426 mg, 1.223 mmol) was dissolved in THF (5 ml) followed by the addition of Water (5.00 ml). Sodium bicarbonate (205 mg, 2.446 mmol) was then added followed by the addition of (9H-fluoren-9-yl)methyl (2,5-dioxopyrrolidin-1-yl) carbonate (412 mg, 1.223 mmol). The reaction was stirred for 2 h. Most of the THF was removed under vacuum then Et₂O was added. The organic layer was discarded and the aqueous layer was again washed with Et₂O. The aqueous phase was collected, acidified with 1 N HCl, and extracted with EtOAc. The organic layer was collected, dried over sodium sulfate, and concentrated under vacuum to give crude product which was not purified further. LC/MS and NMR confirmation obtained. ESI-MS(+) m/z 571.1 (M+H). ¹H NMR (400 MHz, DMSO-d₆) δ12.71 (br. s., 1H), 7.88 (d, J=7.5 Hz, 2H), 7.72 (d, J=8.3 Hz, 1H), 7.66 (t, J=8.3 Hz, 2H), 7.40 (td, J=7.1, 4.1 Hz, 2H), 7.33-7.23 (m, 2H), 7.17 (d, J=8.8 Hz, 1H), 7.13-7.08 (m, 2H), 6.76 (dd, J=8.8, 2.3 Hz, 1H), 4.85 (s, 2H), 4.24-4.14 (m, 3H), 3.76 (s, 3H), 3.14 (dd, J=14.4, 4.4 Hz, 1H), 2.99 (dd, J=14.8, 9.8 Hz, 1H), 1.38 (s, 9H).

Preparation of 2-((((9H-fluoren-9-yl)methoxy)carbonyl)amino)-3-(1-(2-(tert-butoxy)-2-oxoethyl)-1H-pyrrolo[2,3-b]pyridin-3-yl)propanoic acid Scheme:

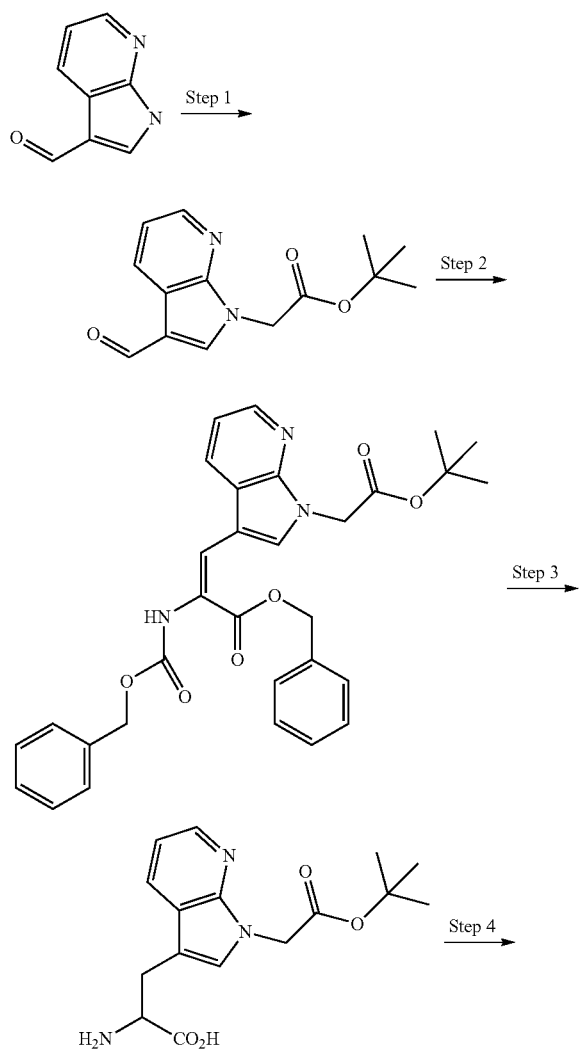

-continued

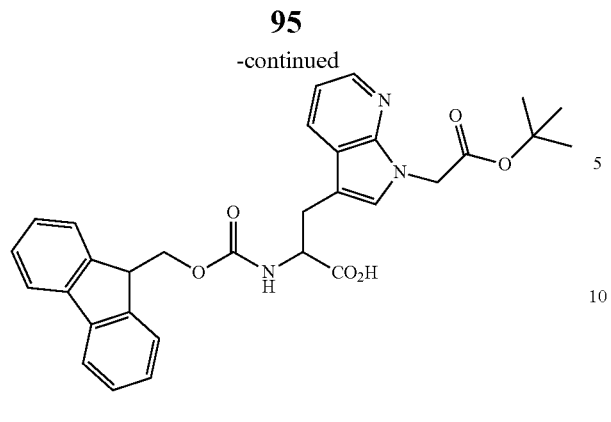

Step 1:
To a 0° C. solution of 1H-pyrrolo[2,3-b]pyridine-3-carbaldehyde (1.5 g, 10.26 mmol) and cesium carbonate (3.68 g, 11.29 mmol) in DMF (41.1 ml) was added tert-butyl 2-bromoacetate (1.646 ml, 11.29 mmol) and was allowed to warm up to RT by removing from ice bath. The reaction was stirred for 2 h. The reaction was poured onto water and Et$_2$O was added. The product was extracted in the Et$_2$O layer. They layers were separated and the aqueous phase was extracted a second time with Et$_2$O. The combined Et$_2$O layers were washed 2× with water then brine. The organic layer was collected dried over sodium sulfate and concentrated under vacuum to give tert-butyl 2-(3-formyl-1H-pyrrolo[2,3-b]pyridin-1-yl)acetate, 2.3 g (86%), which was used in the next step as is. ESI-MS(+) m/z 205.1 (M+1-tBu). $^1$H NMR (400 MHz, CHLOROFORM-d) 10.02 (s, 1H), 8.58 (dd, J=7.8, 1.5 Hz, 1H), 8.42 (dd, J=4.8, 1.5 Hz, 1H), 7.95 (s, 1H), 7.31-7.28 (m, 1H), 5.05 (s, 2H), 1.49 (s, 9H).

Step 2:
Benzyl 2-(((benzyloxy)carbonyl)amino)-2-(dimethoxyphosphoryl)acetate (2.348 g, 5.76 mmol) was dissolved in DCM (12 mL) and stirred under nitrogen. To this solution was added DBU (0.637 ml, 4.23 mmol) and the mixture was stirred for 10 min, followed by dropwise addition of a solution of tert-butyl 2-(3-formyl-1H-pyrrolo[2,3-b]pyridin-1-yl)acetate (1 g, 3.84 mmol) in DCM (12 mL). Stirring was continued at room temperature for 16 h. The reaction mixture was concentrated under vacuum. The residue was diluted with EtOAc and washed with 5% aq. citric acid, and brine, then dried over anhydrous Na$_2$SO$_4$, filtered and evaporated. The crude material was purified by flash chromatography using a gradient of 0-10%% MeOH/DCM. The product fractions were collected and the solvent removed under vacuum to give benzyl (E)-2-(((benzyloxy)carbonyl)amino)-3-(1-(2-(tert-butoxy)-2-oxoethyl)-1H-pyrrolo[2,3-b]pyridin-3-yl)acrylate, 1.54 g (74%).

Preparation of 2-((((9H-fluoren-9-yl)methoxy)carbonyl)amino)-3-(1-(2-(tert-butoxy)-2-oxoethyl)-1H-pyrrolo[3,2-c]pyridin-3-yl)propanoic acid Scheme:

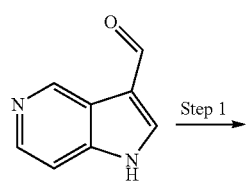

-continued

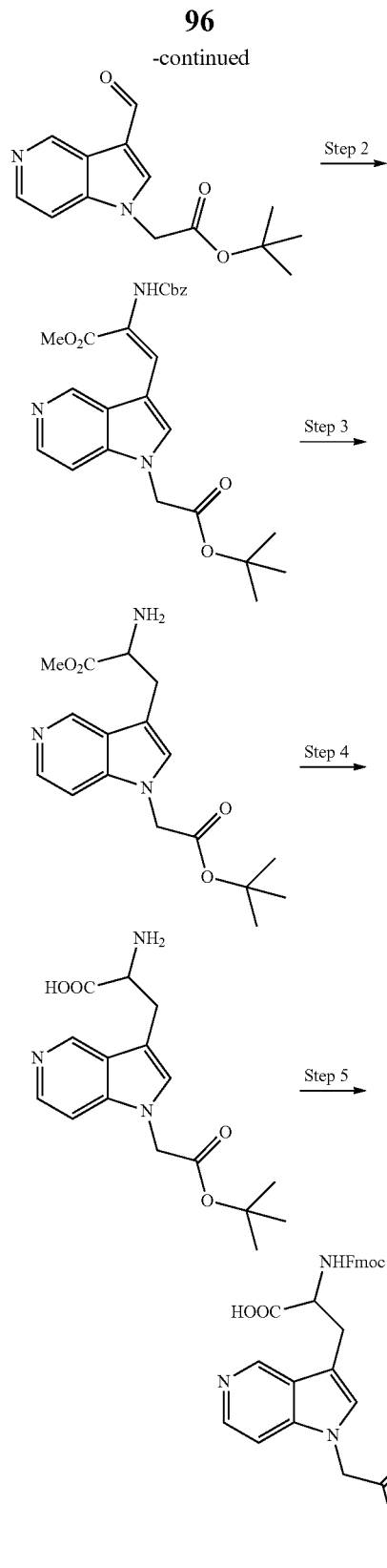

Step 1:
To a 0° C. solution of 1H-pyrrolo[3,2-c]pyridine-3-carbaldehyde (0.95 g, 6.50 mmol) and cesium carbonate (2.330 g, 7.15 mmol) in DMF (26.0 ml) was added tert-butyl 2-bromoacetate (1.042 ml, 7.15 mmol). The mixture was allowed to warm up to RT by removing from ice bath. The reaction was stirred for 2 hs. The reaction was poured onto ice water (100 mL) and EtOAc (50 mL) mixture. The product was extracted in the EtOAc. The layers were separated and the aqueous phase was extracted a second time with EtOAc (2×50 mL). The combined EtOAc layers were washed with brine. The organic layer was collected and dried over sodium sulfate and concentrated under vacuum. The crude product was purified by silica gel chromatography to get tert-butyl 2-(3-formyl-1H-pyrrolo[3,2-c]pyridin-1-yl) acetate 1.24 g (73%) as clean product. ESI-MS(−): MS m/z 259.1.

Step 2:

(±)-Methyl 2-benzyloxycarbonylamino-2-(dimethoxyphosphinyl)acetate (1.596 g, 4.82 mmol) was dissolved in 15 mL DCM and stirred under nitrogen at 0° C. for 5 mins. To this solution was added DBU (0.726 ml, 4.82 mmol), followed by dropwise addition of tert-butyl 2-(3-formyl-1H-pyrrolo[3,2-c]pyridin-1-yl)acetate (1.14 g, 4.38 mmol) in DCM (15 mL) solution during 10 mins. The mixture was stirred at room temperature for overnight. Reaction mixture was diluted with EtOAc and washed with 5% aq. citric acid solution then brine, the organic layer was collected and dried over sodium sulfate and concentrated under vacuum. The crude product was purified by silica gel chromatography to get (E)-methyl 2-(((benzyloxy)carbonyl)amino)-3-(1-(2-(tert-butoxy)-2-oxoethyl)-1H-pyrrolo[3,2-c]pyridin-3-yl) acrylate 1.0 g (49%) as product. ESI-MS(+): MS m/z 466.0.

Step 3:

To the (E)-methyl 2-(((benzyloxy)carbonyl)amino)-3-(1-(2-(tert-butoxy)-2-oxoethyl)-1H-pyrrolo[3,2-c]pyridin-3-yl) acrylate (1.0 g, 2.15 mmol) in methanol (20 mL) solution was added Pd/C (0.5 g). The reaction was carried out at 55 psi for 2 days. The Pd/C was filtered and washed with methanol and DCM. The solvent was concentrated to afford methyl 2-amino-3-(1-(2-(tert-butoxy)-2-oxoethyl)-1H-pyrrolo[3,2-c]pyridin-3-yl)propanoate 0.54 g (75%) as crude product which was used at next step directly. ESI-MS(+): MS m/z 334.1.

Step 4 and 5:

To the methyl 2-amino-3-(1-(2-(tert-butoxy)-2-oxoethyl)-1H-pyrrolo[3,2-c]pyridin-3-yl)propanoate (0.54 g, 1.62 mmol) in THF/H$_2$O (1:1, 10 mL) solution was added LiOH (116 mg, 4.86 mmol). The mixture was stirred at rt for 9 mins. The mixture was adjusted to PH=7 by adding 1 N HCl solution. Sodium bicarbonate (408 mg, 4.86 mmol) and FMOC-OSU (546 mg, 1.620 mmol) were then added to the mixture. The resulting mixture was stirred for 2 hs. 5% citric acid was added to adjust PH=7 and the aqueous was extracted with ethyl acetate, dried over sodium sulfate and concentrated under vacuum. The crude product was purified by silica gel chromatography to get 2-((((9H-fluoren-9-yl)methoxy)carbonyl)amino)-3-(1-(2-(tert-butoxy)-2-oxoethyl)-1H-pyrrolo[3,2-c]pyridin-3-yl)propanoic acid 250 mg (28.5%) as product. ESI-MS(+): MS m/z 542.2. $^1$H NMR (METHANOL-d$_4$) δ 9.17 (s, 1H), 8.28 (d, J=6.3 Hz, 1H), 7.82 (t, J=6.8 Hz, 3H), 7.58 (d, J=7.3 Hz, 1H), 7.62 (d, J=7.3 Hz, 1H), 7.21-7.49 (m, 6H), 7.11-7.19 (m, 1H), 4.98-5.13 (m, 2H), 4.20-4.43 (m, 3H), 4.08-4.20 (m, 1H), 3.47-3.45 (m, 2H), 1.35-1.54 (s, 9H)

Preparation of 2-((((9H-fluoren-9-yl)methoxy)carbonyl)amino)-3-(7-(2-(tert-butoxy)-2-oxoethyl)-7H-pyrrolo[2,3-d]pyrimidin-5-yl)propanoic acid Scheme:

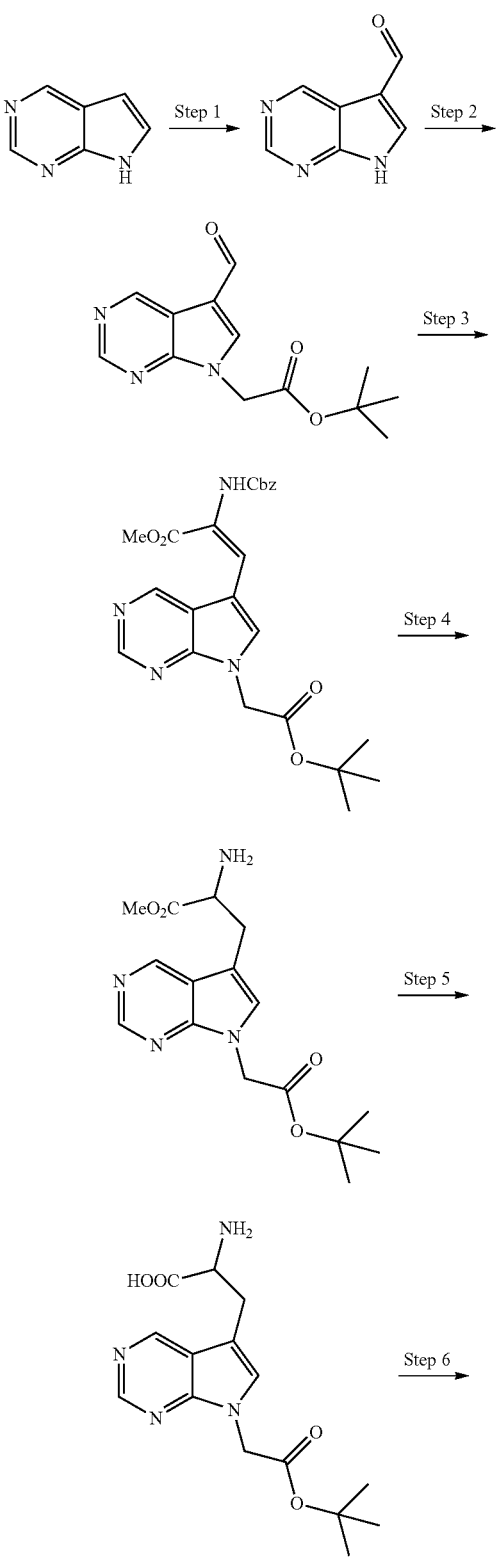

-continued

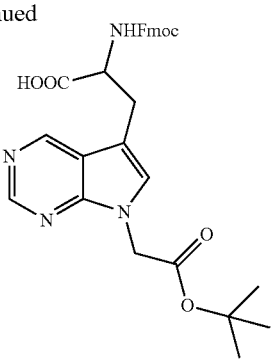

Step 1:

To the 7H-pyrrolo[2,3-d]pyrimidine (6 g, 50.4 mmol) and hexamethylaminetetramine (10.59 g, 76 mmol) were added acetic acid (20.00 mL) and water (40 mL) under nitrogen. The reaction mixture was heated to reflux and stirred for 8 hs. The reaction mixture was cooled to r.t then filtered the solid. The solid was washed with ether for 3 times. The solid was dried to afford 7H-pyrrolo[2,3-d]pyrimidine-5-carbaldehyde 5.6 g (76%) as desired product. ESI-MS(+): MS m/z 148.1. $^1$H NMR (METHANOL-d$_4$) δ: 10.00 (s, 1H), 9.43 (s, 1H), 8.91 (s, 1H), 8.40 (s, 1H).

Step 2:

To a 0° C. solution of 7H-pyrrolo[2,3-d]pyrimidine-5-carbaldehyde (5.41 g, 36.8 mmol) and cesium carbonate (13.18 g, 40.4 mmol) in DMF (147 ml) was added tert-butyl 2-bromoacetate (5.90 ml, 40.4 mmol). The mixture was allowed to warm up to RT by removing from ice bath. The reaction was stirred for 2 hs. The reaction was poured onto ice water (500 mL) and EtOAc (300 mL) mixture. The product was extracted in the EtOAc. The layers were separated and the aqueous phase was extracted a second time with EtOAc (2×150 mL). The combined EtOAc layers were washed with brine. The organic layer was collected and dried over sodium sulfate and concentrated under vacuum. The crude product was purified by silica gel chromatography to get tert-butyl 2-(5-formyl-7H-pyrrolo[2,3-d]pyrimidin-7-yl)acetate 6.60 g (69%) as clean product. ESI-MS(−): MS m/z 262.0.

Step 3:

(±)-Methyl 2-benzyloxycarbonylamino-2-(dimethoxyphosphinyl)acetate (9.07 g, 27.4 mmol) was dissolved in 70 mL DCM and stirred under nitrogen at 0° C. for 5 mins. To this solution was added DBU (4.17 ml, 27.4 mmol), followed by dropwise addition of tert-butyl 2-(5-formyl-7H-pyrrolo[2,3-d]pyrimidin-7-yl)acetate (6.50 g, 24.88 mmol) in DCM (50 mL) solution during 10 mins. The mixture was stirred at room temperature for overnight. Reaction mixture was diluted with EtOAc and washed with 5% aq. citric acid/1 N NaOH PH=4 solution then brine, The organic layer was collected and dried over sodium sulfate and concentrated under vacuum. The crude product was purified by silica gel chromatography to get (E)-methyl 2-(((benzyloxy)carbonyl)amino)-3-(7-(2-(tert-butoxy)-2-oxoethyl)-7H-pyrrolo[2,3-d]pyrimidin-5-yl)acrylate 11.55 g (100%) as product. ESI-MS(+): MS m/z 467.0.

Step 4:

To the (E)-methyl 2-(((benzyloxy)carbonyl)amino)-3-(7-(2-(tert-butoxy)-2-oxoethyl)-7H-pyrrolo[2,3-d]pyrimidin-5-yl)acrylate (5.3 g, 11.36 mmol) in methanol (40 mL) solution was added Pd/C (1.2 g). The reaction was carried out at 55 psi for 2 days. The Pd/C was filtered and washed with methanol and DCM. The solvent was concentrated to afford 3.0 g (79%) of methyl 2-amino-3-(7-(2-(tert-butoxy)-2-oxoethyl)-7H-pyrrolo[2,3-d]pyrimidin-5-yl)propanoate as product. ESI-MS(+): MS m/z 335.1.

Steps 5 and 6:

To the methyl 2-amino-3-(7-(2-(tert-butoxy)-2-oxoethyl)-7H-pyrrolo[2,3-d]pyrimidin-5-yl)propanoate (2.8 g, 8.37 mmol) in THF/H$_2$O (1:1, 40 mL) solution was added LiOH (0.60 g, 25.1 mmol). The mixture was stirred at rt for 8 mins. The mixture was adjusted to PH=7 by adding 1 N HCl solution. Sodium bicarbonate (2.11 g, 25.1 mmol) and FMOC-OSU (2.82 g, 8.37 mmol) were then added to the mixture. The resulting mixture was stirred for 2 hs. 5% citric acid was added to adjust PH=7 and the aqueous was extracted with ethyl acetate, dried over sodium sulfate and concentrated under vacuum. The crude product was purified by silica gel chromatography to get 2-(((((9H-fluoren-9-yl)methoxy)carbonyl)amino)-3-(7-(2-(tert-butoxy)-2-oxoethyl)-7H-pyrrolo[2,3-d]pyrimidin-5-yl)propanoic acid 1.2 g (26.4%) as product. ESI-MS(+): MS m/z 543.1. $^1$H NMR (METHANOL-d$_4$) δ: 8.75 (s, 1H), 7.79 (d, J=7.5 Hz, 2H), 7.60 (t, J=7.4 Hz, 1H), 7.20-7.45 (m, 7H), 4.95 (s, 2H), 4.57 (d, J=8.3 Hz, 1H), 4.23-4.38 (m, 2H), 3.36-3.46 (m, 1H), 2.70 (s, 2H), 2.34 (s, 2H), 1.35-1.50 (s, 9H)

Preparation of benzyl 2-{bis[(tert-butoxy)carbonyl]amino}prop-2-enoate

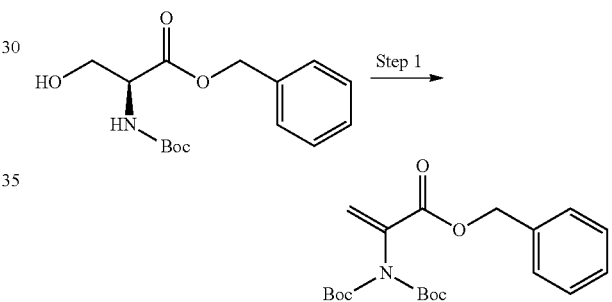

To a solution of (S)-benzyl 2-((tert-butoxycarbonyl)amino)-3-hydroxypropanoate (5.0 g, 17 mmol) and di-tert-butyl dicarbonate (9.6 g, 44 mmol) in acetonitrile (20 mL) was added DMAP (0.21 g, 1.7 mmol) at RT. The solution was stirred for 18 hrs and then concentrated under reduced pressure. The residue was dissolved in diethyl ether, washed sequentially with aqueous 1M potassium hydrogen sulfate (2×), aqueous saturated sodium bicarbonate, brine, then dried over MgSO$_4$, filtered and volatiles evaporated to afford the final product benzyl 2-{bis[(tert-butoxy)carbonyl]amino}prop-2-enoate (6.0 g, 16 mmol, 94% yield) as a white solid. $^1$H NMR (500 MHz, chloroform-d) δ 7.41-7.37 (m, 4H), 7.35-7.31 (m, 1H), 6.45-6.34 (m, 1H), 5.70 (s, 1H), 5.26 (s, 2H), 1.43 (s, 18H).

Preparation of 2-(((((9H-fluoren-9-yl)methoxy)carbonyl)amino)-3-(3-(2-(tert-butoxy)-2-oxoethyl)-1H-pyrrolo[3,2-b]pyridin-1-yl)propanoic acid Scheme:

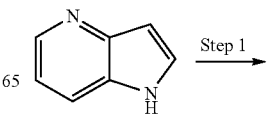

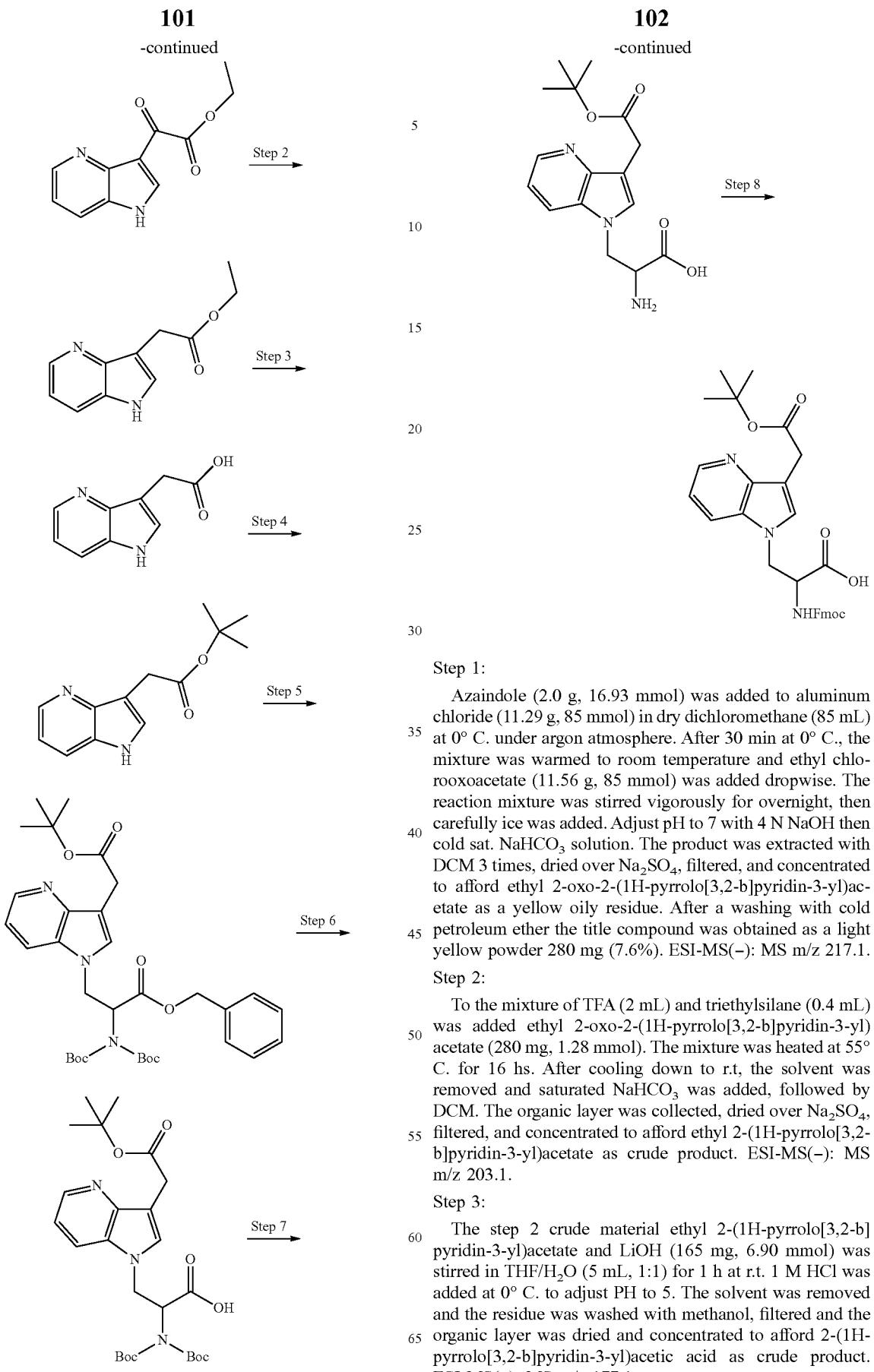

Step 1:

Azaindole (2.0 g, 16.93 mmol) was added to aluminum chloride (11.29 g, 85 mmol) in dry dichloromethane (85 mL) at 0° C. under argon atmosphere. After 30 min at 0° C., the mixture was warmed to room temperature and ethyl chlorooxoacetate (11.56 g, 85 mmol) was added dropwise. The reaction mixture was stirred vigorously for overnight, then carefully ice was added. Adjust pH to 7 with 4 N NaOH then cold sat. NaHCO$_3$ solution. The product was extracted with DCM 3 times, dried over Na$_2$SO$_4$, filtered, and concentrated to afford ethyl 2-oxo-2-(1H-pyrrolo[3,2-b]pyridin-3-yl)acetate as a yellow oily residue. After a washing with cold petroleum ether the title compound was obtained as a light yellow powder 280 mg (7.6%). ESI-MS(−): MS m/z 217.1.

Step 2:

To the mixture of TFA (2 mL) and triethylsilane (0.4 mL) was added ethyl 2-oxo-2-(1H-pyrrolo[3,2-b]pyridin-3-yl)acetate (280 mg, 1.28 mmol). The mixture was heated at 55° C. for 16 hs. After cooling down to r.t, the solvent was removed and saturated NaHCO$_3$ was added, followed by DCM. The organic layer was collected, dried over Na$_2$SO$_4$, filtered, and concentrated to afford ethyl 2-(1H-pyrrolo[3,2-b]pyridin-3-yl)acetate as crude product. ESI-MS(−): MS m/z 203.1.

Step 3:

The step 2 crude material ethyl 2-(1H-pyrrolo[3,2-b]pyridin-3-yl)acetate and LiOH (165 mg, 6.90 mmol) was stirred in THF/H$_2$O (5 mL, 1:1) for 1 h at r.t. 1 M HCl was added at 0° C. to adjust PH to 5. The solvent was removed and the residue was washed with methanol, filtered and the organic layer was dried and concentrated to afford 2-(1H-pyrrolo[3,2-b]pyridin-3-yl)acetic acid as crude product. ESI-MS(+): MS m/z 177.1.

Step 4:

To a solution of 2-(1H-pyrrolo[3,2-b]pyridin-3-yl)acetic acid (375 mg, 2.129 mmol) in DCM (7.0 mL) and tert-butyl acetate (3.0 mL) was added dropwise perchloric acid (0.274 mL, 3.19 mmol). The resulting solution was stirred at rt for 3 hs. Filter the light brown solid and washed with DCM. The DCM layer was concentrated. Water and EtOAc were then added. EtOAc was used to extract product twice. The organic layer was washed with sat.NaHCO₃ for 2 times, dried over Na₂SO₄, concentrated to afford tert-butyl 2-(1H-pyrrolo[3,2-b]pyridin-3-yl)acetate 100 mg (20%) as product. The material was used directly to the next step reaction. ESI-MS(−): MS m/z 231.1.

Step 5:

Potassium carbonate (357 mg, 2.58 mmol) was added to a solution of tert-butyl 2-(1H-pyrrolo[3,2-b]pyridin-3-yl)acetate (100 mg, 0.431 mmol) and benzyl 2-{bis[(tert-butoxy)carbonyl]amino}prop-2-enoate (162 mg, 0.431 mmol) in acetonitrile (5 mL). The reaction mixture was heated to 50° C. for overnight. The reaction was diluted with EtOAc and water. The organic layer was washed with brine, dried over Na₂SO₄, filtered and evaporated to give the crude product. The crude product was purified via silica gel chromatography to afford benzyl 2-{bis[(tert-butoxy)carbonyl]amino}-3-{3-[2-(tert-butoxy)-2-oxoethyl]-1H-pyrrolo[3,2-b]pyridin-1-yl}propanoate as a white solid (100 mg, 38%). ESI-MS(+): MS m/z 610.3.

Step 6:

H₂ was slowly bubbled through a solution of benzyl 2-{bis[(tert-butoxy)carbonyl]amino}-3-{3-[2-(tert-butoxy)-2-oxoethyl]-1H-pyrrolo[3,2-b]pyridin-1-yl}propanoate from step 5 (100 mg, 0.164 mmol) and Pd—C (4.36 mg, 4.10 μmop in MeOH (5 mL) at RT for 6 hs. The reaction mixture was filtered through diatomaceous earth (Celite®) and evaporated to afford 2-{bis[(tert-butoxy)carbonyl]amino}-3-{3-[2-(tert-butoxy)-2-oxoethyl]-1H-pyrrolo[3,2-b]pyridin-1-yl}propanoic acid (80 mg, 94%) which was used for the next step without purification. ESI-MS(+): MS m/z 520.4.

Step 7:

4M HCl in dioxane (2 mL) was added to the 2-{bis[(tert-butoxy)carbonyl]amino}-3-{3-[2-(tert-butoxy)-2-oxoethyl]-1H-pyrrolo[3,2-b]pyridin-1-yl}propanoic acid from step 6. The mixture was stirred for 30 mins before concentrated to afford 2-amino-3-(3-(2-(tert-butoxy)-2-oxoethyl)-1H-pyrrolo[3,2-b]pyridin-1-yl)propanoic acid as crude product. ESI-MS(+): MS m/z 320.1.

Step 8:

Sodium bicarbonate (67.1 mg, 0.8 mmol) and FMOC-OSU (53.9 mg, 0.160 mmol) were added to 2-amino-3-(3-(2-(tert-butoxy)-2-oxoethyl)-1H-pyrrolo[3,2-b]pyridin-1-yl)propanoic acid (51 mg, 0.16 mmol) in THF/water (4 mL, 1:1) solution. The resulting mixture was stirred for 2 hs. 5% citric acid was added to adjust PH=7 and the aqueous was extracted with ethyl acetate, dried over sodium sulfate and concentrated under vacuum. The crude product was purified by silica gel chromatography to get 2-((((9H-fluoren-9-yl)methoxy)carbonyl)amino)-3-(3-(2-(tert-butoxy)-2-oxo-ethyl)-1H-pyrrolo[3,2-b]pyridin-1-yl)propanoic acid 10.7 mg (12%) as product. ESI-MS(+): MS m/z 542.2.

Preparation of (S)-2-((((9H-fluoren-9-yl)methoxy)carbonyl)amino)-3-(3-(2-(tert-butoxy)-2-oxoethyl)-1H-indol-1-yl)propanoic acid and (R)-2-((((9H-fluoren-9-yl)methoxy)carbonyl)amino)-3-(3-(2-(tert-butoxy)-2-oxoethyl)-1H-indol-1-yl)propanoic acid

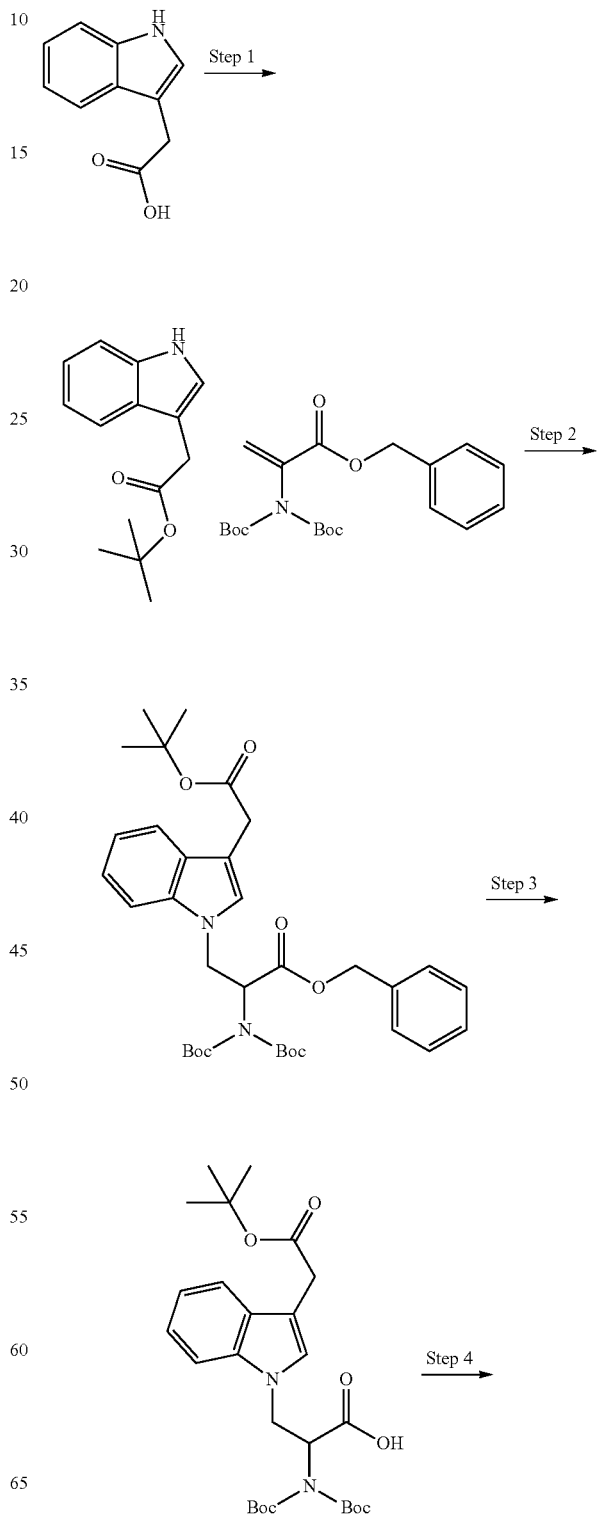

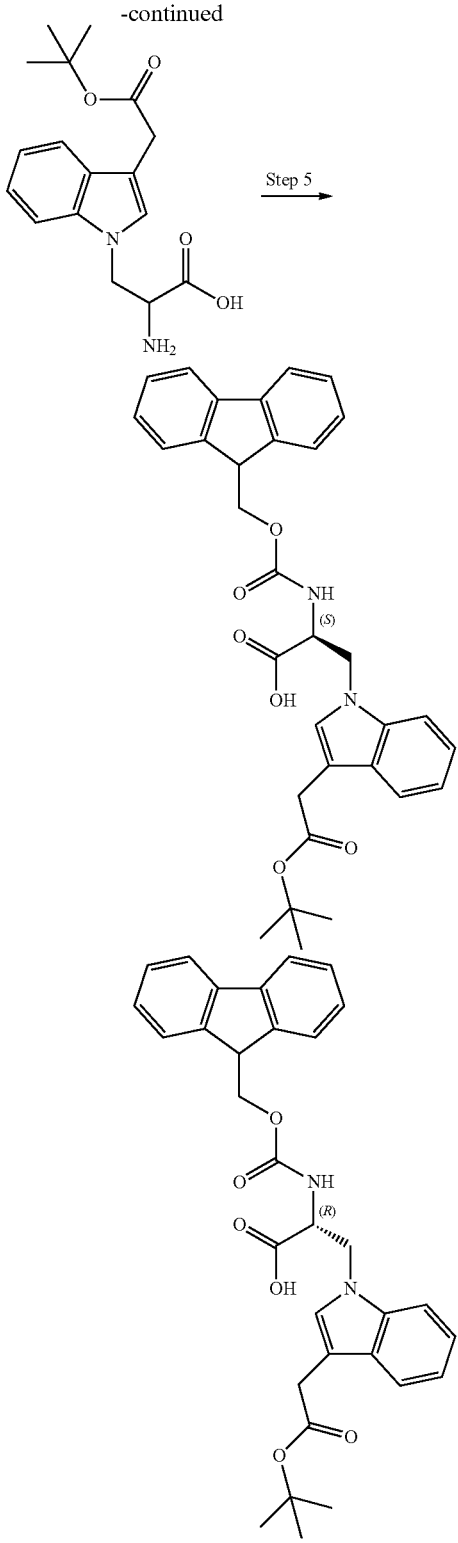

Step 1:

To a solution of 2-(1H-indol-3-yl)acetic acid (500 mg, 2.85 mmol) in DCM (25 mL) and THF (2 mL) was added tert-butyl 2,2,2-trichloroacetimidate (2.041 mL, 11.42 mmol). The reaction was stirred at RT for 18 hrs. The reaction volatiles were evaporated and crude material purified on silica gel (40 g column, 5-50% EtOAc:Hex) to afford the product tert-butyl 2-(1H-indol-3-yl)acetate (200 mg, 0.865 mmol, 30.3% yield) as a yellow oil. $^1$H NMR (500 MHz, methanol-$d_4$) δ 7.55 (dt, J=8.0, 1.0 Hz, 1H), 7.36 (dt, J=8.2, 0.8 Hz, 1H), 7.15 (s, 1H), 7.12 (td, J=7.6, 1.1 Hz, 1H), 7.05-7.01 (m, 1H), 3.67 (d, J=0.8 Hz, 2H), 1.46 (s, 9H).

Step 2:

To a solution of tert-butyl 2-(1H-indol-3-yl)acetate (0.57 g, 2.5 mmol) and benzyl 2-{bis[(tert-butoxy)carbonyl]amino}prop-2-enoate (0.85 g, 2.2 mmol) in acetonitrile (15 mL) was added potassium carbonate (1.9 g, 13 mmol). The reaction was stirred at RT for 18 hrs. After stirring at RT, no reaction had occurred. The reaction was then heated to 50° C. for 24 hr. The reaction was cooled and diluted with EtOAc and washed with water. The organic layer was washed with brine; collected; dried over MgSO$_4$; filtered and evaporated to afford the crude product. The crude product was purified via silica gel (40 g column, 5-40% EtOAc:Hex) to afford benzyl 2-(bis(((2-methyl-2-propanyl)oxy)carbonyl)amino)-3-(3-(2-((2-methyl-2-propanyl)oxy)-2-oxoethyl)-1H-indol-1-yl)propanoate (830 mg, 1.4 mmol, 61% yield) as a clear oil. $^1$H NMR (500 MHz, chloroform-d) δ 7.59 (d, J=7.9 Hz, 1H), 7.41-7.38 (m, 6H), 7.33-7.30 (m, 1H), 7.19 (td, J=7.6, 1.0 Hz, 1H), 7.13-7.08 (m, 1H), 7.05 (s, 1H), 5.28-5.19 (m, 3H), 4.87 (dd, J=15.1, 4.7 Hz, 1H), 3.68-3.55 (m, 2H), 1.47 (s, 9H), 1.43 (s, 9H), 1.28 (s, 9H). Analysis condition A: Retention time=1.69 min; ESI-MS(+) m/z 631.3 (M+Na).

Step 3:

H$_2$ was slowly bubbled through a solution of benzyl 2-(bis(((2-methyl-2-propanyl)oxy)carbonyl)amino)-3-(3-(2-((2-methyl-2-propanyl)oxy)-2-oxoethyl)-1H-indol-1-yl)propanoate (830 mg, 1.4 mmol) and Pd—C (36 mg, 0.034 mmol) in MeOH (10 mL) and then left under positive pressure of H$_2$ at RT for 2 days. The reaction was filtered through a nylon frit filter and the volatiles evaporated to afford 2-(bis(((2-methyl-2-propanyl)oxy)carbonyl)amino)-3-(3-(2-((2-methyl-2-propanyl)oxy)-2-oxoethyl)-1H-indol-1-yl)propanoic acid (700 mg, 1.4 mmol, 100% yield) as a clear oil. Analysis condition A: Retention time=1.46 min; ESI-MS(+) m/z 541.3 (M+Na).

Step 4:

To a 0° C. solution of HCl (4 M, 5.0 ml) in dioxane was added 2-(bis(((2-methyl-2-propanyl)oxy)carbonyl)amino)-3-(3-(2-((2-methyl-2-propanyl)oxy)-2-oxoethyl)-1H-indol-1-yl)propanoic acid (700 mg, 1.4 mmol) while under positive pressure of N$_2$. The ice bath was removed and the reaction was stirred for 30 minutes at RT. The reaction volatiles were evaporated under reduced pressure with no heat to afford 2-amino-3-(3-(2-(tert-butoxy)-2-oxoethyl)-1H-indol-1-yl)propanoic acid as the HCl salt (480 mg, 1.4 mmol, 100% yield) as a sticky oil. Analysis condition A: Retention time=0.91 min; ESI-MS(+) m/z 262.95 (M-t-butyl).

Step 5:

To a solution of 2-amino-3-(3-(2-(tert-butoxy)-2-oxoethyl)-1H-indol-1-yl)propanoic acid, as the HCl salt (480 mg, 1.4 mmol) and sodium bicarbonate (570 mg, 6.8 mmol) in acetone (5.00 mL) and water (10 mL) was added (9H-fluoren-9-yl)methyl (2,5-dioxopyrrolidin-1-yl) carbonate (460 mg, 1.4 mmol). The reaction was stirred for 18 hrs. The reaction was slowly acidified to pH 5 with aqueous HCl (1.0 M) and with vigorous stirring. The reaction solution was separated with DCM. The organic layer was washed with water, followed by brine. The organic layer was collected; dried over MgSO$_4$ and concentrated under reduced pressure to afford the crude product. The crude material was purified on silica gel (40 g column, 20-80% EtOAc:Hex) to afford the product as a white foam. The purified material was submitted to SFC for chiral separation. The first eluting peak from SFC was (S)-2-((((9H-fluoren-9-yl)methoxy)carbonyl)amino)-3-(3-(2-(tert-butoxy)-2-oxoethyl)-1H-indol-1-yl)propanoic acid (90 mg, 0.166 mmol, 12.28% yield). The 2nd eluting peak was (R)-2-((((9H-fluoren-9-yl)methoxy)carbonyl)amino)-3-(3-(2-(tert-butoxy)-2-oxoethyl)-1H-indol-1-yl)propanoic acid (88 mg, 0.16 mmol, 12% yield). Analysis condition A: Retention time=1.44 min; ESI-MS(+) m/z 563.1 (M+Na).

Preparation of (S)-2-((((9H-fluoren-9-yl)methoxy)carbonyl)amino)-3-(1-(2-(methylsulfonamido)-2-oxoethyl)-1H-indol-3-yl)propanoic acid

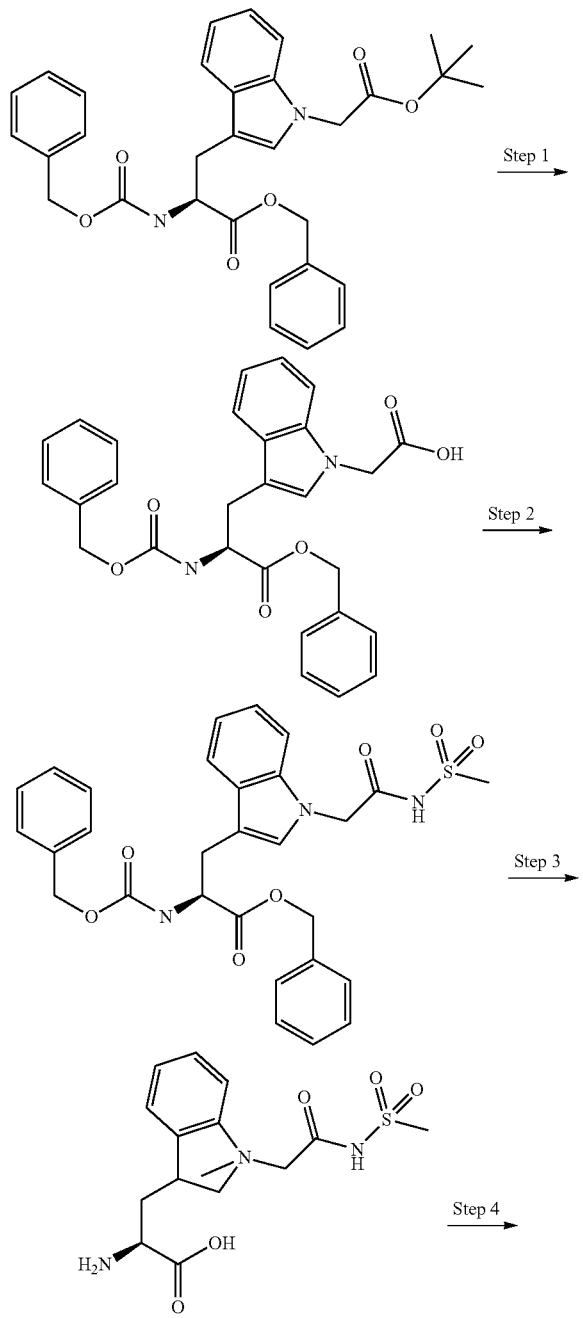

-continued

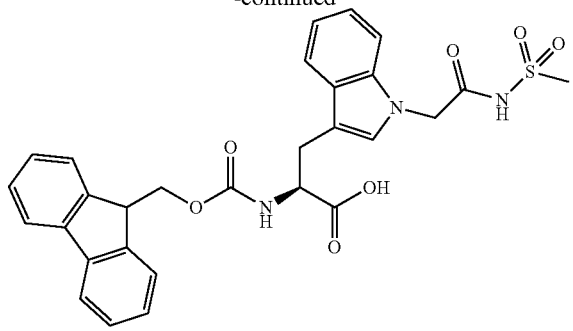

Step 1:
To a solution of (S)-benzyl 2-(((benzyloxy)carbonyl)amino)-3-(1-(2-(tert-butoxy)-2-oxoethyl)-1H-indol-3-yl)propanoate (1.2 g, 2.2 mmol) dissolved in DCM (10 mL) was added TFA (10 mL). The reaction was stirred at RT for 1 hr. The reaction volatiles were evaporated and placed under high vacuum for overnight to afford the product (S)-2-(3-(3-(benzyloxy)-2-(((benzyloxy)carbonyl)amino)-3-oxopropyl)-1H-indol-1-yl)acetic acid (1.0 g, 2.1 mmol, 93% yield). Analysis condition A: Retention time=1.25 min; ESI-MS(+) m/z 509.2 (M+Na).

Step 2:
To a solution of (S)-2-(3-(3-(benzyloxy)-2-(((benzyloxy)carbonyl)amino)-3-oxopropyl)-1H-indol-1-yl)acetic acid (1.01 g, 2.076 mmol) dissolved in dry DCM (20 mL) was added methanesulfonamide (0.197 g, 2.076 mmol), EDC (0.438 g, 2.284 mmol), and DMAP (0.279 g, 2.284 mmol). The reaction was stirred at RT for 4 days. The solution was washed with aqueous HCl (1 M), followed by brine; collected; dried over MgSO$_4$, filtered and evaporated under reduced pressure to afford the crude material (S)-benzyl 2-(((benzyloxy)carbonyl)amino)-3-(1-(2-(methylsulfonamido)-2-oxoethyl)-1H-indol-3-yl)propanoate (900 mg, 1.6 mmol, 77% yield). Analysis condition A: Retention time=1.79 min; ESI-MS(+) m/z 586.1 (M+Na).

Step 3:
H$_2$ was bubbled through a solution of (S)-benzyl 2-(((benzyloxy)carbonyl)amino)-3-(1-(2-(methylsulfonamido)-2-oxoethyl)-1H-indol-3-yl)propanoate (896 mg, 1.590 mmol) and Pd—C (169 mg, 0.159 mmol) in MeOH (20 mL) for 5 minutes. The reaction was then left under positive pressure of H$_2$ for 2 hrs. The reaction was bubbled through with N$_2$, and then filtered through a nylon frit filter. The volatiles were evaporated under reduced pressure to afford the product (S)-2-amino-3-(1-(2-(methylsulfonamido)-2-oxoethyl)-1H-indol-3-yl)propanoic acid (424 mg, 1.25 mmol, 79% yield) as a sticky oil. Analysis condition A: Retention time=0.87 min; ESI-MS(+) m/z 340 (M+H).

Step 4:
To a solution of (S)-2-amino-3-(1-(2-(methylsulfonamido)-2-oxoethyl)-1H-indol-3-yl)propanoic acid (424 mg, 1.249 mmol) and sodium bicarbonate (525 mg, 6.25 mmol) in acetone (8.00 mL) and water (8 mL) was added (9H-fluoren-9-yl)methyl (2,5-dioxopyrrolidin-1-yl) carbonate (421 mg, 1.249 mmol). The reaction was stirred for 18 hrs. The reaction was acidified slowly to pH 5 with aqueous HCl (1 M) with vigorous stirring. The aqueous layer was separated with 25 ml EtOAc. The organic layer was washed with water, followed by brine. The organic layer was collected, dried over MgSO$_4$, and volatiles evaporated under reduced pressure. The crude material was purified via reverse phase chromatography (mobile phase A: 5% acetonitrile, 95% water, 10 mM ammonium acetate. Mobile phase B: 95% acetonitrile, 5% water, 10 mM ammonium acetate. 10% B-50% B over 20 column volumes) to afford the product (S)-2-((((9H-fluoren-9-yl)methoxy)carbonyl)amino)-3-(1-(2-(methylsulfonamido)-2-oxoethyl)-1H-indol-3-yl)propanoic acid (330 mg, 0.59 mmol, 47% yield) as an off-white solid. Analysis condition B: Retention time=1.14 min; ESI-MS(+) m/z 561.9 (M+H).

Preparation of (S)-3-(1-((1H-tetrazol-5-yl)methyl)-1H-indol-3-yl)-2-((((9H-fluoren-9-yl)methoxy)carbonyl)amino)propanoic acid

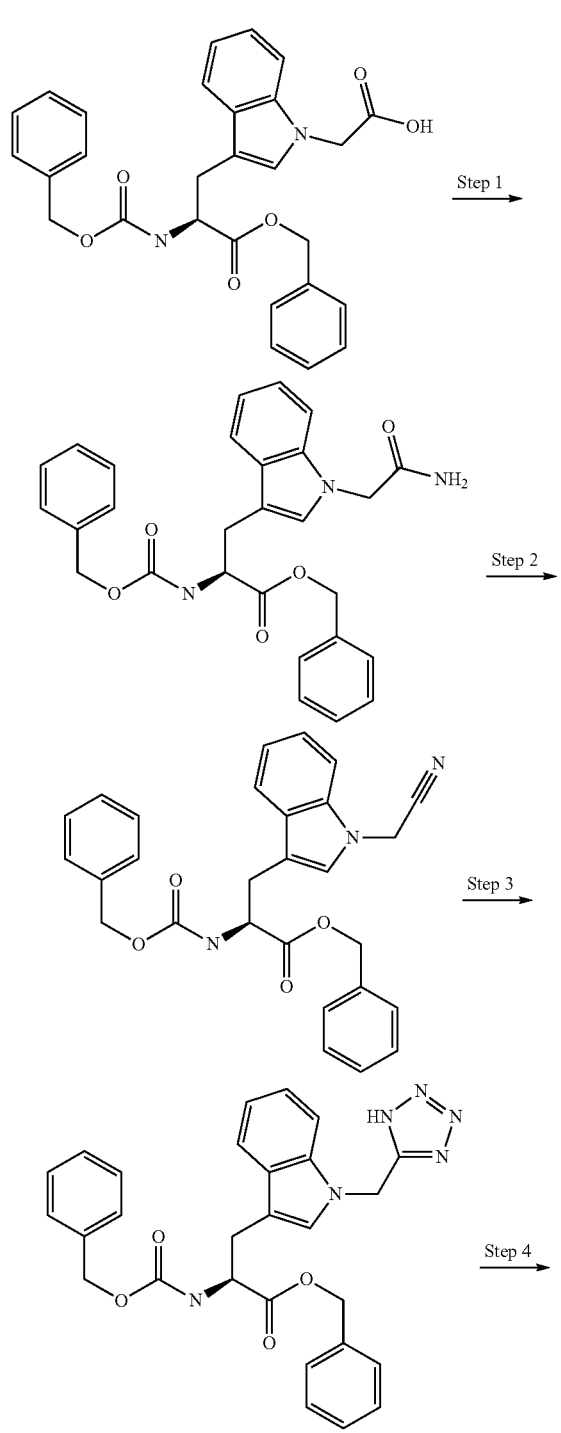

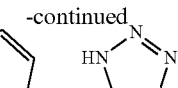

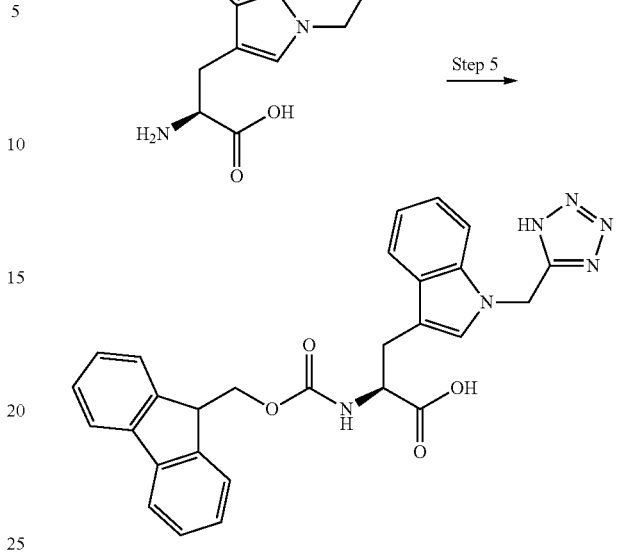

Step 1:
To a solution of (S)-2-(3-(3-(benzyloxy)-2-(((benzyloxy)carbonyl)amino)-3-oxopropyl)-1H-indol-1-yl)acetic acid (0.897 g, 1.844 mmol) was added CDI (0.389 g, 2.397 mmol) and the reaction stirred for 3 hrs. Ammonium hydroxide (0.287 mL, 7.37 mmol) was then added and the reaction stirred for an additional 3 hrs. The reaction was was diluted with DCM (50 mL) and washed with aqueous HCl (1 M). The organic layer was washed with brine; collected; dried over MgSO₄, filtered and evaporated to afford the crude product (S)-benzyl 3-(1-(2-amino-2-oxoethyl)-1H-indol-3-yl)-2-(((benzyloxy)carbonyl)amino)propanoate (865 mg, 1.782 mmol, 97% yield), which was used as is in the next reaction step. Analysis condition A: Retention time=1.14 min; ESI-MS(+) m/z 561.9 (M+H).
Step 2:
To a solution of (S)-benzyl 3-(1-(2-amino-2-oxoethyl)-1H-indol-3-yl)-2-(((benzyloxy)carbonyl)amino)propanoate (865 mg, 1.782 mmol) in DMF (12 mL) was added 2,4,6-trichloro-1,3,5-triazine (164 mg, 0.891 mmol) at RT. The reaction was stirred for 18 hrs. An additional 1 eq of the triazine was added and showed full progression to product in LCMS after 2 hrs. The reaction was diluted with EtOAc and washed with water. The organic layer was washed with brine; collected; dried over MgSO₄, filtered and evaporated. The crude product was purified on silica (40 g column 10-50% EtOAc:Hex) to afford the product (S)-benzyl 2-(((benzyloxy)carbonyl)amino)-3-(1-(cyanomethyl)-1H-indol-3-yl)propanoate (600 mg, 1.28 mmol, 72% yield) as a light brown foam. Analysis condition A: Retention time=1.33 min; ESI-MS(+) m/z 490.2 (M+Na).
Step 3:
To a solution of (S)-benzyl 2-(((benzyloxy)carbonyl)amino)-3-(1-(cyanomethyl)-1H-indol-3-yl)propanoate (300 mg, 0.642 mmol) in water (2.0 ml) and 2-propanol (1.0 ml) were added sodium azide (83 mg, 1.283 mmol) and zinc(II) bromide (72.3 mg, 0.321 mmol) and heated to 90° C. The reaction was heated and stirred for 18 hrs. After the reaction cooled, aqueous HCl (1 M, 10 mL) was added followed by EtOAc (50 mL). The organic layer was washed with brine; collected; dried over MgSO₄; filtered and evaporated to afford the crude material (S)-benzyl 3-(1-((1H-tetrazol-5-yl)methyl)-1H-indol-3-yl)-2-(((benzyloxy)carbonyl)amino)propanoate (328 mg, 0.6 mmol, 100% yield). Analysis condition A: Retention time=1.23 min; ESI-MS(+) m/z 533.3 (M+Na).

Step 4:

H$_2$ was bubbled through a solution of (S)-benzyl 3-(1-((1H-tetrazol-5-yl)methyl)-1H-indol-3-yl)-2-(((benzyloxy)carbonyl)amino)propanoate (160 mg, 0.31 mmol) and Pd—C (33 mg, 0.03 mmol) in MeOH (5 mL) for 5 minutes. The reaction was then left under positive pressure of H$_2$ for 2 days while stirring. The reaction was filtered through a nylon frit filter and evaporated under reduced pressure. The product (S)-3-(1-((1H-tetrazol-5-yl)methyl)-1H-indol-3-yl)-2-aminopropanoic acid (89 mg, 0.311 mmol, 100% yield) was taken directly onto the next step. Analysis condition A: Retention time=0.7 min; ESI-MS(+) m/z 287 (M+H).

Step 5:

To a solution of (S)-3-(1-((1H-tetrazol-5-yl)methyl)-1H-indol-3-yl)-2-aminopropanoic acid (89 mg, 0.31 mmol) and sodium bicarbonate (130 mg, 1.6 mmol) in acetone (2.0 mL) and water (4.0 mL) was added (9H-fluoren-9-yl)methyl (2,5-dioxopyrrolidin-1-yl) carbonate (110 mg, 0.31 mmol). The reaction was stirred for 18 hrs. The reaction was slowly acidified to pH 5 with aqueous HCl (1 M) and with vigorous stirring. The reaction was separated with DCM. The organic layer was washed with water, followed by brine. The organic layer was collected; dried over MgSO$_4$, and the volatiles evaporated under reduced pressure to afford the crude product. The crude material was purified on prep HPLC (SunFire Prep C18 30×100 column size; 10-100% 95:5 CH$_3$CN:Water over a 15 minute gradient with 0.1% TFA buffer) to afford the product (S)-3-(1-((1H-tetrazol-5-yl)methyl)-1H-indol-3-yl)-2-((((9H-fluoren-9-yl)methoxy)carbonyl)amino)propanoic acid (104 mg, 0.205 mmol, 65.8% yield) as a white solid. $^1$H NMR (500 MHz, methanol-d$_4$) δ 7.77 (d, J=7.4 Hz, 2H), 7.66-7.63 (m, 1H), 7.59 (dd, J=7.4, 3.2 Hz, 1H), 7.40-7.34 (m, 3H), 7.33 (d, J=8.2 Hz, 2H), 7.29-7.21 (m, 3H), 7.20-7.15 (m, 2H), 7.11-7.06 (m, 1H), 5.70-5.62 (m, 2H), 4.57-4.51 (m, 1H), 4.36-4.19 (m, 2H), 4.17-4.10 (m, 1H), 3.37 (dd, J=14.7, 4.9 Hz, 1H), 3.23-3.10 (m, 1H). Analysis condition A: Retention time=1.14 min; ESI-MS(+) m/z 509.1 (M+H).

Preparation of benzyl 2-(((benzyloxy)carbonyl)amino)-2-(dimethoxyphosphoryl)acetate

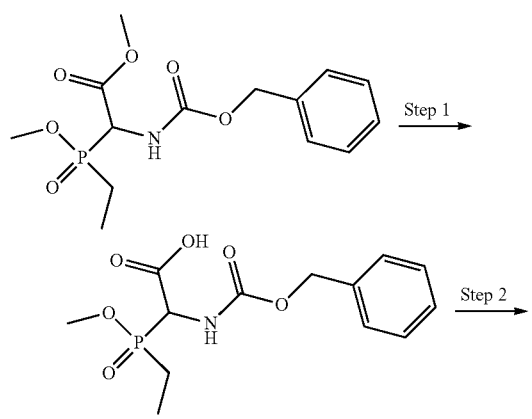

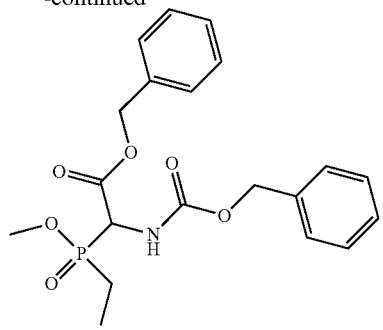

Step 1:

To a solution of methyl 2-(((benzyloxy)carbonyl)amino)-2-(dimethoxyphosphoryl)acetate (10 g, 30 mmol) in THF (50 mL) and MeOH (50 mL) was slowly added dropwise aqueous lithium hydroxide monohydrate (18 mL, 2.0 M). The reaction was stirred at RT for 1 hr. The reaction was acidified with aqueous HCl (1.0 M) and extracted with EtOAc. The organic layer was washed with brine; dried over MgSO$_4$; filtered and evaporated to afford the crude material 2-(((benzyloxy)carbonyl)amino)-2-(dimethoxyphosphoryl)acetic acid (8.0 g, 25 mmol, 84% yield). Analysis condition A: Retention time=1.06 min; ESI-MS(+) m/z 339.8 (M+Na).

Step 2:

To a solution of 2-(((benzyloxy)carbonyl)amino)-2-(dimethoxyphosphoryl)acetic acid (8.0 g, 25 mmol) and DBU (3.8 ml, 25 mmol) in acetonitrile (17 mL) was added (bromomethyl)benzene (3.15 ml, 26.5 mmol). The reaction was stirred at RT for 18 hrs. The reaction was diluted with water and extracted with EtOAc. The organic layer was washed with brine; dried over MgSO$_4$; filtered and evaporated to afford the crude product. The crude product was purified on silica gel (80 g column, 0-100% EtOAc:Hex) to afford the product benzyl 2-(((benzyloxy)carbonyl)amino)-2-(dimethoxyphosphoryl)acetate (4.5 g, 11 mmol, 44% yield) as a white solid. $^1$H NMR (500 MHz, chloroform-d) δ 7.47-7.32 (m, 10H), 5.64 (d, J=7.9 Hz, 1H), 5.33 (d, J=12.1 Hz, 1H), 5.24 (d, J=12.1 Hz, 1H), 5.21-5.11 (m, 2H), 5.04-4.94 (m, 1H), 3.79-3.67 (m, 6H). Analysis condition A: Retention time=1.39 min; ESI-MS(+) m/z 430.0 (M+Na).

Preparation of 2-(trimethylsilyl)ethyl 2-((tert-butoxycarbonyl)amino)-2-(dimethoxyphosphoryl)acetate

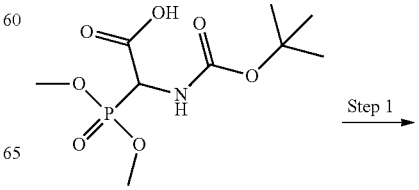

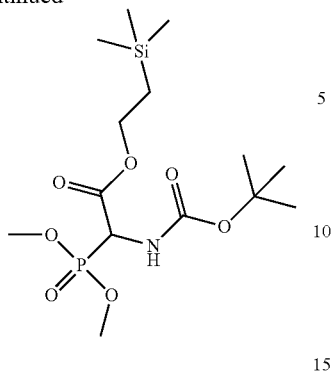

Step 1:

To a solution of 2-((tert-butoxycarbonyl)amino)-2-(dimethoxyphosphoryl)acetic acid (3.44 g, 12.15 mmol) suspended in DCM (100 mL) was added DMAP (0.148 g, 1.215 mmol) followed by 2-(trimethylsilyl)ethanol (1.741 mL, 12.15 mmol) and N1-((ethylimino)methylene)-N3,N3-dimethylpropane-1,3-diamine, HCl (2.79 g, 14.58 mmol). The reaction was stirred at RT for 2 hrs. The organic layer was washed with HCl (1M) followed by brine. The organic layer was collected, dried over MgSO$_4$, filtered and the volatiles evaporated to give the product 2-(trimethylsilyl)ethyl 2-((tert-butoxycarbonyl)amino)-2-(dimethoxyphosphoryl) acetate (4.4 g, 11.47 mmol, 94% yield) as a clear oil. $^1$H NMR (500 MHz, CHLOROFORM-d) δ 4.94-4.78 (m, 1H), 4.39-4.25 (m, 2H), 3.84 (d, J=4.9 Hz, 3H), 3.86 (d, J=5.0 Hz, 3H), 1.48 (s, 9H), 1.15-1.05 (m, 2H), 0.09-0.06 (m, 9H).

Preparation of 2-((((9H-fluoren-9-yl)methoxy)carbonyl)amino)-3-(3-(2-(tert-butoxy)-2-oxoethyl)-5,6,7,8-tetrahydroimidazo[1,5-c]pyridin-1-yl)propanoic acid

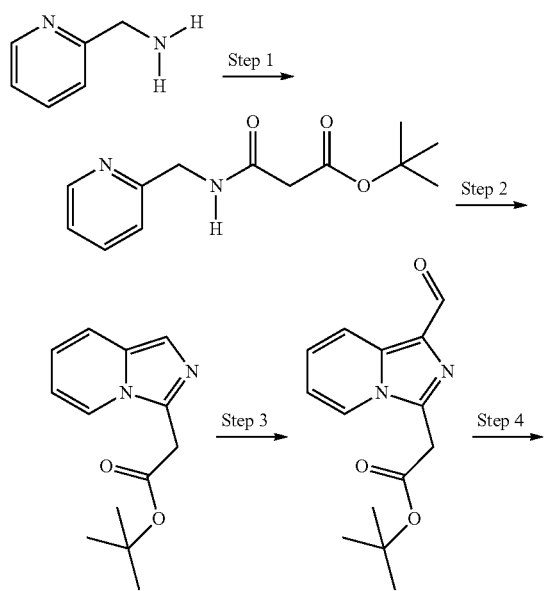

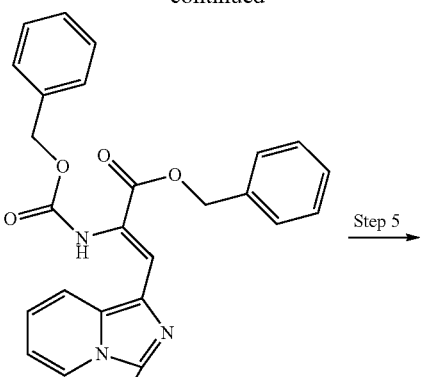

Step 1:

To a solution of 3-(tert-butoxy)-3-oxopropanoic acid (0.7 mL, 4.6 mmol), pyridin-2-ylmethanamine (0.48 mL, 4.6 mmol), and EDC (0.98 g, 5.1 mmol) was added DMAP (0.62 g, 5.1 mmol). The reaction was stirred at RT for 2 hrs. The solvent was evaporated under reduced pressure and then diluted with EtOAc. The organic layer was washed with aqueous saturated sodium bicarbonate and then washed with brine; collected; dried over MgSO$_4$, filtered and evaporated to afford the crude product. The crude product was purified via silica gel (40 g column, 0-5% MeOH:DCM) to afford the product tert-butyl 3-oxo-3-((pyridin-2-ylmethyl)amino)propanoate (830 mg, 3.3 mmol, 72% yield) as a yellow oil. Analysis condition A: Retention time=0.882 min; ESI-MS (+) m/z 251.2 (M+H).

Step 2:

To a solution of tert-butyl 3-oxo-3-((pyridin-2-ylmethyl) amino)propanoate (2 g, 8.0 mmol) and pyridine (3.9 ml, 48 mmol) in DCM (53 ml) at 0° C. was added POCl$_3$ (0.90 ml, 9.6 mmol) and allowed to warm up to RT. The reaction was stirred for 1 hr. The reaction material was transferred to a separatory funnel and washed with aqueous saturated sodium carbonate solution. The organic layer was washed with brine; collected; dried over MgSO$_4$; filtered and evaporated to afford the crude product tert-butyl 2-(imidazo[1,5-a]pyridin-3-yl)acetate (1.8 g, 7.8 mmol, 97% yield). Analysis condition A: Retention time=0.942 min; ESI-MS(+) m/z 233.2 (M+H).

Step 3:

To a solution of DMF (0.40 ml, 5.2 mmol) and pyridine (2.1 ml, 26 mmol) in DCM (29 ml) at 0° C. was added POCl$_3$ (0.50 ml, 5.2 mmol) and stirred for 5 minutes. Tert-butyl 2-(imidazo[1,5-a]pyridin-3-yl)acetate (1.0 g, 4.3 mmol) was then added as a solution in DCM (5.0 mL) and allowed to warm up to RT. The reaction was stirred for 18 hrs. The reaction was then added aqueous saturated sodium carbonate solution and stirred vigorously for 10 minutes. The biphasic mixture was then separated and the organic layer washed with brine; collected; dried over MgSO$_4$; filtered and volatiles evaporated to afford the crude material. The crude material was purified on silica gel (80 g column, 20-80% EtOAc:Hex) to afford the pure product tert-butyl 2-(1-formylimidazo[1,5-a]pyridin-3-yl)acetate (876 mg, 3.37 mmol, 78% yield) as a brown flaky solid. $^1$H NMR (500 MHz, METHANOL-d$_4$) δ 9.97 (s, 1H), 8.41 (d, J=7.1 Hz, 1H), 8.25 (dt, J=9.1, 1.1 Hz, 1H), 7.47 (ddd, J=9.1, 6.7, 0.9 Hz, 1H), 7.13 (td, J=6.9, 1.1 Hz, 1H), 4.24 (s, 2H), 1.49-1.38 (m, 9H). Analysis condition A: Retention time=2.1 min; ESI-MS(+) m/z 261 (M+H).

Step 4:

To a solution of benzyl 2-(((benzyloxy)carbonyl)amino)-2-(dimethoxyphosphoryl)acetate (850 mg, 2.1 mmol) in DCM (15 mL) was added DBU (0.29 mL, 1.9 mmol) slowly under N$_2$ atmosphere. After 10 min. tert-butyl 2-(1-formylimidazo[1,5-a]pyridin-3-yl)acetate (450 mg, 1.729 mmol) (in 2 mL DCM) was added slowly to the reaction mixture. The reaction was stirred for 18 hrs. The reaction was evaporated and purified on silica gel chromatography (80 g column 20-50% EtOAc:Hex) to give the product (Z)-benzyl 2-(((benzyloxy)carbonyl)amino)-3-(3-(2-(tert-butoxy)-2-oxoethyl)imidazo[1,5-a]pyridin-1-yl)acrylate (800 mg, 1.5 mmol, 85% yield) as a clear oil. Analysis condition A: Retention time=1.49 min; ESI-MS(+) m/z 542.5 (M+H).

Step 5:

N$_2$ was bubbled through a solution of (Z)-benzyl 2-(((benzyloxy)carbonyl)amino)-3-(3-(2-(tert-butoxy)-2-oxoethyl) imidazo[1,5-a]pyridin-1-yl)acrylate (400 mg, 0.739 mmol) in MeOH (10 mL) at RT for 5 minutes. Pd—C (79 mg, 0.074 mmol) was then added and then bubbled the reaction solution with H$_2$ for 5 minutes before being left under positive pressure of H$_2$ for 2 hrs while stirring. The reaction was filtered through nylon frit filter and volatiles evaporated to afford the product 2-amino-3-(3-(2-(tert-butoxy)-2-oxoethyl)-5,6,7,8-tetrahydroimidazo[1,5-a]pyridin-1-yl)propanoic acid (239 mg, 0.739 mmol, 100% yield). $^1$H NMR (500 MHz, methanol-d$_4$) δ 3.96-3.82 (m, 2H), 3.82-3.69 (m, 1H), 2.94-2.83 (m, 1H), 2.82-2.63 (m, 2H), 2.02-1.92 (m, 2H), 1.87-1.79 (m, 2H), 1.51-1.45 (m, 9H). Analysis condition A: Retention time=0.747 min; ESI-MS(+) m/z 324.2 (M+H).

Step 6:

To a solution of 2-amino-3-(3-(2-(tert-butoxy)-2-oxoethyl)-5,6,7,8-tetrahydroimidazo[1,5-a]pyridin-1-yl)propanoic acid (240 mg, 0.74 mmol) and sodium bicarbonate (310 mg, 3.7 mmol) in acetone (5 mL) and water (5 mL) was added (9H-fluoren-9-yl)methyl (2,5-dioxopyrrolidin-1-yl) carbonate (250 mg, 0.740 mmol). The reaction was stirred for 18 hrs. The reaction was slowly acidified to pH 5 with aqueous HCl (1.0 M) with vigorous stirring. The reaction was separated with 25 ml EtOAc. The organic layer was washed with water, followed by brine. The organic layer was collected; dried over MgSO$_4$; filtered and volatiles evaporated under reduced pressure to afford the crude product. The crude material was purified reverse phase chromatography (55 g column, 10-100% CH$_3$CN:Water with 0.1% TFA) to afford the product 2-((((9H-fluoren-9-yl)methoxy) carbonyl)amino)-3-(3-(2-(tert-butoxy)-2-oxoethyl)-5,6,7,8-tetrahydroimidazo[1,5-a]pyridin-1-yl)propanoic acid (300 mg, 0.55 mmol, 74% yield) as a white solid. $^1$H NMR (500 MHz, methanol-d$_4$) δ 7.86-7.77 (m, 2H), 7.71-7.61 (m, 2H), 7.45-7.37 (m, 2H), 7.37-7.29 (m, 2H), 4.40-4.17 (m, 5H), 4.00 (t, J=6.0 Hz, 3H), 3.21-3.07 (m, 1H), 2.96 (dd, J=15.0, 8.4 Hz, 1H), 2.80-2.72 (m, 2H), 2.06-1.87 (m, 2H), 1.87-1.75 (m, 2H), 1.51-1.40 (m, 9H). Analysis condition A: Retention time=1.13 min; ESI-MS(+) m/z 546.4 (M+H).

Preparation of (S)-2-((((9H-fluoren-9-yl)methoxy) carbonyl)amino)-3-(3-(2-(tert-butoxy)-2-oxoethyl) imidazo[1,5-a]pyridin-1-yl)propanoic acid

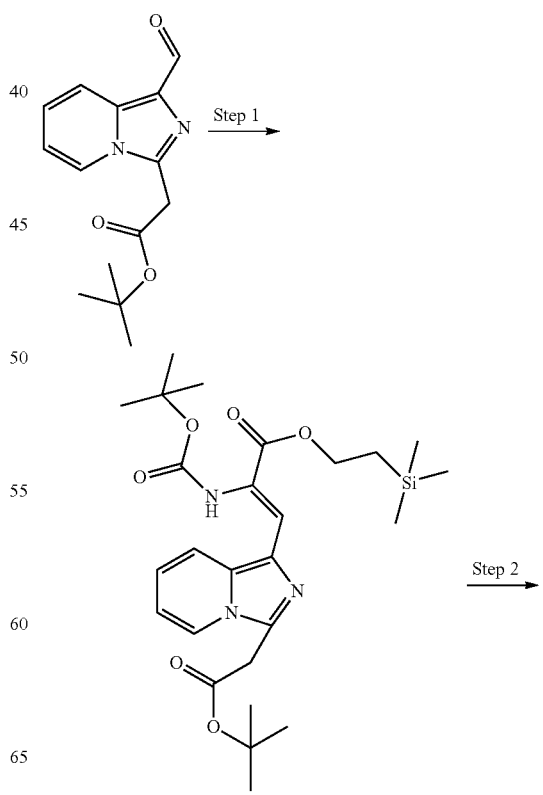

-continued

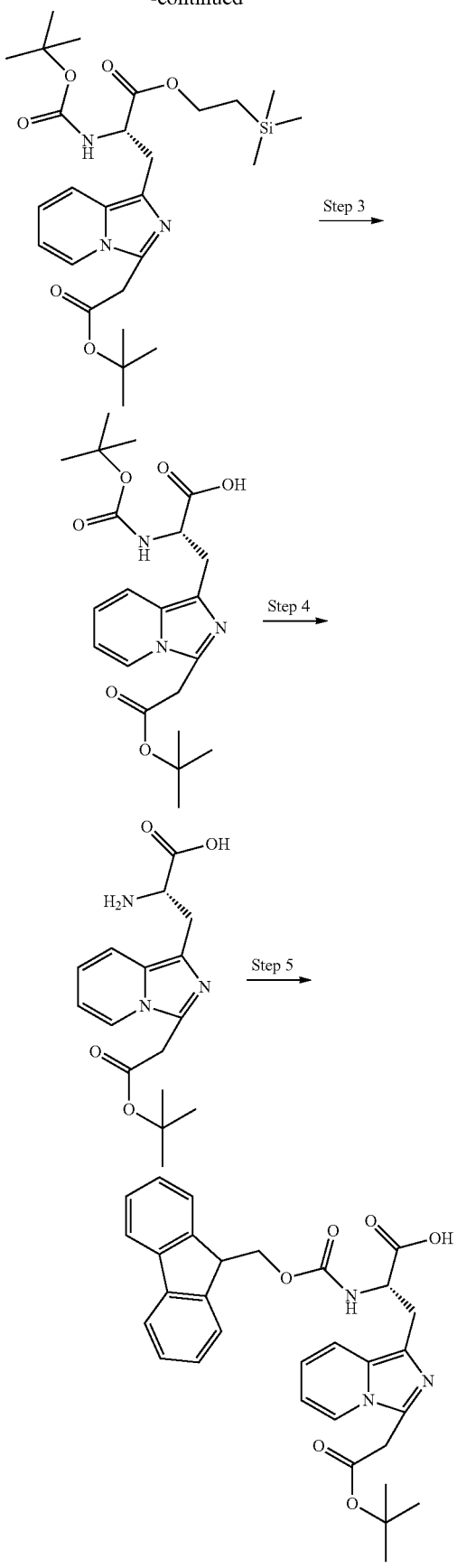

Step 1:

To a solution of 2-(trimethylsilyl)ethyl 2-((tert-butoxycarbonyl)amino)-2-(dimethoxyphosphoryl)acetate (4.75 g, 12.4 mmol) in DCM (25 mL) was added DBU (1.9 mL, 12.3 mmol) slowly under $N_2$ atmosphere. After 10 minutes tert-butyl 2-(1-formylimidazo[1,5-a]pyridin-3-yl)acetate (1.00 g, 3.84 mmol) in DCM (5 mL) was added slowly to the reaction mixture. The reaction was stirred for 18 hrs. The reaction volatiles were evaporated and the crude material purified on silica gel chromatography (80 g column 20-50% EtOAc:Hex) to afford the product (Z)-2-(trimethylsilyl)ethyl 3-(3-(2-(tert-butoxy)-2-oxoethyl)imidazo[1,5-a]pyridin-1-yl)-2-((tert-butoxycarbonyl)amino)acrylate (1.39 g, 2.30 mmol, 70% yield) as a clear oil. $^1$H NMR (500 MHz, METHANOL-$d_4$) δ 8.13 (d, J=7.1 Hz, 1H), 7.74 (dt, J=9.2, 1.1 Hz, 1H), 7.06 (s, 1H), 7.02 (ddd, J=9.3, 6.5, 0.8 Hz, 1H), 6.87-6.79 (m, 1H), 4.43-4.29 (m, 2H), 4.17 (s, 2H), 1.52-1.48 (m, 9H), 1.46 (s, 9H), 1.17-1.10 (m, 2H), 0.13-0.09 (m, 9H). Analysis condition F: Retention time=2.24 min; ESI-MS(+) m/z 518.4 (M+H).

Step 2:

To a solution of (Z)-2-(trimethylsilyl)ethyl 3-(3-(2-(tert-butoxy)-2-oxoethyl)imidazo[1,5-a]pyridin-1-yl)-2-((tert-butoxycarbonyl)amino)acrylate (1.40 g, 2.69 mmol) in tetrahydrofuran (30 ml) was treated with (+)-1,2-bis((2s,5s)-2,5-diethylphospholano)benzene(cyclooctadiene)rhodium (i) trifluoromethanesulfonate (0.06 g, 0.081 mmol), and placed under a hydrogen atmosphere (20 bar) in a PARR bomb. The reaction was stirred for 72 hrs. The reaction volatiles were evaporated and the crude material purified on silica gel (80 g column, 5-40% EtOAc:Hex) to afford the product (S)-2-(trimethylsilyl)ethyl 3-(3-(2-(tert-butoxy)-2-oxoethyl)imidazo[1,5-a]pyridin-1-yl)-2-((tert-butoxycarbonyl)amino)propanoate (380 mg, 0.729 mmol, 27% yield) as a light orange foam. Analysis condition F: Retention time=1.64 min; ESI-MS(+) m/z 520.5 (M+H).

Step 3:

To a solution of (S)-2-(trimethylsilyl)ethyl 3-(3-(2-(tert-butoxy)-2-oxoethyl)imidazo[1,5-a]pyridin-1-yl)-2-((tert-butoxycarbonyl)amino)propanoate (240 mg, 0.462 mmol) in THF (4 mL) at rt was added tetra-n-butylammonium fluoride (0.460 mL, 0.462 mmol) and stirred for 1 hr. The reaction volatiles were then evaporated and diluted with EtOAc (10 mL). The organic layer was then dried over $MgSO_4$, filtered through a nylon frit filter and the volatiles evaporated under reduced pressure. The residue was then placed under high vacuum for 30 minutes to afford the product (S)-3-(3-(2-(tert-butoxy)-2-oxoethyl)imidazo[1,5-a]pyridin-1-yl)-2-((tert-butoxycarbonyl)amino)propanoic acid (194 mg, 0.462 mmol, 100% yield) as a dark orange residue. Analysis condition A: Retention time=0.93 min; ESI-MS(+) m/z 420.2 (M+H).

Step 4:

To a vial containing (S)-3-(3-(2-(tert-butoxy)-2-oxoethyl)imidazo[1,5-a]pyridin-1-yl)-2-((tert-butoxycarbonyl)amino)propanoic acid (194 mg, 0.462 mmol) under positive pressure of $N_2$, was added HCl (1.2 mL, 4M in dioxane) and stirred at RT for 1 hr. The reaction volatiles were then evaporated under reduced pressure at rt to afford the product (S)-2-amino-3-(3-(2-(tert-butoxy)-2-oxoethyl)imidazo[1,5-a]pyridin-1-yl)propanoic acid, as the HCl salt (165 mg, 0.464 mmol, 100% yield) as a sticky foam. Analysis condition F: Retention time=0.96 min; ESI-MS(+) m/z 320.1 (M+H).

Step 5:

(9H-fluoren-9-yl)methyl (2,5-dioxopyrrolidin-1-yl) carbonate (203 mg, 0.603 mmol) was added to a solution of (S)-2-amino-3-(3-(2-(tert-butoxy)-2-oxoethyl)imidazo[1,5-a]pyridin-1-yl)propanoic acid, HCl (195 mg, 0.548 mmol) and sodium bicarbonate (230 mg, 2.74 mmol) in acetone (3 mL) and water (3 mL) and stirred at RT for 1 hr. The reaction was neutralized with HCl (1M) to reach pH 5-6. The neutralized solution was then diluted with EtOAc and water. The organic layer was washed with brine; collected; dried over MgSO₄; filtered and the volatiles evaporated to afford the crude material. The crude material was purified on prep HPLC (SunFire Prep C18 30×100 column size; 10-100% 95:5 CH₃CN:Water over a 15 minute gradient with 0.1% TFA buffer) to afford the pure product (S)-2-((((9H-fluoren-9-yl)methoxy)carbonyl)amino)-3-(3-(2-(tert-butoxy)-2-oxoethyl)imidazo[1,5-a]pyridin-1-yl)propanoic acid (165 mg, 0.305 mmol, 55.6% yield) as a brown foam. Analysis condition A: Retention time=1.09 min; ESI-MS(+) m/z 542.3 (M+H).

Preparation of (S)-2-((((9H-fluoren-9-yl)methoxy)carbonyl)amino)-3-(1-(2-(tert-butoxy)-2-oxoethyl)imidazo[1,5-a]pyridin-3-yl)propanoic acid

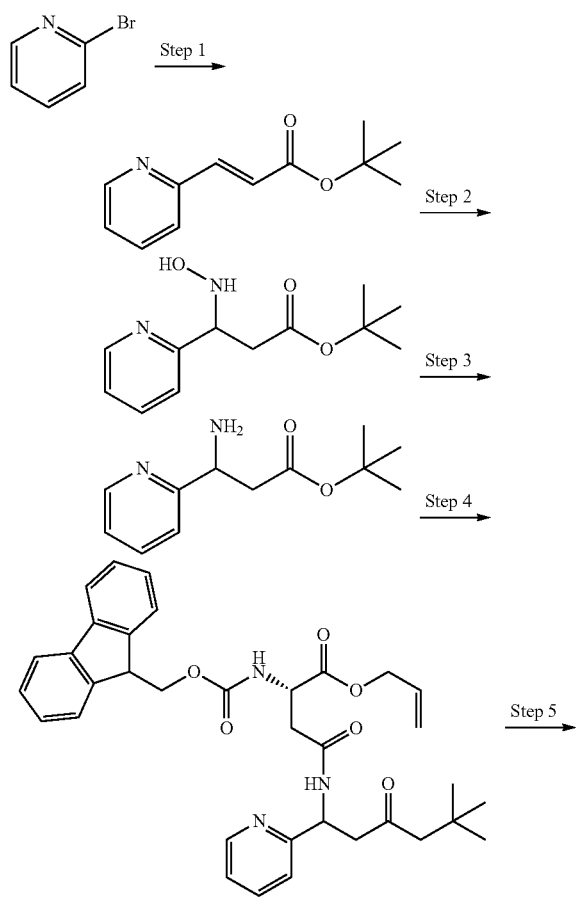

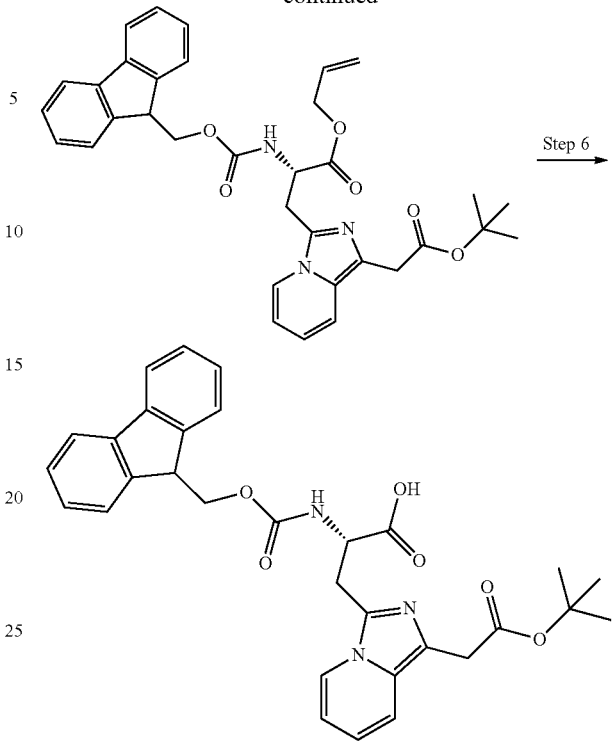

Step 1:

To a solution of 2-bromopyridine (2.50 ml, 25.3 mmol), tert-butyl acrylate (18.4 ml, 127 mmol), 1,4-diazabicyclo[2.2.2]octane (0.114 g, 1.013 mmol), potassium carbonate (3.50 g, 25.3 mmol), and tetrabutylammonium bromide (8.16 g, 25.3 mmol) in degassed DMF (100 ml) was added palladium(II) acetate (0.114 g, 0.506 mmol) and heated to 120° C. in a pressure vessel and stirred for 14 hrs. After 14 hrs, the reaction was cooled and poured into water (100 ml) and extracted with EtOAc (100 ml). The organic layer was washed with water; brine; collected; dried over MgSO₄; filtered and the volatiles evaporated to afford the crude product. The crude product was purified via silica gel chromatography (120 g column, 5-25% EtOAc:Hex) to afford the product (E)-tert-butyl 3-(pyridin-2-yl)acrylate (1.5 g, 7.31 mmol, 28.9% yield) as a brown oil. ¹H NMR (500 MHz, chloroform-d) δ 8.69-8.59 (m, 1H), 7.76-7.68 (m, 1H), 7.65-7.55 (m, 1H), 7.47-7.40 (m, 1H), 7.27 (ddd, J=7.6, 4.8, 1.1 Hz, 1H), 6.85 (d, J=15.8 Hz, 1H), 1.60-1.50 (m, 9H). Analysis condition A: Retention time=1.02 min; ESI-MS(+) m/z 206.1 (M+H).

Step 2:

To a solution of (E)-tert-butyl 3-(pyridin-2-yl)acrylate (1.00 g, 4.87 mmol) in 1,4-dioxane (35 mL) was added hydroxylamine (50% in water, 3.22 g, 48.7 mmol) followed by tetra-n-butylammonium sulfate (50% in water 0.06 g, 0.049 mmol). The reaction was stirred for 4 days. The reaction was then diluted with EtOAc and washed with water. The organic layer was then washed with brine; collected; dried over MgSO₄; filtered and volatiles evaporated to afford the product tert-butyl 3-(hydroxyamino)-3-(pyridin-2-yl)propanoate (1.10 g, 4.62 mmol, 95% yield). ¹H NMR (500 MHz, methanol-d₄) δ 8.58-8.41 (m, 1H), 7.82 (td, J=7.7, 1.7 Hz, 1H), 7.52 (d, J=7.9 Hz, 1H), 7.33 (ddd, 5.0, 1.3 Hz, 1H), 4.43 (t, J=7.1 Hz, 1H), 2.85-2.67 (m, 2H), 1.38 (s, 9H). Analysis condition A: Retention time=0.80 min; ESI-MS(+) m/z 239.2 (M+H).

Step 3:

To a solution of tert-butyl 3-(hydroxyamino)-3-(pyridin-2-yl)propanoate (500 mg, 2.10 mmol) in acetic acid (5 mL) cooled to 0° C. was added zinc (500 mg, 7.65 mmol). The reaction was then warmed up to RT and stirred for 3 hrs. The reaction slurry was diluted with MeOH (5 mL) and filtered through a nylon frit filter. The solvent was evaporated under reduced pressure then azeotroped (3 times) with toluene (20 mL×3) to afford a sticky residue. The sticky residue was placed under high vacuum for 24 hrs to afford the product tert-butyl 3-amino-3-(pyridin-2-yl)propanoate (466 mg, 2.096 mmol, 100% yield) as a white foam. $^1$H NMR (500 MHz, methanol-d$_4$) δ 8.63 (d, J=4.9 Hz, 1H), 8.11-8.05 (m, 1H), 7.65 (d, J=8.0 Hz, 1H), 7.60-7.55 (m, 1H), 4.69 (dd, J=7.7, 4.7 Hz, 1H), 3.02-2.83 (m, 2H), 1.48-1.43 (m, 9H). Analysis condition A: Retention time=1.10 min; ESI-MS(+) m/z 223.1 (M+H).

Step 4:

To a solution of (S)-3-((((9H-fluoren-9-yl)methoxy)carbonyl)amino)-4-(allyloxy)-4-oxobutanoic acid (740 mg, 1.87 mmol) in DCM (15 mL) was added HATU (712 mg, 1.871 mmol) followed by Hunig's Base (1.634 mL, 9.36 mmol) and stirred at RT for 20 minutes. Tert-butyl 3-amino-3-(pyridin-2-yl)propanoate (416 mg, 1.871 mmol) was then added and stirred at RT for 1 hr. The reaction was then diluted with water and DCM. The organic layer was washed with brine; collected; dried over MgSO$_4$; filtered and evaporated to afford the crude material. The crude material was purified via silica gel (40 g column, 10-70% EtOAc:Hex) to afford the product (2S)-allyl 2-((((9H-fluoren-9-yl)methoxy)carbonyl)amino)-4-((3-(tert-butoxy)-3-oxo-1-(pyridin-2-yl)propyl)amino)-4-oxobutanoate (263 mg, 0.439 mmol, 23.43% yield) as a light brown oil. Analysis condition A: Retention time=1.22 min; ESI-MS(+) m/z 600.3 (M+H).

Step 5:

To a solution of (2S)-allyl 2-((((9H-fluoren-9-yl)methoxy)carbonyl)amino)-4-((3-(tert-butoxy)-3-oxo-1-(pyridin-2-yl)propyl)amino)-4-oxobutanoate (263 mg, 0.439 mmol) and pyridine (0.210 mL, 2.63 mmol) in DCM (3.00 mL) in a 1 dram vial at 0° C. was added POCl$_3$ (0.05 mL, 0.526 mmol) and allowed to warm up to RT and then stirred for 18 hrs. After stirring for 18 hrs the reaction was diluted with DCM and washed aqueous sat. sodium carbonate solution. The organic layer was then washed with brine; collected; dried over MgSO$_4$; filtered and volatiles evaporated to afford the crude product. The crude product was purified via silica gel chromatography (40 g column, 10-60% EtOAc:Hex) to afford the product (S)-allyl 2-((((9H-fluoren-9-yl)methoxy)carbonyl)amino)-3-(1-(2-(tert-butoxy)-2-oxoethyl)imidazo[1,5-a]pyridin-3-yl)propanoate (136 mg, 0.234 mmol, 53.3% yield) as a light brown foam. Analysis condition A: Retention time=1.20 min; ESI-MS(+) m/z 582.3 (M+H).

Step 6:

To a solution of (S)-allyl 2-((((9H-fluoren-9-yl)methoxy)carbonyl)amino)-3-(1-(2-(tert-butoxy)-2-oxoethyl)imidazo[1,5-a]pyridin-3-yl)propanoate (136 mg, 0.234 mmol) in THF (5 mL) at 0° C. was added N-methylaniline (0.130 mL, 1.17 mmol) followed by Pd(Ph$_3$P)$_4$ (27.0 mg, 0.023 mmol). The reaction was then allowed to warm up to RT and stirred for 1 hr. The reaction volatiles were evaporated to afford the crude material. The crude material was purified via prep HPLC (SunFire Prep C18 30×100 column size; 10-100% 95:5 CH$_3$CN:Water over a 15 minute gradient with 0.1% TFA buffer) to afford the product (S)-2-((((9H-fluoren-9-yl)methoxy)carbonyl)amino)-3-(1-(2-(tert-butoxy)-2-oxoethyl)imidazo[1,5-a]pyridin-3-yl)propanoic acid (105 mg, 0.194 mmol, 83% yield) as a white foam.

Preparation of 2-((((9H-fluoren-9-yl)methoxy)carbonyl)amino)-3-(3-(2-(tert-butoxy)-2-oxoethyl)-1H-indazol-1-yl)propanoic acid

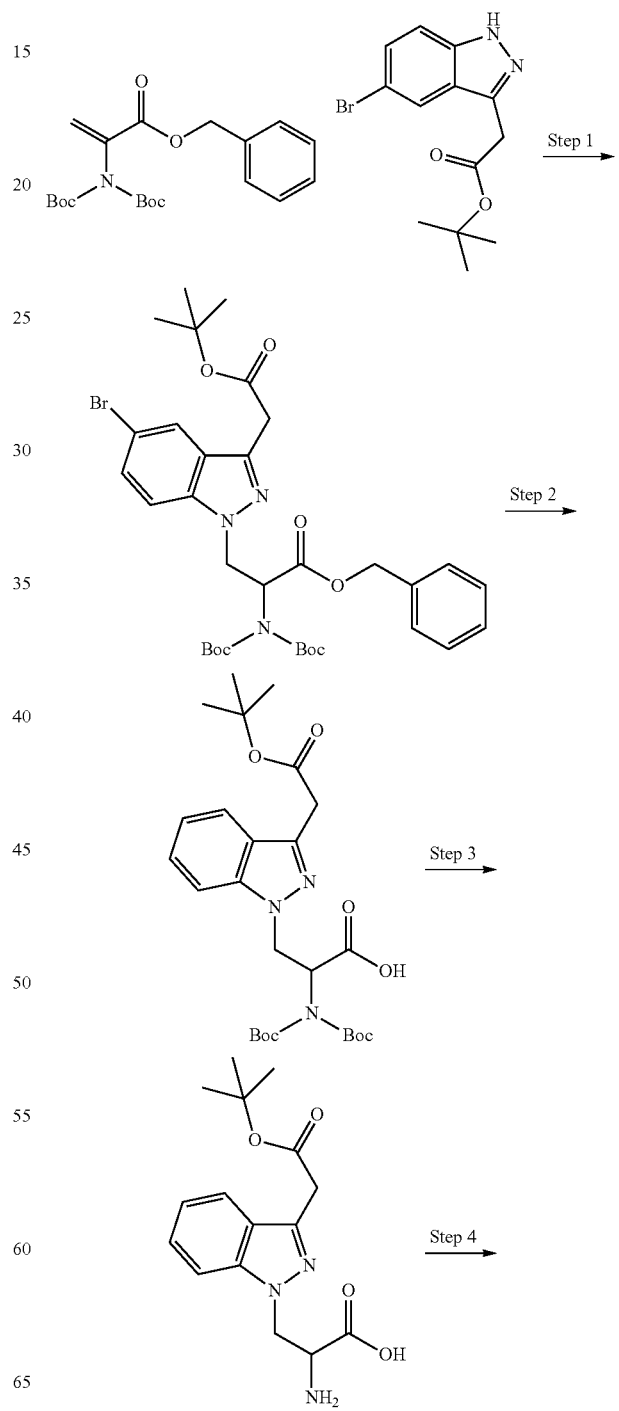

-continued

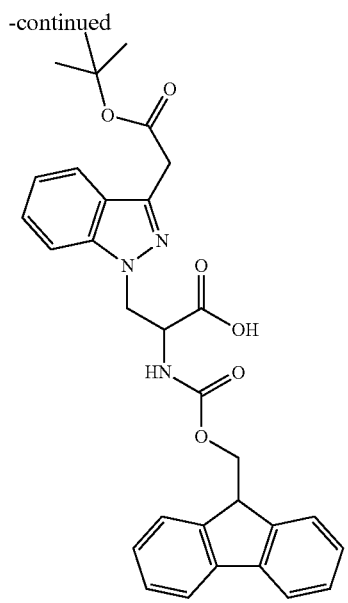

Step 1:

To a solution of tert-butyl 2-(5-bromo-1H-indazol-3-yl)acetate (500 mg, 1.6 mmol) and benzyl 2-{bis[(tert-butoxy)carbonyl]amino}prop-2-enoate (640 mg, 1.7 mmol) in acetonitrile (10 mL) was added potassium carbonate (1.3 g, 9.6 mmol) was added. The reaction was stirred at RT for 18 hrs. The reaction was diluted with EtOAc and washed with water. The organic layer was washed with brine; collected; dried over MgSO$_4$; filtered and volatiles evaporated to afford the crude product. The crude product was purified via reverse phase chromatography (55 g column, 5-100% CH$_3$CN:Water with 01.% TFA) to afford benzyl 2-(bis(((2-methyl-2-propanyl)oxy)carbonyl)amino)-3-(5-bromo-3-(2-((2-methyl-2-propanyl)oxy)-2-oxoethyl)-1H-indazol-1-yl)propanoate (1.12 g, 1.626 mmol, 101% yield) as a white solid. $^1$H NMR (500 MHz, methanol-d$_4$) δ 7.98-7.90 (m, 1H), 7.49 (dd, J=8.9, 1.8 Hz, 1H), 7.43-7.33 (m, 6H), 5.49 (t, J=7.2 Hz, 1H), 5.26 (d, J=2.7 Hz, 2H), 5.04 (d, J=7.1 Hz, 2H), 3.93-3.82 (m, 2H), 1.48-1.45 (m, 9H), 1.31-1.27 (m, 18H). Analysis condition A: Retention time=1.84 min; ESI-MS(+) m/z 712.2 (M+Na).

Step 2:

H$_2$ was bubbled through a solution of benzyl 2-(bis(((2-methyl-2-propanyl)oxy)carbonyl)amino)-3-(5-bromo-3-(2-((2-methyl-2-propanyl)oxy)-2-oxoethyl)-1H-indazol-1-yl)propanoate (1.0 g, 1.5 mmol) and Pd—C (0.16 g, 0.15 mmol) in MeOH (20 mL) for 5 minutes. The reaction was then left under positive pressure of H$_2$ for 2 hrs while stirring. The reaction was bubbled through with N$_2$, and then the slurry filtered through a nylon frit filter. The volatiles were evaporated under reduced pressure to afford 2-(bis(((2-methyl-2-propanyl)oxy)carbonyl)amino)-3-(3-(2-((2-methyl-2-propanyl)oxy)-2-oxoethyl)-1H-indazol-1-yl)propanoic acid (0.76 g, 1.5 mmol, 100% yield) as a sticky oil. Analysis condition A: Retention time=1.63 min; ESI-MS(+) m/z 542.2 (M+Na).

Step 3:

HCl (5.0 ml, 4.0 M) in dioxane was added to 2-(bis(((2-methyl-2-propanyl)oxy)carbonyl)amino)-3-(3-(2-((2-methyl-2-propanyl)oxy)-2-oxoethyl)-1H-indazol-1-yl)propanoic acid (781 mg, 1.503 mmol) and was stirred at 0° C. for 30 minutes then warmed up to RT and stirred for 30 min. The reaction volatiles were evaporated on under reduced pressure with no heat to afford 2-amino-3-(3-(2-(tert-butoxy)-2-oxoethyl)-1H-indazol-1-yl)propanoic acid, as the HCl salt (540 mg, 1.5 mmol, 100% yield) as a white solid. Analysis condition A: Retention time=1.18 min; ESI-MS(+) m/z 320 (M+H).

Step 4:

To a solution of 2-amino-3-(3-(2-(tert-butoxy)-2-oxoethyl)-1H-indazol-1-yl)propanoic acid, as the HCl salt (540 mg, 1.5 mmol) and sodium bicarbonate (630 mg, 7.5 mmol) in acetone (10 mL) and water (10 mL) was added (9H-fluoren-9-yl)methyl (2,5-dioxopyrrolidin-1-yl) carbonate (510 mg, 1.5 mmol). The reaction was stirred at RT for 18 hrs. The reaction was slowly acidified to pH 5 with aqueous HCl (1.0 M) with vigorous stirring. The aqueous layer was separated with 25 ml EtOAc. The organic layer was washed with water, followed by brine. The organic layer was collected; dried over MgSO$_4$ and volatiles evaporated under reduced pressure to afford the crude product. The crude material was purified via prep HPLC (10-100% CH$_3$CN:Water with 0.1% TFA) to afford the pure product 2-((((9H-fluoren-9-yl)methoxy)carbonyl)amino)-3-(3-(2-(tert-butoxy)-2-oxoethyl)-1H-indazol-1-yl)propanoic acid (131 mg, 0.242 mmol, 16.1% yield) as an off white solid. $^1$H NMR (500 MHz, methanol-d$_4$) δ 7.79 (d, J=7.4 Hz, 2H), 7.71 (d, J=8.2 Hz, 1H), 7.58-7.50 (m, 3H), 7.41-7.34 (m, 3H), 7.26 (q, J=7.4 Hz, 2H), 7.13 (t, J=7.5 Hz, 1H), 4.85-4.81 (m, 2H), 4.79-4.68 (m, 1H), 4.17 (dd, J=7.3, 1.7 Hz, 2H), 4.08 (d, J=7.3 Hz, 1H), 3.92 (s, 2H), 1.46-1.39 (m, 9H). Analysis condition A: Retention time=1.75 min; ESI-MS(+) m/z 542.1 (M+H).

Preparation of (S)-2-((((9H-fluoren-9-yl)methoxy)carbonyl)amino)-3-(1-(2-(tert-butoxy)-2-oxoethyl)-2-(tert-butoxycarbonyl)-1H-indol-3-yl)propanoic acid and (R)-2-((((9H-fluoren-9-yl)methoxy)carbonyl)amino)-3-(1-(2-(tert-butoxy)-2-oxoethyl)-2-(tert-butoxycarbonyl)-1H-indol-3-yl)propanoic acid

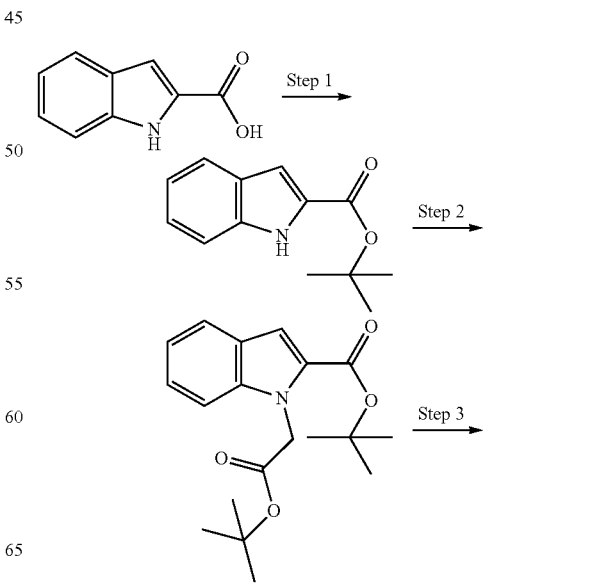

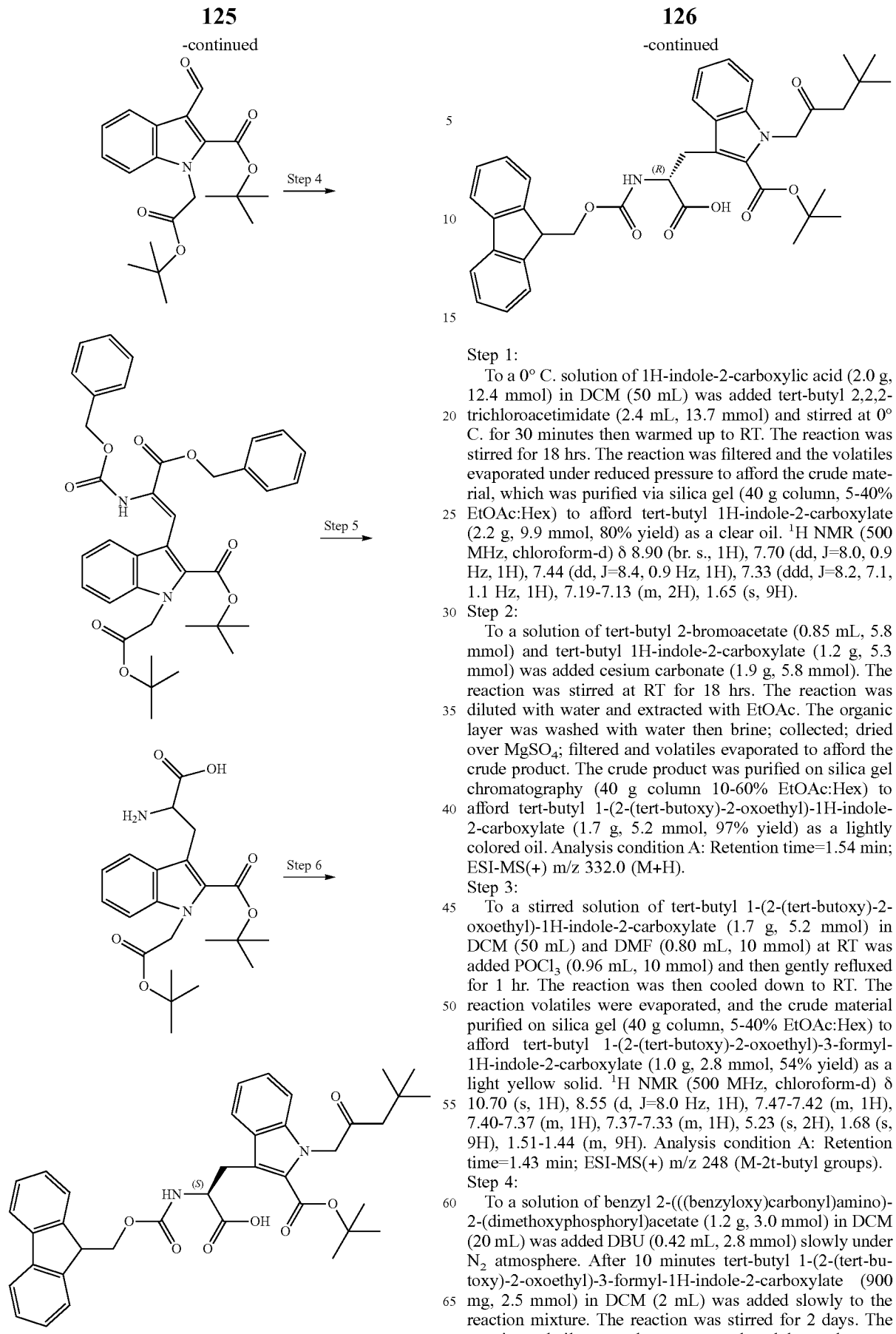

Step 1:
To a 0° C. solution of 1H-indole-2-carboxylic acid (2.0 g, 12.4 mmol) in DCM (50 mL) was added tert-butyl 2,2,2-trichloroacetimidate (2.4 mL, 13.7 mmol) and stirred at 0° C. for 30 minutes then warmed up to RT. The reaction was stirred for 18 hrs. The reaction was filtered and the volatiles evaporated under reduced pressure to afford the crude material, which was purified via silica gel (40 g column, 5-40% EtOAc:Hex) to afford tert-butyl 1H-indole-2-carboxylate (2.2 g, 9.9 mmol, 80% yield) as a clear oil. $^1$H NMR (500 MHz, chloroform-d) δ 8.90 (br. s., 1H), 7.70 (dd, J=8.0, 0.9 Hz, 1H), 7.44 (dd, J=8.4, 0.9 Hz, 1H), 7.33 (ddd, J=8.2, 7.1, 1.1 Hz, 1H), 7.19-7.13 (m, 2H), 1.65 (s, 9H).

Step 2:
To a solution of tert-butyl 2-bromoacetate (0.85 mL, 5.8 mmol) and tert-butyl 1H-indole-2-carboxylate (1.2 g, 5.3 mmol) was added cesium carbonate (1.9 g, 5.8 mmol). The reaction was stirred at RT for 18 hrs. The reaction was diluted with water and extracted with EtOAc. The organic layer was washed with water then brine; collected; dried over MgSO$_4$; filtered and volatiles evaporated to afford the crude product. The crude product was purified on silica gel chromatography (40 g column 10-60% EtOAc:Hex) to afford tert-butyl 1-(2-(tert-butoxy)-2-oxoethyl)-1H-indole-2-carboxylate (1.7 g, 5.2 mmol, 97% yield) as a lightly colored oil. Analysis condition A: Retention time=1.54 min; ESI-MS(+) m/z 332.0 (M+H).

Step 3:
To a stirred solution of tert-butyl 1-(2-(tert-butoxy)-2-oxoethyl)-1H-indole-2-carboxylate (1.7 g, 5.2 mmol) in DCM (50 mL) and DMF (0.80 mL, 10 mmol) at RT was added POCl$_3$ (0.96 mL, 10 mmol) and then gently refluxed for 1 hr. The reaction was then cooled down to RT. The reaction volatiles were evaporated, and the crude material purified on silica gel (40 g column, 5-40% EtOAc:Hex) to afford tert-butyl 1-(2-(tert-butoxy)-2-oxoethyl)-3-formyl-1H-indole-2-carboxylate (1.0 g, 2.8 mmol, 54% yield) as a light yellow solid. $^1$H NMR (500 MHz, chloroform-d) δ 10.70 (s, 1H), 8.55 (d, J=8.0 Hz, 1H), 7.47-7.42 (m, 1H), 7.40-7.37 (m, 1H), 7.37-7.33 (m, 1H), 5.23 (s, 2H), 1.68 (s, 9H), 1.51-1.44 (m, 9H). Analysis condition A: Retention time=1.43 min; ESI-MS(+) m/z 248 (M-2t-butyl groups).

Step 4:
To a solution of benzyl 2-(((benzyloxy)carbonyl)amino)-2-(dimethoxyphosphoryl)acetate (1.2 g, 3.0 mmol) in DCM (20 mL) was added DBU (0.42 mL, 2.8 mmol) slowly under N$_2$ atmosphere. After 10 minutes tert-butyl 1-(2-(tert-butoxy)-2-oxoethyl)-3-formyl-1H-indole-2-carboxylate (900 mg, 2.5 mmol) in DCM (2 mL) was added slowly to the reaction mixture. The reaction was stirred for 2 days. The reaction volatiles were then evaporated, and the crude material purified on silica gel (80 g column 0-25% EtOAc:Hex) to afford (Z)-tert-butyl 3-(3-(benzyloxy)-2-(((benzyloxy)carbonyl)amino)-3-oxoprop-1-en-1-yl)-1-(2-(tert-butoxy)-2-oxoethyl)-1H-indole-2-carboxylate (680 mg, 1.1 mmol, 43% yield) as a clear oil. Analysis condition A: Retention time=1.61 min; ESI-MS(+) m/z 663.2 (M+Na).

Step 5:

H$_2$ was slowly bubbled through a solution of (Z)-tert-butyl 3-(3-(benzyloxy)-2-(((benzyloxy)carbonyl)amino)-3-oxoprop-1-en-1-yl)-1-(2-(tert-butoxy)-2-oxoethyl)-1H-indole-2-carboxylate (680 mg, 1.1 mmol) and Pd—C (28 mg, 0.027 mmol) in MeOH (10 mL) and stirred at RT for 2 days. The reaction slurry was filtered through a nylon frit filter and the volatiles evaporated to afford the crude product 2-amino-3-(1-(2-(tert-butoxy)-2-oxoethyl)-2-(tert-butoxycarbonyl)-1H-indol-3-yl)propanoic acid (440 mg, 1.1 mmol, 99% yield). Analysis condition A: Retention time=1.04 min; ESI-MS(+) m/z 419.3 (M+H).

Step 6:

To a solution of 2-amino-3-(1-(2-(tert-butoxy)-2-oxoethyl)-2-(tert-butoxycarbonyl)-1H-indol-3-yl)propanoic acid (440 mg, 1.1 mmol) and sodium bicarbonate (450 mg, 5.3 mmol) in acetone (5.00 mL) and water (10 mL) was added (9H-fluoren-9-yl)methyl (2,5-dioxopyrrolidin-1-yl)carbonate (358 mg, 1.061 mmol). The reaction was stirred for 18 hrs. The reaction was slowly acidified to pH 5 with aqueous HCl (1.0 M) with vigorous stirring. The acidified solution was then separated with DCM. The organic layer was washed with water, followed by brine. The organic layer was collected; dried over MgSO$_4$, and the volatiles evaporated under reduced pressure to afford the crude product. The crude material was purified on silica gel (40 g column, 20-80% EtOAc:Hex) to give the product as a white foam. The material was further purified via SFC chiral purification team to get the products (S)-2-(((((9H-fluoren-9-yl)methoxy)carbonyl)amino)-3-(1-(2-(tert-butoxy)-2-oxoethyl)-2-(tert-butoxycarbonyl)-1H-indol-3-yl)propanoic acid (100 mg, 0.156 mmol, 14.71% yield) and (R)-2-(((((9H-fluoren-9-yl)methoxy)carbonyl)amino)-3-(1-(2-(tert-butoxy)-2-oxoethyl)-2-(tert-butoxycarbonyl)-1H-indol-3-yl)propanoic acid (98 mg, 0.153 mmol, 14.42% yield) as white foams. Analysis condition A: Retention time=1.53 min; ESI-MS(+) m/z 663.2 (M+Na).

Preparation of (R)-2-(((((9H-fluoren-9-yl)methoxy)carbonyl)amino)-3-(3-((R)-1-(tert-butoxy)-1-oxopropan-2-yl)-2-oxo-2,3-dihydro-1H-benzo[d]imidazol-1-yl)propanoic acid

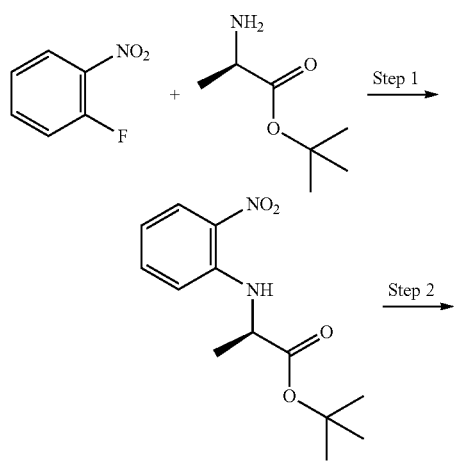

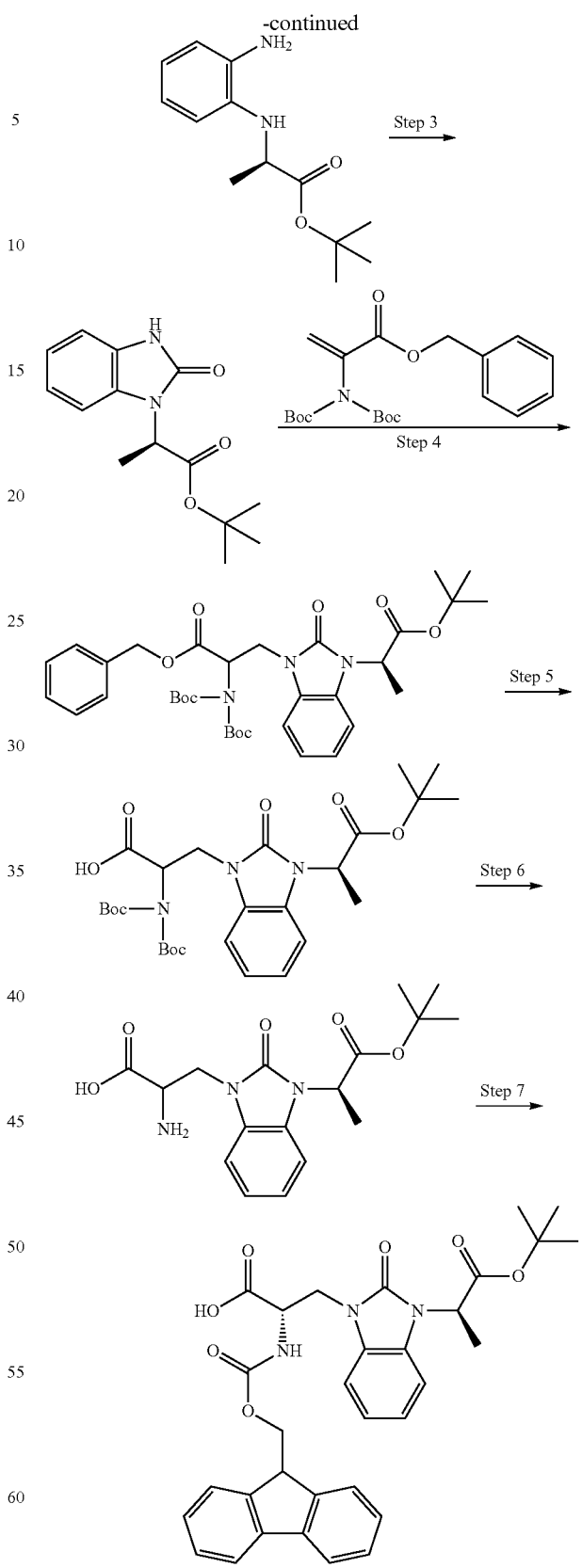

Step 1:

A 40 mL vial equipped with a stir bar was charged with (R)-tert-butyl 2-aminopropanoate mono HCl salt (2.0 g, 11 mmol), 1-fluoro-2-nitrobenzene (1.553 g, 11.01 mmol), potassium carbonate (3.04 g, 22.0 mmol) and DMF (30 mL). The vial was placed in a 70° C. heating block with for 18 h. The reaction mixture was transferred to a 500 mL separatory funnel and was diluted with water (100 mL). The mixture was extracted with EtOAc (2×100 mL). The combined organics were washed with water (100 mL); then brine (75 mL); dried over $MgSO_4$; filtered; then concentrated in vacuo. The resulting residue was dissolved in a minimum of acetone and then was concentrated onto diatomaceous earth (Celite®) in vacuo. The resulting powder was subjected to silica gel chromatography (40 g column, hexanes:EtOAc 100:0→90:10) to afford (R)-tert-butyl 2-((2-nitrophenyl) amino)propanoate as an orange oil (2.359 g, 80%).
Step 2:
To a 100 mL r.b. flask equipped with a stir bar and charged with (R)-tert-butyl 2-((2-nitrophenyl)amino)propanoate (2.359 g, 8.86 mmol) was added MeOH (40 mL) and palladium on carbon (Degussa type E101 NE/W, 10% Pd dry basis, ca 50% wt water, 0.471 g, 0.221 mmol). The flask was sealed with a rubber septum and the mixture was sparged with $N_2$ for 15 minutes, then mixture was then sparged with $H_2$ for 5 minutes. The mixture was stirred under balloon pressure of $H_2$ for 16 h. The mixture was filtered through diatomaceous earth (Celite®) and the filter pad was extracted with MeOH. The combined filtrate was concentrated in vacuo, and the resulting residue was subjected to silica gel chromatography (25 g Interchim 25 micron column, hexanes:EtOAc 100:0→50:50) to afford (R)-tert-butyl 2-((2-aminophenyl)amino)propanoate as a red liquid (1.100 g, 53%). 13C-NMR (100 MHz, $CDCl_3$) δ 173.86, 135.61, 134.82, 119.89, 119.25, 116.36, 113.07, 80.95, 52.65, 27.59, 18.73.
Step 3:
To a 50 mL flask charged equipped with a stir bar and charged with (R)-tert-butyl 2-((2-aminophenyl)amino)propanoate (1.100 g, 4.66 mmol) was added THF (25 mL), DIPEA (3.00 mL, 17.5 mmol) and 1,1'-Carbonyldiimidazole (2.83 g, 17.5 mmol), respectively. The vial was sealed and the solution was stirred at room temperature for 2 h. The reaction solution was transferred to a 250 mL separatory funnel and was diluted with $Et_2O$ (75 mL), then washed with aq HCl (1M, 50 mL). The organic phase was washed with water (50 mL); then brine (50 mL); dried over $MgSO_4$; filtered; then concentrated in vacuo onto diatomaceous earth (Celite®). The resulting powder was subjected to silica gel chromatography (40 g $SiO_2$ column, hexanes:EtOAc 90:10→50:50) to afford (R)-tert-butyl 2-(2-oxo-2,3-dihydro-1H-benzo[d]imidazol-1-yl)propanoate as an off-white solid foam (828.1 mg, 68%). 1H-NMR (500 MHz, $CDCl_3$) δ 9.09 (br. s., 1H), 7.13-7.03 (m, 3H), 7.02-6.95 (m, 1H), 5.19 (q, J=7.4 Hz, 1H), 1.70 (d, J=7.4 Hz, 3H), 1.41 (s, 9H)
Step 4:
To a 40 mL vial equipped with a stir bar was added benzyl 2-{bis[(tert-butoxy)carbonyl]amino}prop-2-enoate (1.192 g, 3.16 mmol), (R)-tert-butyl 2-(2-oxo-2,3-dihydro-1H-benzo[d]imidazol-1-yl)propanoate (828.1 mg, 3.16 mmol), and MeCN (15 mL). To the solution was added potassium carbonate (2.618 g, 18.94 mmol). The vial was capped and placed in a 60° C. heating block with stirring for 2 h. The reaction mixture was filtered and the filtrate was concentrated in vacuo. The resulting residue was dissolved in acetone and then was concentrated onto diatomaceous earth (Celite®) in vacuo. The resulting powder was subjected to $SiO_2$ chromatography (80 g silica gel column, hexanes: EtOAc 100:0→50:50) to afford benzyl 2-{bis[(tert-butoxy) carbonyl]amino}-3-{3-[(2R)-1-(tert-butoxy)-1-oxopropan-2-yl]-2-oxo-2,3-dihydro-1H-1,3-benzodiazol-1-yl}propanoate as a colorless solid foam (1:1 ratio of diastereomers, 1.841 g, 91%).
Step 5:
To a 100 mL r.b. flask equipped with a stir bar and charged with benzyl 2-{bis[(tert-butoxy)carbonyl]amino}-3-{3-[(2R)-1-(tert-butoxy)-1-oxopropan-2-yl]-2-oxo-2,3-dihydro-1H-1,3-benzodiazol-1-yl}propanoate (920.3 mg, 1.439 mmol) in MeOH (20 mL) was added palladium on carbon (Degussa type E101 NE/W, 10% Pd dry basis, ca 50% wt water, 153 mg, 0.072 mmol). The flask was capped with a rubber septum. The solution was sparged with $N_2$ for 15 minutes, then the solution was then sparged with $H_2$ for 5 minutes. The system was then placed under balloon pressure $H_2$ while the mixture was stirred for 1.5 h. The solution was sparged with $N_2$ for 15 minutes, then was filtered through diatomaceous earth (Celite®). The filter cake was extracted with MeOH and the combined filtrate was concentrated in vacuo to afford 2-{bis[(tert-butoxy) carbonyl]amino}-3-{3-[(2R)-1-(tert-butoxy)-1-oxopropan-2-yl]-2-oxo-2,3-dihydro-1H-1,3-benzodiazol-1-yl}propanoic acid as a colorless solid foam (1:1 ratio of diastereomers, 791 mg, 100%).
Step 6:
To a 100 mL r.b. flask charged with 2-{bis[(tert-butoxy) carbonyl]amino}-3-{3-[(2R)-1-(tert-butoxy)-1-oxopropan-2-yl]-2-oxo-2,3-dihydro-1H-1,3-benzodiazol-1-yl}propanoic acid (0.791 g, 1.44 mmol) and cooled with a 0° C. bath was added a 0° C. solution of HCl in dioxane (5 mL, 4 M, 20 mmol). The solution was stirred at 0° C. for 1 h and then was concentrated in vacuo and analyzed to find partial conversion to the desired product. The 100 mL r.b. flask containing the solids was returned to the 0° C. bath and to the flask was added a 0° C. solution of HCl in dioxane (5 mL, 4 M, 20 mmol). The solution was stirred at 0° C. for 1.5 h and then was concentrated in vacuo to afford crude 2-amino-3-(3-((R)-1-(tert-butoxy)-1-oxopropan-2-yl)-2-oxo-2,3-dihydro-1H-benzo[d]imidazol-1-yl)propanoic acid HLC salt as a white solid which was used in its entirety in the next step.
Step 7:
To a solution of 2-amino-3-(3-((R)-1-(tert-butoxy)-1-oxopropan-2-yl)-2-oxo-2,3-dihydro-1H-benzo[d]imidazol-1-yl) propanoic acid (1.439 mmol) in water (12 mL) and acetone (6 mL) was added sodium bicarbonate (604 mg, 7.20 mmol), then (9H-fluoren-9-yl)methyl (2,5-dioxopyrrolidin-1-yl) carbonate (485 mg, 1.44 mmol). The solution was stirred overnight (18 h). The reaction mixture was concentrated onto diatomaceous earth (Celite®) in vacuo and the resulting powder was subjected to C18 chromatography (column=55 g Interchim Puriflash C18-HP 30 micron; Solvent A=0.1% TFA in water; Solvent B=0.1% TFA in acetonitrile; gradient=15% B to 80% B over 15 column volumes). The product-containing fractions were pooled and concentrated in vacuo to remove the volatiles and afforded an aqueous solution which was transferred to a 125 mL separatory funnel with EtOAc. The mixture was further diluted with brine (10 mL). The mixture was extracted with EtOAc (2×50 mL). The combined organics were washed with brine (25 mL); dried over $MgSO_4$; filtered; then concentrated in vacuo to afford a yellow solid foam, the product as a mixture of diastereomers, 468.2 mg. A portion of the material was subjected to SFC purification as follows: Column=Chiralpak AD-H preparative column, 30×250 mm, 5 μm; Mobile Phase=20% MeOH in CO2, 150 bar; Temp=35° C.; Flow rate=70.0 mL/min. for 19 min.; UV monitored @ 220 nm; Injection=0.25 ml of ~30 mg/mL solution in 2:1 MeOH:CHCl₃ (~246 mg purified by stacked injection). The peak at 7.63 min. was collected to afford (S)-2-((((9H-fluoren-9-yl)methoxy)carbonyl)amino)-3-(3-((R)-1-(tert-butoxy)-1-oxopropan-2-yl)-2-oxo-2,3-dihydro-1H-benzo[d]imidazol-1-yl)propanoic acid. ¹H NMR (400 MHz, CD₃OD) δ 7.78 (d, J=7.5 Hz, 2H), 7.57 (d, J=7.5 Hz, 2H), 7.37 (t, J=7.4 Hz, 2H), 7.32-7.22 (m, 3H), 7.13-7.03 (m, 3H), 5.09 (q, J=7.3 Hz, 1H), 4.68 (d, J=4.3 Hz, 1H), 4.47-4.38 (m, 1H), 4.27 (dd, J=14.7, 8.9 Hz, 1H), 4.17-4.11 (m, 2H), 4.10-4.03 (m, 1H), 1.59 (d, J=7.3 Hz, 3H), 1.36 (s, 9H).

Preparation of 2-((((9H-fluoren-9-yl)methoxy)carbonyl)amino)-3-(3-(2-(tert-butoxy)-2-oxoethyl)-2-oxo-2,3-dihydro-1H-benzo[d]imidazol-1-yl)propanoic acid

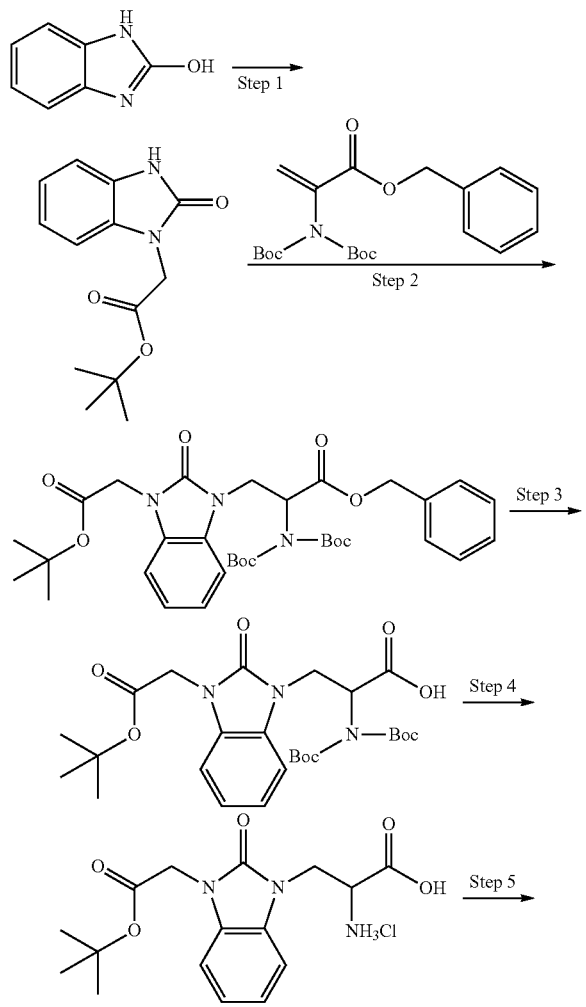

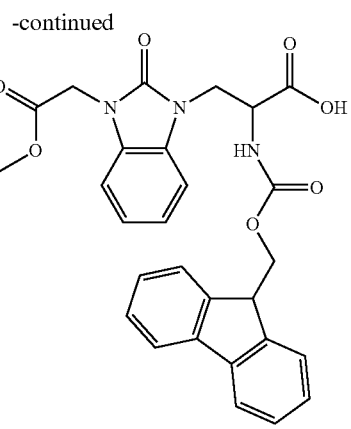

Step 1:

To a dry 250 mL r.b. flask equipped with a Schlenk adapter and placed under N₂ atm was added DMF (60 mL), 1H-benzo[d]imidazol-2-ol (6.93 g, 51.7 mmol) and tert-butyl 2-bromoacetate (9.6 g, 49.2 mmol). The solution was cooled to 0° C. To the solution was added sodium hydride (60% w/w dispersion in oil, 2.264 g, 56.6 mmol). The mixture was stirred at 0° C. (t=0) for 1 h. To the solution was added sat. aq. NaHCO₃ (60 mL). The mixture became very thick and not possible to stir. The mixture was briefly warmed to room temperature, then the mixture was transferred to a 1 L separatory funnel using water (250 mL). The mixture was extracted with EtOAc (400 mL) and the organic phase was dried over MgSO₄; filtered, then concentrated in vacuo. The residue was dissolved in a minimum of acetone and then was concentrated onto diatomaceous earth (Celite®) in vacuo. This powder was subjected to SiO₂ chromatography (hexanes:EtOAc 100:0→0:100, product is second major peak to elute) to afford tert-butyl 2-(2-oxo-2,3-dihydro-1H-benzo[d]imidazol-1-yl)acetate as a pale yellow solid (3.301 g, 27%). 1H-NMR (500 MHz, CDCl₃) δ 8.60 (br. s., 1H), 7.12-7.04 (m, 3H), 6.92-6.86 (m, 1H), 4.53 (s, 2H), 1.47 (s, 9H).

Step 2:

To a 40 mL vial equipped with a stir bar was added benzyl 2-{bis[(tert-butoxy)carbonyl]amino}prop-2-enoate (1.382 g, 3.66 mmol), tert-butyl 2-(2-oxo-2,3-dihydro-1H-benzo[d]imidazol-1-yl)acetate (1.00 g, 4.03 mmol), and MeCN (18 mL). To the solution was added potassium carbonate (3.04 g, 22.0 mmol). The vial was capped and placed in a 50° C. heating block with stirring for 2 h. The reaction mixture was filtered through diatomaceous earth (Celite®) and the filter cake was extracted with MeCN (20 mL). The filtrate was concentrated in vacuo and the residue was dissolved in a minimum of acetone and then concentrated onto diatomaceous earth (Celite®) in vacuo. The resulting powder was subjected to SiO₂ chromatography (80 g silica gel column, hexanes:EtOAc 100:0→50:50) to afford benzyl 2-{bis[(tert-butoxy)carbonyl]amino}-3-{3-[2-(tert-butoxy)-2-oxoethyl]-2-oxo-2,3-dihydro-1H-1,3-benzodiazol-1-yl}propanoate as a yellow oil (2.167 g, 95% yield). 1H-NMR (500 MHz, CDCl₃) δ 7.38-7.29 (m, 5H), 7.06-7.01 (m, 2H), 7.00-6.95 (m, 1H), 6.85-6.80 (m, 1H), 5.47 (dd, J=9.8, 4.3 Hz, 1H), 5.22 (s, 2H), 4.66-4.49 (m, 3H), 4.40 (d, J=17.7 Hz, 1H), 1.44 (s, 9H), 1.31 (s, 18H).

Step 3:

To a 100 mL r.b. flask equipped with a stir bar and charged with benzyl 2-{bis[(tert-butoxy)carbonyl]amino}-3-{3-[2-(tert-butoxy)-2-oxoethyl]-2-oxo-2,3-dihydro-1H-1,3-benzodiazol-1-yl}propanoate (1.083 g, 1.731 mmol) in methanol (20 mL) was added palladium on carbon (Degussa type E101 NE/W, 10% Pd dry basis, ca 50% wt water, 0.184 g, 0.087 mmol). The flask was capped with a rubber septum. The solution was sparged with $N_2$ for 15 minutes, then the solution was then sparged with $H_2$ for 5 minutes. The system was then placed under balloon pressure $H_2$ while the mixture was stirred for 2 h. The solution was sparged with $N_2$ for 15 minutes, then to the solution was added diatomaceous earth (Celite®). The mixture was filtered and the filter cake was extracted with methanol. The filtrate was concentrated in vacuo to afford 2-{bis[(tert-butoxy)carbonyl]amino}-3-{3-[2-(tert-butoxy)-2-oxoethyl]-2-oxo-2,3-dihydro-1H-1,3-benzodiazol-1-yl}propanoic acid as (917.7 mg, 99%).

Step 4:

To a 100 mL r.b. flask charged with 2-{bis[(tert-butoxy)carbonyl]amino}-3-{3-[2-(tert-butoxy)-2-oxoethyl]-2-oxo-2,3-dihydro-1H-1,3-benzodiazol-1-yl}propanoic acid (917.7 mg, 1.713 mmol) and cooled with a 0° C. bath was added a 0° C. solution of HCl in dioxane (5 mL, 4 M, 20 mmol). The solution was stirred at 0° C. for 1 h and then was concentrated in vacuo. Co-evaporation with dichloroethane (50 mL) was used to remove trace solvent to afford 2-amino-3-(3-(2-(tert-butoxy)-2-oxoethyl)-2-oxo-2,3-dihydro-1H-benzo[d]imidazol-1-yl)propanoic acid HCl salt as a colorless solid (710.8 mg). The entirety of this material was used in step 6.

Step 5:

To a solution of 2-amino-3-(3-(2-(tert-butoxy)-2-oxoethyl)-2-oxo-2,3-dihydro-1H-benzo[d]imidazol-1-yl)propanoic acid mono HCl salt (1.713 mmol) in water (12 mL) and acetone (6 mL) was added sodium bicarbonate (720 mg, 8.57 mmol), then (9H-fluoren-9-yl)methyl (2,5-dioxopyrrolidin-1-yl) carbonate (578 mg, 1.71 mmol). The solution was stirred at room temperature for 18 h. The reaction solution was concentrated onto diatomaceous earth (Celite®) in vacuo and the resulting solid was subjected to C18 chromatography (Interchim C18 55 g 30 micron column, gradient=water:MeCN 50:50 to water:MeCN 0:100 over 10 CV, hold at 100% MeCN for 5 CV). The combined product fractions were concentrated in vacuo to afford an aqueous phase that was then extracted with EtOAc (2×100 mL). The combined organic phase was dried over $MgSO_4$; filtered; then concentrated in vacuo to afford 2-((((9H-fluoren-9-yl)methoxy)carbonyl)amino)-3-(3-(2-(tert-butoxy)-2-oxoethyl)-2-oxo-2,3-dihydro-1H-benzo[d]imidazol-1-yl)propanoic acid as a white solid (483.2 mg, 22% over two steps). $^1$H-NMR (500 MHz, acetone-$d_6$) □ 7.84 (d, J=7.6 Hz, 2H), 7.71-7.61 (m, 2H), 7.40 (t, J=7.4 Hz, 2H), 7.34-7.26 (m, 3H), 7.12-7.00 (m, 4H), 4.72 (td, J=8.0, 4.8 Hz, 1H), 4.63-4.54 (m, 2H), 4.47-4.36 (m, 2H), 4.25-4.21 (m, 2H), 4.20-4.14 (m, 1H), 1.43 (s, 9H).

PREPARATION OF EXAMPLE 1001

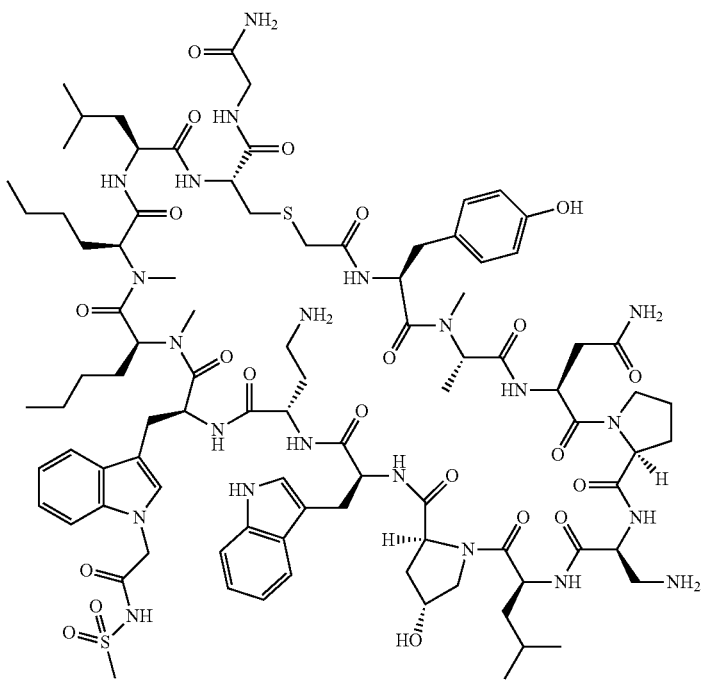 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)NS(C)(=O)=O)c3ccccc23)C(=O)N1C]

EXAMPLE 1001

Example 1001 was prepared following "General Synthetic Sequence A". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 8.5 mg, and its estimated purity by LCMS analysis was 100%.

Analysis condition C: Retention time=1.59 min; ESI-MS(+) m/z 983.1 (M+2H)

Analysis condition D: Retention time=1.32 min; ESI-MS(+) m/z 983.0 (M+2H)

ESI-HRMS(+) m/z: Calculated: 982.4750 Found: 982.4796.

PREPARATION OF EXAMPLE 1002

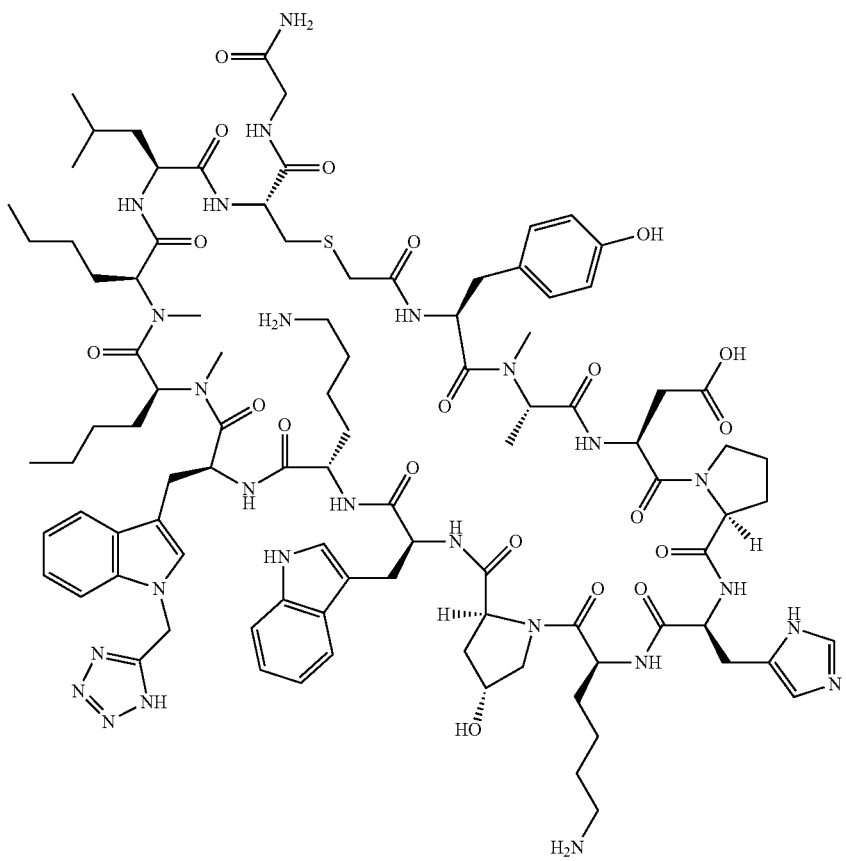 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(Cc3nnn[nH]3)c3ccccc23)C(=O)N1C]

EXAMPLE 1002

Example 1002 was prepared following "General Synthetic Sequence A". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 30 minutes, then a 3-minute hold at 100% B; Flow: 20 mL/min. Fractions containing the desired product were combined and dried via centrifugal evaporation. The yield of the product was 2.1 mg, and its estimated purity by LCMS analysis was 100%.
Analysis condition C: Retention time=1.45 min; ESI-MS(+) m/z 1003.2 (M+2H)
Analysis condition D: Retention time=1.17 min; ESI-MS(+) m/z 1004.1 (M+2H)
ESI-HRMS(+) m/z: Calculated: 1003.5145 Found: 1003.5111.

PREPARATION OF EXAMPLE 1003

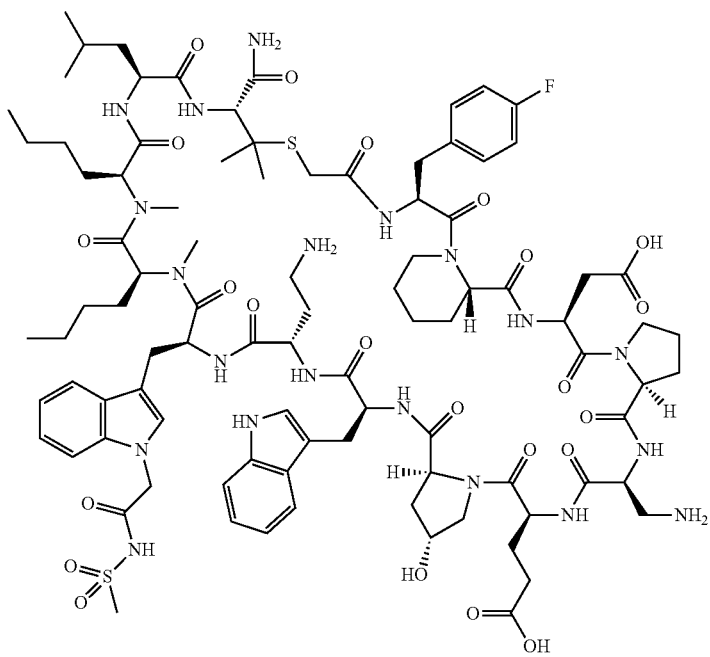 [SMILES: CCCC[C@H]1C(=O)N(C)[C@@H](CCCC)C(=O)N[C@@H](CC(C)C)C(=O)N[C@H](C(N)=O)C(C)(C)SCC(=O)N[C@@H](Cc2ccc(F)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)NS(C)(=O)=O)c3ccccc23)C(=O)N1C]

EXAMPLE 1003

Example 1003 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 96%.

Analysis condition C: Retention time=1.76 min; ESI-MS(+) m/z 1979.0 (M+H)

Analysis condition D: Retention time=1.63 min; ESI-MS(+) m/z 991.2 (M+2H)

ESI-HRMS(+) m/z: Calculated: 990.4633 Found: 990.4601.

PREPARATION OF EXAMPLE 1004

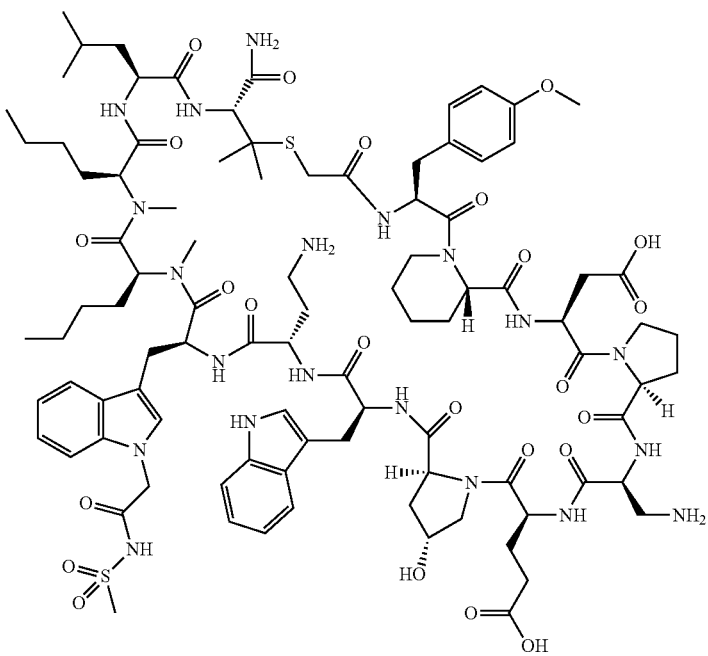 [SMILES: CCCC[C@H]1C(=O)N(C)[C@@H](CCCC)C(=O)N[C@@H](CC(C)C)C(=O)N[C@H](C(N)=O)C(C)(C)SCC(=O)N[C@@H](Cc2ccc(OC)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)NS(C)(=O)=O)c3ccccc23)C(=O)N1C]

EXAMPLE 1004

Example 1004 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 12-52% B over 30 minutes, then a 5-minute hold at 100% B; Flow: 20 mL/min. Fractions containing the desired product were combined and dried via centrifugal evaporation. The yield of the product was 7.3 mg, and its estimated purity by LCMS analysis was 100%.

Analysis condition C: Retention time=1.33 min; ESI-MS(+) m/z 996.6 (M+2H)

Analysis condition D: Retention time=1.62 min; ESI-MS(+) m/z 996.5 (M+2H)

ESI-HRMS(+) m/z: Calculated: 996.4733 Found: 996.4698.

PREPARATION OF EXAMPLE 1005

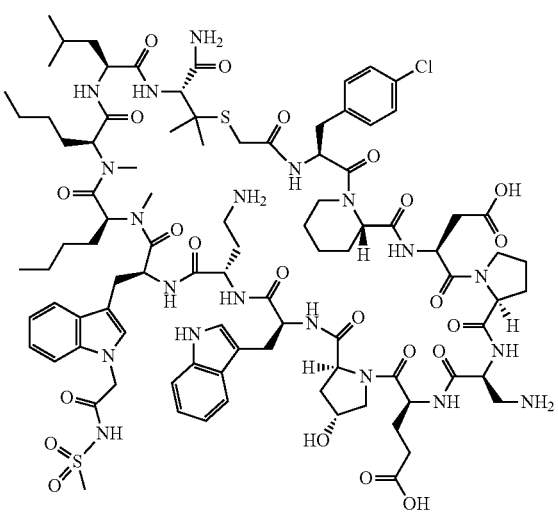 [SMILES: CCCC[C@H]1C(=O)N(C)[C@@H](CCCC)C(=O)N[C@@H](CC(C)C)C(=O)N[C@H](C(N)=O)C(C)(C)SCC(=O)N[C@@H](Cc2ccc(Cl)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)NS(C)(=O)=O)c3ccccc23)C(=O)N1C]

EXAMPLE 1005

Example 1005 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 12-52% B over 30 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 98%.

Analysis condition C: Retention time=1.82 min; ESI-MS(+) m/z 999.1 (M+2H).

Analysis condition D: Retention time=1.67 min; ESI-MS(+) m/z 999.6 (M+2H)

ESI-HRMS(+) m/z: Calculated: 998.4486 Found: 998.4448.

PREPARATION OF EXAMPLE 1006

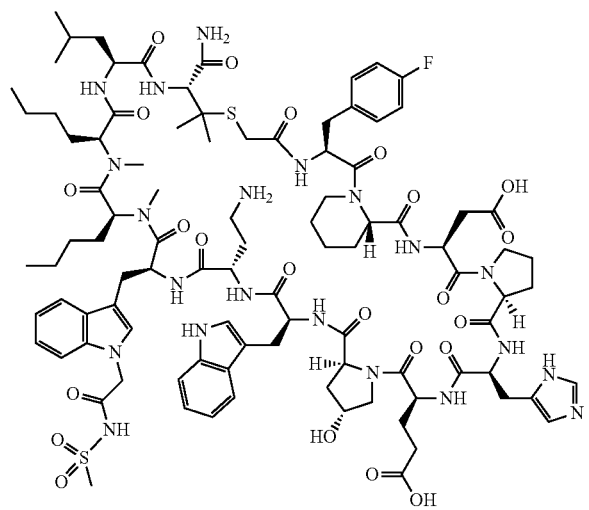 [SMILES: CCCC[C@H]1C(=O)N(C)[C@@H](CCCC)C(=O)N[C@@H](CC(C)C)C(=O)N[C@H](C(N)=O)C(C)(C)SCC(=O)N[C@@H](Cc2ccc(Cl)cc2)C(=O)N2CCCC[C@H]2C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)NS(C)(=O)=O)c3ccccc23)C(=O)N1C]

EXAMPLE 1006

Example 1006 was prepared following "General Synthetic Sequence A". The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 8-48% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 12-52% B over 30 minutes, then a 5-minute hold at 100% B; Flow: 20 mL/min. Fractions containing the desired product were combined and dried via centrifugal evaporation. The yield of the product was 4.8 mg, and its estimated purity by LCMS analysis was 99%.

Analysis condition C: Retention time=1.72 min; ESI-MS(+) m/z 1016.6 (M+2H)

Analysis condition D: Retention time=1.62 min; ESI-MS(+) m/z 1015.9 (M+2H)

PREPARATION OF EXAMPLE 1007

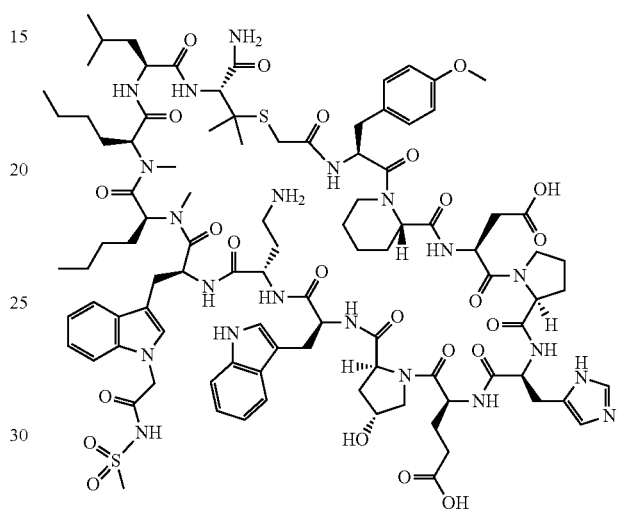

EXAMPLE 1007

Example 1007 was prepared following "General Synthetic Sequence A". The crude material was purified via preparative LC/MS with the following conditions: Column: waters xbridge c-18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 8-48% B over 30 minutes, then a 5-minute hold at 100% B; Flow: 20 mL/min. Fractions containing the desired product were combined and dried via centrifugal evaporation. The yield of the product was 6.6 mg, and its estimated purity by LCMS analysis was 96%.

Analysis condition C: Retention time=1.58 min; ESI-MS(+) m/z 1022.5 (M+2H)

Analysis condition D: Retention time=1.56 min; ESI-MS(+) m/z 1022.3 (M+2H)

ESI-HRMS(+) m/z: Calculated: 1021.9788 Found: 1021.9747.

143
PREPARATION OF EXAMPLE 1008

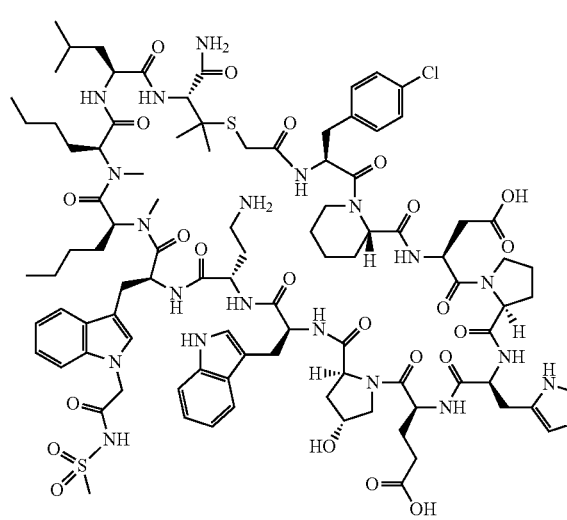

EXAMPLE 1008

Example 1008 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 12-52% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 12-52% B over 30 minutes, then a 5-minute hold at 100% B; Flow: 20 mL/min. Fractions containing the desired product were combined and dried via centrifugal evaporation. The yield of the product was 3.5 mg, and its estimated purity by LCMS analysis was 98%.

Analysis condition C: Retention time=1.75 min; ESI-MS(+) m/z 1024.8 (M+2H)

Analysis condition D: Retention time=1.98 min; ESI-MS(+) m/z 1024.7 (M+2H)

ESI-HRMS(+) m/z: Calculated: 1023.9540 Found: 1023.9506.

144
PREPARATION OF EXAMPLE 1009

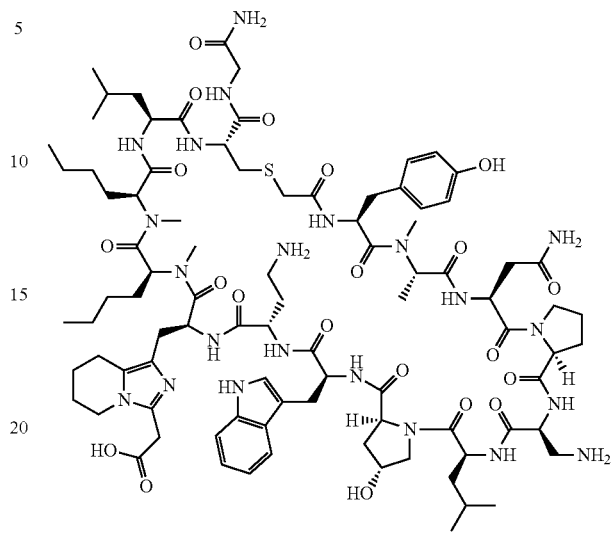

EXAMPLE 1009

Example 1009 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 8-48% B over 30 minutes, then a 5-minute hold at 100% B; Flow: 20 mL/min. Fractions containing the desired product were combined and dried via centrifugal evaporation. The yield of the product was 1.8 mg, and its estimated purity by LCMS analysis was 96%.

Analysis condition C: Retention time=1.58 min; ESI-MS(+) m/z 947.1 (M+2H)

Analysis condition D: Retention time=1.44 min; ESI-MS(+) m/z 946.4 (M+2H)

ESI-HRMS(+) m/z: Calculated: 946.4980 Found: 946.4946.

PREPARATION OF EXAMPLE 1010

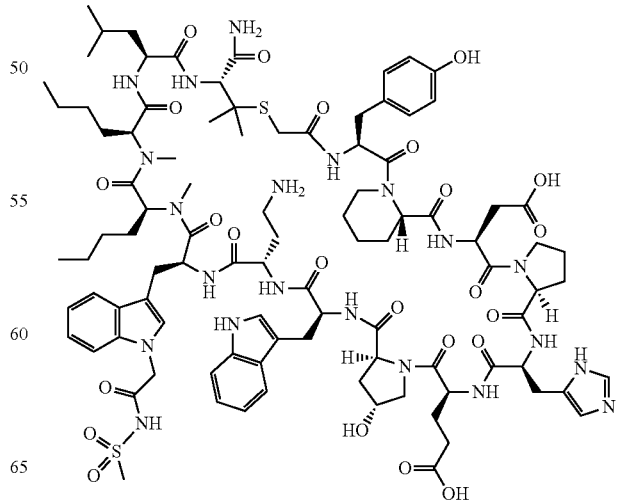

EXAMPLE 1010

Example 1010 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-45% B over 35 minutes, then a 5-minute hold at 100% B; Flow: 20 mL/min. Fractions containing the desired product were combined and dried via centrifugal evaporation. The yield of the product was 2.0 mg, and its estimated purity by LCMS analysis was 93%.

Analysis condition C: Retention time=1.54 min; ESI-MS(+) m/z 1015.6 (M+2H).

PREPARATION OF EXAMPLE 1011

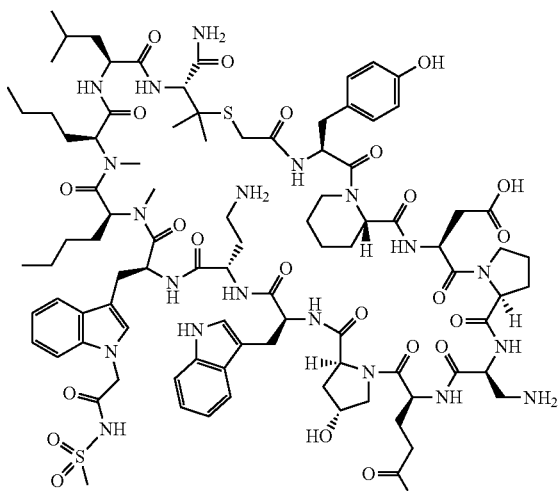

EXAMPLE 1011

Example 1011 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-100% B over 30 minutes, then a 5-minute hold at 100% B; Flow: 20 mL/min. Fractions containing the desired product were combined and dried via centrifugal evaporation. The yield of the product was 2.0 mg, and its estimated purity by LCMS analysis was 94%.

Analysis condition C: Retention time=1.52 min; ESI-MS(+) m/z 989.7 (M+2H)

Analysis condition D: Retention time=1.43 min; ESI-MS(+) m/z 1975.9 (M−H)

ESI-HRMS(+) m/z: Calculated: 989.4655 Found: 989.4619.

PREPARATION OF EXAMPLE 1012

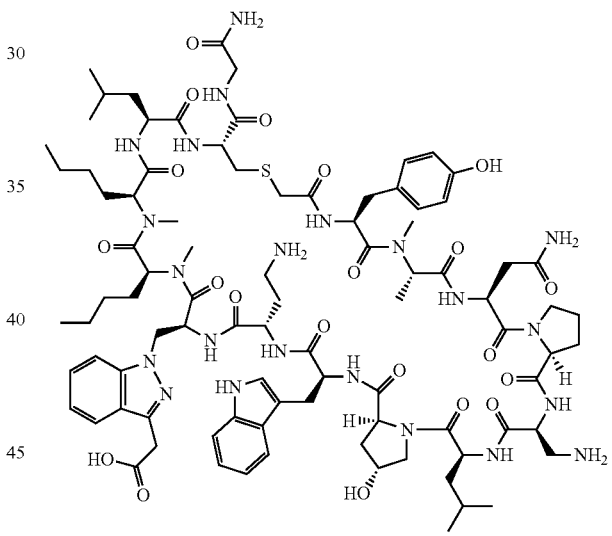

EXAMPLE 1012

Example 1012 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 2-42% B over 30 minutes, then a 5-minute hold at 100% B; Flow: 20 mL/min. Fractions containing the desired product were combined and dried via centrifugal evaporation. The yield of the product was 9.8 mg, and its estimated purity by LCMS analysis was 97%.

Analysis condition C: Retention time=1.56 min; ESI-MS(+) m/z 944.5 (M+2H)

Analysis condition D: Retention time=1.38 min; ESI-MS(+) m/z 944.6 (M+2H).

PREPARATION OF EXAMPLE 1013

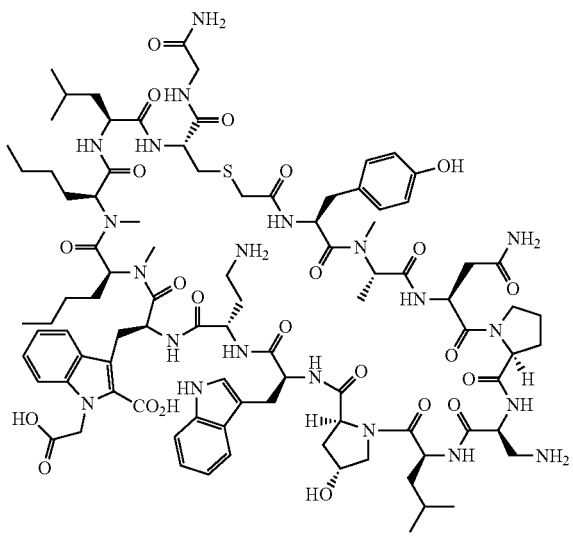 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2c(C(=O)O)n(CC(=O)O)c3ccccc23)C(=O)N1C]

EXAMPLE 1013

Example 1013 was prepared following "General Synthetic Sequence A". The crude material was purified via preparative LC/MS with the following conditions: Column: XBridge C18, 19×mm, 5-µm particles; Mobile Phase A: 5:95 methanol: water with 10-mM ammonium acetate; Mobile Phase B: 95:5 methanol: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 22.5 mg, and its estimated purity by LCMS analysis was 98%.
Analysis condition C: Retention time=1.63 min; ESI-MS(+) m/z 966.0 (M+2H)
Analysis condition D: Retention time=1.53 min; ESI-MS(+) m/z 967.2 (M+2H)
ESI-HRMS(+) m/z: Calculated: 965.9796 Found: 965.9790.

PREPARATION OF EXAMPLE 1014

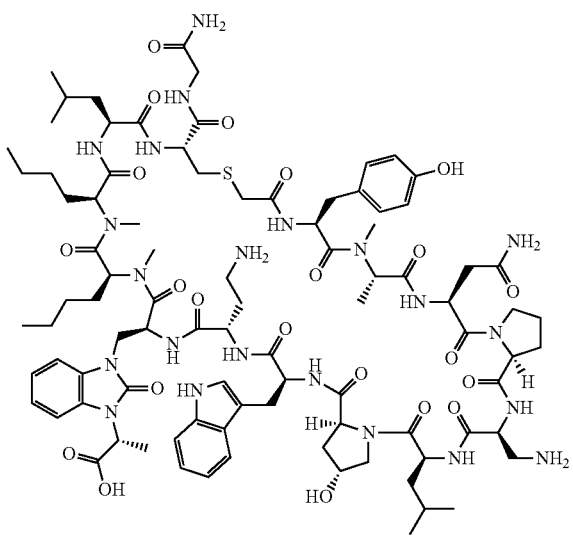 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cn2c(=O)n([C@H](C)C(=O)O)c3ccccc32)C(=O)N1C]

EXAMPLE 1014

Example 1014 was prepared following "General Synthetic Sequence A". The crude material was purified via preparative LC/MS with the following conditions: Column: XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 8-48% B over 30 minutes, then a 3-minute hold at 100% B; Flow: 20 mL/min. Fractions containing the desired product were combined and dried via centrifugal evaporation. The yield of the product was 3.3 mg, and its estimated purity by LCMS analysis was 96%.
Analysis condition C: Retention time=1.59 min; ESI-MS(+) m/z 960.6 (M+2H)
Analysis condition D: Retention time=1.39 min; ESI-MS(+) m/z 959.2 (M+2H)
ESI-HRMS(+) m/z: Calculated: 959.4879 Found: 959.4848.

PREPARATION OF EXAMPLE 1015

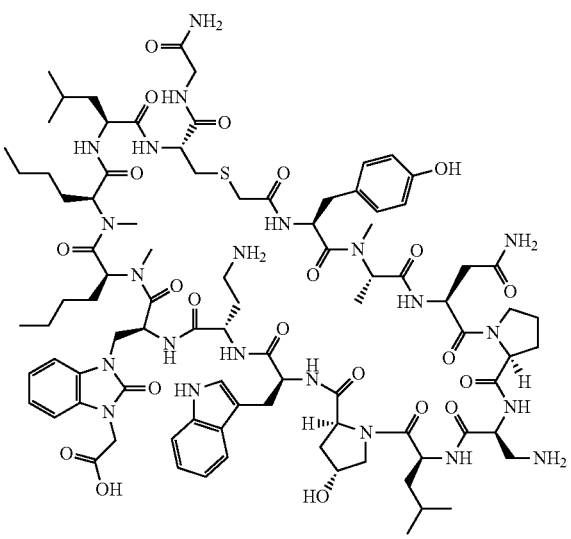 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cn2c(=O)n(CC(=O)O)c3ccccc32)C(=O)N1C]

EXAMPLE 1015

Example 1015 was prepared following "General Synthetic Sequence A". The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 8-48% B over 30 minutes, then a 5-minute hold at 100% B; Flow: 20 mL/min. Fractions containing the desired product were combined and dried via centrifugal evaporation. The yield of the product was 43.1 mg, and its estimated purity by LCMS analysis was 96%.
Analysis condition C: Retention time=1.56 min; ESI-MS(+) m/z 1901.9 (M−H)
Analysis condition D: Retention time=1.31 min; ESI-MS(+) m/z 952.3 (M+2H)
ESI-HRMS(+) m/z: Calculated: 952.4798 Found: 952.4758.

PREPARATION OF EXAMPLE 1016

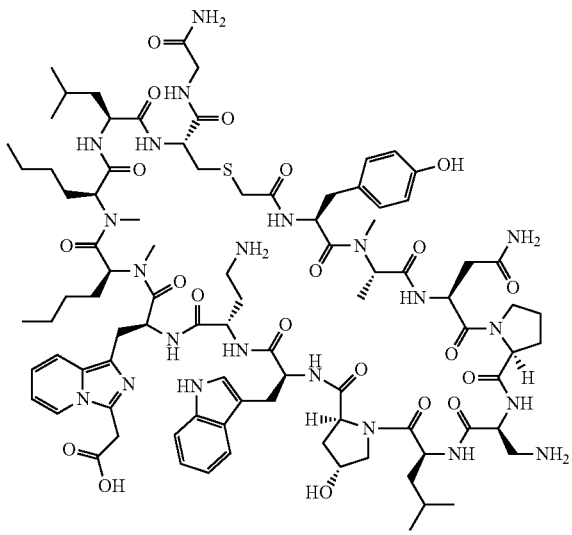 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2nc(CC(=O)O)n3ccccc23)C(=O)N1C]

EXAMPLE 1016

Example 1016 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 8-48% B over 30 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 98%.
Analysis condition C: Retention time=1.52 min; ESI-MS(+) m/z 945.1 (M+2H)
Analysis condition D: Retention time=1.36 min; ESI-MS(+) m/z 945.0 (M+2H).

PREPARATION OF EXAMPLE 1017

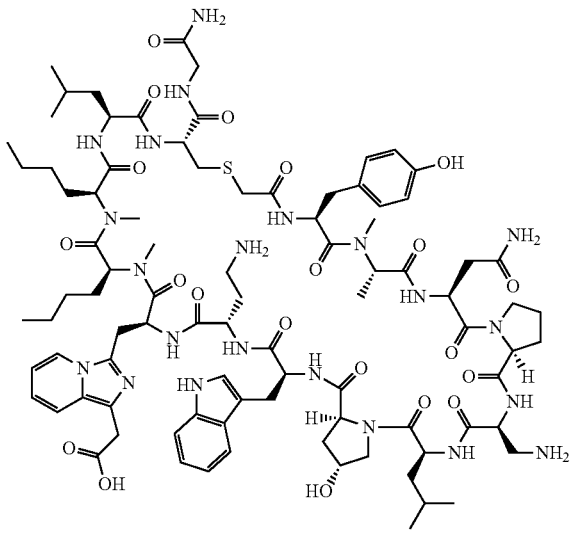 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2nc(CC(=O)O)c3ccccn23)C(=O)N1C]

EXAMPLE 1017

Example 1017 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 6.9 mg, and its estimated purity by LCMS analysis was 97%. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm
Analysis condition C: Retention time=1.56 min; ESI-MS(+) m/z 945.1 (M+2H)
Analysis condition D: Retention time=1.23 min; ESI-MS(+) m/z 944.4 (M+2H)
ESI-HRMS(+) m/z: Calculated: 944.4824 Found: 944.4783.

PREPARATION OF EXAMPLE 1018

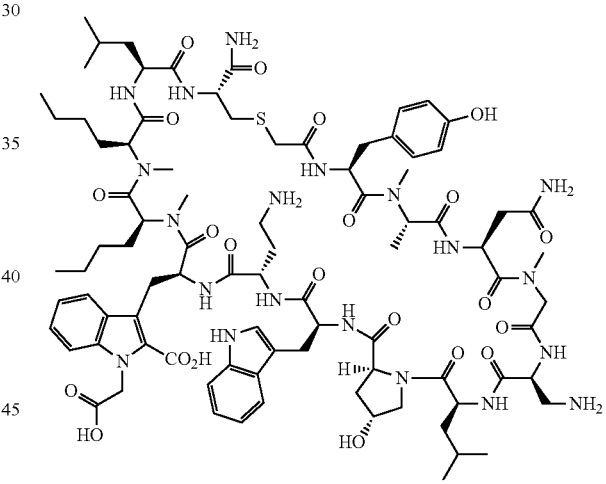

EXAMPLE 1018

Example 1018 was prepared following "General Synthetic Sequence A". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 14.8 mg, and its estimated purity by LCMS analysis was 100%.
Analysis condition C: Retention time=1.54 min; ESI-MS(+) m/z 925.0 (M+2H)
Analysis condition D: Retention time=1.38 min; ESI-MS(+) m/z 925.2 (M+2H)
ESI-HRMS(+) m/z: Calculated: 924.4611 Found: 924.4596.

PREPARATION OF EXAMPLE 1019

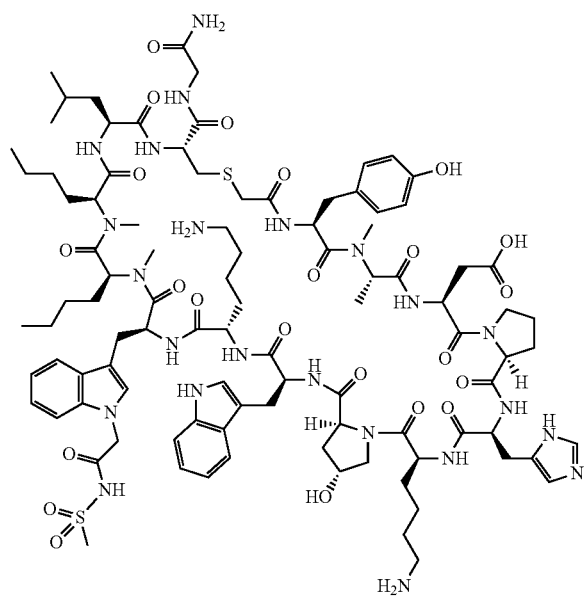 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)NS(C)(=O)=O)c3ccccc23)C(=O)N1C]

EXAMPLE 1019

Example 1019 was prepared following "General Synthetic Sequence A". The crude material was purified via preparative LC/MS with the following conditions: Column: XBridge C18, 19×mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 3.6 mg, and its estimated purity by LCMS analysis was 97%.

Analysis condition C: Retention time=1.46 min; ESI-MS(+) m/z 687.3 (M+3H)

Analysis condition D: Retention time=1.17 min; ESI-MS(+) m/z 687.4 (M+3H).

PREPARATION OF EXAMPLE 1020

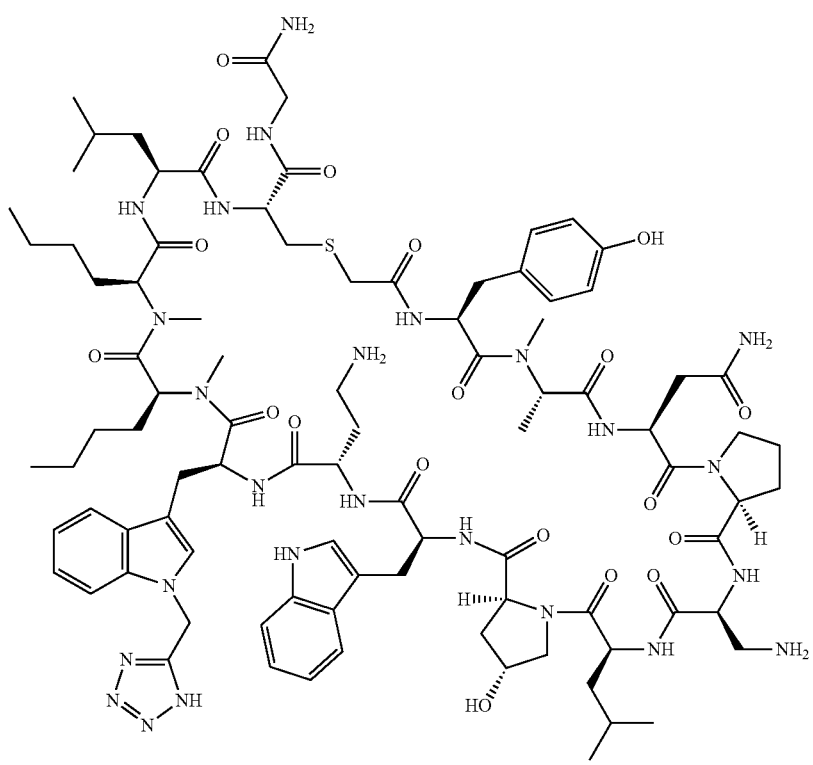 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(Cc3nnn[nH]3)c3ccccc23)C(=O)N1C]

EXAMPLE 1020

Example 1020 was prepared following "General Synthetic Sequence A". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 8.5 mg, and its estimated purity by LCMS analysis was 100%.

Analysis condition C: Retention time=1.56 min; ESI-MS(+) m/z 956.2 (M+2H)

Analysis condition D: Retention time=1.31 min; ESI-MS(+) m/z 957.1 (M+2H).

EXAMPLE 10001

Example 10001 was prepared following "General Synthetic Sequence A". The crude material of Example 10001 was purified via preparative LC/MS with the following conditions: Analysis LCMS Condition C: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0% B, 0-100% B over 3 minutes, then a 2.0-minute hold at 100% B; Flow: 0.75 mL/min; Detection: UV at 220 nm. Analysis LCMS Condition D: Column: Waters CSH C18, 2.1×50 mm, 1.7-μm particles; Mobile Phase A: 5:95 acetonitrile: water with trifluoroacetic acid; Mobile Phase B: 95:5 acetonitrile: water with trifluoroacetic acid; Temperature: 70° C.; Gradient: 0% B, 0-100% B over 3 minutes, then a 2.0-minute hold at 100% B; Flow: 0.75 mL/min; Detection: UV at 220 nm. Fractions containing the desired product were combined and dried via centrifugal evaporation. The yield of the product was 26.9 mg, and its estimated purity by LCMS analysis was 93%.

Analysis condition C: Retention time=1.40 min; ESI-MS(+) m/z 944.60 (M+2H).

Analysis condition D: Retention time=1.12 min; ESI-MS(+) m/z 944.80 (M+2H).

PREPARATION OF EXAMPLE 10001

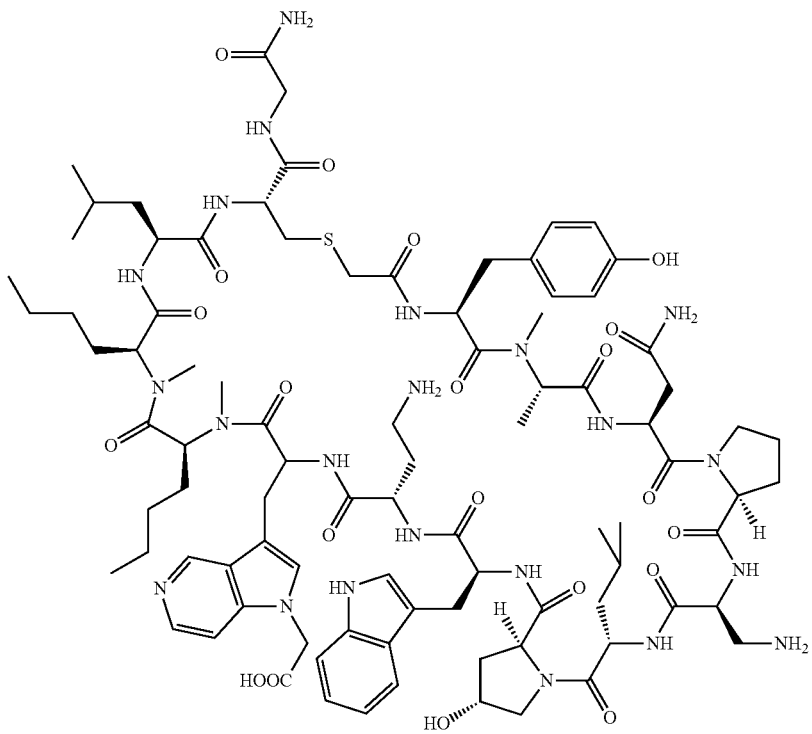 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)NC(Cc2cn(CC(=O)O)c3ccncc23)C(=O)N1C]

PREPARATION OF EXAMPLE 10002

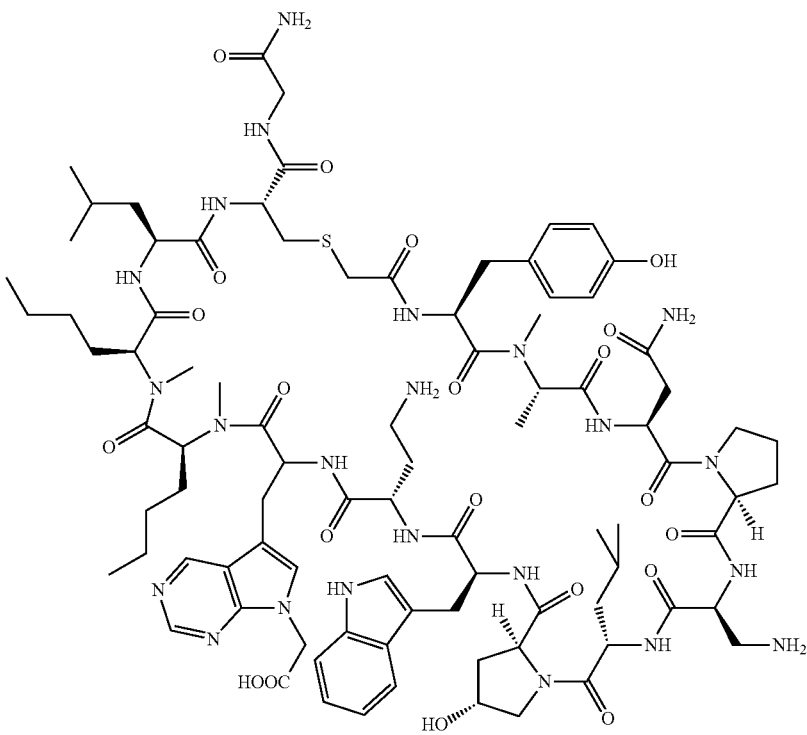

EXAMPLE 10002

Example 10002 was prepared following "General Synthetic Sequence A". The crude material of Example 10002 was purified via preparative LC/MS with the following conditions: Analysis LCMS Condition C: Column: Waters BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0% B, 0-100% B over 3 minutes, then a 2.0-minute hold at 100% B; Flow: 0.75 mL/min; Detection: UV at 220 nm. Analysis LCMS Condition D: Column: Waters CSH C18, 2.1×50 mm, 1.7-µm particles; Mobile Phase A: 5:95 acetonitrile: water with trifluoroacetic acid; Mobile Phase B: 95:5 acetonitrile: water with trifluoroacetic acid; Temperature: 70° C.; Gradient: 0% B, 0-100% B over 3 minutes, then a 2.0-minute hold at 100% B; Flow: 0.75 mL/min; Detection: UV at 220 nm. Fractions containing the desired product were combined and dried via centrifugal evaporation. The yield of the product was 22.6 mg, and its estimated purity by LCMS analysis was 98%.

Analysis condition C: Retention time=1.44 min; ESI-MS(+) m/z 945.30 (M+2H).

Analysis condition D: Retention time=1.15 min; ESI-MS(+) m/z 945.25 (M+2H).

PREPARATION OF EXAMPLE 10003

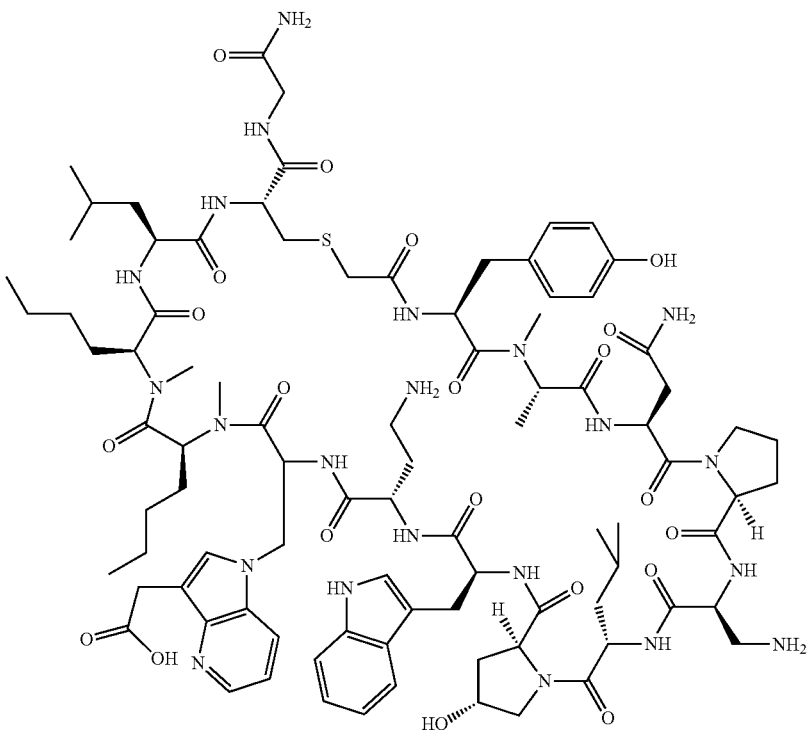 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)NC(Cn2cc(CC(=O)O)c3ncccc32)C(=O)N1C]

EXAMPLE 10003

Example 10003 was prepared following "General Synthetic Sequence A". The crude material of Example 10003 was purified via preparative LC/MS with the following conditions: Analysis LCMS Condition C: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0% B, 0-100% B over 3 minutes, then a 2.0-minute hold at 100% B; Flow: 0.75 mL/min; Detection: UV at 220 nm. Analysis LCMS Condition D: Column: Waters CSH C18, 2.1×50 mm, 1.7-μm particles; Mobile Phase A: 5:95 acetonitrile: water with trifluoroacetic acid; Mobile Phase B: 95:5 acetonitrile: water with trifluoroacetic acid; Temperature: 70° C.; Gradient: 0% B, 0-100% B over 3 minutes, then a 2.0-minute hold at 100% B; Flow: 0.75 mL/min; Detection: UV at 220 nm. Fractions containing the desired product were combined and dried via centrifugal evaporation. The yield of the product was 1.2 mg, and its estimated purity by LCMS analysis was 94%.

Analysis condition C: Retention time=1.48 min; ESI-MS(+) m/z 944.70 (M+2H).

Analysis condition D: Retention time=1.26 min; ESI-MS(+) m/z 944.45 (M+2H).

PREPARATION OF EXAMPLE 10500

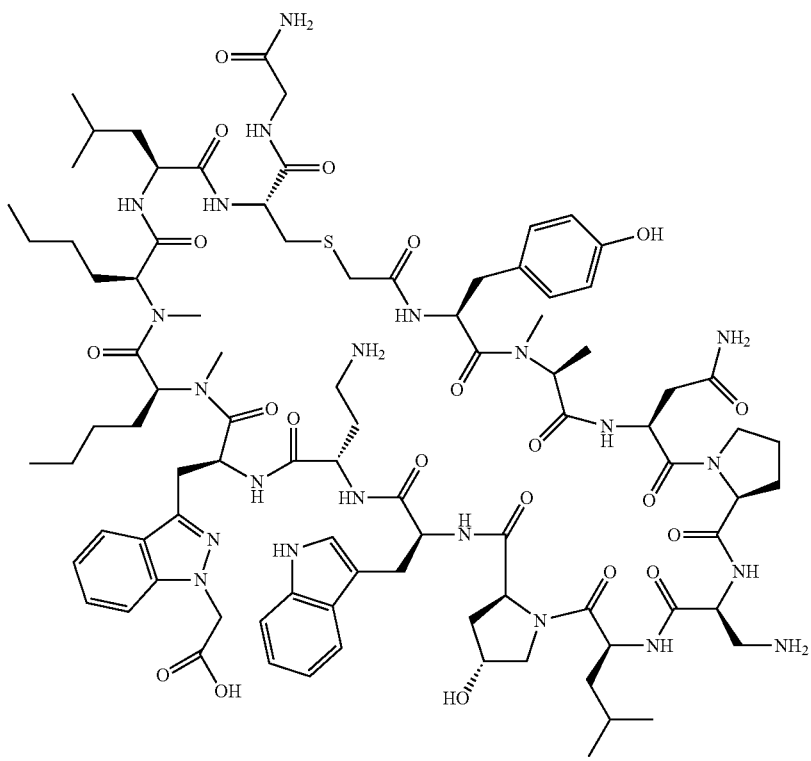 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2nn(CC(=O)O)c3ccccc23)C(=O)N1C]

EXAMPLE 10500

Example 10500 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 8-48% B over 30 minutes, then a 5-minute hold at 100% B; Flow: 20 mL/min. Fractions containing the desired product were combined and dried via centrifugal vaporation. The material was further purified via preparative LC/MS with the following conditions: Column: Waters CSH C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-70% B over 15 minutes, then a 5-minute hold at 100% B; Flow: 20 mL/min. Fractions containing the desired product were combined and dried via centrifugal evaporation. The yield of the product was 20.0 mg, and its estimated purity by LCMS analysis was 91%.
Analysis condition C: Retention time=1.66 min; ESI-MS(+) m/z 944.3 (M+2H)
Analysis condition E: Retention time=1.40 min; ESI-MS(+) m/z 944.2 (M+2H).

PREPARATION OF EXAMPLE 10501

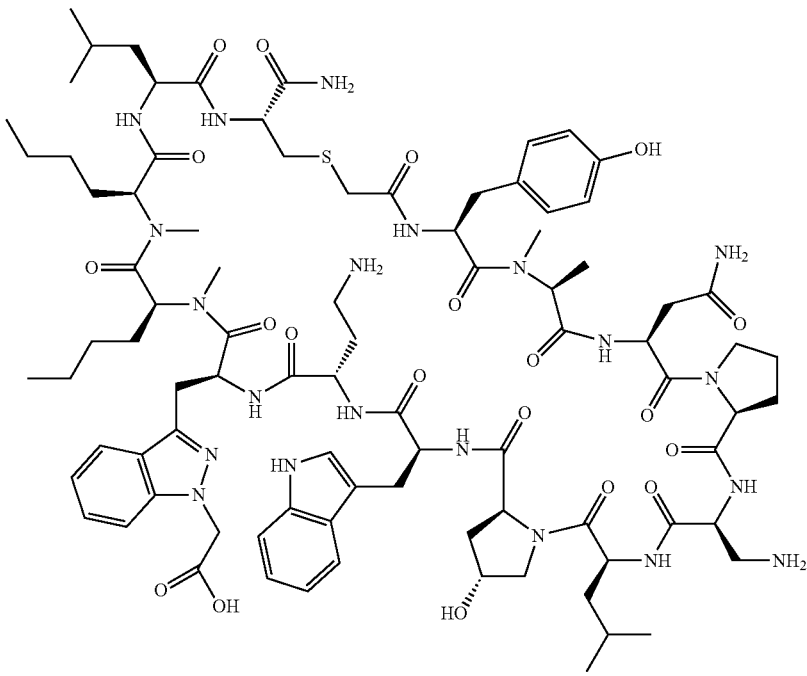 [SMILES: CCCC[C@H]1C(=O)N(C)[C@@H](CCCC)C(=O)N[C@@H](CC(C)C)C(=O)N[C@H](C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2nn(CC(=O)O)c3ccccc23)C(=O)N1C]

EXAMPLE 10501

Example 10501 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 8-48% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-70% B over 15 minutes, then a 5-minute hold at 100% B; Flow: 20 mL/min. Fractions containing the desired product were combined and dried via centrifugal evaporation. The yield of the product was 21.1 mg, and its estimated purity by LCMS analysis was 92%.

Analysis condition C: Retention time=1.70 min; ESI-MS(+) m/z 916.0 (M+2H)

Analysis condition E: Retention time=1.37 min; ESI-MS(+) m/z 916.0 (M+2H).

PREPARATION OF EXAMPLE 10502

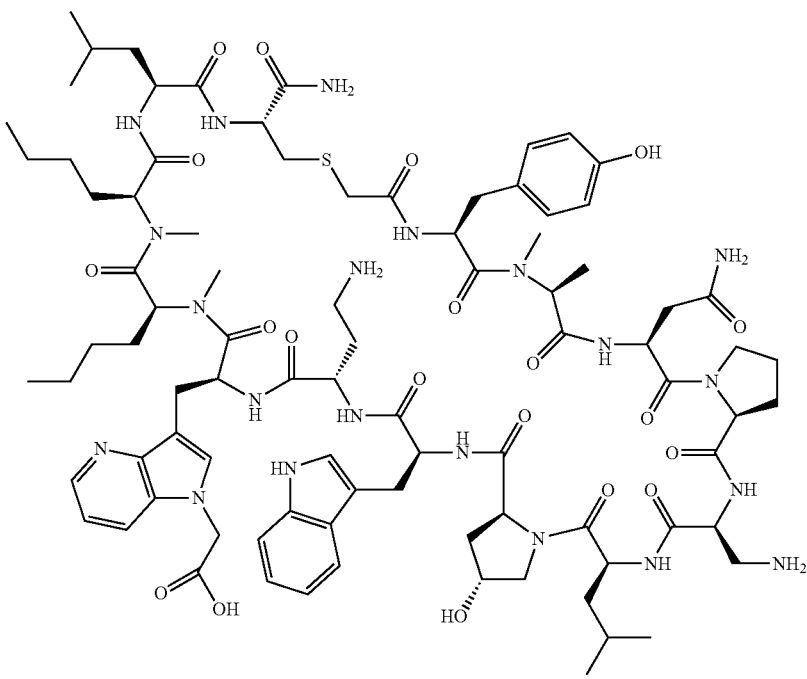 [SMILES: CCCC[C@H]1C(=O)N(C)[C@@H](CCCC)C(=O)N[C@@H](CC(C)C)C(=O)N[C@H](C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3cccnc23)C(=O)N1C]

EXAMPLE 10502

Example 10502 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 8-48% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-70% B over 15 minutes, then a 5-minute hold at 100% B; Flow: 20 mL/min. Fractions containing the desired product were combined and dried via centrifugal evaporation. The yield of the product was 1.4 mg, and its estimated purity by LCMS analysis was 94%.

Analysis condition C: Retention time=1.30 min; ESI-MS(+) m/z 916.2 (M+2H)

Analysis condition E: Retention time=1.16 min; ESI-MS(+) m/z 916.1 (M+2H.

PREPARATION OF EXAMPLE 10503

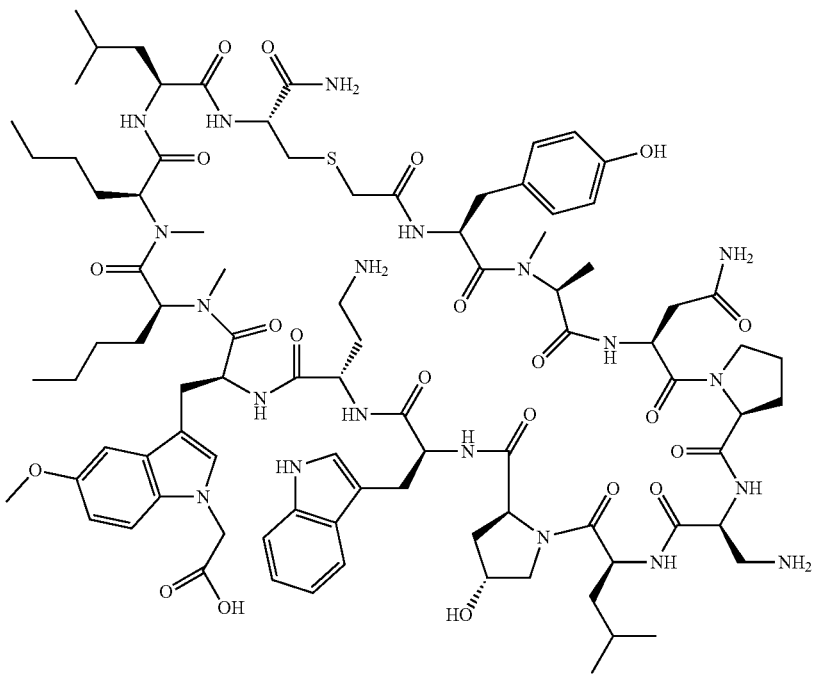 [SMILES: CCCC[C@H]1C(=O)N(C)[C@@H](CCCC)C(=O)N[C@@H](CC(C)C)C(=O)N[C@H](C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccc(OC)cc23)C(=O)N1C]

EXAMPLE 10503

Example 10503 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 23.1 mg, and its estimated purity by LCMS analysis was 96%.

Analysis condition C: Retention time=1.61 min; ESI-MS(+) m/z 930.1 (M+2H)

Analysis condition E: Retention time=1.37 min; ESI-MS(+) m/z 930.1 (M+2H).

PREPARATION OF EXAMPLE 10504

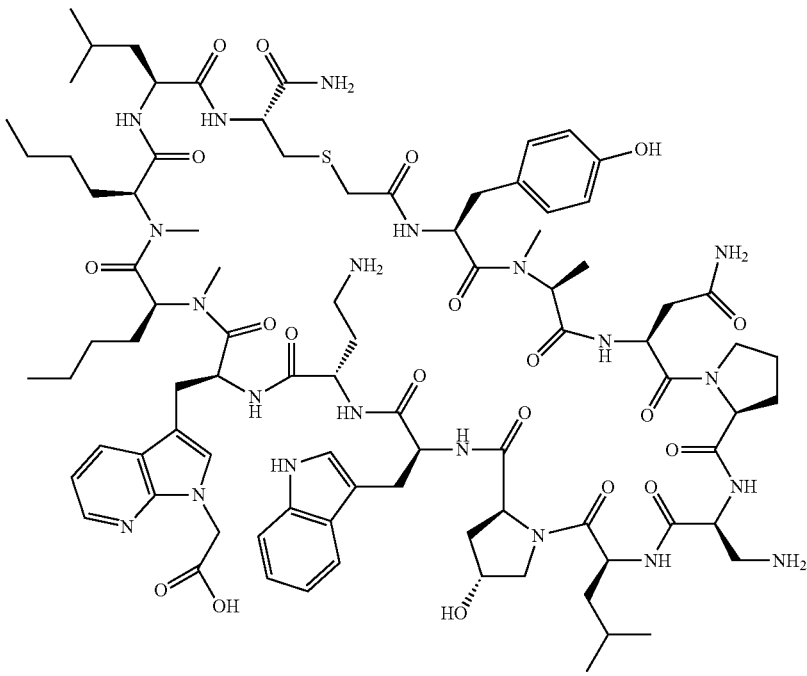 [SMILES: CCCC[C@H]1C(=O)N(C)[C@@H](CCCC)C(=O)N[C@@H](CC(C)C)C(=O)N[C@H](C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ncccc23)C(=O)N1C]

EXAMPLE 10504

Example 10504 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 2-42% B over 40 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-100% B over 10 minutes, then a 5-minute hold at 100% B; Flow: 20 mL/min. Fractions containing the desired product were combined and dried via centrifugal evaporation. The yield of the product was 6.5 mg, and its estimated purity by LCMS analysis was 97%.

Analysis condition C: Retention time=1.57 min; ESI-MS(+) m/z 916.0 (M+2H)

Analysis condition E: Retention time=1.32 min; ESI-MS(+) m/z 915.9 (M+2H).

PREPARATION OF EXAMPLE 10505

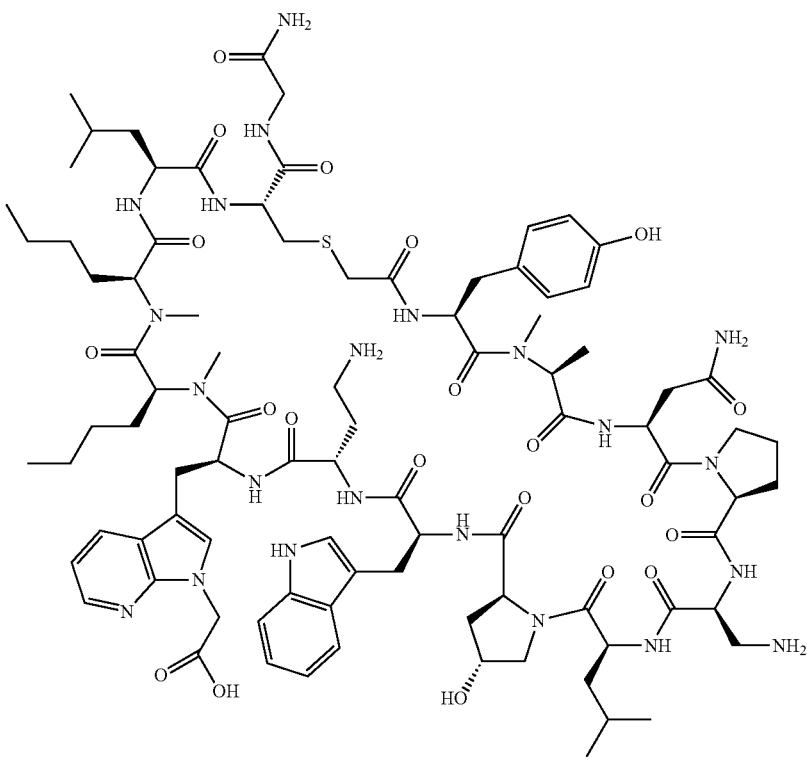 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ncccc23)C(=O)N1C]

EXAMPLE 10505

Example 10505 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 2-42% B over 40 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-100% B over 15 minutes, then a 5-minute hold at 100% B; Flow: 20 mL/min. Fractions containing the desired product were combined and dried via centrifugal evaporation. The yield of the product was 7.4 mg, and its estimated purity by LCMS analysis was 96%.
Analysis condition C: Retention time=1.53 min; ESI-MS(+) m/z 944.1 (M+2H)
Analysis condition E: Retention time=1.29 min; ESI-MS(+) m/z 944.4 (M+2H).

PREPARATION OF EXAMPLE 10506

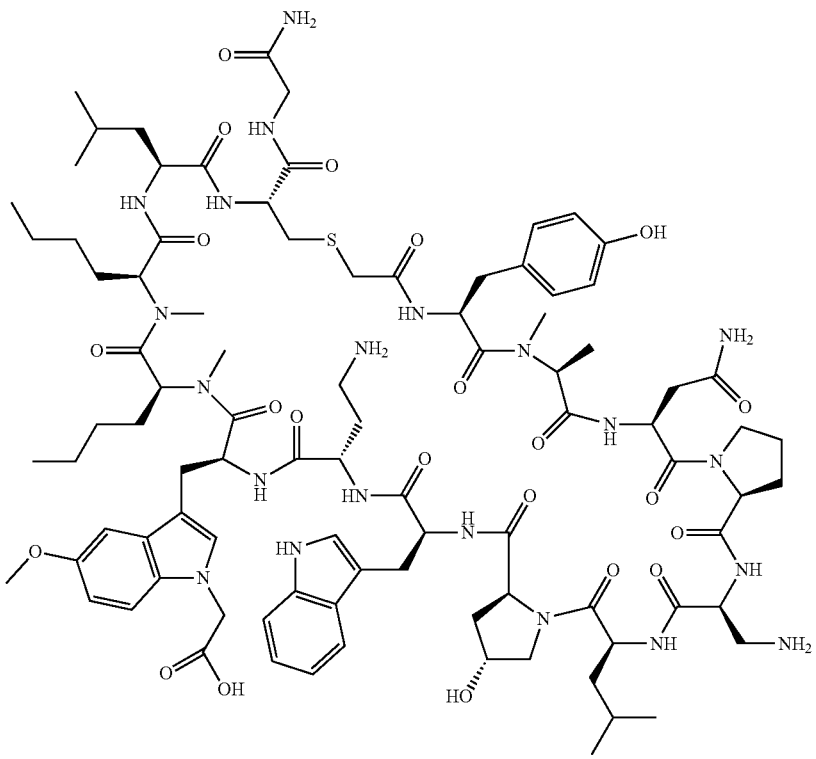 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccc(OC)cc23)C(=O)N1C]

EXAMPLE 10506

Example 10506 was prepared following "General Synthetic Sequence A". The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 8-48% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-100% B over 10 minutes, then a 5-minute hold at 100% B; Flow: 20 mL/min. Fractions containing the desired product were combined and dried via centrifugal evaporation. The yield of the product was 9.3 mg, and its estimated purity by LCMS analysis was 100%.

Analysis condition C: Retention time=1.57 min; ESI-MS(+) m/z 959.2 (M+2H)

Analysis condition E: Retention time=1.35 min; ESI-MS(+) m/z 959.3 (M+2H).

Methods for Testing the Ability of Macrocyclic Peptides to Compete for the Binding of Pd-1 to Pd-L1 Using Homogenous Time-Resolved Fluorescence (HTRF) Binding Assays The ability of the macrocyclic peptides of the present disclosure to bind to PD-L1 was investigated using a PD-1/PD-L1 Homogenous Time-Resolved Fluorescence (HTRF) binding assay.

Methods

Homogenous Time-Resolved Fluorescence (HTRF) Assays of Binding of Soluble PD-1 to Soluble PD-L1. Soluble PD-1 and soluble PD-L1 refers to proteins with carboxyl-end truncations that remove the transmembrane-spanning regions and are fused to heterologous sequences, specifically the Fc portion of the human immunoglobuling G sequence (Ig) or the hexahistidine epitope tag (His). All binding studies were performed in an HTRF assay buffer consisting of dPBS supplemented with 0.1% (w/v) bovine serum albumin and 0.05% (v/v) Tween-20. For the PD-1-Ig/PD-L1-His binding assay, inhibitors were pre-incubated with PD-L1-His (10 nM final) for 15 m in 4 µl of assay buffer, followed by addition of PD-1-Ig (20 nM final) in 1 µl of assay buffer and further incubation for 15 m. PD-L1 fusion proteins from either human, cynomologous macaques, mouse, or other species were used. HTRF detection was achieved using europium crypate-labeled anti-Ig monoclonal antibody (1 nM final) and allophycocyanin (APC) labeled anti-His monoclonal antibody (20 nM final). Antibodies were diluted in HTRF detection buffer and 5 µl was dispensed on top of binding reaction. The reaction was allowed to equilibrate for 30 minutes and signal (665 nm/620 nm ratio) was obtained using an EnVision fluorometer. Additional binding assays were established between PD-1-Ig/PD-L2-His (20 and 5 nM, respectively), CD80-His/PD-L1-Ig (100 and 10 nM, respectively) and CD80-His/CTLA4-Ig (10 and 5 nM, respectively). Binding/competition studies between biotinylated Compound No. 71 and human PD-L1-His were performed as follows. Macrocyclic peptide inhibitors were pre-incubated with PD-L1-His (10 nM final) for 60 minutes in 4 µl of assay buffer followed by addition of biotinylated Compound No. 71 (0.5 nM final) in 1 µl of assay buffer. Binding was allowed to equilibrate for 30 minutes followed by addition of europium crylated labeled Streptavidin (2.5 pM final) and APC-labeled anti-His (20 nM final) in 5 µl of HTRF buffer. The reaction was allowed to equilibrate for 30 m and signal (665 nm/620 nm ratio) was obtained using an EnVision fluorometer.

Recombinant Proteins. Carboxyl-truncated human PD-1 (amino acids 25-167) with a C-terminal human Ig epitope tag [hPD-1 (25-167)-3S-IG] and human PD-L1 (amino acids 18-239) with a C-terminal His epitope tag [hPD-L1(19-239)-tobacco vein mottling virus protease cleavage site (TVMV)-His] were expressed in HEK293T cells and purified sequentially by recombinant Protein A affinity chromatography and size exclusion chromatography. Human PD-L2-His (Sino Biologicals), CD80-His (Sino Biologicals), CTLA4-Ig (RnD Systems) were all obtained through commercial sources.

The results are shown in Table 1. As shown, the macrocyclic peptides of the present disclosure demonstrated potent inhibition of PD-1-Ig binding activity to PD-L1-TVMV-His (PD-L1-His). Ranges are as follows: A=>1 µM; B=0.10-0.99 µM; C=0.01-0.099 µM; D=0.001-0.0099 µM.

TABLE 1

| Example Number | HTRF IC50 (µM) |
| --- | --- |
| Example 0001 | B |
| Example 1254 | C |
| Example 1271 | C |
| Example 1284 | B |
| Example 1286 | B |
| Example 1287 | C |
| Example 1288 | 7.14 |
| Example 1000 | C |
| Example 1001 | 0.004 |
| Example 1002 | D |
| Example 1003 | D |
| Example 1004 | D |
| Example 1005 | D |
| Example 1006 | D |
| Example 1007 | D |
| Example 1008 | D |
| Example 1009 | C |
| Example 1010 | D |
| Example 1011 | D |
| Example 1012 | C |
| Example 1013 | C |
| Example 1014 | D |
| Example 1015 | D |
| Example 1016 | D |
| Example 1017 | D |
| Example 1018 | C |
| Example 1019 | D |
| Example 1020 | A |
| Example 10001 | C |
| Example 10002 | B |
| Example 10003 | B |
| Example 10500 | D |
| Example 10501 | D |
| Example 10502 | 0.013 |
| Example 10503 | D |

```
Sequence of Recombinant Human PD-1-IG
hPD1 (25-167)-3S-IG
                                                          (SEQ ID NO: 1)
  1    LDSPDRPWNP PTFSPALLVV TEGDNATFTC SFSNTSESFV LNWYRMSPSN

51    QTDKLAAFPE DRSQPGQDCR PRVTQLPNGR DFHMSVVRAR RNDSGTYLCG

101    AISLAPKAQI KESLRAELRV TERRAEVPTA HPSPSPRPAG QFQGSPGGGG

151    GREPKSSDKT HTSPPSPAPE LLGGSSVFLF PPKPKDTLMI SRTPEVTCVV

201    VDVSHEDPEV KFNWYVDGVE VHNAKTKPRE EQYNSTYRVV SVLTVLHQDW

251    LNGKEYKCKV SNKALPAPIE KTISKAKGQP REPQVYTLPP SRDELTKNQV

301    SLTCLVKGFY PSDIAVESES NGQPENNYKT TPPVLDSDGS FFLYSKLTVD

351    KSRWQQGNVF SCSVMHEALH NHYTQKSLSL SPGK

Sequence of Recombinant Human Pd-L1-TVMV-His (PD-L1-His)
hPDL1 (19-239)-TVMV-His
                                                          (SEQ ID NO: 2)
  1    FTVTVPKDLY VVEYGSNMTI ECKFPVEKQL DLAALIVYWE MEDKNIIQFV

51    HGEEDLKVQH SSYRQRARLL KDQLSLGNAA LQITDVKLQD AGVYRCMISY

101    GGADYKRITV KVNAPYNKIN QRILVVDPVT SEHELTCQAE GYPKAEVIWT

151    SSDHQVLSGK TTTTNSKREE KLFNVTSTLR INTTTNEIFY CTFRRLDPEE

201    NHTAELVIPE LPLAHPPNER TGSSETVRFQ GHHHHHH
```

TABLE 1-continued

| Example Number | HTRF IC50 (μM) |
|---|---|
| Example 10504 | D |
| Example 10505 | C |
| Example 10506 | D |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

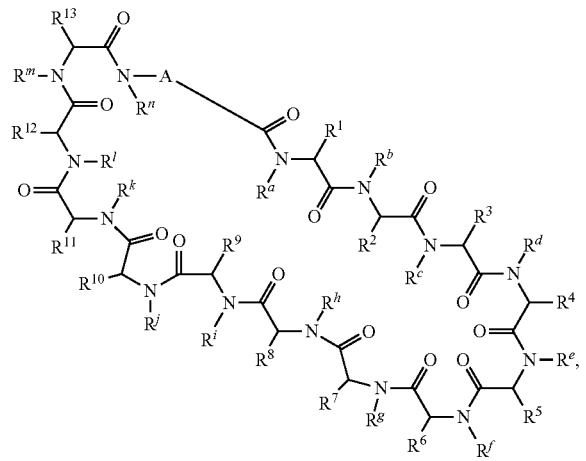

or a pharmaceutically acceptable salt thereof, wherein:

A is selected from a bond,

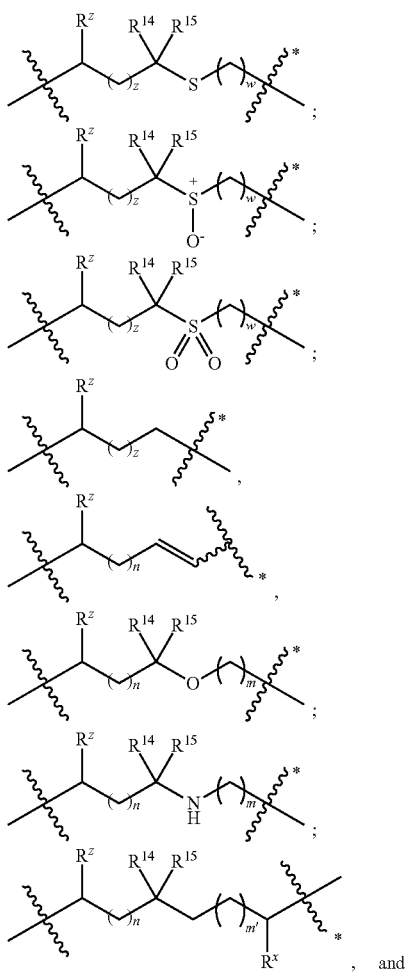

and

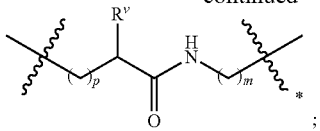

wherein:

⌇* denotes the point of attachment to the carbonyl group and *⌇ denotes the point of attachment to the nitrogen atom;

z is 0, 1, or 2;
w is 1 or 2;
n is 0 or 1;
m is 1 or 2;
m' is 0 or 1;
p is 0, 1, or 2;
$R^x$ is selected from hydrogen, amino, hydroxy, and methyl;
$R^{14}$ and $R^{15}$ are independently selected from hydrogen and methyl; and
$R^z$ is selected from hydrogen and —C(O)NHR$^{16}$; wherein R$^{16}$ is selected from hydrogen, —CHR$^{17}$C(O)NH$_2$, —CHR$^{17}$C(O)NHCHR$^{18}$C(O)NH$_2$, and —CHR$^{17}$C(O)NHCHR$^{18}$C(O)NHCH$_2$C(O)NH$_2$; wherein R$^{17}$ is selected from hydrogen and —CH$_2$OH and wherein R$^{18}$ is selected from hydrogen and methyl;
$R^v$ is hydrogen or a natural amino acid side chain;

⌇* denotes the point of attachment to the carbonyl group and *⌇ denotes the point of attachment to the nitrogen atom;

$R^c$, $R^f$, $R^h$, $R^i$, $R^m$, and $R^n$ are hydrogen;
$R^a$, $R^e$, $R^j$, and $R^k$, are each independently selected from hydrogen and methyl;
$R^{10}$ is —(CH$_2$)$_n$Q', wherein n is 1-3 and Q' is a five, six-fused saturated or unsaturated ring system containing one, two, three, or four nitrogen atoms, wherein said ring system is optionally substituted with one, two, or three groups selected from C$_1$-C$_6$alkoxy, C$_1$-C$_6$alkoxycarbonyl, C$_1$-C$_6$alkoxycarbonylC$_1$-C$_3$alkyl, C$_1$-C$_3$alkyl, (C$_1$-C$_6$alkyl)S(O)$_2$NHC(O)C$_1$-C$_3$alkyl, arylS(O)$_2$NHC(O)C$_1$-C$_3$alkyl, arylC$_1$-C$_3$alkylS(O)$_2$NHC(O)C$_1$-C$_3$alkyl, carboxy, carboxyC$_1$-C$_3$alkyl, cyano, C$_3$-C$_6$cycloalkylS(O)$_2$NHC(O)C$_1$-C$_3$alkyl, C$_3$-C$_6$cycloalkylC$_1$-C$_3$alkylS(O)$_2$NHC(O)C$_1$-C$_3$alkyl, halo, haloC$_1$-C$_3$alkoxy, haloC$_1$-C$_3$alkyl, heteroarylS(O)$_2$NHC(O)C$_1$-C$_3$alkyl, heteroarylC$_1$-C$_3$alkylS(O)$_2$NHC(O)C$_1$-C$_3$alkyl, hydroxy, —NR$^p$R$^q$, (NR$^p$R$^q$)C$_1$-C$_3$alkyl, tetrazolyl, tetrazolylC$_1$-C$_3$alkyl, and phenyl, wherein the phenyl is further optionally substituted by one, two, or three groups independently selected from C$_1$-C$_3$alkoxy, C$_1$-C$_3$alkyl, and halo; provided Q' is other than azaindolyl or indolyl; or
$R^{10}$ is —(CH$_2$)$_n$Z', wherein n is 1-3 and Z' is a six, six-fused saturated or unsaturated ring system containing one, two, three or four nitrogen atoms, wherein said ring system is optionally substituted with one, two, or three groups selected from C$_1$-C$_6$alkoxy, C$_1$-C$_6$alkoxycarbonyl, C$_1$-C$_6$alkoxycarbonylC$_1$-C$_3$alkyl, C$_1$-C$_3$alkyl, (C$_1$-C$_6$alkyl)S(O)$_2$NHC(O)C$_1$-C$_3$alkyl, arylS(O)$_2$NHC (O)C$_1$-C$_3$alkyl, arylC$_1$-C$_3$alkylS(O)$_2$NHC(O)C$_1$-C$_3$alkyl, carboxy, carboxyC$_1$-C$_3$alkyl, cyano, C$_3$-C$_6$cycloalkylS(O)$_2$NHC(O)C$_1$-C$_3$alkyl, C$_3$-C$_6$cycloalkylC$_1$-C$_3$alkylS(O)$_2$NHC(O)C$_1$-C$_3$alkyl, halo, haloC$_1$-C$_3$alkoxy, haloC$_1$-C$_3$alkyl, heteroarylS(O)$_2$NHC(O)C$_1$-C$_3$alkyl, heteroarylC$_1$-C$_3$alkylS(O)$_2$NHC(O)C$_1$-C$_3$alkyl, hydroxy, —NR$^p$R$^q$, (NR$^p$R$^q$)C$_1$-C$_3$alkyl, tetrazolyl, tetrazolylC$_1$-C$_3$alkyl, and phenyl, wherein the phenyl is further optionally substituted by one, two, or three groups independently selected from C$_1$-C$_3$alkoxy, C$_1$-C$_3$alkyl, and halo;

R$^p$ and R$^q$ are independently selected from hydrogen and C$_1$-C$_6$alkyl;

R$^{13}$ is selected from a natural amino acid side chain, an unnatural amino acid side chain, and —C(R$^{17a}$)$_2$)$_2$—X—R$^{30}$; —C(R$^{17a}$)$_2$C(O)N(R$^{16a}$)C(R$^{17a}$)$_2$—X'—R$^{31}$; —C(R$^{17a}$)$_2$[C(O)N(R$^{16a}$)C(R$^{17a}$)$_2$]$_{w'}$—X—R$^{31}$; —(C(R$^{17a}$)(R$^{17}$)C(O)NR$^{16a}$)$_{n'}$—H; and —(C(R$^{17a}$)(R$^{17}$)C(O)NR$^{16a}$)$_{m'}$—C(R$^{17a}$)(R$^{17}$)—CO$_2$H;

w' is 2 or 3;

n' is 1-6;

m' is 0-5;

X is a chain of between 1 and 172 atoms wherein the atoms are selected from carbon and oxygen and wherein the chain may contain one, two, three, or four groups selected from —NHC(O)NH—, and —C(O)NH— embedded therein; and wherein the chain is optionally substituted with one to six groups independently selected from —CO$_2$H, —C(O)NH$_2$, —CH$_2$C(O)NH$_2$, and —(CH$_2$)CO$_2$H;

X' is a chain of between 1 and 172 atoms wherein the atoms are selected from carbon and oxygen and wherein the chain may contain one, two, three, or four groups selected from —NHC(O)NH—, and —C(O)NH— embedded therein; and wherein the chain is optionally substituted with one to six groups independently selected from —CO$_2$H, —C(O)NH$_2$, and —CH$_2$CO$_2$H, provided that X' is other than unsubstituted PEG;

R$^{30}$ is selected from —CO$_2$H, —C(O)NR$^w$R$^x$, and —CH$_3$ wherein R$^w$ and R$^x$ are independently selected from hydrogen and C$_1$-C$_6$alkyl, provided that when X is all carbon, R$^{30}$ is other than —CH$_3$;

R$^{31}$ is —CO$_2$H, —C(O)NR$^w$R$^x$, —CH$_3$, alexa-5-SDP, and biotin;

each R$^{17a}$ is independently selected from hydrogen, C$_1$-C$_6$alkyl, —CH$_2$OH, —CH$_2$CO$_2$H, —(CH$_2$)$_2$CO$_2$H, each R$^{17}$ is independently selected from hydrogen, —CH$_3$, (CH$_2$)$_z$N$_3$, —(CH$_2$)$_z$NH$_2$, —X—R$^{31}$, —(CH$_2$)$_z$CO$_2$H, —CH$_2$OH, CH$_2$C≡CH, and —(CH$_2$)$_z$-triazolyl-X—R$^{35}$, wherein z is 1-6 and R$^{35}$ is selected from —CO$_2$H, —C(O)NR$^w$R$^x$, CH$_3$, biotin, -2-fluoropyridine, —C(O)—(CH$_2$)$_2$—C(O)O-vitamin E, —C(O)O-vitamin E; and

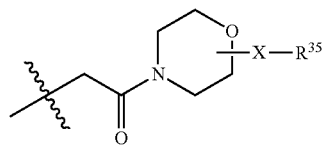

provided at least one R$^{17}$ is other than hydrogen, —CH$_3$, or —CH$_2$OH;

R$^1$, R$^2$, R$^3$, R$^4$, R$^5$, R$^6$, R$^7$, R$^8$, R$^9$, R$^{11}$, and R$^{12}$ are independently selected from a natural amino acid side chain and an unnatural amino acid side chain or form a ring with the corresponding vicinal R group as described below;

R$^e$ and R$^k$ can each form a ring with the corresponding vicinal R group and the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, and hydroxy;

R$^b$ is methyl or, R$^b$ and R$^2$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, and hydroxy;

R$^d$ is hydrogen or methyl, or, R$^d$ and R$^4$, together with the atoms to which they are attached, can form a ring selected from azetidine, pyrollidine, morpholine, piperidine, piperazine, and tetrahydrothiazole; wherein each ring is optionally substituted with one to four groups independently selected from amino, cyano, methyl, halo, hydroxy, and phenyl;

R$^g$ is hydrogen or methyl or R$^g$ and R$^7$, together with the atoms to which they are attached, can form a ring selected from azetidine, pyrollidine, morpholine, piperidine, piperazine, and tetrahydrothiazole; wherein each ring is optionally substituted with one to four groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and R$^L$ is methyl or, R$^L$ and R$^{12}$, together with the atoms to which they are attached, form a ring selected from azetidine and pyrollidine, wherein each ring is optionally substituted with one to four independently selected from amino, cyano, methyl, halo, and hydroxy; and wherein each unnatural amino acid side chain is independently selected from:

C$_2$-C$_7$alkenyl, C$_1$-C$_3$alkoxyC$_1$-C$_3$alkyl, C$_1$-C$_6$alkoxycarbonylC$_1$-C$_3$alkyl, C$_1$-C$_7$alkyl, C$_1$-C$_3$alkylsulfanylC$_1$-C$_3$alkyl, amidoC$_1$-C$_3$alkyl, aminoC$_1$-C$_3$alkyl, benzothiazolylC$_1$-C$_3$alkyl, benzothienylC$_1$-C$_3$alkyl, benzyloxyC$_1$-C$_3$alkyl, carboxyC$_1$-C$_3$alkyl, C$_3$-C$_{14}$cycloalkylC$_1$-C$_3$alkyl, C$_3$-C$_6$cycloalkylC$_1$-C$_3$alkyl, diphenylmethyl, furanylC$_1$-C$_3$alkyl, imidazolylC$_1$-C$_3$alkyl, naphthylC$_1$-C$_3$alkyl, pyridinylC$_1$-C$_3$alkyl, thiazolylC$_1$-C$_3$alkyl, thienylC$_1$-C$_3$alkyl, azaindolylC$_1$-C$_3$alkyl, wherein the azaindolyl part of the azaindolylC$_1$-C$_3$alkyl is optionally substituted with one or two substituents independently selected from C$_1$-C$_6$alkoxy, C$_1$-C$_6$alkyl, (C$_1$-C$_6$alkyl)S(O)$_2$NHC(O)C$_1$-C$_3$alkyl, carboxy, carboxyC$_1$-C$_3$alkyl, cyano, halo, hydroxy, tetrazolyl, tetrazolylC$_1$-C$_3$alkyl, and phenyl, wherein the phenyl is further optionally substituted by one, two, or three groups independently selected from $C_1$-$C_3$alkoxy, $C_1$-$C_3$alkyl, and halo, biphenyl$C_1$-$C_3$alkyl wherein the biphenyl is optionally substituted with a methyl group, —$(CH_2)_nQ'$, wherein n is 1-3 and Q' is a five, six-fused saturated or unsaturated ring system containing two, three, or four nitrogen atoms, wherein said ring system is optionally substituted with one, two, or three groups selected from $C_1$-$C_6$alkoxy, $C_1$-$C_6$alkyl, $(C_1$-$C_6$alkyl$)S(O)_2NHC(O)C$-$C_3$alkyl, $(C_1$-$C_6$alkyl) sulfamidyl$C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; provided Q' is other than azaindolyl or indolyl, —$(CH_2)_nZ'$, wherein n is 1-3 and Z' is a six, six-fused saturated or unsaturated ring system containing one, two, three or four nitrogen atoms, wherein said ring system is optionally substituted with one, two, or three groups selected from $C_1$-$C_6$alkoxy, $C_1$-$C_6$alkyl, $(C_1$-$C_6$alkyl$)S(O)NHC(O)C_1$-$C_3$alkyl, carboxy, carboxy$C_1$-$C_3$alkyl, cyano, halo, hydroxy, tetrazolyl, tetrazolyl$C_1$-$C_3$alkyl and phenyl, wherein the phenyl is further optionally substituted by one, two, or three groups independently selected from $C_1$-$C_3$alkoxy, $C_1$-$C_3$alkyl, and halo, heterorocyclyl optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, —$NC(NH_2)_2$, nitro, and —$OP(O)(OH)_2$, indolyl$C_1$-$C_3$alkyl, wherein the indolyl part is optionally substituted with one or two groups selected from $(C_{1-6}$alkyl$)S(O)_2NHC(O)C_1$-$C_3$alkyl, $C_1$-$C_6$alkoxy, $C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo, phenyl optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl hydroxy, —$NC(NH_2)_2$, nitro, and —$OP(O)(OH)_2$, $NR^aR^b(C_1$-$C_7$alkyl), wherein $R^a$ and $R^b$ are independently selected from hydrogen, $C_2$-$C_4$alkenyloxycarbonyl, $C_1$-$C_3$alkyl, $C_1$-$C_3$alkylcarbonyl, $C_3$-$C_6$cycloalkylcarbonyl, furanylcarbonyl, and phenylcarbonyl, wherein when the alkyl linker contains more than one carbon an additional $NR^aR^b$ group can be on the chain, $NR^cR^d$carbonyl$C_1$-$C_3$alkyl, wherein $R^c$ and $R^d$ are independently selected from hydrogen, $C_1$-$C_3$alkyl, and triphenylmethyl, phenyl$C_1$-$C_3$alkyl wherein the phenyl part is optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, —$NC(NH_2)_2$, nitro, and —$OP(O)(OH)_2$, and phenoxy$C_1$-$C_3$alkyl wherein the phenyl is optionally substituted with a $C_1$-$C_3$alkyl group.

2. A compound of claim 1, or a pharmaceutically acceptable salt thereof, wherein $R^{13}$ is a natural amino acid side chain or an unnatural amino acid side chain.

3. A compound of claim 2, or a pharmaceutically acceptable salt thereof, wherein $R^{10}$ is —$(CH_2)_nQ'$, wherein n is 1-3 and Q' is a five, six-fused saturated or unsaturated ring system containing two, three, or four nitrogen atoms, wherein said ring system is optionally substituted with one, two, or three groups selected from $C_1$-$C_6$alkoxy, $C_1$-$C_6$alkyl, $(C_1$-$C_6$alkyl$)S(O)_2NHC(O)C_1$-$C_3$alkyl, carboxy, carboxy$C_1$-$C_3$alkyl, cyano, halo, hydroxy, oxo, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo; provided Q' is other than azaindolyl or indolyl; or $R^{10}$ is —$(CH_2)_nZ'$, wherein n is 1-3 and Z' is a six, six-fused saturated or unsaturated ring system containing one, two, three or four nitrogen atoms, wherein said ring system is optionally substituted with one, two, or three groups selected from $C_1$-$C_6$alkoxy, $C_1$-$C_6$alkyl, $(C_1$-$C_6$alkyl$)S(O)_2NHC(O)C_1$-$C_3$alkyl, carboxy, carboxy$C_1$-$C_3$alkyl, cyano, halo, hydroxy, tetrazolyl, tetrazolyl$C_1$-$C_3$alkyl, and phenyl, wherein the phenyl is further optionally substituted by one, two, or three groups independently selected from $C_1$-$C_3$alkoxy, $C_1$-$C_3$alkyl, and halo.

4. A compound of claim 3, or a pharmaceutically acceptable salt thereof, wherein A is

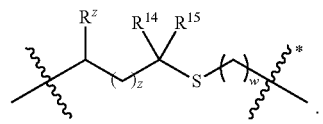

5. A compound of claim 4, or a pharmaceutically acceptable salt thereof, wherein w is 1;

z is 0; and $R^z$ is —$C(O)NHR^{16}$; wherein $R^{16}$ is selected from hydrogen and —$CHR^{17}C(O)NH_2$, wherein $R^{17}$ is hydrogen.

6. A compound of claim 5, or a pharmaceutically acceptable salt thereof, wherein $R^d$ and $R^4$, together with the atoms to which they are attached, form a pyrollidine ring;

$R^g$ and $R^7$, together with the atoms to which they are attached, form a pyrollidine ring, wherein said ring is optionally substituted with one hydroxy group; and $R^k$ is methyl.

7. A compound of claim 6, or a therapeutically acceptable salt thereof, wherein:

$R^a$, $R^e$, and $R^j$ hydrogen;

$R^b$ and $R^2$ are each methyl, or, $R^b$ and $R^2$, together with the atoms to which they are attached, form a piperidine ring;

$R^L$ is methyl;

$R^n$ is hydrogen;

$R^1$ is phenylmethyl wherein the phenyl is optionally substituted with one group selected from $C_1$-$C_6$alkoxy, halo, and hydroxy;

$R^3$ is selected from —CH$_2$C(O)NH$_2$ and —CH$_2$CO$_2$H;

$R^5$ is selected from —CH$_2$(imidazolyl), —CH$_2$NH$_2$, and —CH$_2$CH$_2$CO$_2$H;

$R^6$ is selected from —CH$_2$CH(CH$_3$)$_2$, —(CH$_2$)$_4$NH$_2$, and (CH$_2$)$_2$C(O)NH$_2$;

$R^8$ is —CH$_2$(indolyl);

$R^9$ is selected from —(CH$_2$)$_2$NH$_2$ and CH$_2$OH;

$R^{10}$ is —(CH$_2$)$_n$Q', wherein n is 1 and Q' is a five, six-fused saturated or unsaturated ring system containing two or three nitrogen atoms, wherein said ring system is optionally substituted with one or two groups selected from —CH$_3$, —CH$_2$CO$_2$H, and oxo; provided Q' is other than azaindolyl or indolyl; or $R^{10}$ is —(CH$_2$)$_n$Z', wherein n is 1 and Z' is a six, six-fused saturated or unsaturated ring system containing one nitrogen atom;

$R^{11}$ and $R^{12}$ are —(CH$_2$)$_3$CH$_3$; and $R^{13}$ is selected from methyl, —CH$_2$CH(CH$_3$)$_2$, and —(CH$_2$)$_3$NHC(NH)NH$_2$.

8. A compound selected from:

Example 0001, Example 1254, Example 1271, Example 1286, Example 1287, Example 1288, Example 1009, Example 1012, Example 1014, Example 1015, Example 1016, Example 1017, Example 10001, Example 10002, Example 10003, Example 10500, Example 10501, Example 10502, Example 10504, and Example 10505, or a pharmaceutically acceptable salt thereof.

9. A method of enhancing, stimulating, and/or increasing the immune response in a subject in need thereof, said method comprising administering to the subject a therapeutically effective amount of a compound of claim 1 or a therapeutically acceptable salt thereof.

10. A method of inhibiting growth, proliferation, or metastasis of cancer cells in a subject in need thereof, said method comprising administering to the subject a therapeutically effective amount a compound of claim 1 or a therapeutically acceptable salt thereof.

11. The method of claim 10 wherein the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and hematological malignancies.

12. A method of treating an infectious disease in a subject in need thereof, the method comprising administering to the subject a therapeutically effective amount of a compound of claim 1 or a therapeutically acceptable salt thereof.

13. The method of claim 12 wherein the infectious disease is caused by a virus.

14. A method of treating septic shock in a subject in need thereof, the method comprising administering to the subject a therapeutically effective amount of a compound of claim 1 or a therapeutically acceptable salt thereof.

15. A method blocking the interaction of PD-L1 with PD-1 and/or CD80 in a subject, said method comprising administering to the subject a therapeutically effective amount of a compound of claim 1 or a therapeutically acceptable salt thereof.

* * * * *